(12) United States Patent
Valenzuela et al.

(10) Patent No.: US 7,741,437 B2
(45) Date of Patent: Jun. 22, 2010

(54) P. ARIASI POLYPEPTIDES, P. PERNICIOSUS POLYPEPTIDES AND METHODS OF USE

(75) Inventors: Jesus G. Valenzuela, Rockville, MD (US); Jose M. C. Ribiero, Rockville, MD (US); Shaden Kamhawi, Rockville, MD (US); Yasmine Belkaid, Norwood, OH (US); Laurent Fischer, Lyons (FR); Jean-Christophe Audonnet, Lyons (FR); Francis Milward, Bogart, GA (US)

(73) Assignees: The United States of America as represented by the Department of Health and Human Services, Washington, DC (US); Merial Limited, Duluth, GA (US)

( * ) Notice: Subject to any disclaimer, the term of this patent is extended or adjusted under 35 U.S.C. 154(b) by 897 days.

(21) Appl. No.: 10/527,500

(22) PCT Filed: Sep. 18, 2003

(86) PCT No.: PCT/US03/29833

§ 371 (c)(1),
(2), (4) Date: Mar. 11, 2005

(87) PCT Pub. No.: WO2004/027041

PCT Pub. Date: Apr. 1, 2004

(65) Prior Publication Data

US 2006/0004186 A1    Jan. 5, 2006

Related U.S. Application Data

(60) Provisional application No. 60/412,327, filed on Sep. 19, 2002, provisional application No. 60/425,852, filed on Nov. 12, 2002.

(51) Int. Cl.
C07K 14/00 (2006.01)

(52) U.S. Cl. .................................... 530/350

(58) Field of Classification Search ............... None
See application file for complete search history.

(56) References Cited

U.S. PATENT DOCUMENTS 6,248,329 B1 * 6/2001 Chandrashekar et al. . 424/191.1

FOREIGN PATENT DOCUMENTS

| WO | WO 95/06729 | 3/1995 |
| WO | WO/9920644 | * 4/1999 |
| WO | WO 02/102324 | 12/2002 |
| WO | WO 2004/039958 | 5/2004 |

OTHER PUBLICATIONS

Gerhold et al [BioEssays, vol. 18, pp. 973-981 {1996}].*
Bowie et al (Science, 1990, 247:1306-1310).*
(Chapter 29 of Vaccines, Plotkin, et al. (eds) WB Saunders, Philadelphia, 1998, especially p. 571, paragraph 2.*
Lederman et al. (Molecular Immunology 28: 1171-1181, 1991).*
Colman et al Research in Immunology 145: 33-36, 1994.*
Greenspan et al. (Nature Biotechnology 7: 936-937, 1999).*
Barral et al., "Human immune response to sand fly salivary gland products is a useful epidemiological marker," *Am. J. Trop. Med. Hyg.* 62:740-745, 2000.
Belkaid et al., "Development of a natural model of cutaneous leishmaniasis: powerful effects of vector saliva and saliva preexposure on the long-term outcome of *Leishmania* major infection in the mouse ear dermis," *J Exp Med* 188, 1941-1953, 1998.
Belkaid et al., "Delayed-type hypersensitivity to *Phlebotomus papatasi* sand fly bite: An adaptive response induced by the fly?" *Proc Natl Acad Sci U S A* 97, 6704-6709, 2000.
Campbell, *Monoclonal Antibody Technology*. New York: Elsevier Science Publishing Co., Inc., pp. 1-32, 1984.
Sambrook et al., eds., *Molecular Cloning: A Laboratory Manual*, 2nd edition. Cold Spring Harbor Laboratory Press, vol. 3, pp. 16.2-16.81, 1989.
Titus et al., "Salivary gland lysates of the sand fly *Lutzomyia longipalpis* enhance *Leishmania* infectivity," *Science* 239(4845):1306-1308, 1988.
Valenzuela et al., "Toward a defined anti-*Leishmania* vaccine targeting vector antigens: Characterization of a protective salivary protein," *J. Exp. Med.* 194:331-342, 2001.
Database A_Genseq_Jun. 29, 2004 Accession No. ABB71995, Mar. 26, 2005, 1 page.
Database A_Genseq_Jun. 29, 2004 Accession No. ABG718028, Feb. 18, 2002, 1 page.
Database SPTrEMBL Accession No. Q95WD8, Dec. 19, 2001, 6 pages.
Database SPTrEMBL Accession No. Q23404, Jun. 6, 1998, 5 pages.
Database A_Genseq_Jun. 29, 2004 Accession No. AAG03191, Oct. 6, 2000, 1 page.
Database A_Genseq_Jun. 29, 2004 Accession No. ABG24332, Feb. 18, 2002, 1 page.
Database SPTrEMBL Accession No. Q9HNC7 Mar. 16, 2001, 4 pages.
Database A_Genseq_Jun. 29, 2004 Accession No. AAU48010, Feb. 27, 2002, 1 page.
Database SPTrEMBL Accession No. Q95WE2, Dec. 1, 2001, 1 page.
Database PIR_78 Accession No. G81431, Mar. 31, 2000, 2 pages.
Database SPTrEMBL Accession No. Q9XZ44, Nov. 12, 1999, 4 pages.
Database A_Genseq_Jun. 29, 2004 Accession No. AAB94843 Jun. 26, 2001, 1 page.

(Continued)

Primary Examiner—Robert B Mondesi
Assistant Examiner—Nina A Archie
(74) Attorney, Agent, or Firm—Klarquist Sparkman, LLP.

(57) ABSTRACT

Substantially purified salivary *P. ariasi* and *P. perniciosus* polypeptides, and polynucleotides encoding these polypeptides are disclosed. Vectors and host cells including the *P. ariasi* and *P. perniciosus* polynucleotides are also disclosed. In one embodiment, a method is disclosed for inducing an immune response to sand fly saliva. In other embodiments, methods for treating or preventing *Leishmaniasis* are disclosed.

10 Claims, No Drawings

OTHER PUBLICATIONS

Database A_Genseq_Jun. 29, 2004 Accession No. ABB61398, Mar. 26, 2002, 1 page.
Database A_Genseq_Jun. 29, 2004 Accession No. AAB42952, Feb. 8, 2001, 1 page.
Database SPTrEMBL Accession No. Q9RVD4, May 1, 2000, 1 page.
Database SPTrEMBL Accession No. Q95WE2, Dec. 1, 2001, 2 pages.
Database PIR_78 Accession No. B64020, Sep. 10, 1999, 1 page.
Database A_Genseq_Jun. 29, 2004 Accession No. ABB57882, Mar. 26, 2002, 1 page.
Database PIR_78 Accession No. T50116, Jun. 9, 2000, 1 page.
Database PIR_78 Accession No. F90270, May 24, 2001, 1 page.
Database A_Genseq_Jun. 29, 2004 Accession No. ABB58845, Mar. 26, 2002, 1 page.
Database A_Genseq_Jun. 29, 2004 Accession No. AAB83185, Jul. 9, 2001, 1 page.
Database Swissprot_42 Accession No. Q57124, Nov. 10, 1997, 1 page.
Adler et al., "The mouthparts, alimentary tract and salivary apparatus of the female *Phlebotomus papatasi*," *Ann. Trop. Med. Parasitol.* 20:109, 1926.
Belkaid et al., "A natural model of *Leishmania major* infection reveals a prolonged "silent" phase of parasite amplification in the skin before the onset of lesion formation and immunity," *J. Immunol.* 165:969-977, 2000.
Charlab et al., "Toward an understanding of the biochemical and pharmacological complexity of the saliva of a hematophagous sand fly *Lutzomyia longipalpis*," *Proc. Natl. Acad. Sci., USA.* 96(26):15155-15160, 1999.
Haskó et al., "Adenosine receptor agonists differentially regulate IL-10, TNF-alpha, and nitric oxide production in RAW 264.7 macrophages and in endotoxemic mice," *J. Immunol.*, 157(10):4634-4640, 1996.
Haskó et al., "Adenosine inhibits IL-12 and TNF-[alpha] production via adenosine A2a receptor-dependent and independent mechanisms," *FASEB J.*, 14(13):2065-2074, 2000.
Gurunathan et al., "Vaccination with DNA encoding the immunodominant LACK parasite antigen confers protective immunity to mice infected with *Leishmania major*," *J. Exp. Med.* 186:1137-1147, 1997.
Gurunathan et al., "Vaccine requirements for sustained cellular immunity to an intracellular parasitic infection," *Nat. Med.* 4:1409-1415, 1998.
Kamhawi et al., "Protection against cutaneous leishmaniasis resulting from bites of uninfected sand flies," *Science* 290:1351-1354, 2000.
Katz et al., "Adenosine, AMP, and protein phosphatase activity in sand fly saliva," *Am. J. Trop. Med. Hyg.* 62:145-150, 2000.
Killick-Kendrick, Biology of *Leishmania* in phlebotomine sand flies. In Biology of the Kinetoplastida. W. Lumsden and D. Evans, editors. Academic Press, New York. 395, 1979.
Lerner et al., "Isolation of maxadilan, a potent vasodilatory peptide from the salivary glands of the sand fly *Lutzomyia longipalpis*," *J. Biol. Chem.*, 266(17):11234-11236, 1991.
Makoul et al., "Prostaglandin E2 inhibits the activation of cloned T cell hybridomas," *J. Immunol.*, 134(4):2645-2650, 1985.
Mellanby, "Man's Reaction to Mosquito Bites," *Nature* 158(4016):554-555, 1946.
Méndez et al., "The potency and durability of DNA- and protein-based vaccines against *Leishmania major* evaluated using low dose, intradermal challenge," *J. Immunol.* 166(8):5122-5128, 2001.

Modi et al., "A simple technique for mass rearing *Lutzomyia longipalpis* and *Phlebotomus papatasi* (Diptera: Psychodidae) in the laboratory," *J. Med. Ent.* 20:568-569, 1983.
Nong et al., "Peptides encoded by the calcitonin gene inhibit macrophage function," *J. Immunol.*, 143(1):45-49, 1989.
Qureshi et al., "Immunomodulatory properties of maxadilan, the vasodilator peptide from sand fly salivary gland extracts," *Am. J. Trop. Med. Hyg.*, 54(6):665-671, 1996.
Ribeiro et al., "Blood-finding strategy of a capillary-feeding sandfly, *Lutzomyia longipalpis*," *Comp. Biochem. Physiol.*, 83(4):683-686, 1986.
Ribeiro et al., "Salivary apyrase activity of some Old World phlebotomine sand flies," *Insect Biochem.* 19:409-412, 1989.
Ribeiro et al., "Salivary glands of the sand fly *Phlebotomus papatasi* contain pharmacologically active amounts of adenosine and 5'-AMP,"-0 *J. Exp. Biol.*, 202(Pt. 11):1551-1559, 1999.
Santoli et al., "Prostaglandin E precursor fatty acids inhibit human IL-2 production by a prostaglandin E-independent mechanism," and Zurier, *J. Immunol.*, 143(4):1303-1309, 1989.
Sjölander et al., "Induction of a Th 1 immune response and simultaneous lack of activation of a Th2 response are required for generation of immunity to *leishmaniasis*," *J. Immunol.* 160:3949-3957, 1998.
Smelt et al., "B cell-deficient mice are highly resistant to *Leishmania donovani* infection, but develop neutrophil-mediated tissue pathology," *J. Immunol.* 164:3681-3688, 2000.
Soares et al., "The vasoactive peptide maxadilan from sand fly saliva inhibits TNF-alpha and induces IL-6 by mouse macrophages through interaction with the pituitary adenylate cyclase-activating polypeptide (PACAP) receptor," *J. Immunol.* 160:1811-1816, 1998.
Stockman et al., "The effect of prostaglandins on the in vitro blastogenic response of human peripheral blood lymphocytes," *Exp. Hematol.*, 2(2):65-72, 1974.
Theodos et al., "Analysis of enhancing effect of sand fly saliva on *Leishmania* infection in mice," *Infect. Immun.* 59:1592-1598, 1991.
Titus et al., "The role of vector saliva in transmission of arthropod-borne disease," *Parasitology Today* 6(5):157-160, 1990.
Valenzuela et al., "The salivary apyrase of the blood-sucking sand fly *Phlebotomus papatasi* belongs to the novel Cimex family of apyrases," *J. Experimental Biology*, 204:229-237, 2001.
Webster, "Role of purines in lymphocyte function," *Asian Pac. J. Allergy Immunol.*, 2(2):311-317, 1984.
Xu et al., "Protection against *leishmaniasis* by injection of DNA encoding a major surface glycoprotein, gp63, of *L. major*," *Immunology* 84:173-176, 1995.
Killick-Kendrick et al., "Mark-release-recapture of sand flies fed on leishmanial dogs: the natural life-cycle of *Leishmania infantum* in *Phlebotomus ariasi*," *Parassitologia*, 44(1-2):67-71, 2002.
Supplementary Partial European Search Report issued on Nov. 30, 2005, for European Patent Application No. 03759395.1.
Volf and Rohousova, "Species-specific antigens in salivary glands of phlebotomine sandflies," *Parasitology*, 122:37-41, 2001.
Volf et al., "Salivary proteins and glycoproteins in phlebotomine sandflies of various species, sex and age," *Medical and Veterinary Entomology*, 14:251-256, 2000.
Supplementary Partial European Search Report issued on Feb. 21, 2006, for European Patent Application No. 03759395.1.
Accession No. ABG 18028, Feb. 18, 2002, 1 page.
EMBL database accession No. ABR92010.
EMBL database accession No. ABR91965.

* cited by examiner

SEQUENCE LISTING

```
<160> NUMBER OF SEQ ID NOS: 87

<210> SEQ ID NO 1
<211> LENGTH: 446
<212> TYPE: PRT
<213> ORGANISM: Phlebotomus ariasi

<400> SEQUENCE: 1

Met Lys Leu Val Pro Leu Cys Ile Leu Val Cys Phe Leu Ile Ile Ala
 1               5                  10                  15

Gln Gln Val Ala Gln Asn Glu Ala Ser Pro Ala Lys Ser Gln Asp Ala
            20                  25                  30

Met Tyr Gly Asp Trp Ser Arg Trp Ser Ser Cys Asp Glu Thr Cys His
        35                  40                  45

Gln Thr Lys Val Arg Ser Cys Leu Gly Ala Val Cys Glu Arg Asn Arg
    50                  55                  60

Leu Met Lys Glu Arg Lys Cys Pro Gly Cys Gly Thr Lys Val Arg Ile
65                  70                  75                  80

Val Gln Lys Leu Leu Gln Leu Phe Gly Met Gly Asp Ser Ile Glu Thr
                85                  90                  95
```

```
Asp Tyr Glu Asp Asp Tyr Gly Glu His Trp Leu Thr Asp Asp Arg Val
            100                 105                 110

Ile Ser Ser Arg Asn Asp Pro Glu Ser Ala Glu Ser Asp Glu Leu Gly
        115                 120                 125

Ser Phe Phe Arg Asp Phe His Ser Phe Asp Phe Glu Trp Lys Asn
    130                 135                 140

Pro Phe Ser Asn Pro His Glu Asn Asn Asp Val Asp Leu Glu Val Glu
145                 150                 155                 160

Glu Asp Glu Glu Val Glu Glu Leu Pro Glu Ile Arg Thr Ser Asn Glu
                165                 170                 175

Glu Asp Ser Val Ser Gly Ala Asp His Val Cys Gly Val Thr Lys Asn
            180                 185                 190

Glu Arg Ser Ser Gly Met Met Ala Lys Thr Ile Gly Gly Arg Asn Ser
        195                 200                 205

Lys Lys Gly Arg Trp Pro Trp Gln Val Ala Leu Tyr Asn Gln Glu Tyr
    210                 215                 220

Glu Asn Phe Phe Cys Gly Gly Thr Leu Ile Ser Lys Tyr Trp Val Ile
225                 230                 235                 240

Thr Ala Ala His Cys Leu Ile Ser Asp Phe Gly Ser Asp Ile Thr Ile
                245                 250                 255

Phe Ser Gly Leu Tyr Asp Thr Gly Asp Leu Val Glu Ser Pro Tyr Ser
            260                 265                 270

Ile His Leu Val Arg Asp Arg Val Ile His Pro Arg Tyr Asp Ala Glu
        275                 280                 285

Thr Asn Asp Asn Asp Ile Ala Leu Leu Arg Leu Tyr Asn Glu Val Lys
    290                 295                 300

Leu Ser Asp Asp Val Gly Ile Ala Cys Leu Pro Ser Tyr Ser Gln Ala
305                 310                 315                 320

Ser Pro Gly Arg Ser Glu Val Cys Lys Val Leu Gly Trp Gly Gln Gly
                325                 330                 335

Thr Arg Arg Thr Lys Leu Gln Glu Ala Asp Met His Ile Gln Pro Ala
            340                 345                 350

Asn Ser Cys Lys Arg His Tyr Tyr Gly Thr Gly Gln Leu Val Thr Arg
        355                 360                 365

His Met Leu Cys Ala Ser Ser Arg Asn Tyr Val Ser Asp Thr Cys Gly
    370                 375                 380

Gly Asp Ser Gly Gly Pro Leu Leu Cys Arg Asp Thr Lys Ser Pro Ala
385                 390                 395                 400

Arg Pro Trp Thr Leu Phe Gly Ile Thr Ser Phe Gly Asp Asp Cys Thr
                405                 410                 415

Val Ser Glu Ser Pro Gly Val Tyr Ala Arg Val Ala Ser Phe Arg Lys
            420                 425                 430

Trp Ile Asp Ser Val Ile Glu Cys Asp Gly Ser Cys Asp Asn
        435                 440                 445

<210> SEQ ID NO 2
<211> LENGTH: 1520
<212> TYPE: DNA
<213> ORGANISM: Phlebotomus ariasi

<400> SEQUENCE: 2
acttgtcgat cacttttcac tcgctccaga cgcattttg cgctcttcag ccgtgattag      60
cacaaagtgt tttagaattt ggtgaaaaaa tagcaagata aggatgaaat tagtgccatt    120
gtgtatttta gtgtgttttc taatcatcgc gcagcaggtg gctcagaatg aagcatctcc    180
```

```
cgccaaaagc caagacgcca tgtacggtga ttggagtcgt tggagctcct gtgacgagac    240
ttgccatcag acgaaggtga gatcgtgcct aggggctgtc tgtgagcgga atcgactgat    300
gaaggagcga aaatgtccag gatgtggtac aaaagtgcga attgtacaga aacttcttca    360
gctcttcggc atgggagact ccatagagac tgactatgaa gatgactatg agagcactg     420 gctaactgat gacagagtca ttagttctag gaatgatcct gaaagtgcag aaagtgatga    480
attgggatca ttcttcaggg atttcttcca ttcattcgat tttgagtgga aaaatccatt    540
tagcaatccc catgagaaca atgatgtgga cttggaggtg gaggaagatg aggaagttga    600
agaacttccc gaaattagga cttctaatga ggaggattct gtctctgggg cggatcacgt    660
gtgtggagtg accaagaatg agagatcttc agggatgatg gcaaaaacta tcggcgggag    720
gaactcgaag aagggtcgat ggccctggca gtggctctt tataaccagg aatatgagaa     780
tttcttctgc ggcgggactc ttatctcaaa atactgggtc ataacggccg ctcactgtct    840
gatatctgac ttcggcagtg acatcacgat cttctccggc ctgtacgaca ccggagatct    900
cgtggagtcg ccctacagca tccacctggt gcgggatcga gtgattcatc gcgctacga    960 cgccgaaacc aatgacaatg atatcgccct gctgaggctc tacaacgaag tgaaattgag    1020
cgatgatgtg gtatcgcttt gtctgccag ctactcgcaa gcctccccgg acgcagtga     1080 ggtgtgcaag gtgctgggct ggggccaagg gacacgtcga accaaactcc aggaggccga    1140
catgcacatc caacccgcca actcctgcaa gcgccactac tacggcaccg gacaactcgt    1200
cacgcgtcac atgctgtgcg cctcctcccg gaactacgtc agcgacacgt gtggcggtga    1260
ttccggtgga ccactgctgt gtcgcgacac caaatccccc gcccgaccct ggacgctgtt    1320
cggcatcacg agcttcggtg acgattgcac ggtgagcgag agtccgggtg tttatgcgcg    1380
cgtcgcctcc ttccggaagt ggattgactc cgtcatcgag tgcgacggct cttgtgacaa    1440
ttaataaact cacaatatta tcagtgaaaa aataaattag caaatttaat gcaaaaaaaa    1500
aaaaaaaaaa aaaaaaaaa                                                 1520
```

<210> SEQ ID NO 3
<211> LENGTH: 251
<212> TYPE: PRT
<213> ORGANISM: Phlebotomus ariasi

<400> SEQUENCE: 3

```
Met Asn Ile Leu Leu Lys Val Ala Ile Leu Val Ser Leu Cys Glu Ile
1               5                   10                  15

Gly Tyr Ser Trp Lys Tyr Pro Arg Asn Ala Asp Gln Thr Leu Trp Ala
            20                  25                  30

Trp Arg Ser Cys Gln Lys Gly Asn Tyr Asp Pro Glu Leu Val Lys Lys
        35                  40                  45

Trp Met Ala Phe Glu Ile Pro Asp Asp Glu Val Thr His Cys Tyr Ile
    50                  55                  60

Lys Cys Val Trp Thr His Leu Gly Met Tyr Asp Glu Thr Ser Gln Thr
65                  70                  75                  80

Ile Arg Ala Asp Arg Val Lys Gln Gln Phe Lys Ala Arg Gly Leu Ser
                85                  90                  95

Val Pro Ala Glu Ile Ser His Leu Glu Gly Ser Thr Gly Gly Ser Cys
            100                 105                 110

Val Thr Ile Tyr Lys Lys Thr Arg Ala Phe Leu Glu Thr Gln Met Pro
        115                 120                 125
```

-continued

Asn Tyr Arg Ile Ala Phe Tyr Gly Thr Val Glu Glu Ser Asp Lys Trp
    130                 135                 140

Phe Ala Asn Asn Pro Glu Thr Lys Pro Lys Arg Ile Lys Ile Ser Asp
145                 150                 155                 160

Phe Cys Lys Gly Arg Glu Ala Gly Thr Glu Gly Thr Cys Lys His Ala
                165                 170                 175

Cys Ser Met Tyr Tyr Tyr Arg Leu Val Asp Glu Asp Asn Leu Val Ile
            180                 185                 190

Pro Phe Arg Lys Leu Pro Gly Ile Leu Asp Ser Gln Leu Glu Gln Cys
        195                 200                 205

Arg Asp Gln Ala Ser Ser Glu Thr Gly Cys Lys Val Gly Asp Thr Ile
    210                 215                 220

Tyr Asn Cys Leu Asn Arg Ile Asn Pro Glu Gly Leu Lys Lys Ala Leu
225                 230                 235                 240

Asn Thr Leu Asp Glu Gln Ser Leu Thr Leu Tyr
                245                 250

<210> SEQ ID NO 4
<211> LENGTH: 815
<212> TYPE: DNA
<213> ORGANISM: Phlebotomus ariasi

<400> SEQUENCE: 4
aaaatgaata tcttattgaa agttgcgatt ttggtgagct tgtgcgaaat tgggtactct      60
tggaaatatc ccaggaatgc cgatcaaact ctctgggctt ggagatcatg ccaaaaggga     120
aactatgacc cagaattagt gaagaaatgg atggcttttg aaatcccaga cgacgaagta     180
actcattgtt acattaagtg tgtttggact catttgggaa tgtacgatga actagccaa      240 actattagag ctgatagagt caagcaacaa ttcaaggctc gtggactatc agttcctgct     300
gaaataagcc atttagaggg atctacagga ggatcctgtg taacgattta caaaaaaact     360
agggctttcc ttgaaactca aatgccgaat tatcgcattg cattctatgg cactgtggaa     420
gaatcagata gtggttcgc gaataatccc gaaactaaac ccaagagaat taagatttct     480
gacttctgca aggtcgcga agctggaacg gaaggaactt gcaagcatgc ttgcagcatg     540
tactactacc gcttagtcga tgaggataat cttgtgattc ccttcaggaa gttgccagga     600
atcttagatt cccaacttga acaatgcagg gatcaagcta gttcggaaac tggatgcaaa     660
gttggtgata caatctacaa ttgtcttaac agaattaatc cggaaggtct aaaaaagca     720 ttgaatacac tcgatgaaca atcattgacg ttgtattaga aagcaataaa cttgattaag     780 aaaacaaaa aaaaaaaaa aaaaaaaaa aaaaa                                  815

<210> SEQ ID NO 5
<211> LENGTH: 388
<212> TYPE: PRT
<213> ORGANISM: Phlebotomus ariasi

<400> SEQUENCE: 5

Met Lys Ile Phe Leu Cys Leu Phe Ala Ala Val Ser Ile Gln Gly Ala
1               5                   10                  15

Leu Ala Ser Gln Ile Glu Arg Glu Tyr Ala Trp Lys Asn Ile Ile Tyr
            20                  25                  30

Glu Gly Ile Asp Gln Gly Ser Tyr Asn Ile Glu Asn Ser Ile Pro Thr
        35                  40                  45

Ala Phe Ala His Asp Ala Ala Ser Lys Lys Ile Phe Ile Thr Ile Pro
    50                  55                  60

```
Arg Ile Asn Gln Val Pro Ile Thr Leu Thr Glu Phe Asp Ser Ile Lys
 65                  70                  75                  80

Tyr Pro Gly Gly Ser Pro Pro Leu Ser Lys Phe Pro Gly Ser Asp Asn
                 85                  90                  95

Ile Ile Ser Val Tyr Gln Pro Val Ile Asp Glu Cys Arg Arg Leu Trp
                100                 105                 110

Ile Val Asp Ala Gly Gln Val Glu Tyr Lys Gly Asp Glu Gln Lys Tyr
                115                 120                 125

Pro Lys Lys Asn Pro Ala Ile Ile Ala Tyr Asp Leu Thr Lys Asp Asn
130                 135                 140

Tyr Pro Glu Ile Asp Arg Tyr Glu Ile Pro Ile Asn Ile Ala Gly Asn
145                 150                 155                 160

Pro Leu Gly Phe Gly Gly Phe Thr Val Asp Val Thr Asn Pro Lys Glu
                165                 170                 175

Gly Cys Gly Lys Thr Phe Ile Tyr Ile Thr Asn Phe Glu Asp Asn Thr
                180                 185                 190

Leu Ile Val Tyr Asp Gln Glu Lys Asp Ser Trp Lys Ile Ser His
                195                 200                 205

Gly Ser Phe Lys Pro Glu His Glu Ser Ile Leu Ile His Asn Gly Val
210                 215                 220

Asp His Ile Leu Lys Leu Gly Ile Phe Gly Ile Thr Leu Gly Asp Arg
225                 230                 235                 240

Asp Ser Glu Gly Asn Arg Pro Ala Tyr Tyr Leu Gly Gly Ser Ser Thr
                245                 250                 255

Lys Leu Phe Glu Val Asn Thr Lys Ala Leu Lys Lys Lys Glu Gly Glu
                260                 265                 270

Ile Glu Pro Ile Thr Leu Gly Asp Arg Gly Pro His Ser Glu Ala Ile
                275                 280                 285

Ala Leu Ala Tyr Asp Pro Lys Thr Lys Val Ile Phe Phe Thr Glu Tyr
290                 295                 300

Asn Ser Lys Lys Ile Ser Cys Trp Asn Ile Lys Lys Pro Leu Ile His
305                 310                 315                 320

Asp Asn Met Asp Lys Ile Tyr Ala Ser Pro Glu Phe Ile Phe Gly Thr
                325                 330                 335

Asp Ile Ser Val Asp Ser Glu Ser Lys Leu Trp Phe Phe Ser Asn Gly
                340                 345                 350

His Pro Pro Ile Glu Asn Leu Gln Leu Ser Ser Asp Lys Pro His Ile
                355                 360                 365

His Leu Ile Ser Val Asp Thr Glu Lys Ala Ile Arg Gly Thr Lys Cys
370                 375                 380

Glu Val Lys Ala
385

<210> SEQ ID NO 6
<211> LENGTH: 1268
<212> TYPE: DNA
<213> ORGANISM: Phlebotomus ariasi

<400> SEQUENCE: 6
gtcagtcttt tggaaacaaa acatgaagat ctttctgtgc cttttgctg cagtttccat      60 tcagggagct ttagcttctc aaattgaaag ggaatacgcg tggaaaaaca ttatttatga    120
agggatagat caaggatcct acaacattga aaacagcatc ccaactgctt cgctcacga    180 tgcagctagt aagaagattt tcatcactat tccaagaata aaccaagtac caataaccct    240
```

```
aactgaattt gatagcatca agtatccggg aggttctcct cctcttagca aattccctgg      300
aagcgataac ataatttccg tttatcaacc ggtcattgac gaatgtcgta gactttggat      360
tgtggacgct ggacaggttg agtacaaggg agatgagcag aagtatccca agaaaaatcc      420
tgctatcata gcttatgacc tgactaagga caattatcct gagattgatc gatacgagat      480
accgattaat attgctggta atccattagg atttggagga tttaccgttg atgttaccaa      540
tccgaaggag ggatgtggta aaacttttat ctacatcaca aacttcgaag acaacactct      600
gattgtgtac gatcaggaga agaaagattc ttggaagatc agtcatggtt catttaaacc      660
cgaacatgag tcgattctaa tccataacgg ggttgatcat atttttaaaac tgggtatttt      720 cggaatcacc cttggagatc gggattcgga gggaaaccgt ccggcttact acttaggagg      780
aagcagtacg aagctctttg aagtcaacac aaaggctctt aagaagaagg agggtgaaat      840
cgaaccaatc actctgggag atcgtggacc tcattccgaa gccattgctt tggcatacga      900
tcccaagacc aaagtgattt cttcactga atataactct aagaagatct catgctggaa      960
catcaagaaa cccttattc atgacaacat ggataagatt tatgctagtc ctgaattat      1020 tttcggcact gatatttcgg ttgatagtga atccaaattg tggttcttct ccaacggaca      1080
tccacccatt gagaatctgc agttgagctc tgataagcct catattcatc ttataagcgt      1140
ggatacggaa aaggcaattc gtggcactaa atgtgaagtg aaggcctaag tcaaaaatat      1200
aacaatttta caacaaattg taaatttaac gatgataata aaaaaaaaaa aaaaaaaaa      1260 aaaaaaaa                                                              1268

<210> SEQ ID NO 7
<211> LENGTH: 393
<212> TYPE: PRT
<213> ORGANISM: Phlebotomus ariasi

<400> SEQUENCE: 7

Met Lys Ile Phe Met Gly Leu Ile Ala Val Val Ser Leu Gln Gly Ala
1               5                   10                  15

Leu Ala Tyr His Val Glu Arg Glu Tyr Ala Trp Lys Asn Ile Thr Phe
            20                  25                  30

Glu Gly Ile Asp Gln Ala Ser Tyr Asn Ile Glu Asn Ser Ile Pro Thr
        35                  40                  45

Ala Phe Val His Asp Ala Leu Ser Lys Lys Ile Ile Ala Ile Pro
    50                  55                  60

Arg Leu Tyr Pro Gln Val Pro Ile Thr Leu Thr Gln Leu Asp Thr Thr
65                  70                  75                  80

Lys His Pro Glu Arg Ser Pro Leu Glu Lys Phe Pro Gly Ser Asp
                85                  90                  95

Lys Leu Thr Ser Val Tyr Gln Pro Met Leu Asp Glu Cys Arg Arg Leu
            100                 105                 110

Trp Ile Val Asp Val Gly Gln Val Glu Tyr Lys Gly Asp Glu Gln Lys
        115                 120                 125

Tyr Pro Lys Lys Asn Pro Ala Ile Ile Ala Tyr Asp Leu Thr Lys Asp
    130                 135                 140

Asn Tyr Pro Glu Ile Asp Arg Tyr Glu Ile Pro Ile Asn Ile Ala Gly
145                 150                 155                 160

Asn Gln Ile Gly Phe Gly Gly Phe Thr Val Asp Val Thr Asn Pro Lys
                165                 170                 175

Glu Gly Cys Gly Lys Thr Phe Ile Tyr Ile Thr Asn Phe Glu Asp Asn
```

```
                    180                 185                 190
Thr Leu Ile Val Tyr Asp Gln Glu Lys Lys Asp Ser Trp Lys Ile Ser
                195                 200                 205

His Gly Ser Phe Lys Pro Glu His Glu Ser Asn Phe Ser His Asn Gly
            210                 215                 220

Ala Gln Tyr Lys Tyr Lys Ala Gly Ile Phe Gly Ile Thr Leu Gly Asp
225                 230                 235                 240

Arg Asp Pro Glu Gly Asn Arg Pro Ala Tyr Tyr Leu Gly Gly Ser Ser
                    245                 250                 255

Thr Lys Leu Phe Glu Val Ser Thr Glu Ala Leu Lys Lys Lys Gly Ala
                260                 265                 270

Lys Phe Asp Pro Val Arg Leu Gly Asp Arg Gly Arg His Thr Glu Ala
            275                 280                 285

Ile Ala Leu Val Tyr Asp Pro Lys Thr Lys Val Ile Phe Phe Ala Glu
        290                 295                 300

Ser Asp Ser Arg Gln Ile Ser Cys Trp Asn Thr Gln Lys Pro Leu Asn
305                 310                 315                 320

His Lys Asn Thr Asp Val Ile Tyr Ala Ser Ser Lys Phe Ile Phe Gly
                    325                 330                 335

Thr Asp Ile Gln Ile Asp Ser Asp Ser Gln Leu Trp Phe Leu Ser Asn
                340                 345                 350

Gly Gln Pro Pro Ile Asp Asn Leu Lys Leu Thr Phe Asp Lys Pro His
            355                 360                 365

Ile Arg Leu Met Arg Val Asp Thr Lys Asn Ser Ile Arg Arg Thr Arg
        370                 375                 380

Cys Glu Val Lys Pro Ile Lys Lys Pro
385                 390

<210> SEQ ID NO 8
<211> LENGTH: 1306
<212> TYPE: DNA
<213> ORGANISM: Phlebotomus ariasi

<400> SEQUENCE: 8 gtcttttgg aaacaaagat gaagatcttt atgggcctaa ttgctgtggt ttcccttcag      60
ggagctttag cttatcacgt tgaaagggag tacgcgtgga agaacattac ttttgaaggg    120
atagatcaag catcctacaa cattgaaaac agcatcccaa ctgcattcgt tcacgatgca    180
cttagtaaga agattatcat cgctattcct aggctatatc ctcaggtgcc aattacttta    240
actcaacttg ataccaccaa gcatccggaa cgttctcctc ctctcgaaaa attccctgga    300
agcgataaat taacctctgt ttatcaaccg atgcttgacg aatgtcgtag actttggatt    360
gttgacgttg acaggtcga gtacaaggga gatgagcaga agtaccccaa gaaaaatcct    420
gctatcatag cctatgacct gactaaggac aattatccag agattgatcg atatgagata    480
ccgattaata ttgctggtaa tcaaatagga tttggaggat ttaccgttga tgttacgaat    540
ccgaaggagg gatgtggtaa aacctttatc tacatcacga acttcgaaga caacactctg    600
attgtgtacg atcaggagaa gaaagattct tggaagatca gtcatggttc atttaaaccc    660
gaacatgagt ctaatttctc ccacaacggt gctcagtaca agtacaaagc gggtattttc    720
ggaatcaccc ttggagatcg ggatccggag ggaaatcgtc cggcttacta cttaggagga    780
agcagtacga agctctttga agtgagcact gaggctctca agaagaaggg tgcaaagttc    840
gatcctgttc gtctgggtga tcgtgggcgt cacactgaag ccattgctct ggtatatgat    900
```

```
cccaagacta aagttatttt ctttgctgaa tctgactcga gacaaatctc atgctggaac    960
acccagaagc cactaaatca taagaatact gatgtaattt atgcgagttc caaatttatt   1020
ttcggcaccg acattcaaat tgacagtgac tcccaattgt ggttcttatc caacggacaa   1080 cccccattg ataatctcaa attgactttt gataagcccc atattcgtct tatgagggta    1140
gatacgaaaa attcaattcg taggactaga tgtgaagtga agcccatcaa gaagccataa   1200
gacaatctat taaaaatgta acaatttccc caaaaaaaga aattgtaaat tttacgatga   1260
taataaaaaa attttatgct tgtgaaaaaa aaaaaaaaaa aaaaaa                   1306
```

<210> SEQ ID NO 9
<211> LENGTH: 292
<212> TYPE: PRT
<213> ORGANISM: Phlebotomus ariasi

<400> SEQUENCE: 9

```
Met Phe Lys Glu Ile Ile Val Val Ala Leu Ala Val Ile Val Ala Gln
1               5                   10                  15

Cys Ala Pro Pro Ala Ile Pro Ile Ala Lys Gln Gly Asn Asp Phe Pro
            20                  25                  30

Val Pro Ile Val Asp Glu Lys Glu Thr Asp Asp Phe Phe Asp Asp Arg
        35                  40                  45

Phe Tyr Pro Asp Ile Asp Asp Glu Arg Val Gly Ala Arg Ala Pro Val
    50                  55                  60

Gly Gly Lys Gln Thr Ser Asn Arg Gly Thr Ser Ser Gln Ser Asp Lys
65                  70                  75                  80

Val Pro Arg Pro Gln Gly Ser Asn Arg Gly Pro Ser Ser Gln Thr Thr
                85                  90                  95

Asp Lys Val Pro Arg Pro Gln Trp Pro Ser Arg Gly Thr Asn Ser Gln
            100                 105                 110

Asn Asp Lys Val Pro Arg Pro Gln Gly Ser Ser Gly Gln Thr Pro Pro
        115                 120                 125

Arg Thr Pro Gly Lys Val Glu Gln Ser Gly Arg Thr Asn Thr Lys Asp
    130                 135                 140

Gln Ile Pro Arg Pro Leu Thr Asn Arg Asn Pro Thr Lys Asn Pro Thr
145                 150                 155                 160

Glu Gln Ala Arg Arg Pro Gly Asn Arg Glu Leu Leu Ile Arg Asp Lys
                165                 170                 175

Thr Pro Gly Ser Gln Gly Gly Lys Gln Gly Thr Gly Asn Arg Gln Lys
            180                 185                 190

Leu Ser Ser Tyr Lys Asp Ala Gln Pro Lys Leu Ile Phe Lys Ser Ser
        195                 200                 205

Gln Phe Asn Thr Asp Gly Gln Asn Pro Tyr Leu Thr Arg Leu Phe Lys
    210                 215                 220

Thr Lys Lys Val Glu Val Ile Ala Lys Gly Ser Pro Thr Asp Glu
225                 230                 235                 240

Tyr Val Leu Glu Leu Leu Asp Gly Lys Pro Asp Asn Leu Ser Leu Val
                245                 250                 255

Ile Arg Thr Asn Gly Lys Thr Ser Gln Ala Val Leu Arg Asn Pro Thr
            260                 265                 270

Arg Asn Arg Ile Val Gly Arg Ile Lys Ser Tyr Asn Pro Gly Pro Arg
        275                 280                 285

Arg Met Ser Tyr
    290
```

<210> SEQ ID NO 10
<211> LENGTH: 992
<212> TYPE: DNA
<213> ORGANISM: Phlebotomus ariasi

<400> SEQUENCE: 10

```
attcagtcat aaacctgggg taatgtttaa ggaaattatc gtagtggctc tagccgtgat      60
cgtggcacaa tgtgctcctc ctgcaattcc aattgcaaaa cagggaaacg atttccctgt     120
cccaattgtt gatgaaaagg aaacggatga tttctttgac gatcgattct atccggacat     180
agatgatgag cgtgtaggtg ctagggctcc ggtgggtggc aaacagacat ctaatagagg     240
aaccagttct cagagtgata aggttcctcg tcctcaaggg tccaatagag ggcctagctc     300
tcagactact gacaaggttc cccgtcctca atggcccagt agaggaacca attctcagaa     360
tgacaaggtt cctcgtcctc aagggtctag tggacaaact ccacctagaa cgcctggaaa     420
ggttgaacaa gtggaagga ccaacacaaa ggaccaaata cctcgtccac tgactaacag     480
aaacccaacc aagaacccaa ctgaacaggc tagaagacca ggaaacaggg agctactcat     540
tagggataaa accccaggga gtcaaggtgg aaaacaggga acaggcaata ggcagaaact     600
gtcgagttat aaagacgctc agccgaagtt gattttcaaa tcgagtcaat tcaatactga     660
tggccaaaat ccatatttaa cgaggttgtt caagacgaag aaagtcgaag aagttatagc     720
taaaggaagt cccactgatg aatatgtcct ggagcttttg gatggaaagc cagataatct     780
gagcttggtc atcagaacaa atggcaagac gagccaagcg gttctcagga atccccactcg     840
caacagaatt gtgggccgta tcaagtcgta caaccccggc ccgaggcgaa tgtcctatta     900
atttttttt ctctttttc tcctaaatac aactcccaca ataaaatttc agttgtacgc     960
agcaaaaaaa aaaaaaaaaa aaaaaaaaaa aa                                  992
```

<210> SEQ ID NO 11
<211> LENGTH: 312
<212> TYPE: PRT
<213> ORGANISM: Phlebotomus ariasi

<400> SEQUENCE: 11

```
Met Ala Ser Ile Lys Leu Ser Thr Cys Ser Phe Val Leu Leu Asn Leu
1               5                   10                  15

Ile Leu Pro Thr Ile Ser Met Lys Val Ile Ser Phe Asp Asp Arg Asp
            20                  25                  30

Glu Tyr Leu Leu Gly Lys Pro Ala Asn Ser Asp Asp Glu Leu Leu Tyr
        35                  40                  45

Ser Thr Phe Asp Phe Gln Arg Asp Pro Cys Ser Lys Ser Tyr Val Lys
    50                  55                  60

Cys Thr Asn Asn Asn Thr His Phe Ile Leu Asp Phe Val Asp Pro Lys
65                  70                  75                  80

Lys Arg Cys Ile Ser Ile His Val Phe Ser Tyr Pro Asp Arg Pro
            85                  90                  95

Pro Ser Phe Glu Glu Lys Arg Ile Pro Ser Lys Ser Ala Ile Tyr Cys
        100                 105                 110

Gln Lys Gly Gly Ile Gly Lys Ser His Cys Leu Leu Val Phe Arg Lys
    115                 120                 125

Lys Glu Pro Arg Glu Asp Ala Leu Val Asp Ile Arg Gly Ile Pro Ala
130                 135                 140

Asp Gln Thr Cys Ser Leu Lys Glu Arg Tyr Thr Ser Gly Asp Pro Lys
145                 150                 155                 160
```

Lys Thr Asp Ala Tyr Gly Met Ala Tyr Gln Phe Asp Arg Lys Asp Asp
                165                 170                 175

Trp His Ile Gln Arg Thr Gly Ile Lys Thr Trp Lys Arg Ser Gly Asn
            180                 185                 190

Glu Ile Phe Tyr Arg Lys Asn Gly Leu Met Asn His Gln Ile Arg Tyr
        195                 200                 205

Leu Ser Lys Phe Asp Lys Tyr Thr Val Thr Arg Glu Leu Val Val Lys
    210                 215                 220

Asn Asn Ala Lys Lys Phe Thr Leu Glu Phe Ser Asn Phe Arg Gln Tyr
225                 230                 235                 240

Arg Ile Ser Phe Leu Asp Ile Tyr Trp Phe Gln Glu Ser Gln Arg Asn
                245                 250                 255

Lys Pro Arg Leu Pro Tyr Ile Tyr Tyr Asn Gly His Cys Leu Pro Ser
            260                 265                 270

Asn Lys Thr Cys Gln Leu Val Phe Asp Thr Asp Glu Pro Ile Thr Tyr
        275                 280                 285

Ala Phe Val Lys Val Phe Ser Asn Pro Asp His Asn Glu Pro Arg Leu
    290                 295                 300

Arg His Glu Asp Leu Gly Arg Gly
305                 310

<210> SEQ ID NO 12
<211> LENGTH: 1047
<212> TYPE: DNA
<213> ORGANISM: Phlebotomus ariasi

<400> SEQUENCE: 12
taacgctcaa gctttgtctt caatatggct tccatcaagc tcagtacttg ctctttcgtt     60
ttgctaaacc tcattctacc aacaatctct atgaaagtta tcagtttcga cgatagagat    120
gagtatctac ttggtaaacc tgcaaattct gacgatgaac ttctctattc aacctttgac    180
ttccagagag atccctgttc taagtcttac gtgaagtgca ccaacaacaa cacccacttt    240
attctggatt tcgttgatcc gaagaagaga tgcatctctt caattcacgt tttctcctac    300
cccgatagac ctcccagctt tgaggagaag aggattccct cgaagagtgc aatttactgc    360
caaaagggcg gcattgggaa gagtcactgt ttgctggtgt tcaggaagaa ggaacctcga    420
gaggacgcac tggttgatat ccggggaatc cccgctgatc aaacatgctc cctcaaggag    480
cgctacacat cgggagatcc taagaaaacc gatgcttacg gaatggccta tcagtttgat    540
agaaaagatg attggcacat tcaaagaaca ggtatcaaga catggaaaag atcaggaaac    600
gagatcttct accgtaagaa tggtttaatg aaccatcaaa taggtacttt gagcaagttc    660
gacaaataca cggttaccag agaattggtg gtgaagaaca cgctaagaa attcaccttg    720
gaattttcaa acttccgtca ataccgaatc agtttcttgg acatctactg gttccaggag    780
tctcagagga ataaacccag attaccttat atttactaca cggtcattg cttgcctagc    840
aacaagacat gccagttggt cttcgacact gatgagccta ttacttatgc ttttgtgaaa    900
gtgtttagta atccggatca caatgaacca cgactaagac atgaagatct aggacgaggg    960
taagaatgga ctagtccggg gttgaaaaat cgcctaaaat atgggggaatc tattattgaa   1020
aaaaaaaaaa aaaaaaaaa aaaaaaa                                        1047

<210> SEQ ID NO 13
<211> LENGTH: 375
<212> TYPE: PRT

<213> ORGANISM: Phlebotomus ariasi

<400> SEQUENCE: 13

```
Met Val Ile Tyr Leu Thr Gln Asn Ile Ser Arg Ala Leu Leu Thr Leu
1               5                   10                  15
Leu Pro Asn Pro Glu Asp Val Arg Ser Ala Ala Asp Val Leu Glu Ser
            20                  25                  30
Phe Thr Asp Asp Leu Lys Ser Phe Tyr Pro Pro Asp Asp Val Asn
        35                  40                  45
Glu Glu Val Ser Glu Thr Glu Ser Arg Thr Lys Arg Ser Leu Ile Glu
    50                  55                  60
Gln Leu Lys Glu Ser Gln Pro Leu Lys Gln Ile Arg Glu Thr Val Ala
65                  70                  75                  80
Glu Thr Thr Lys Tyr Leu Lys Gly Phe Leu Lys Thr Lys Pro Ser Gly
                85                  90                  95
Asn Gln Thr Glu Ser Ser Asn Ser Thr Ser Thr Lys Thr Gln Ser Arg
            100                 105                 110
Lys Arg Arg Gly Leu Thr Asp Phe Ile Pro Val Asn Ser Leu Lys Asp
        115                 120                 125
Ala Ile Ser Gln Ala Thr Ser Gly Ala Met Lys Ala Phe Lys Pro Ser
    130                 135                 140
Ser Glu Asn Lys Thr Ser Ser Asn Pro Leu Asp Phe Leu Ala Ser Leu
145                 150                 155                 160
Ser Asp Ile Ser Arg Asp Leu Val Gln Asn Ser Ile Lys Glu Val Ser
                165                 170                 175
Gly Asn Leu Val Ser Ser Val Ala Leu Tyr Gln Val Asn Ser Lys Leu
            180                 185                 190
Asp Ala Ile Lys Gln Ser Ile Gly Ile Ile Asn Gln Glu Ile Asp Arg
        195                 200                 205
Thr Lys Lys Val Gln Gln Tyr Val Met Asn Ala Leu Gln Gln Ala Ser
    210                 215                 220
Asn Ile Thr Asn Ser Ile Gly Glu Gln Leu Lys Ser Asn Asn Cys Phe
225                 230                 235                 240
Ala Gln Phe Ile Asn Pro Phe Lys Leu Phe Glu Val Ile Thr Cys
                245                 250                 255
Val Lys Asn Lys Ile Glu Asn Gly Leu Lys Ile Ala Glu Glu Thr Phe
            260                 265                 270
Lys Asn Leu Asn Gln Ala Leu Ser Val Pro Ser Asp Ile Val Ser Glu
        275                 280                 285
Val Ser Lys Cys Ser Gln Asn Gln Asn Leu Asn Pro Leu Thr Lys Leu
    290                 295                 300
Leu Cys Tyr Leu Arg Val Pro Leu Gln Leu Asp Glu Lys Leu Leu
305                 310                 315                 320
Leu Pro Ile Glu Phe Ala Arg Arg Ile Arg Glu Ile Thr Asn Tyr Phe
                325                 330                 335
Ala Thr Met Arg Met Asp Leu Ile Gln Cys Gly Ile Ala Thr Ile Gln
            340                 345                 350
Ser Ile Gly Asp Lys Val Glu Asn Cys Ala Ile Glu Ala Ile Leu Ala
        355                 360                 365
Val Lys Asp Thr Leu Lys Gly
    370                 375
```

<210> SEQ ID NO 14
<211> LENGTH: 1263

<212> TYPE: DNA
<213> ORGANISM: Phlebotomus ariasi

<400> SEQUENCE: 14

```
atgtatcaaa catcacggat atggtgattt atctcacgca gaatatcagt agagctcttc      60
tcacgcttct accaaatcct gaagatgtcc gatcagcagc ggatgtccta gaaagtttta     120
cagacgacct caagtctttc tacccacctc ctgatgatgt gaatgaagag gtatcagaga     180
cagagtcaag aactaagaga tcattgattg agcaactcaa agagtcgcaa cctctaaaac     240
aaatcagaga aacagttgct gagacaacca agtacctaaa ggattcttaa aaacgaaac     300
cttctggaaa tcaaacggag agttctaact caacaagtac gaagactcag tcaagaaaga     360
gacgtggatt aactgatttt ataccagtga attctctaaa ggatgcaatt tcacaagcaa     420
cttcaggtgc catgaaagcg ttcaaacctt caagtgaaaa taaacaagt tcaaatcctc     480
tagatttcct cgcaagcctc tcagatattt ccagagatct tgtacaaaat tcaattaagg     540
aagtctctgg caatttagtt tcaagcgttg ctttatacca agtcaactca aagttagatg     600
ccattaaaca atccattggt atcataaatc aagaaattga taggaccaaa aaagttcagc     660
aatacgtcat gaatgctctt caacaagcca gcaatattac taactcaatt ggagagcaac     720
tcaagtccaa caactgtttc gcacaattta taaacccatt caaacttttc gaagaagtaa     780
taacttgtgt gaaaaataaa atcgaaaatg gattgaaaat tgcggaagag acatttaaaa     840
atttaaatca ggctttaagt gtgccctcag atattgtaag tgaagtgtcc aaatgttccc     900
aaaaccagaa cttgaatccc ttgacgaaac ttctgtgcta cttgagggta ccctgcaat     960
tggatgagga gaaactgctg cttcctattg aatttgcgag gcgaattaga gaataaacca    1020
actattttgc caccatgaga atggacctca ttcaatgtgg catagcaact attcaatcaa    1080
tcggagacaa ggttgagaat tgtgcaatag aagcaatatt ggctgtaaag gacactttga    1140
agggataaag tccgtatttt atgctgtcca attgggctaa cccaatcatt gatataccga    1200
attgtgtatg tatattgaga aaatgaataa atgcttcaaa atgaaaaaaa aaaaaaaaa    1260
aaa                                                                  1263
```

<210> SEQ ID NO 15
<211> LENGTH: 138
<212> TYPE: PRT
<213> ORGANISM: Phlebotomus ariasi

<400> SEQUENCE: 15

```
Met Lys Gln Phe Pro Val Ile Leu Leu Thr Leu Gly Leu Leu Val Val
1               5                   10                  15

Lys Cys Arg Ser Glu Arg Pro Glu Trp Lys Cys Glu Arg Asp Phe Lys
            20                  25                  30

Lys Ile Asp Gln Asn Cys Phe Arg Pro Cys Thr Phe Ala Ile Tyr His
        35                  40                  45

Phe Val Asp Asn Lys Phe Arg Ile Ala Arg Lys Asn Ile Glu Asn Tyr
    50                  55                  60

Lys Lys Phe Leu Ile Asp Tyr Asn Thr Val Lys Pro Glu Val Asn Asp
65                  70                  75                  80

Leu Glu Lys His Leu Leu Asp Cys Trp Asn Thr Ile Lys Ser Ile Glu
                85                  90                  95

Ala Ser Ser Arg Thr Glu Lys Cys Glu Gln Val Asn Asn Phe Glu Arg
            100                 105                 110

Cys Val Ile Asp Lys Asn Ile Leu Asn Tyr Pro Val Tyr Phe Asn Ala
```

Leu Lys Lys Ile Asn Lys Asn Thr Asn Val
    130             135

<210> SEQ ID NO 16
<211> LENGTH: 530
<212> TYPE: DNA
<213> ORGANISM: Phlebotomus ariasi

<400> SEQUENCE: 16

```
acatacgatt cctaaccaac catgaagcag ttcccagtga tccttttgac cttaggcctt      60
ttggtcgtga aatgccgatc agaacggccg gaatggaaat gtgaaagaga cttcaagaaa     120
atcgaccaaa attgctttcg tccttgtaca tttgcaattt accactttgt tgataacaag    180
ttcaggattg ccaggaagaa tattgaaaac tacaagaagt tcttaattga ctataacacc    240
gtgaagcccg aagttaatga tttggaaaaa cacctgttag attgttggaa tacaatcaaa    300
tccattgaag catcatccag gacggaaaaa tgtgaacaag ttaacaactt tgaacgatgt    360
gttattgaca gaacattcct taattatcct gtttacttca atgctttgaa gaaaataaat    420
aagaatacaa atgtttaatt aaataaagat gtgaaatatt gcagtgcaca aatataaaaa    480
aaaaaaaaaa aaaaaaaaaa aaaaaaaaaa aaaaaaaaa aaaaaaaaaa                530
```

<210> SEQ ID NO 17
<211> LENGTH: 388
<212> TYPE: PRT
<213> ORGANISM: Phlebotomus ariasi

<400> SEQUENCE: 17

Met Ile Asn Pro Ile Val Leu Arg Phe Thr Phe Leu Leu Val Ile Leu
1               5                   10                  15

Leu Pro Gly Lys Cys Lys Ser Ala Pro Lys Ser Cys Thr Ile Asn Leu
            20                  25                  30

Pro Thr Ser Ile Pro Lys Lys Gly Glu Pro Ile Tyr Leu Asn Ser Asn
        35                  40                  45

Gly Ser Val Phe Arg Pro Ile Gly Gly Leu Thr Gln Leu Asn Ile Gly
    50                  55                  60

Asp Ser Leu Ser Ile Tyr Cys Pro Pro Leu Lys Lys Leu Lys Ser Val
65                  70                  75                  80

Pro Cys Ser Arg Lys Phe Ser Leu Glu Ser Tyr Ser Cys Asn Ser
            85                  90                  95

Ser Gln Ser Glu Leu Val Gln Thr Glu Glu Cys Gly Gln Glu Gly
            100                 105                 110

Lys Trp Tyr Asn Ile Gly Phe Pro Leu Pro Thr Asn Ala Phe His Thr
            115                 120                 125

Ile Tyr Arg Thr Cys Phe Asn Lys Gln Lys Leu Thr Pro Ile Tyr Ser
        130                 135                 140

Tyr His Val Ile Asn Gly Lys Ala Val Gly Tyr His Val Lys Gln Pro
145                 150                 155                 160

Arg Gly Asn Phe Arg Pro Gly Lys Gly Val Tyr Arg Lys Ile Asn Ile
                165                 170                 175

Asn Glu Leu Tyr Lys Thr His Ile Ser Arg Phe Lys Lys Val Phe Gly
            180                 185                 190

Asp Lys Gln Thr Phe Phe Arg Lys Pro Leu His Tyr Leu Ala Arg Gly
            195                 200                 205

His Leu Ser Pro Glu Val Asp Phe Val Phe Gly Thr Glu Gln His Ala

```
                210                 215                 220
Thr Glu Phe Tyr Ile Asn Thr Ala Pro Gln Tyr Gln Ser Ile Asn Gln
225                 230                 235                 240

Gly Asn Trp Leu Arg Val Glu Lys His Val Arg Gly Leu Ala Lys Ala
                245                 250                 255

Leu Gln Asp Asn Leu Leu Val Val Thr Gly Ile Leu Asp Ile Leu Lys
                260                 265                 270

Phe Ser Asn Lys Arg Ala Asp Thr Glu Ile Tyr Leu Gly Asp Gly Ile
            275                 280                 285

Ile Pro Val Pro Gln Ile Phe Trp Lys Ala Ile Phe His Leu Arg Thr
        290                 295                 300

Ser Ser Ala Ile Val Phe Val Thr Ser Asn Asn Pro His Glu Thr Thr
305                 310                 315                 320

Phe Asn Asn Ile Cys Lys Asp Ala Cys Glu Met Ala Gly Phe Gly Asp
                325                 330                 335

Lys Gln His Gly Asn Gln Asn Phe Ser Asn Tyr Ser Leu Gly Phe Thr
                340                 345                 350

Ile Cys Cys Glu Leu Gln Asp Phe Ile Gly Asn Ser Lys Val Val Leu
            355                 360                 365

Pro Lys Asp Ile Gln Val Lys Asn His Arg Lys Leu Leu Gln Leu Pro
        370                 375                 380

Lys Pro Lys Gln
385

<210> SEQ ID NO 18
<211> LENGTH: 1268
<212> TYPE: DNA
<213> ORGANISM: Phlebotomus ariasi

<400> SEQUENCE: 18
agaagttatt ttacacctgt gcaatgataa acccaatagt gctgagattt acttttctct      60
tggtgatttt gttgcctggc aaatgtaaaa gtgccccaaa gtcttgcacc attaatcttc     120
ccaccagcat tcccaagaaa ggtgaaccga tttacctcaa cagtaatgga tcagttttcc     180
gacctattgg aggtttaact caactcaaca ttggggactc cctctccatc tactgtccac     240
cactgaagaa gctcaagagt gttccttgca gtcgaaaatt ctcccttgag agctactctt     300
gcaacaacag ctctcagagt gaactcgtgc agacggagga ggagtgcgga caagagggga     360
aatggtacaa cattggcttt ccattgccca caaatgcctt ccacacaatc tacagaactt     420
gcttcaataa gcagaaacta acaccaattt actcttatca cgtcatcaat ggaaaggccg     480
ttggatatca cgtgaagcag ccgcgaggaa acttccgacc aggaaaaggt gtctacagga     540
aaatcaacat caatgagctg tacaagacgc acatttcgcg cttcaagaaa gtcttcggtg     600
acaaacagac attcttccgg aagccactgc actacctggc tcgcggacat ctctcccctg     660
aagtggactt tgtcttcggc accgaacaac acgccactga gttctacatc aacaccgccc     720
cccagtatca gtccatcaac cagggaaatt ggctgcgagt tgaaaaacac gtgcgcggtc     780
tggccaaggc gctccaggac aatctcctcg tcgtcactgg cattttggac atcctaaagt     840
tctcaaacaa acgagccgac acagaaatct acttgggcga cggaataatt cctgttccgc     900
aaatattctg gaaggcaatc ttccacctca gaacatcttc cgccattgtc tttgtcacct     960
ccaacaaccc tcacgagacg accttcaaca atatctgcaa ggacgcgtgt gaaatggcag    1020
gattcggaga caaacaacat ggaaatcaaa attttttccaa ctactccttg ggattcacca    1080
```

```
tctgttgcga actacaggac ttcattggga actcgaaagt tgttcttcca aaggatattc   1140
aagtcaaaaa ccaccgcaaa cttcttcagt tgccaaaacc gaagcaataa actttaattt   1200
tggtcttgca agtgtgagt atattttaaa taaacagcaa atcaaaaaaa aaaaaaaaa    1260 aaaaaaaa                                                            1268
```

<210> SEQ ID NO 19
<211> LENGTH: 252
<212> TYPE: PRT
<213> ORGANISM: Phlebotomus ariasi

<400> SEQUENCE: 19

```
Met Asn Ala Leu Leu Cys Val Leu Leu Ser Leu Gly Ile Gly
1               5                   10                  15

Tyr Ser Trp Lys Tyr Pro Arg Asn Ala Asp Gln Thr Leu Trp Ala Tyr
            20                  25                  30

Arg Thr Cys Gln Arg Glu Gly Lys Asp Pro Ala Leu Val Ser Lys Trp
        35                  40                  45

Met Asn Trp Val Leu Pro Asp Asp Pro Glu Thr His Cys Tyr Val Lys
    50                  55                  60

Cys Val Trp Thr Asn Leu Gly Ser Tyr Asp Asp Asn Thr Gly Ser Ile
65                  70                  75                  80

Met Ile Asn Thr Val Ala Thr Gln Phe Ile Thr Arg Gly Met Lys Val
                85                  90                  95

Pro Ala Glu Val Asn Asn Leu Ser Gly Ser Thr Ser Gly Ser Cys Ser
            100                 105                 110

Asp Ile Tyr Lys Lys Thr Ile Gly Phe Phe Lys Ser Gln Lys Ala Asn
        115                 120                 125

Ile Gln Lys Ala Tyr Tyr Gly Thr Lys Glu Glu Ser Asp Asn Trp Tyr
    130                 135                 140

Ser Lys His Pro Asn Val Lys Pro Lys Gly Thr Lys Ile Ser Asp Phe
145                 150                 155                 160

Cys Lys Gly Arg Glu Gly Gly Thr Glu Gly Thr Tyr Lys His Ala Cys
                165                 170                 175

Ser Met Tyr Tyr Tyr Arg Leu Val Asp Glu Asp Asn Leu Val Ile Pro
            180                 185                 190

Phe Arg Lys Leu Lys Ile Pro Gly Ile Pro Gly Pro Lys Ile Asp Glu
        195                 200                 205

Cys Arg Arg Lys Ala Ser Ser Lys Thr Gly Cys Lys Val Ala Asp Ala
    210                 215                 220

Leu Tyr Lys Cys Leu Lys Ala Ile Asn Gly Lys Ser Phe Glu Asn Ala
225                 230                 235                 240

Leu Lys Lys Leu Asp Glu Glu Ser Ser Arg Thr Tyr
                245                 250
```

<210> SEQ ID NO 20
<211> LENGTH: 838
<212> TYPE: DNA
<213> ORGANISM: Phlebotomus ariasi

<400> SEQUENCE: 20

```
agtctctccc agggttttat tgtggaaaat gaacgcttta ttgctttgtg ttttgttgag    60
tttaagtgga atagggtact cttggaaata ccctaggaat gccgatcaaa ctctctgggc   120
ttacagaacg tgccaaagag aagggaaaga tccggcatta gtatccaagt ggatgaattg   180
ggtgttacca gatgatccgg aaactcactg ctacgttaag tgcgtttgga ccaatttagg   240
```

-continued

```
atcctacgat gataacaccg gttccattat gattaacaca gtggctacac aatttataac       300
acgcggcatg aaagtcccag ccgaagtaaa taatttaagt gggtcgacaa gtggatcttg       360
ttcagatatt tacaagaaaa ccattgggtt cttcaaaagt caaaggcga acatacagaa        420 agcgtattac ggaactaagg aagagtcaga taactggtat tcgaaacatc caaatgtaaa       480
gccgaaagga acgaagattt ctgacttctg caaaggtcgc gaaggtggaa cggaaggaac       540
ttacaagcat gcttgcagca tgtactacta ccgcttagtc gatgaggata atcttgtgat       600
tccgttcagg aagttgaaaa ttccgggaat tccaggaccc aaaatagatg agtgtaggag       660
gaaggctagc tcgaaaactg gatgcaaagt tgccgatgca ctatacaaat gtcttaaggc       720
tataaacggt aaaagttttg aaaatgcttt aaagaagttg gacgaagaat catccagaac       780
ttattaaaat aaaagaaact tgagttgcta aaaaaaaaaa aaaaaaaaa aaaaaaa           838
```

<210> SEQ ID NO 21
<211> LENGTH: 113
<212> TYPE: PRT
<213> ORGANISM: Phlebotomus ariasi

<400> SEQUENCE: 21

```
Met Ile Arg Ile Leu Phe Pro Leu Phe Ile Leu Ser Leu Gly Ile Tyr
1               5                   10                  15

Gln Val Thr Cys Leu Met Cys His Ser Cys Thr Leu Asp Gly Glu Leu
            20                  25                  30

Glu Ser Cys Glu Asp Ser Ile Asn Glu Thr Tyr Val Val Lys Ile Glu
        35                  40                  45

Glu Lys Glu Cys Lys Pro Ala Gln Ser Cys Gly Lys Val Ser Phe Thr
    50                  55                  60

Ala Asn Gly Thr Val Arg Ile Gly Arg Gly Cys Ile Arg Ser Ser Ser
65                  70                  75                  80

Ser Trp Lys Ile Asp Cys Arg Ile Leu Ala Lys Glu Val Arg Asp Glu
                85                  90                  95

Gly Ile Ala Val Thr His Cys Ser Leu Cys Asp Thr Asp Leu Cys Asn
            100                 105                 110

Glu
```

<210> SEQ ID NO 22
<211> LENGTH: 492
<212> TYPE: DNA
<213> ORGANISM: Phlebotomus ariasi

<400> SEQUENCE: 22

```
atatctagag gaaatatta agtgaaaagt gaaatgatta ggattctgtt tcctctcttt        60
attcttagtc ttggaattta tcaagtaact tgccttatgt gccactcatg tactcttgat      120
ggggagcttg agtcatgtga agattctatc aatgagactt atgtagttaa gattgaggaa     180
aaggagtgca aacctgcgca atcttgcgga aaagtctcat ttactgcgaa tggaacagtt     240
cgaatcggaa gaggatgtat tcgctcaagc agtagttgga aaatcgattg cagaatactt    300
gcaaaggaag ttagagatga aggcattgcg gtaacacact gttccttatg cgacacggac    360
ttgtgcaatg aataaataaa attgtgaaga aaaagtatt gtaactgtta ctggaaaac     420 aatttcagaa atatccacaa taaaagaga gcatttcgct gtaaaaaaaa aaaaaaaaaa    480
aaaaaaaaaa aa                                                         492
```

<210> SEQ ID NO 23
<211> LENGTH: 277
<212> TYPE: PRT
<213> ORGANISM: Phlebotomus ariasi

<400> SEQUENCE: 23

Met Leu Gln Ile Lys His Phe Leu Phe Phe Val Val Leu Phe Val Val
1               5                   10                  15

Ala His Ser Asn Asp Tyr Cys Glu Pro Lys Leu Cys Lys Phe Asn Asn
            20                  25                  30

Gln Val Lys Thr His Ile Gly Cys Lys Asn Asp Gly Lys Phe Val Glu
        35                  40                  45

Ser Thr Cys Pro Lys Pro Asn Asp Ala Gln Met Ile Asp Met Thr Glu
    50                  55                  60

Gln Arg Lys Asn Leu Phe Leu Lys Ile His Asn Arg Leu Arg Asp Arg
65                  70                  75                  80

Leu Ala Arg Gly Ser Val Ser Asn Phe Lys Ser Ala Ala Lys Met Pro
                85                  90                  95

Met Leu Lys Trp Asp Asn Glu Leu Ala Arg Leu Ala Glu Tyr Asn Val
            100                 105                 110

Arg Thr Cys Lys Phe Ala His Asp Gln Cys Arg Ser Thr Lys Ala Cys
        115                 120                 125

Pro Tyr Ala Gly Gln Asn Leu Gly Gln Met Leu Ser Ser Pro Asp Phe
    130                 135                 140

Leu Asp Pro Asn Tyr Val Ile Lys Asn Ile Thr Arg Glu Trp Phe Leu
145                 150                 155                 160

Glu Tyr Lys Trp Ala Asn Gln Gly His Thr Asp Lys Tyr Met Thr Gly
                165                 170                 175

Ser Gly Lys Asn Gly Lys Ala Ile Gly His Phe Thr Ala Phe Ile His
            180                 185                 190

Glu Lys Ser Asp Lys Val Gly Cys Ala Val Ala Lys Leu Thr Asn Gln
        195                 200                 205

Gln Tyr Asn Met Lys Gln Tyr Leu Val Ala Cys Asn Tyr Cys Tyr Thr
    210                 215                 220

Asn Met Leu Lys Glu Gly Ile Tyr Thr Thr Gly Lys Pro Cys Ser Gln
225                 230                 235                 240

Cys Gln Gly Lys Lys Cys Asp Ser Val Tyr Lys Asn Leu Cys Asp Ala
                245                 250                 255

Ser Glu Lys Val Asp Pro Ile Pro Asp Ile Phe Lys Gln Ser Arg Gln
            260                 265                 270

Gln Arg Ser Arg Lys
        275

<210> SEQ ID NO 24
<211> LENGTH: 1067
<212> TYPE: DNA
<213> ORGANISM: Phlebotomus ariasi

<400> SEQUENCE: 24
tccagttaat attccgacat gttgcaaatt aaacacttct gttctttgt ggtgttgttc      60 gttgtcgctc actccaatga ttattgtgag ccgaaattgt gcaaatttaa caaccaagtg     120
aagactcaca ttggatgcaa gaatgatgga aagttcgtgg aaagcacttg cccaaaacca     180
aatgatgctc aaatgattga tatgactgaa cagaggaaga atctcttct caagattcac      240 aatcgccttc gcgataggct cgctcgtggt tctgtgtcta atttcaagtc agccgccaag     300

```
atgccaatgc tgaaatggga caatgaattg gccaggttgg cagaatacaa tgtgagaacg    360
tgcaaatttg ctcacgatca gtgtcgctca accaaggctt gtccttatgc tggccagaac    420
ttgggccaaa tgttgtcttc tccagatttc ttggaccccca actatgtcat caagaatatc   480
actagggagt ggttcttgga gtataagtgg gcaaatcaag acatactga taaatatatg     540 acaggatctg gtaagaatgg caaagcaatt ggtcactttta ctgccttcat ccatgagaaa   600
agcgacaagg ttggatgcgc tgttgctaaa ttaaccaacc agcagtacaa catgaagcag    660
tacctcgtgg cctgcaacta ctgctacacg aatatgctaa aggaagggat ctacacgaca    720
ggaaagcctt gttctcagtg ccagggaaag aagtgtgatt ccgtctacaa gaacttatgc    780
gatgcgagtg agaaagtcga tcccatccca gacatcttta gcaatcgag acaacagagg     840 agcaggaaat aattctctgc tttcccattt ggtataaaat gttaaattta ttgttttccc    900
atctattggg tgaattggcg aaaaaggtga agatgaaaaa aggtataaga aaataagaga    960
taaacagaaa ctgagatatc tgaaaaaaaa aaaaaaaaa aaaaaaaaaa aaaaaaaaa     1020 aaaaaaaaaa aaaacccaaa aaaaaaaaaa aaaaaaaaa aaaaaaa                  1067
```

<210> SEQ ID NO 25
<211> LENGTH: 249
<212> TYPE: PRT
<213> ORGANISM: Phlebotomus ariasi

<400> SEQUENCE: 25

```
Met Ile Val Lys Ser Phe Leu Gly Val Phe Leu Val Ile Leu Leu Val
1               5                   10                  15

Ser Val Thr Glu Gln Asp Arg Gly Val Asp Gly His Arg Thr Gln
        20                  25                  30

Asp Asp His Asp Tyr Ser Glu Leu Ala Glu Tyr Asp Glu Asp Pro
        35                  40                  45

His Gln Glu Val Ile Asp Gly Asp Glu Glu His Glu Leu Ser Gly
    50                  55                  60

Gly Arg Arg Leu Ser His Glu Asp Glu Asp Asp Asp Arg His Tyr
65                  70                  75                  80

Gly His Arg Gly Glu Asp Arg Glu Asn Ser Arg Gly Arg Asn Gly Gly
                85                  90                  95

Ser Arg Asn Arg Gly Ser Glu Glu Gln Ser Tyr Asp Pro Tyr Ser His
            100                 105                 110

Glu Arg Ala Pro Thr Tyr Ser Glu Ser Ser Glu Tyr Asp His Ser Gly
        115                 120                 125

Asp Tyr Asp Asn Ser Asn Tyr Gln Gln His Ser Ser Thr Pro Ser Ser
    130                 135                 140

Tyr Ser Asn Ile Asp His Tyr Leu His Leu Ile Gln Leu His Ser Val
145                 150                 155                 160

Pro Ser Asp Leu Ala Gln Tyr Ala Asp Ser Tyr Leu Gln His Ser Lys
                165                 170                 175

Asn Ser Ile Arg Tyr Tyr Ala Ser His Ala Lys Asp Phe Glu Lys Ile
            180                 185                 190

Arg Pro Cys Leu Glu Ser Val Val Lys Tyr Ser Asn Leu Leu Asn Asp
        195                 200                 205

Asp Leu Ala Lys Glu Tyr Ile Arg Cys Gln Arg Lys Cys Tyr Leu Glu
    210                 215                 220

Arg Leu Asn Ser Tyr Thr Ser Ala Ile Ser Gln Tyr Thr Val Thr Thr
225                 230                 235                 240
```

-continued

Asn Ala Cys Ile Asn Asn Arg Leu His
            245

<210> SEQ ID NO 26
<211> LENGTH: 914
<212> TYPE: DNA
<213> ORGANISM: Phlebotomus ariasi

<400> SEQUENCE: 26
tcagtttcac tttgaccatc gatggtgcaa ttacttcaat tcaatttacg aaatcacttt      60
gattgagaaa cgatgatcgt gaagagtttc cttggggtgt tcttgtgat cttgctcgtg     120
tccgtgacag aacaggatcg tggagtagac ggacacagga ggactcaaga tgaccatgat     180
tacagcgaat tggcggaata tgacgacgaa gatcctcatc aagaggtaat tgacggtgat     240
gaggaggaac atgagttgtc cggaggacgt cgactatccc acgaagacga agacgacgac     300
gacagacact atggccatcg tggagaggat cgagagaatt ctcgaggcag aaatggtgga     360
tctcgtaatc gtggtagtga ggaacaatca tacgatccct acagccacga gagagctcct     420
acctactcag aatccagtga atacgaccac agcggtgact acgacaattc caactaccag     480
caacattcct ccactccctc ctcctacagc aacatcgatc actatctcca tctcatccaa     540
ttgcacagcg tccccagtga tttagcccag tacgccgatt cctaccttca acactccaag     600
aactccatca gatactacgc ttcgcatgcc aaagactttg agaagattcg accctgtctg     660
gagagcgtcg tgaagtactc caatctcctc aatgacgatc ttgccaagga gtacatcaga     720
tgccaacgaa agtgttacct tgaacgtctc aatagctaca catcggctat ctctcagtac     780
acagtcacca caaatgcctg cataaacaac cgattgcatt aaagctgagg attatcttgt     840
gaaatattta tttgaatcga tcagtgaaaa taaatttcca atagcaaaaa aaaaaaaaca     900
aaaaaaaaa aaaa                                                        914

<210> SEQ ID NO 27
<211> LENGTH: 333
<212> TYPE: PRT
<213> ORGANISM: Phlebotomus ariasi

<400> SEQUENCE: 27

Met Ile Ile Lys Leu Cys Ala Ile Ala Val Ala Cys Leu Leu Thr Gly
1               5                   10                  15

Asp Gly Glu Ala Ala Pro Arg Ala Thr Arg Phe Ile Pro Phe Ala Val
            20                  25                  30

Ile Ser Asp Leu Asp Lys Lys Ser Ile Lys Ser Asp Gln Lys Ser Phe
        35                  40                  45

Thr Ser Ile Val Arg Tyr Gly Glu Leu Lys Asp Asn Gly Glu Arg Tyr
    50                  55                  60

Thr Leu Ser Ile Lys Ser Glu Asn Leu His Tyr Phe Thr Arg Tyr Ala
65                  70                  75                  80

Tyr Asn Gly Arg Gly Ala Glu Leu Ser Glu Leu Leu Tyr Phe Asn Asn
                85                  90                  95

Lys Leu Tyr Thr Ile Asp Asp Lys Thr Gly Ile Ile Phe Glu Val Lys
            100                 105                 110

His Gly Gly Asp Leu Ile Pro Trp Val Ile Leu Ser Asn Gly Asp Gly
        115                 120                 125

Asn Gln Lys Asn Gly Phe Lys Ala Glu Trp Ala Thr Val Lys Gly Asp
    130                 135                 140

Lys Leu Ile Val Gly Ser Thr Gly Ile Pro Trp Phe Glu Glu Lys Thr

```
            145                 150                 155                 160
Gln Ser Leu Asn Thr Tyr Ser Leu Trp Val Lys Glu Ile Ser Lys Glu
                165                 170                 175

Gly Glu Val Thr Asn Ile Asn Trp Lys Ser Gln Tyr Ser Lys Val Lys
            180                 185                 190

Asn Ala Met Gly Ile Pro Ser Ser Val Gly Phe Val Trp His Glu Ala
        195                 200                 205

Val Asn Trp Ser Pro Arg Lys Asn Leu Trp Val Phe Met Pro Arg Lys
    210                 215                 220

Cys Thr Thr Glu Tyr Phe Thr Ser Gln Val Glu Glu Lys Thr Gly Cys
225                 230                 235                 240

Asn Gln Ile Ile Thr Ala Asn Glu Asp Phe Thr Gln Val Lys Ala Ile
                245                 250                 255

Arg Ile Asp Gly Pro Val Gln Asp Gln Ala Ala Gly Phe Ser Ser Phe
            260                 265                 270

Lys Phe Ile Pro Gly Thr Gln Asn Asn Asp Ile Phe Ala Leu Lys Thr
        275                 280                 285

Ile Glu Arg Asn Gly Gln Thr Ala Thr Tyr Gly Thr Val Ile Asn Ile
    290                 295                 300

Glu Gly Lys Thr Leu Leu Asn Glu Lys Arg Ile Leu Asp Asp Lys Tyr
305                 310                 315                 320

Glu Gly Val Ala Phe Phe Lys Asn Pro Glu Gly Ile Ile
                325                 330

<210> SEQ ID NO 28
<211> LENGTH: 1161
<212> TYPE: DNA
<213> ORGANISM: Phlebotomus ariasi

<400> SEQUENCE: 28
aaagtattca gttgtgagaa atctttccaa atacacatca tgattatcaa attgtgcgct      60
attgctgttg cttgtctcct cactggagat ggagaagcag ctcccagagc aacaagattc     120 atcccttttcg ctgttatctc cgacttggac aagaagtcca ttaaatccga tcagaagagt    180
ttcaccagca tcgtgagata tggcgaattg aaggacaatg agagagata tacgttatcc     240 atcaagagtg aaaatcttca ctacttcacg cgatacgctt acaatggacg cggagccgaa     300
ttatctgaat tgttgtactt caacaacaaa ctctacacca ttgatgacaa acaggaatt     360 atctttgagg tgaaacatgg tggggatctc attccatggg tgatcctgtc gaatggcgat     420
ggaaatcaaa agaatggctt taaagccgaa tgggcgacag ttaagggtga caagttgatt     480
gtcggatcaa caggaatccc ctggtttgag gagaaaaccc agtctcttaa cacctacagc     540
ctttgggtga agagatcag caaggaaggc gaagtcacca acatcaattg gaagagtcaa     600
tacagcaaag tgaagaatgc aatgggaatt ccttcctctg tgggattcgt ctggcatgag     660
gctgtaaatt ggtcaccgag gaagaatcta tgggtcttca tgcccagaaa atgtacaact     720
gaatatttca ccagtcaagt ggaagagaaa actggatgca atcagattat acggctaat      780 gaagatttca ctcaagtgaa agcaattagg atcgatggac ctgttcagga tcaagctgct     840
ggattctcct cctttaagtt catcccaggc actcaaaaca atgatatctt cgcactgaag     900
actatcgaga ggaacggcca aacagccact tacgggacag taattaacat cgaagggaag     960
actttgttga acgaaaaacg aattctcgat gataaatacg aaggagttgc attttttcaag   1020 aatcccgaag gcattatata aaataataat gatggagtga aaaacaaatt gaataaaaat    1080
```

```
gctaaagctc ataaaattaa aaaaaaaaaa aaaaaaaaaa aaaaaaaaaa aaaaaaaaaa    1140
aaaaaaaaaa aaaaaaaaaa a                                               1161

<210> SEQ ID NO 29
<211> LENGTH: 137
<212> TYPE: PRT
<213> ORGANISM: Phlebotomus ariasi

<400> SEQUENCE: 29
```

Met His Phe Lys Ile Ile Phe Cys Ser Leu Phe Ile Val Leu Leu Gly
1               5                   10                  15

His Met Ala Phe Ala Glu Ser Ser Glu Ser Ser Ser Glu Ser Ser
            20                  25                  30

Ser Ser Glu Thr Ser Glu Glu Ser Ser Glu Glu Val Val Pro Ser Pro
        35                  40                  45

Ser Pro Ser Pro Lys His Arg Pro His Phe Gly Pro His His Pro His
    50                  55                  60

Gly Gly Arg Pro Lys Pro Pro His Pro Pro Pro Lys Pro Glu Pro
65                  70                  75                  80

Glu Pro Asp Asn Gly Ser Asp Gly Gly Asn Gln Asp Asn Ser Asn Gly
                85                  90                  95

Gln Asp Asn Ser Asn Gly Asn Ser Gln Asn Asp Glu Gln Asp Asn Ser
            100                 105                 110

Gln Ser Gly Ser Ala Lys Arg Phe Arg Gln Pro Ala Val Asn Ile Val
        115                 120                 125

Asn Leu Val Ile Pro Phe Ser Thr Ile
    130                 135

```
<210> SEQ ID NO 30
<211> LENGTH: 530
<212> TYPE: DNA
<213> ORGANISM: Phlebotomus ariasi

<400> SEQUENCE: 30
atcaattgtt attgaaataa tcttcaagat gcatttcaag attatcttct gctccctctt     60
cattgtcctg ctgggacata tggcgtttgc tgaatcttct gagtcatcat cttcagagtc    120
gtcgtcttca gaaacatctg aagagtcatc tgaagaagtt gttccatccc cttctccctc    180
acctaagcat cggccgcatt ttggtcccca tcacccacat ggaggccgac ctaagcctcc    240
ccatccgccg ccaccgaaac ctgagccgga gccagataat ggctcagatg gtggcaatca    300
ggataattca aatggtcagg ataactctaa tggaaactct cagaatgatg aacaggataa    360
ctctcaatcg ggatccgcta agcgattcag acaacctgca gtgaatattg ttaatcttgt    420
gattcctttt tctacgattt aactttcctt ttgtctactt taatcacttt aatgcacgta    480
ataataaaaa atactttcag caaaaaaaaa aaaaaaaaaa aaaaaaaaaa                530

<210> SEQ ID NO 31
<211> LENGTH: 170
<212> TYPE: PRT
<213> ORGANISM: Phlebotomus ariasi

<400> SEQUENCE: 31
```

Met Phe Ser Lys Ile Phe Ser Leu Ala Ile Leu Ala Leu Ala Leu Ser
1               5                   10                  15

Thr Val Ser Ser Glu Thr Cys Ser Asn Pro Gln Val Lys Gly Ala Ser
            20                  25                  30

```
Ser Tyr Thr Thr Thr Asp Ala Thr Ile Val Ser Gln Ile Ala Phe Ile
        35                  40                  45

Thr Glu Phe Ser Leu Glu Cys Ser Asn Pro Gly Ala Glu Lys Val Ser
 50                  55                  60

Leu Phe Ala Glu Val Asp Gly Arg Ile Thr Pro Val Ala Val Ile Gly
 65                  70                  75                  80

Asp Thr Lys Tyr Gln Val Ser Trp Asn Glu Glu Val Lys Lys Ala Arg
                 85                  90                  95

Ser Gly Asp Tyr Asn Val Arg Leu Tyr Asp Glu Glu Gly Tyr Gly Ala
                100                 105                 110

Val Arg Lys Ala Gln Arg Ser Gly Glu Glu Asn Asn Ala Lys Pro Leu
                115                 120                 125

Ala Thr Val Val Arg His Ser Gly Ser Tyr Thr Gly Pro Trp Phe
130                 135                 140

Asn Ser Glu Ile Leu Ala Ser Gly Leu Ile Ala Val Val Ala Tyr Phe
145                 150                 155                 160

Ala Phe Ala Thr Arg Ser Lys Ile Leu Ser
                165                 170

<210> SEQ ID NO 32
<211> LENGTH: 674
<212> TYPE: DNA
<213> ORGANISM: Phlebotomus ariasi

<400> SEQUENCE: 32
tttctcaatt tgtgtgtgat tgctctagac gtggccggtg aattttccca aaatgttttc      60
caaaatcttc tctttggcta tcctcgctct cgccttgtcc actgtgtcca gtgagacttg     120
cagtaatcct caagtgaagg gcgcttcctc ctacacaacc acggatgcaa cgatagtcag     180
ccaaattgcc ttcatcactg aattctcact ggagtgctcg aatcccggag ctgagaaggt     240
ctccctgttc gccgaagttg acggacggat cactccagtt gcggtaattg gagatactaa     300
atatcaggtg agctggaatg aggaggtcaa gaaggctcgc agtggagatt acaatgtaag     360
actgtacgac gaggagggat acggagctgt gcgcaaagcc cagagatcag gagaggagaa     420
caatgcgaag ccactggcta cagttgttgt tcgccattcc ggatcctaca ctggcccttg     480
gttcaattct gaaatcttag cctccggtct catcgccgtc gtagcatatt ttgctttcgc     540
caccagaagc aaaatcctgt cgtagagacg catcaataat ttcacaaaaa tgtagccaga     600
aggctgttct tggcactcag actgtttctg tgaaatacaa caacatatca aaaaaaaaa     660 aaaaaaaaaa aaaa                                                      674

<210> SEQ ID NO 33
<211> LENGTH: 250
<212> TYPE: PRT
<213> ORGANISM: Phlebotomus ariasi

<400> SEQUENCE: 33

Met Ser Asn Leu Leu Thr Ile Phe Gly Ala Ile Cys Phe Leu Gly Val
 1               5                  10                  15

Ala Asn Ser Leu Gln Phe Pro Arg Asn Pro Asp Gln Thr Arg Trp Ala
                20                  25                  30

Glu Lys Thr Cys Leu Lys Glu Ser Trp Ala Pro Pro Asn Leu Ile Asn
             35                  40                  45

Lys Trp Lys Gln Leu Glu Phe Pro Ser Thr Asn Leu Thr Tyr Cys Tyr
 50                  55                  60
```

```
Val Lys Cys Phe Val Met Tyr Leu Gly Val Tyr Asn Glu Thr Thr Lys
 65                  70                  75                  80

Lys Phe Asn Val Asp Gly Ile Arg Ser Gln Phe Thr Ser Gln Gly Leu
                 85                  90                  95

Arg Pro Pro Asn Gly Leu Glu Ser Leu Gln Lys Thr Ser Lys Gly Thr
            100                 105                 110

Cys Lys Asp Val Phe Arg Met Ser Ala Gly Leu Ile Lys Lys Tyr Lys
        115                 120                 125

Leu Glu Phe Val Lys Ala Phe His Gly Asp Ser Ala Glu Ala Ala Lys
    130                 135                 140

Trp Tyr Ile Glu His Lys Gly Asn Val Lys Ala Lys Tyr Gln Lys Ala
145                 150                 155                 160

Ser Glu Phe Cys Lys Thr Gln Lys Asp Glu Cys Arg Leu His Cys Arg
                165                 170                 175

Phe Tyr Tyr Tyr Arg Leu Val Asp Glu Asp Phe Gln Ile Phe Asn Arg
            180                 185                 190

Lys Phe Lys Ile Tyr Gly Ile Ser Asp Ser Gln Leu Arg Gln Cys Arg
        195                 200                 205

Ser Lys Ala Ser Gln Ala Lys Gly Cys Lys Val Ala Lys Val Leu Lys
    210                 215                 220

Asn Cys Leu Asp Lys Ile Asp Ser Glu Lys Val Lys Thr Ala Leu Lys
225                 230                 235                 240

Thr Leu Asp Glu Ile Ser Ala Asn Tyr Val
                245                 250

<210> SEQ ID NO 34
<211> LENGTH: 977
<212> TYPE: DNA
<213> ORGANISM: Phlebotomus ariasi

<400> SEQUENCE: 34
gtttcttata catcactttg aagcagcaat gagtaacttg ctaactatct ttggggcaat      60
ttgtttcttg ggcgttgcca actctctgca attccctcgg aacccagacc aaaccagatg    120
ggcagaaaag acatgtttaa agaatcttg gcaccacct aatctgataa acaagtggaa     180
gcaattggaa tttcccagta ccaatctcac ctactgctac gtgaagtgct ttgttatgta    240
tttaggagtc tacaacgaga cgaccaagaa attcaacgta gacggtatca gatcccaatt    300
tacaagtcaa ggacttcgtc cacctaacgg tctagagagc ctacaaaaga catctaaagg    360
aacctgcaag gatgtcttcc gaatgtccgc tggcctaatc aagaagtaca aattggaatt    420
cgtaaaagct ttccatggag attctgccga agctgcgaag tggtacatcg aacataaagg    480
aaatgttaag gcaaagtatc agaaagcttc ggaattctgc aaaactcaga aggatgagtg    540
taggctgcat tgtcgtttct actactaccg cttagttgac gaagacttcc aaatattcaa    600
tagaaaattc aagatctacg gcatttcgga ctcacagcta cggcagtgta ggagtaaagc    660
cagtcaagct aagggttgca aggttgccaa agtccttaaa aattgcctcg acaagattga    720
ttctgagaaa gtgaaaaccg ctcttaagac tttggatgag atatcagcaa attacgttta    780
acagtaatct ccaagttagc cccatcagcc taatttagcg ccacctttaa atcaaccccc    840
agctaatttc tcgaacgtta gaaaaggtgt ttaacttac gggtgattga gtgtaagtaa    900
tttagcggct gtggagatga aatgactatt aaatcgtgca caatggggca aaaaaaaaa    960 aaaaaaaaaa aaaaaaa                                                    977
```

<210> SEQ ID NO 35
<211> LENGTH: 45
<212> TYPE: PRT
<213> ORGANISM: Phlebotomus ariasi

<400> SEQUENCE: 35

Met Tyr Phe Thr His Thr Leu Asn Phe Leu Leu Val Ile Leu Leu
1               5                   10                  15

Ile Met Ala Gly Phe Ser Gln Ala Asn Pro Glu Lys Arg Pro Cys Thr
            20                  25                  30

Asn Cys Glu Arg Pro Lys Leu Ser Ala Lys Thr Pro Leu
        35                  40                  45

<210> SEQ ID NO 36
<211> LENGTH: 346
<212> TYPE: DNA
<213> ORGANISM: Phlebotomus ariasi

<400> SEQUENCE: 36
acaattcata tttcctttag tgaagttgtt gaaaatcaag caagatgtac tttacccata      60
ccctcaattt tcttcttctt gtaattctat taataatggc tggttttttcc caggcaaatc    120 ccgagaaaag gccctgcaca aactgtgagc gtcccaagtt atcggctaaa actcctttgt    180
aaccctttta atcatataa tcggtgatta agatttacc agcagagcta ccgcaatgtg      240
aaatcgaaaa attataccta cctacagaaa aactaaaatg taataagaat tagaaaaaat    300
aaaaatgatc caagaacaaa aaaaaaaaaa aaaaaaaaaa aaaaaa                   346

<210> SEQ ID NO 37
<211> LENGTH: 232
<212> TYPE: PRT
<213> ORGANISM: Phlebotomus ariasi

<400> SEQUENCE: 37

Met Thr Trp Val Ile Leu Cys Val Ala Leu Leu Val Ala Ser Val Val
1               5                   10                  15

Ala Glu Gly Gly Ile Asp Ala Glu Gly Asn Arg Thr Lys Ile Glu Lys
            20                  25                  30

Ile Thr Ala Gly Ala Gly Ser Asp Gly Lys Val Val Tyr Thr Glu Gly
        35                  40                  45

Gly Ser Phe Pro Glu Lys Leu Glu Lys Glu Gln Lys Ser Val Lys Lys
50                  55                  60

Glu Leu Gly Glu Leu Pro Lys Pro Thr Asn Ala Thr Phe Ser Pro Pro
65                  70                  75                  80

Val Lys Val Glu Asn Lys Thr Glu Glu Val Arg Asn Ala Thr Leu Pro
                85                  90                  95

Val Asn Ala Thr Thr Glu Ala Pro Lys Val Val Asn Thr Thr Ala Ser
            100                 105                 110

Thr Thr Thr Val Lys Leu Thr Ser Thr Ser Thr Thr Thr Thr Thr Pro
        115                 120                 125

Lys Pro Lys Lys Pro Ser Leu Thr Ile Ser Val Glu Asp Asp Pro Ser
130                 135                 140

Leu Leu Glu Val Pro Val Lys Val Gln His Pro Gln Thr Gly Gly Arg
145                 150                 155                 160

Leu Asp Val Glu Glu Pro Val Ala Gln Leu Ser His Glu Asn Ile Leu
                165                 170                 175

Glu Met Pro Val Asn His Arg Asp Tyr Ile Val Pro Ile Val Val Leu
            180                 185                 190

```
Ile Phe Ala Ile Pro Met Ile Leu Gly Leu Ala Thr Val Val Ile Arg
        195                 200                 205

Arg Phe Arg Asp Tyr Arg Leu Thr Arg His Tyr Arg Arg Met Asp Tyr
    210                 215                 220

Leu Val Asp Gly Met Tyr Asn Glu
225                 230

<210> SEQ ID NO 38
<211> LENGTH: 899
<212> TYPE: DNA
<213> ORGANISM: Phlebotomus ariasi

<400> SEQUENCE: 38
atcgcgattc tgttgcaacg tcacagagta cttccttctt ttcctttcgg tttcctatca      60
tttcatttgt tatctcgcac ccaaatgacg tgggtgattc tttgtgtcgc cctcctggtt    120
gcttccgttg tcgcggaggg cggaatcgat gcggagggga atcgcacgaa aatcgagaag    180
ataaccgcgg gtgcaggaag tgatggcaag gtggtctaca cagagggtgg aagcttcccg    240
gagaagctag agaaggagca aagagcgtg aagaaggagc ttggagaatt gccaaagccc    300
acaaatgcca cattttcacc tcccgtgaag gtggagaata agacggagga ggtgaggaat    360
gctacactgc cggtgaatgc cacaactgag gcccctaagg tggtcaatac gacagccagc    420
accaccacgg tgaagctaac atccaccagc accacaacaa ctactcccaa gcccaagaag    480
cccagcctca cgattagcgt ggaggacgat ccgagcctcc tggaggtgcc agtcaaggtg    540
cagcatccac agaccggagg acgactggat gtggaggagc ctgtggctca gctgtcgcat    600
gagaacatcc tggagatgcc cgtgaatcac cgggactaca ttgttcccat tgtggtgctt    660
atctttgcca ttcccatgat cctgggactc gccactgttg tcatccgacg tttcagggac    720
taccggctca ctcgccacta ccgccggatg gactacctcg tggatggaat gtataatgag    780
tagtttccgg ctcgcactaa ccgcccaagc aataatctaa ttaatgctta atcgttttat    840
actatgtaaa taaatgtaca ttttaataat aaaaaaaaaa aaaaaaaaa aaaaaaaa      899

<210> SEQ ID NO 39
<211> LENGTH: 65
<212> TYPE: PRT
<213> ORGANISM: Phlebotomus ariasi

<400> SEQUENCE: 39

Met Lys Lys Ile Leu Leu Phe Ser Val Ile Phe Val Ala Leu Leu Ile
1               5                   10                  15

Thr Ala Glu Ala Ile Pro Gly Lys Arg Ala Arg Pro Lys Ala Pro Ala
            20                  25                  30

Val Thr Lys Gly Arg Asp Val Pro Lys Pro Arg Pro Gly Gln Gly Gly
        35                  40                  45

Gln Val Pro Val Glu Pro Asp Phe Pro Met Glu Asn Leu Arg Ser Arg
    50                  55                  60

Ile
65

<210> SEQ ID NO 40
<211> LENGTH: 303
<212> TYPE: DNA
<213> ORGANISM: Phlebotomus ariasi

<400> SEQUENCE: 40
```

```
cgtcagtttg ttgaaagttg ggaaaatgaa gaaaattctg ctattcagtg ttatattcgt      60
tgctttgttg atcactgccg aagccattcc gggaaaacgg gcaagaccga agctcccgc      120 ggtcactaaa ggtcgggatg ttccaaaacc aagacctggt caaggaggac aagtgccagt    180
tgaaccagat tttcctatgg aaaacttaag aagtagaatt tagtagatct tcagctttct    240
cggccccttt aataaaattc gtctactgat aaaaaaaaaa aaaaaaaaaa aaaaaaaaa     300 aaa                                                                   303
```

<210> SEQ ID NO 41
<211> LENGTH: 114
<212> TYPE: PRT
<213> ORGANISM: Phlebotomus ariasi

<400> SEQUENCE: 41

```
Met Ala Val Lys Asn Leu His Lys Phe Leu Val Val Gly Phe Val
1               5                   10                  15

Ser Leu Ile His Ala Ala Tyr Ser Ala Ala Gln His Arg Thr Tyr Leu
            20                  25                  30

Arg Ile Thr Glu Gln Glu Phe Asn Ser Leu Pro Phe Asp Ile Val Leu
        35                  40                  45

Gln Ala Val Val Ser Leu Ile Ile Leu Val Tyr Ser Ile Leu Gln Val
    50                  55                  60

Val Gly Glu Phe Arg Glu Ile Arg Ala Ala Val Asp Leu Gln Ala Lys
65                  70                  75                  80

Ser Trp Glu Thr Leu Gly Asn Ile Pro Ser Phe Tyr Met Phe Asn His
                85                  90                  95

Arg Gly Lys Ser Leu Ser Gly Gln Tyr Glu Asp Asn Ile Asp Thr Ser
            100                 105                 110

Ala Asp
```

<210> SEQ ID NO 42
<211> LENGTH: 536
<212> TYPE: DNA
<213> ORGANISM: Phlebotomus ariasi

<400> SEQUENCE: 42

```
atatatctat cgatttctcg tgttttgatt tgcttaggtg gccccatttt tccaagaaaa     60
ttcctgaaat ggcagttaaa aatcttcaca aattcctcct ggtcgtggga ttcgtgtccc    120
tgatccatgc ggcttattcg gcagcacagc acagaacgta cctgagaatc acggagcagg    180
agtttaattc tctcccattt gacattgtgc tccaagctgt ggtgagtctg atcattctgg    240
tgtacagcat tctgcaggtt gttggggagt tccgggagat cgagcagct gtggacttgc     300 aagcgaaatc atgggagact ttgggtaaca tcccctcctt ctacatgttc aatcaccgtg    360
ggaagagcct atccggccag tatgaggata cattgacac gagtgccgat gaatgcccg      420 gaagaagcct tcccgtaaat ctatttgaat gtaaggaatc cgattaattg aattaacacc    480
aaaggagagc tgagggaaaa aaaaaaaaaa aaaaaaaaaa aaaaaaaaaa aaaaaa        536
```

<210> SEQ ID NO 43
<211> LENGTH: 291
<212> TYPE: PRT
<213> ORGANISM: Phlebotomus ariasi

<400> SEQUENCE: 43

```
Met Met Ser Arg Trp Ser Lys Ser Val Lys Phe Val Cys Leu Leu Leu
1               5                   10                  15
```

Cys Gly Gly Phe Thr Phe Leu Thr Thr Ser Ala Arg Ala Lys Pro Thr
            20                  25                  30

Leu Thr Phe Gln Leu Pro Pro Ala Leu Thr Asn Leu Pro Pro Phe Val
            35                  40                  45

Gly Ile Ser Arg Phe Val Glu Arg Lys Met Gln Asn Glu Gln Met Lys
        50                  55                  60

Thr Tyr Thr Gly Val Arg Gln Thr Asn Glu Ser Leu Val Met Ile Tyr
 65                  70                  75                  80

His His Asp Leu Thr Ile Ala Ile Val Glu Leu Gly Pro Glu Lys Ser
                85                  90                  95

Leu Leu Gly Cys Glu Leu Ile Glu Ile Asn Asn Asp Asp Glu Gly Ala
            100                 105                 110

Lys Val Leu Lys Glu Leu Ala Thr Val Asn Ile Pro Leu Glu Ile Asp
            115                 120                 125

Phe Arg Glu Met Val Lys Leu Met Lys Gln Cys Glu Lys Ile Asp Tyr
130                 135                 140

Ile Arg Lys Val Lys Arg Gln Gly Ala Pro Glu Ser Asp Gln Thr Thr
145                 150                 155                 160

Asn Arg Gln His Gln Thr Gly Tyr Phe Thr Gly Ala Thr Ala Gly Leu
                165                 170                 175

Ser Ile Leu Ser Gly Ile Leu Pro Gly Thr Lys Trp Cys Gly Thr Gly
            180                 185                 190

Asp Ile Ala Arg Thr Tyr His Asp Leu Gly Thr Glu Ala Thr Met Asp
            195                 200                 205

Met Cys Cys Arg Thr His Asp Leu Cys Pro Val Lys Val Arg Ser Tyr
210                 215                 220

Gln Gln Arg Tyr Asn Leu Thr Asn Lys Ser Ile Tyr Thr Lys Ser His
225                 230                 235                 240

Cys Lys Cys Asp Asp Met Leu Phe Asn Cys Leu Lys Arg Thr Asn Thr
                245                 250                 255

Ser Ala Ser Gln Phe Met Gly Thr Ile Tyr Phe Asn Val Val Gln Val
            260                 265                 270

Pro Cys Val Leu Asp Thr Asp Arg Gly Tyr Arg Phe Arg Lys Ala Arg
            275                 280                 285

Thr Phe Ser
        290

<210> SEQ ID NO 44
<211> LENGTH: 1087
<212> TYPE: DNA
<213> ORGANISM: Phlebotomus ariasi

<400> SEQUENCE: 44
cacgaattag aaaacggtcc cagtgattct ctcggtggct gatttataag agaatgtgaa      60
gagttgagga tgatgtctcg ctggagcaaa agtgtgaaat ttgtgtgcct cctcctgtgt     120
ggcggattca cgtttctcac aacatcagca cgtgccaaac ccacactgac ctttcagcta     180
ccgcccgcac tcacgaacct accccccttc gtgggcatct cacgattcgt cgaacgcaaa     240
atgcagaatg agcagatgaa gacctacact ggcgttcggc agacgaatga gtctctcgtg     300
atgatctacc accatgatct gacgatcgcc atcgtggaat tgggaccaga gaagagtctc     360
ttgggttgtg aattgataga aattaacaac gatgacgaag cgccaaagt gctgaaagaa     420 ctggccacgg tgaatatacc actggagatc gacttccggg agatggtgaa gctcatgaag     480

```
cagtgcgaga agatcgatta catacggaaa gtgaaacgcc aaggagcacc agagagtgac      540
cagacgacaa atcgtcaaca ccagacgggc tacttcacgg gcgccactgc cggcctgagt      600
atcctcagtg gcatccttcc cggcaccaag tggtgtggca caggagacat cgccaggaca      660
tatcacgatc tcggcacaga ggctaccatg gacatgtgct gtcgcactca cgatctctgt      720
ccagtgaaag tgcgctcata tcagcaacgc tacaatctca ccaataagtc aatctacaca      780
aaatctcact gtaaatgtga tgacatgctg ttcaattgcc tcaagaggac caacacgtca      840
gcctcgcaat tcatggggac catctacttc aacgtggtcc aagtgccatg tgttctggac      900
acagacagag gctacagatt cagaaaagcg agaaccttct cctgatcatc gcaatgcaac      960
gaaatctgag gatattttat ttttggggac ttttttttgc gtgtaaagac catttctgtg     1020
attttcagct gaggtgctct ttcaaatgaa ttatttatat gttacaaaaa aaaaaaaaaa     1080
aaaaaaa                                                               1087
```

<210> SEQ ID NO 45
<211> LENGTH: 139
<212> TYPE: PRT
<213> ORGANISM: Phlebotomus ariasi

<400> SEQUENCE: 45

```
Met Lys Leu Leu Pro Ile Ile Leu Leu Ala Leu Thr Val Leu Ile Val
1               5                   10                  15

Thr Cys Gln Ala Glu His Pro Gly Thr Lys Cys Arg Arg Glu Phe Ala
            20                  25                  30

Ile Glu Glu Glu Cys Ile Asn His Cys Glu Tyr Lys His Phe Gly Phe
        35                  40                  45

Thr Asp Asp Gln Phe Arg Ile Lys Lys His His Arg Glu Asn Phe Lys
    50                  55                  60

Asn Ala Met Ser His Tyr Gly Ala Ile Arg Lys Asp Gln Glu Gly Glu
65                  70                  75                  80

Leu Asp Lys Leu Leu Asn Arg Cys Ala Lys Lys Ala Lys Glu Ser Pro
                85                  90                  95

Ala Thr Ser Lys Arg Asp Lys Cys Tyr Arg Ile Ile Asn Tyr Tyr Arg
            100                 105                 110

Cys Val Val Asp Asn Asn Leu Ile Asn Tyr Ser Val Tyr Val Lys
        115                 120                 125

Ala Val Thr Lys Ile Asn Asp Ser Ile Asn Val
    130                 135
```

<210> SEQ ID NO 46
<211> LENGTH: 518
<212> TYPE: DNA
<213> ORGANISM: Phlebotomus ariasi

<400> SEQUENCE: 46

```
aacatatctg aaccagccat gaagttgtta cctataattc tgttggcgtt gacagtcttg       60
atcgtgactt gtcaagctga acatcccggt actaagtgta aagagaatt cgcaatagaa      120 gaagaatgta tcaatcattg tgaatacaaa cactttggct tcacagatga ccaattccgg      180
attaaaaagc atcatagaga aaatttcaaa acgctatga gtcattacgg tgcaatcaga      240
aaggatcaag aaggtgaact ggataagctt ttgaatagat gtgccaagaa agccaaagag      300
tctcctgcta catcgaaaag agacaaatgt tacagaatta ttaactacta ccgttgtgtt      360
gttgtagata ataatctgat caattattct gtttacgtca aagctgttac caagattaat      420
```

```
gattcaatca atgtataaaa atcaaatatt actttgaaat aaaagaagaa acaatgttgt      480
atgcaaggcc aaaaaaaaaa aaaaaaaaaa aaaaaaaa                              518
```

<210> SEQ ID NO 47
<211> LENGTH: 137
<212> TYPE: PRT
<213> ORGANISM: Phlebotomus ariasi

<400> SEQUENCE: 47

```
Met Lys Glu Leu Val Val Phe Leu Thr Leu Ile Val Leu Val Val Ile
1               5                   10                  15

Cys His Ala Glu Arg Pro Ser Gln Lys Cys Arg Arg Glu Leu Lys Thr
                20                  25                  30

Glu Glu Glu Cys Ile Leu His Cys Glu Tyr Lys His Tyr Arg Phe Thr
            35                  40                  45

Asp Asp Gln Phe Arg Leu Asn Ala Asp Gln Arg Gly Asp Phe Arg Asn
        50                  55                  60

Ile Met Arg Arg Tyr Gly Ala Ile Arg Val Asp Gln Glu Ser Gln Leu
65                  70                  75                  80

Asp Lys His Leu Lys Lys Cys Ala Asn Lys Val Ala Lys Thr Pro Ala
                85                  90                  95

Thr Ser Arg Lys Asp Lys Cys Arg Lys Ile Ser Arg Tyr Tyr His Cys
            100                 105                 110

Ala Val Asp Asn Lys Leu Phe Lys Tyr Asn Asp Tyr Ala Asn Ala Ile
        115                 120                 125

Ile Lys Tyr Asp Lys Thr Ile Asn Val
    130                 135
```

<210> SEQ ID NO 48
<211> LENGTH: 507
<212> TYPE: DNA
<213> ORGANISM: Phlebotomus ariasi

<400> SEQUENCE: 48

```
atagaaatcg aatcatgaag gagcttgttg tattttttgac actgatagtt ttggtcgtga      60
tttgtcacgc agaacgacct tcacaaaagt gtaggaggga actgaagaca gaggaagagt     120
gtatactgca ttgtgagtac aaacattatc gctttactga tgaccagttt cgacttaacg     180
cagatcaaag aggagacttt aggaatatca tgaggaggta cggcgcaatt agggtggatc     240
aggaaagtca attggataag catttgaaaa aatgtgccaa caaagttgct aagactccgg     300
caacatcgag gaaggataag tgtaggaaaa tttctcggta ctatcactgt gctgtggata     360
ataaactttt caaatataat gattatgcca atgccataat taaatatgat aagcaataa      420 atgtttaaag atgaatgtat cgctcaaata aagaagcaaa gctaaccata ttcaaatcaa     480
aaaaaaaaaa aaaaaaaaaa aaaaaaa                                          507
```

<210> SEQ ID NO 49
<211> LENGTH: 393
<212> TYPE: PRT
<213> ORGANISM: Phlebotomus perniciosus

<400> SEQUENCE: 49

```
Met Lys Ile Phe Leu Cys Leu Ile Ala Val Val Phe Leu Gln Gly Val
1               5                   10                  15

Val Gly Phe His Val Glu Arg Glu Tyr Ala Trp Lys Asn Ile Ser Tyr
                20                  25                  30
```

Glu Gly Val Asp Pro Ala Leu Phe Asn Ile Asp Asn Ile Ile Pro Thr
        35                  40                  45
Gly Phe Val His Asp Ala Ile Asn Lys Lys Ile Phe Ile Ala Val Pro
 50                  55                  60
Arg Arg Ser Pro Gln Ile Pro Phe Thr Leu Thr Glu Leu Asp Thr Thr
65                  70                  75                  80
Lys His Pro Glu Arg Ser Pro Pro Leu Ser Lys Phe Pro Gly Ser Asp
                85                  90                  95
Lys Leu Ile Asn Val Tyr Gln Pro Val Ile Asp Glu Cys Arg Arg Leu
            100                 105                 110
Trp Ile Ala Asp Val Gly Arg Val Asp Tyr Lys Gly Asp Glu Gln Lys
        115                 120                 125
Tyr Pro Asn Gln Asn Ala Val Leu Ile Ala Tyr Asp Leu Thr Lys Glu
    130                 135                 140
Asn Tyr Pro Glu Ile His Arg Tyr Glu Ile Pro Ser Lys Ile Ala Gly
145                 150                 155                 160
Ser Asn Thr Ile Pro Phe Gly Phe Ala Val Asp Val Thr Asn Pro
                165                 170                 175
Lys Glu Gly Cys Gly Lys Thr Phe Val Tyr Ile Thr Asn Phe Glu Asp
            180                 185                 190
Asn Thr Leu Ile Val Tyr Asp Gln Glu Lys Lys Asp Ser Trp Lys Ile
        195                 200                 205
Ser His Gly Ser Phe Lys Pro Glu His Asp Ser Thr Leu Ser His Asp
    210                 215                 220
Gly Lys Gln Tyr Lys Tyr Arg Val Gly Leu Phe Gly Ile Thr Leu Gly
225                 230                 235                 240
Asp Arg Asp Pro Glu Gly Asn Arg Pro Ala Tyr Tyr Ile Ala Gly Ser
                245                 250                 255
Ser Thr Lys Leu Phe Glu Ile Ser Thr Lys Ile Leu Lys Glu Lys Gly
            260                 265                 270
Ala Lys Phe Asp Pro Val Asn Leu Gly Asn Arg Gly Pro His Thr Glu
        275                 280                 285
Ala Val Ala Leu Val Tyr Asp Pro Lys Thr Lys Val Ile Phe Phe Ala
    290                 295                 300
Glu Ser Asp Ser Arg Gln Val Ser Cys Trp Asn Thr Gln Lys Pro Leu
305                 310                 315                 320
Asn His Lys Asn Thr Asp Val Ile Phe Ala Ser Ala Lys Phe Ile Tyr
                325                 330                 335
Gly Ser Asp Ile Ser Val Asp Ser Glu Ser Gln Leu Trp Phe Leu Ser
            340                 345                 350
Thr Gly His Pro Pro Ile Pro Asn Leu Lys Leu Thr Phe Asp Lys Pro
        355                 360                 365
His Ile Arg Leu Met Arg Val Asp Thr Ala Lys Ala Ile Arg Arg Thr
    370                 375                 380
Arg Cys Glu Val Lys Pro Arg Lys Pro
385                 390

<210> SEQ ID NO 50
<211> LENGTH: 1341
<212> TYPE: DNA
<213> ORGANISM: Phlebotomus perniciosus

<400> SEQUENCE: 50
tatatataac ttttgaaatg ttcagtcagt cttttggaag caaagatgaa gatctttctg    60

```
tgcctaattg ctgtggtttt ccttcaggga gttgtaggct ttcacgttga acgagaatat    120
gcgtggaaaa acattagtta cgaaggagta gatccagcat tattcaatat tgataatatc    180
attccgactg gtttcgttca cgatgcaatt aataagaaga ttttcattgc tgttccaagg    240
agatctcctc aaataccatt taccctaact gaacttgata ccaccaagca tccggaacgt    300
tctcctcctc taagcaaatt tcctggtagc gataaattaa tcaacgttta tcaaccggtc    360
attgacgaat gtcgccgact ttggattgcg gacgtcggac gggttgacta caaggggat    420 gagcagaagt atccaaacca aaatgctgtt ctcatagctt atgacctgac gaaggaaaat    480
tacccagaga ttcatcgata cgagatacca agtaaaattg ctggttcaaa tacaattcca    540
tttggaggat ttgccgttga tgttacgaat ccgaaggagg gatgcggcaa aacctttgtc    600
tacatcacga acttcgaaga caacactctg attgtgtacg atcaggagaa gaaagattct    660
tggaagatca gtcatgggtc attcaaacca gagcatgact cgactctctc ccatgacggt    720
aaacagtaca gtatagagt gggtttattc ggaattactc ttggagatcg ggatccggaa    780
ggaaatcgtc cggcttacta catagccgga agcagtacga agctctttga gatcagcact    840
aagattttga aggagaaggg tgccaaattt gatcctgtta atttgggaaa tcgtggtccc    900
cacactgaag ctgttgccct ggtatatgat cccaagacaa agttatctt ctttgctgaa    960 tctgactcca ggcaggtctc ttgctggaat acccagaagc cactgaatca taagaacact    1020
gatgtgattt ttgccagtgc caaatttatt tacggctccg atatttcagt tgatagtgaa    1080
tctcaattgt ggttcttatc cacgggacat ccacccattc ctaatctcaa gttgaccttt    1140
gataaacccc atattcgtct tatgagggtg gatacggcta agcaattcg tagaactaga    1200 tgcgaagtga agccccgcaa gccataagac gaatatctaa tatcaaaaat gttacaattc    1260
tgctaaaatg tctaaaaata aagataataa taaataaata aaaatattgt gcaacacaca    1320
gaaacaaacc aaaaaaaaaa a                                             1341
```

<210> SEQ ID NO 51
<211> LENGTH: 388
<212> TYPE: PRT
<213> ORGANISM: Phlebotomus perniciosus

<400> SEQUENCE: 51

```
Met Lys Ile Phe Leu Cys Leu Ile Ala Val Val Ser Leu Gln Gly Val
  1               5                  10                  15

Leu Ala Tyr Asp Ile Glu Arg Glu Tyr Ala Trp Lys Asn Ile Ser Phe
             20                  25                  30

Glu Gly Ile Asp Pro Ala Ser Tyr Ser Val Lys Asn Ser Ile Val Thr
         35                  40                  45

Gly Phe Ala His Asp Ala Asp Ser Lys Lys Ile Phe Ile Thr Ile Pro
     50                  55                  60

Arg Leu Asn Pro Val Pro Ile Thr Leu Thr Glu Leu Asp Thr Thr Lys
 65                  70                  75                  80

His Pro Glu Gly Ser Pro Pro Leu Ser Lys Phe Pro Gly Ser Asp Lys
                 85                  90                  95

Leu Ile Ser Val Tyr Gln Pro Val Ile Asp Glu Cys Arg Arg Leu Trp
            100                 105                 110

Ile Val Asp Ala Gly Gln Val Glu Tyr Lys Gly Asp Glu Gln Lys Ile
        115                 120                 125

Pro Lys Lys Asn Ala Ala Ile Ile Ala Tyr Asp Leu Thr Lys Asp Asn
    130                 135                 140
```

Tyr Pro Glu Ile Asp Arg Tyr Glu Ile Pro Asn Asn Val Ala Gly Asn
145                 150                 155                 160

Pro Leu Gly Phe Gly Gly Phe Ala Val Asp Val Thr Asn Pro Lys Glu
            165                 170                 175

Gly Cys Gly Lys Thr Phe Val Tyr Ile Thr Asn Phe Glu Asp Asn Thr
        180                 185                 190

Leu Ile Val Tyr Asp Gln Glu Lys Lys Asp Ser Trp Lys Ile Ser His
        195                 200                 205

Asp Ser Phe Lys Pro Glu His Glu Ser Ile Leu Thr His Asn Gly Ala
    210                 215                 220

Gln His Ile Leu Lys Leu Gly Ile Phe Gly Ile Thr Leu Gly Asp Leu
225                 230                 235                 240

Asp Glu Glu Gly Asn Arg Gln Ala Tyr Tyr Leu Gly Gly Ser Ser Thr
                245                 250                 255

Lys Leu Phe Arg Val Asn Thr Lys Asp Leu Lys Lys Ala Gly Gln
            260                 265                 270

Ile Glu Phe Thr Pro Leu Gly Asp Arg Gly Ser His Ser Glu Ala Leu
        275                 280                 285

Ala Leu Ala Tyr Asp Pro Lys Thr Lys Val Ile Phe Phe Ile Glu Tyr
    290                 295                 300

Asn Ser Lys Arg Ile Ser Cys Trp Asn Thr Gln Lys Ser Leu Asn Pro
305                 310                 315                 320

Asp Asn Ile Asp Val Ile Tyr His Ser Pro Asp Phe Ile Phe Gly Thr
                325                 330                 335

Asp Ile Ser Met Asp Ser Glu Ser Lys Leu Trp Phe Phe Ser Asn Gly
            340                 345                 350

His Pro Pro Ile Glu Asn Val Gln Leu Thr Phe Asp Lys Pro His Phe
        355                 360                 365

Arg Leu Ile Ser Met Asp Thr Lys Lys Ser Ile His Gly Thr Lys Cys
    370                 375                 380

Glu Val Lys Pro
385

<210> SEQ ID NO 52
<211> LENGTH: 1273
<212> TYPE: DNA
<213> ORGANISM: Phlebotomus perniciosus

<400> SEQUENCE: 52
caagatgaaa atctttctgt gcctaattgc tgtggtttcc cttcaggag ttttagctta      60 tgatattgag agggaatacg cgtggaaaaa catcagtttt gaaggaatag acccagcatc     120
ctacagcgtt aaaaatagta tcgtaactgg tttcgctcac gatgcagata gtaagaagat     180
tttcattact attccaaggc taaacccagt tccgattact ctaactgaac tggataccac     240
taagcatccg gaaggatctc ctccactaag caaatttcct ggtagtgata aattaatctc     300
tgtttatcaa ccggtcattg acgaatgtcg ccgactttgg attgtggacg ctggacaggt     360
tgagtacaaa ggagatgagc agaagattcc caagaaaaat gctgctatta tagcttatga     420
tctgacgaag gacaattatc agaaattga tcgatacgag ataccgaata atgttgctgg     480
taatccactt ggatttggag gatttgccgt tgatgttaca aatccgaaag agggatgtgg     540
taaaaccttt gtctacatca cgaacttcga agacaacact ctaatagtgt atgatcagga     600
gaagaaagat tcctggaaga tcagtcatga ttcattcaaa cctgagcatg aatcgatcct     660
gacccacaac ggtgctcaac acattttaaa gttgggtata ttcggaatca ccttaggaga     720

```
tctggatgag gagggaaatc gtcaggctta ctacttggga ggtagtagta cgaagctctt      780
tagagtgaac accaaggatc tcaagaagaa agccggtcaa attgaattca ctcctctggg      840
agatcgtgga tctcactctg aagcccttgc tctggcttat gatcccaaga ctaaagttat      900 cttttcatt gaatataatt ctaagcgaat ctcctgctgg aacactcaga atcactaaa        960 tcctgacaac attgatgtga tttatcacag tcctgatttt atcttcggca ctgatatttc     1020
aatggatagt gaatccaaat tgtggttctt ttccaacggt catccaccaa ttgagaatgt     1080
tcaactaact tttgataagc cacattttcg tcttataagc atggatacga aaaaatcaat     1140
tcatggtact aaatgcgaag taaaacctta agtcaaactt ggaaaataaa acacttctta     1200
aagaaattgt aattttatg atggtaataa attttgtgt gccgaaaaaa aaaaaaaaa        1260 aaaaaaaaaa aaa                                                       1273
```

<210> SEQ ID NO 53
<211> LENGTH: 208
<212> TYPE: PRT
<213> ORGANISM: Phlebotomus perniciosus

<400> SEQUENCE: 53

```
Met Phe Lys Lys Phe Ile Leu Val Ala Leu Val Val Val Ala Gln
1               5                   10                  15

Cys Ala Leu Pro Ala Ile Pro Ile Ala Arg Gln Gly Lys Asp Phe Pro
                20                  25                  30

Val Pro Phe Val Ser Glu Asp Asn Pro Asp Asp Tyr Phe Asp Asp
            35                  40                  45

Gln Tyr Tyr Pro Asp Ile Asn Asp Ala Gly Val Gly Ser Lys Ala Pro
    50                  55                  60

Gln Gly Ser Arg Lys Pro Pro Asn Arg Gly Thr Ile Pro Pro Arg
65                  70                  75                  80

Gly Asp Gln Val Ser Ser Gly Gly Arg Thr Pro Pro Gly Arg Val Gly
                85                  90                  95

Gln Gly Thr Ser Pro Thr Lys Asp Lys Arg Ala Arg Pro Gln Ile Asn
            100                 105                 110

Arg Asn Pro Thr Gly Thr Val Gly Gln Gly Gly Ser Pro Gly Thr Lys
        115                 120                 125

Asp Lys Arg Ala Arg Pro Gln Ile Asn Arg Asn Pro Thr Gly Ser Gly
    130                 135                 140

Thr Lys Pro Arg Asp Arg Glu Leu Val Ile Arg Asp Lys Pro Pro Ser
145                 150                 155                 160

Gly Ser Gln Gly Gly Lys Pro Gly Arg Gln Val Arg Gly Pro Lys Glu
                165                 170                 175

Asp Leu Ser Arg Tyr Gln Asn Ala Pro Ala Lys Leu Ile Phe Lys Ser
            180                 185                 190

Ser Asn Ile Asn Thr Ala Gly Lys Thr Pro Lys Arg Cys Glu Val Val
        195                 200                 205
```

<210> SEQ ID NO 54
<211> LENGTH: 954
<212> TYPE: DNA
<213> ORGANISM: Phlebotomus perniciosus

<400> SEQUENCE: 54

```
cactttagtc tcaaatcttg gatcatgttt aagaaattta tcttggtggc ccttgtcgtt       60
gtcgtggcac aatgtgctct tcccgcaatc ccaattgcaa gacagggaaa agatttcccc      120
```

```
gtcccgtttg taagtgaaga taataatccg gatgattatt ttgacgatca gtactatccg    180
gacataaacg atgcgggtgt aggttcaaag gctccgcagg gaagcagaaa gccacccaat    240
agaggcacca tccctcctcc tcgtggtgac caagtgtcat ctggtggacg aactccaccc    300
ggaagggttg gacagggtac aagccctaca aggataaaaa gagctcgtcc tcagattaac    360
agaaacccaa ccggaacggt tggacagggt ggaagccctg gtacaaagga taaaagagct    420
cgtcctcaga ttaacagaaa cccaaccgga agtggtacaa acccagaga tagggagctt    480 gtgattaggg ataagccccc atccggaagt caaggtggta acctggaag acaggtcaga     540 ggcccaaagg aagatttgtc gcgttatcaa aacgctccgg caaagttgat tttcaaatcg    600
agtaatatca atactgctgg taaaaccccg aagcgctgtg aagttgttta agacgaagaa    660
ggacaaaaca gttgttgcta agggaggtcc caacgatgtt tatgaggtgg agcttctcga    720
tggaaatttc aataatatga gcttgaggat ccagataatg gacaggaaga gcagcacagc    780
gatcctcagc aatccagatc gcaacttaat tgttggccgt gtcaagacgt accgcggatt    840
aagatgaggt gctgaatttt taaattttat tttattttt tgctcctaaa tccaaaatcc     900
ccccaaataa atcagtttga acgcaaaaaa aaaaaaaaa aaaaaaaaa aaaa            954
```

<210> SEQ ID NO 55
<211> LENGTH: 310
<212> TYPE: PRT
<213> ORGANISM: Phlebotomus perniciosus

<400> SEQUENCE: 55

```
Met Thr Tyr Phe Lys Ile Ser Thr Cys Cys Leu Val Leu Ile Ser Leu
1               5                   10                  15

Ile Leu Pro Ile Ile Cys Ile Lys Val Ile Arg Phe Asp Asp Arg Asp
            20                  25                  30

Glu Tyr Leu Leu Gly Lys Pro Asp Asn Thr Asp Glu Glu Leu Leu Tyr
        35                  40                  45

Ser Thr Phe Asp Phe Ile Lys Asn Thr Cys Ala Asn Pro Lys Met Lys
    50                  55                  60

Cys Thr Asn Asn Ala Thr His Phe Val Leu Asp Phe Ser Asp Pro Lys
65                  70                  75                  80

Lys Arg Cys Ile Ser Ser Ile His Val Phe Ser Thr Pro Asp Gly Pro
                85                  90                  95

Val Asn Leu Glu Glu Glu Asn Lys Pro Arg Ser Lys Ser Ser Ile Tyr
            100                 105                 110

Cys Gln Val Gly Gly Ile Gly Gln Ser Tyr Cys Leu Leu Val Phe Lys
        115                 120                 125

Lys Lys Glu Arg Arg Glu Asp Ala Leu Val Asp Ile Arg Gly Leu Lys
    130                 135                 140

Thr Cys Ser Leu Lys Glu Arg Tyr Thr Ser Gly Asp Pro Lys Lys Thr
145                 150                 155                 160

Asp Ala Tyr Gly Met Ala Tyr Lys Phe Asp Lys Asn Asp Asn Trp Ser
                165                 170                 175

Ile Lys Arg Glu Gly Val Lys Gln Trp Lys Arg Ser Gly Asn Glu Ile
            180                 185                 190

Phe Tyr Arg Lys Asn Gly Leu Met Asn His Gln Ile Arg Tyr Leu Ser
        195                 200                 205

Lys Phe Asp Lys Tyr Thr Val Thr Arg Glu Met Val Val Lys His Arg
    210                 215                 220
```

```
Ala Lys Lys Phe Thr Met Asp Phe Ser Asn Tyr Gly Gln Tyr Arg Ile
225                 230                 235                 240

Ser Phe Leu Asp Val Tyr Trp Phe Gln Glu Ser Val Lys His Lys Pro
            245                 250                 255

Lys Leu Pro Tyr Ile Tyr Tyr Asn Gly Glu Cys Leu Pro Ser Asn Lys
            260                 265                 270

Thr Cys Gln Leu Val Phe Asp Ala Asp Glu Pro Ile Thr Tyr Ala Phe
        275                 280                 285

Val Lys Val Phe Ser Asn Pro Asp His Asn Glu Pro Arg Leu Arg His
    290                 295                 300

Ala Asp Leu Gly Arg Gly
305                 310
```

<210> SEQ ID NO 56
<211> LENGTH: 1081
<212> TYPE: DNA
<213> ORGANISM: Phlebotomus perniciosus

<400> SEQUENCE: 56

```
ggccattacg gccaggggga ataagttagt gtcttcacgt ttattgaagc tttcacttca     60
atatgactta cttcaagatc agtacttgtt gtttagtttt aataagcctc attctaccta    120
taatttgtat taaagttatt cgttttgatg atagagatga atatcttctt ggtaaacctg    180
ataatactga tgaagaactc ctctattcaa cctttgactt cattaagaat acctgcgcta    240
atcctaaaat gaaatgcacc aataacgcca ctcatttcgt tctggatttc tctgatccga    300
agaagagatg tatctcctcc atccatgtat tttccactcc cgatggacct gttaatcttg    360
aggaggagaa taagcctcga tcaaagagtt caatttactg ccaagtgggc ggcattggac    420
agagttactg tttgctggtg tttaaaaaga aggaacgtcg tgaggatgct ctggttgata    480
tccggggact caaaacatgc tccctcaagg agcgctacac atctggagat cccaagaaaa    540
ccgatgctta cggaatggca tacaaattcg acaagaatga taattggagc atcaagagag    600
aaggtgttaa gcaatggaaa agatcaggaa atgagatctt ctaccgcaag aatggtttga    660
tgaaccatca aataagatac ttgagcaagt ttgataagta cacggttacc agagaaatgg    720
tcgtgaagca ccgcgctaag aaattcacca tggacttctc caactatggc cagtacagaa    780
tcagtttctt ggacgtctac tggttccagg agtccgtgaa gcacaagccg aagttaccct    840
acatctacta caatggcgaa tgcttgccta gcaataagac gtgtcagttg gttttcgacg    900
ctgatgagcc tattacttat gcttttgtga agtgttcag taatccggac acaacgaac     960
cacgattgag gcatgcagat ctgggacgag gataggagtg gattagtccg ttgttgaaat   1020
ttgaataaaa tgctatgaag atgttaaatt tgcctcaaaa aaaaaaaaaa aaaaaaaaa   1080
a                                                                   1081
```

<210> SEQ ID NO 57
<211> LENGTH: 431
<212> TYPE: PRT
<213> ORGANISM: Phlebotomus perniciosus

<400> SEQUENCE: 57

```
Met Lys Leu Leu Ile Thr Ile Gly Ala Val Cys Val Leu Gln Val Val
1               5                   10                  15

Thr Val Ser Ser Ile Phe Phe Pro Ile Pro Ile Asn Ile Gln Thr Gly
            20                  25                  30

Thr Thr Ser Ser Ser Ser Gly Gln Pro Gly Gln Gln Val Thr Thr Ser
```

-continued

```
                35                  40                  45
Ile Ser Phe Ser Asn Val Ser Asn Ile Thr Asp Met Val Ile Tyr Leu
 50                  55                  60

Thr Gln Asn Ile Ser Arg Ala Leu Leu Thr Arg Val Pro Asn Pro Asp
 65                  70                  75                  80

Asp Ile Lys Ser Ala Asp Ile Leu Glu Ser Phe Thr Gly Ser Leu
                 85                  90                  95

Lys Tyr Phe Gln Thr Pro Pro Asp Val Asp Gln Glu Glu Ser Glu
                100                 105                 110

Thr Lys Ser Arg Ser Lys Arg Ser Phe Thr Asp Ile Phe Lys Gln Ser
                115                 120                 125

Ser Pro Leu Lys Glu Ile Gly Glu Arg Ile Glu Glu Ile Lys Lys Lys
130                 135                 140

Leu Lys Gly Met Leu Lys Pro Lys Pro Gln Thr Pro Ser Gly Asn Gln
145                 150                 155                 160

Thr Asp Ser Ser Asn Thr Thr Ser Glu Thr Gln Ser Arg Lys Lys Arg
                165                 170                 175

Ala Leu Thr Asp Phe Ile Pro Met Asp Ser Leu Lys Asp Ala Ile Ser
                180                 185                 190

Lys Thr Gly Glu Val Leu Ile Pro Ser Ser Ala Ser Ala Asn Ser Ser
                195                 200                 205

Pro Leu Asp Phe Met Ser Lys Leu Ser Asp Ile Ala Asn Asp Leu Ile
210                 215                 220

Gln Asn Ser Met Lys Glu Ile Ser Glu Asn Leu Ala Ser Ser Val Ala
225                 230                 235                 240

Met Tyr Gln Val Asn Ser Gln Leu Asp Ala Ile Lys Gln Ser Met Asp
                245                 250                 255

Ile Ile Lys Gln Glu Ile Asp Lys Thr Gln Lys Ile Gln Lys Tyr Val
                260                 265                 270

Lys Glu Ala Leu Asn Gln Ala Lys Asn Ala Thr Lys Ser Leu Gly Glu
                275                 280                 285

Lys Leu Lys Ser Ser Asn Cys Phe Ala Gln Phe Ile Asn Pro Phe Lys
290                 295                 300

Leu Phe Glu Lys Gly Ile Thr Cys Val Lys Asn Lys Ile Asp Asn Gly
305                 310                 315                 320

Leu Lys Ile Ala Lys Asp Thr Phe Lys Asn Leu Gln Gln Ala Met Ser
                325                 330                 335

Val Pro Ser Asp Ile Gln Ser Glu Val Ser Lys Cys Ser Gln Asn Gln
                340                 345                 350

Gln Leu Asn Pro Ile Ala Lys Leu Leu Cys Tyr Leu Arg Thr Pro Leu
                355                 360                 365

Gln Leu Asp Asp Glu Lys Leu Leu Leu Pro Phe Glu Phe Thr Arg Arg
                370                 375                 380

Ile Arg Glu Ile Thr Asn Tyr Phe Ala Thr Met Arg Met Asp Leu Ile
385                 390                 395                 400

Arg Cys Gly Ile Glu Thr Ile Gln Ser Ile Gly Asp Lys Val Glu Asp
                405                 410                 415

Cys Ala Arg Glu Ala Ile Leu Ala Val Lys Asp Thr Leu Lys Gly
                420                 425                 430
```

<210> SEQ ID NO 58
<211> LENGTH: 1471
<212> TYPE: DNA
<213> ORGANISM: Phlebotomus perniciosus

<400> SEQUENCE: 58

```
aaaacatctt cgcgttttcg tgctatttga acggagaaac atcgagtaaa gaatatgaag    60
ttactaatta ctatcggtgc ggtttgtgtg ttacaagtcg ttacagtatc atccatcttc   120
tttcccattc caatcaacat ccaaacaggg acgacatcat catcatcagg acaaccagga   180
cagcaagtta aacgagtat aagtttcagt aatgtatcaa acatcacgga tatggtgatt   240
tatctcacgc agaatatcag tagagctctc cttacgcgtg taccaaaccc tgatgatatc   300
aaatcagcag cggatatctt ggaaagtttt acaggaagcc tcaagtattt ccaaacacct   360
ccggatgatg tggatcaaga ggaatcagag acaaagtcac gatctaagag atcatttact   420
gatatattca acaatcttc gcctttaaaa gaaatcggag aaaggatcga agaaataaaa   480
aagaaactaa aaggaatgct caaaccaaaa ccgcaaacac cttctggaaa tcaaactgat   540
agctcgaaca caacttcgga gactcaatcg agaaagaaac gggctttaac tgactttata   600
ccaatggatt ctctgaaaga tgcgatttca aaaacagggg aagtgttgat accttcaagt   660
gcaagtgcaa actctagtcc tctagatttt atgtcaaaac tatccgatat cgcaaatgat   720
cttattcaaa actcaatgaa ggaaatctcc gaaaatttag cctcaagcgt tgctatgtac   780
caagtcaact cacagttaga tgccattaaa caatccatgg atattataaa acaagaaatt   840
gataagaccc aaaagatcca gaaatacgta aaggaagctc ttaatcaagc caaaaatgct   900
actaaatctt taggagaaaa gcttaagtcc agtaactgtt tcgctcaatt tataaatccc   960
tttaaacttt ttgaaaaagg aattacttgt gtgaaaaata aaatcgataa tggattaaaa  1020
atcgcaaaag acacctttaa gaatttacaa caggcaatga gtgtgccctc agatattcaa  1080
agtgaagtgt ccaaatgctc ccaaaatcag caattgaatc ccattgccaa actcctgtgc  1140
tacttgagga caccactgca attggacgac gagaagttgc tgcttccctt tgaatttacg  1200
aggagaatta gagaaataac taactatttt gccaccatga gaatggacct cattcgttgt  1260
ggcatagaaa ctattcagtc gatcggagac aaggttgagg attgtgcaag agaagcaata  1320
ttggctgtaa aggacactct gaagggataa agtccgcatt ttctggctgt ccaattggga  1380
ctaacccaat cattgatgat gccgagctat tgtatgttgg agaaaatgaa taaaaggctt  1440
cgcaaaaaaa aaaaaaaaaa aaaaaaaaaa a                                 1471
```

<210> SEQ ID NO 59
<211> LENGTH: 131
<212> TYPE: PRT
<213> ORGANISM: Phlebotomus perniciosus

<400> SEQUENCE: 59

```
Met Lys Gln Leu Val Val Phe Leu Ala Leu Ile Val Leu Ile Val Ile
1               5                   10                  15
Cys His Ala Glu Pro Pro Ser Lys Lys Cys Arg Ser Gly Leu Val Lys
                20                  25                  30
Asp Glu Glu Cys Ile Leu His Cys Glu Tyr Lys Tyr Tyr Gly Phe Thr
            35                  40                  45
Asp Asp Asn Phe Glu Leu Asp Ser Asp Leu Arg Gly His Phe Arg Thr
        50                  55                  60
Ala Met Arg Lys His Gly Ala Ile Arg Ile Asp Gln Glu Arg Gln Leu
65                  70                  75                  80
Asp Lys His Leu Lys Lys Cys Ala Gln Glu Ala Lys Lys Ser Glu Lys
                85                  90                  95
```

```
Cys Arg Lys Ile Ile Gln Tyr Tyr Arg Cys Ala Val Asn Asn Lys Leu
            100                 105                 110

Phe Gln Tyr Asn Ala Tyr Ala Lys Ala Ile Ile Ala Leu Asp Lys Thr
        115                 120                 125

Ile Asn Val
    130

<210> SEQ ID NO 60
<211> LENGTH: 499
<212> TYPE: DNA
<213> ORGANISM: Phlebotomus perniciosus

<400> SEQUENCE: 60
attagaaaac caatcatgaa gcagcttgtt gtattttttgg cgttgatagt tctgatagtg     60
atttgtcacg cagaaccacc ttcgaagaag tgtaggagtg gactggtgaa agatgaggag    120
tgtatactcc attgtgaata caaatactat ggctttactg atgataattt cgaacttgat    180
tcagatctaa gaggacactt tagaactgct atgaggaagc acggcgcaat taggatcgat    240
caggaaagac aacttgataa gcatttgaaa aaatgtgctc aggaagctaa aaagtcggaa    300
aagtgtagga aaatcattca gtactatcgc tgtgctgtga ataataaact tttccaatat    360
aatgcttatg ctaaagcaat tattgcgctt gataagacaa taaatgttta aaaaagaaag    420
tgaaatgtat ctatcgctca aataaagaag gaagctaaga tcgttgaaag aaaaaaaaaa    480
aaaaaaaaaa aaaaaaaaa                                                 499

<210> SEQ ID NO 61
<211> LENGTH: 388
<212> TYPE: PRT
<213> ORGANISM: Phlebotomus perniciosus

<400> SEQUENCE: 61

Met Ile Asn Ser Thr Val Ile Gln Phe Ile Phe Leu Phe Val Ile Phe
1               5                   10                  15

Leu Pro Gly Lys Ser Lys Ser Ala Pro Lys Thr Cys Glu Ile Asn Leu
            20                  25                  30

Pro Thr Ser Ile Pro Thr Lys Gly Glu Ser Ile Tyr Leu Leu Asn Gly
        35                  40                  45

Asn Gly Ser Val Phe Arg Pro Asp Gly Lys Leu Thr Gln Leu Asn Ile
    50                  55                  60

Gly Asp Ser Leu Ser Ile Tyr Cys Pro Gly Gln Lys Glu Leu Lys Arg
65                  70                  75                  80

Val Pro Cys Ser Pro Lys Phe Ser Leu Glu Asn Ile Thr Cys Asn Ser
                85                  90                  95

Asn Val His Ser Glu Leu Val Asp Thr Glu Glu Lys Cys Gly Lys Asp
            100                 105                 110

Gly Lys Cys Tyr Asn Ile Ser Phe Pro Leu Pro Thr Asn Thr Phe His
        115                 120                 125

Thr Ile Tyr Arg Thr Cys Phe Asn Lys Gln Lys Leu Thr Pro Ile Tyr
    130                 135                 140

Ser Tyr His Val Ile Asn Gly Lys Ala Val Gly Tyr His Val Lys Gln
145                 150                 155                 160

Pro Arg Gly Asn Phe Arg Pro Gly Lys Gly Val Tyr Arg Lys Ile Asn
                165                 170                 175

Ile Asn Glu Leu Tyr Lys Thr His Ile Ser Arg Phe Lys Arg Ile Ile
            180                 185                 190
```

```
Gly Ser Thr Gln Thr Phe Phe Arg Lys Pro Leu His Tyr Leu Ala Arg
        195                 200                 205

Gly His Leu Ser Pro Glu Val Asp Phe Val Phe Gly Asn Glu Gln His
        210                 215                 220

Ala Thr Glu Phe Tyr Ile Asn Thr Ala Pro Gln Tyr Gln Ser Ile Asn
225                 230                 235                 240

Gln Gly Asn Trp Leu Arg Val Glu Lys His Val Arg Lys Leu Ala Lys
                245                 250                 255

Ala Leu Gln Asp Asp Leu His Val Val Thr Gly Ile Leu Gly Ile Leu
            260                 265                 270

Lys Phe Ser Asn Lys Arg Ala Glu Arg Glu Ile Tyr Leu Gly Glu Gly
        275                 280                 285

Val Ile Pro Val Pro Gln Ile Phe Trp Lys Ala Val Phe His Pro Lys
        290                 295                 300

Thr Ser Ser Ala Ile Val Phe Val Ser Ser Asn Asn Pro His Glu Lys
305                 310                 315                 320

Thr Phe Asn Pro Met Cys Lys Asp Val Cys Glu Thr Ala Arg Phe Gly
                325                 330                 335

Gly Lys Gln His Glu Asn Gln Asn Phe Ser Asn His Thr Val Gly Phe
            340                 345                 350

Thr Ile Cys Cys Glu Leu Pro Asp Phe Leu Gly Asn Ser Lys Val Ile
        355                 360                 365

Leu Pro Lys Glu Phe Gln Gly Lys Asn Tyr Arg Lys Leu Leu Lys Met
        370                 375                 380

Pro Gly Lys Pro
385

<210> SEQ ID NO 62
<211> LENGTH: 1772
<212> TYPE: DNA
<213> ORGANISM: Phlebotomus perniciosus

<400> SEQUENCE: 62
gctttagaag ttatttaca tctgtgcaat gattaactca acagtgattc aatttatttt    60 tcttttgtg attttttcttc ctggaaaatc taaaagtgcc ccaaagactt gcgaaattaa   120
tcttcccacc agtattccga caaaaggtga atcaatttat cttctcaatg gaaatggatc   180
ggtcttccga ccggatggaa aattgactca actcaatatt ggggattccc tgtccatcta   240
ctgtcctgga cagaaggagc tcaagagagt cccttgcagt cccaaatttt cccttgagaa   300
catcacttgc aacagcaatg ttcacagtga attggttgac acggaggaaa agtgcggaaa   360
agatggaaaa tgttacaata ttagctttcc attgccaaca ataccttcc atacaatcta    420 cagaacttgc ttcaacaagc agaaactaac accaatctat tcttatcacg tcatcaatgg   480
aaaggcagtt ggatatcatg tgaaacagcc acgaggaaac tttcgaccgg aaaaggtgt    540 ctacaggaag atcaacatca tgagctcta caagacccac atttcgcgct tcaagagaat   600
catcggatcc acccagacat tcttccggaa gcccctgcac tatctggctc gtggacatct   660
ctcacctgaa gtggactttg tctttggcaa cgaacaacac gccactgagt tctacatcaa   720
caccgccccc caatatcaat ccatcaacca gggaaattgg cttcgagtgg agaaacacgt   780
gcgcaaactg gccaaggccc tccaggatga tctccacgtt gtcactggaa ttttgggcat   840
cctcaagttc tcaaacaaac gagccgaaag agaaatctat ctgggcgaag gagttattcc   900
tgtaccgcaa atattttgga aggctgtctt ccaccctaaa acctcttccg ccattgtctt   960
```

```
cgtgtcctct aacaaccctc atgagaagac cttcaatcca atgtgcaagg atgtttgtga   1020
aacagcaaga ttcggaggca acaacatga aaatcaaaat ttttccaatc acacagtggg   1080
attcaccatc tgttgtgaat taccagactt tcttggaaac tcaaaagtta ttcttcctaa   1140
ggagtttcaa ggcaaaaact accgcaagtt gcttaaaatg ccaggaaagc cataaaaact   1200
ttcatcttat ggtgttgtca cacggcaata gttttgacaa cagatcctag ctcaaacgga   1260
attcaatagc atttttcctttagaaaactat catattttca tcgaaaaaca gtctcttaca   1320
attctgagga ttttttaaaaa agaatttcaa ttgaatcaga atctcttttta agcactgaag   1380 agaatctcct gtcattttct gatcttctat gggtcttttc cagaaaattc ttgattattc   1440
ctaagaagaa attgatattt agtgaagact gtaattgttt agcattcaac agtaaaaatt   1500
tgttgacaga gctataattc cgtgtgacaa caccattagt ggaagactca acaaatcgat   1560
aaaaaaaatg atttcaaaat ggtataatag taaaaataaa aacctttccg gcaataaatt   1620
attcctttga ggatcacaat gtcctgaata ttcacacagt gactgagttt taagattatt   1680
ttactctcaa atcgtataat aaaggacaaa aaacatgcgt aaataaagaa atttgcagta   1740
cgtaaaaaaa aaaaaaaaaa aaaaaaaaaa aa                                 1772

<210> SEQ ID NO 63
<211> LENGTH: 249
<212> TYPE: PRT
<213> ORGANISM: Phlebotomus perniciosus

<400> SEQUENCE: 63

Met Asn Asn Leu Leu Thr Phe Phe Gly Val Leu Cys Phe Leu Gly Phe
1               5                   10                  15

Ala Asn Ser Leu Arg Phe Pro Arg Asp Pro Asp Gln Thr Arg Trp Ala
            20                  25                  30

Glu Lys Thr Cys Leu Arg Glu Phe Ser Arg Ala Pro Pro Ser Leu Leu
        35                  40                  45

Lys Lys Trp Gln Gln Leu Asp Phe Pro Asn Thr Asn Leu Thr His Cys
    50                  55                  60

Phe Ile Lys Cys Phe Thr Ser Tyr Leu Gly Val Tyr Asn Asp Thr Thr
65                  70                  75                  80

Lys Lys Phe Asn Val Asp Gly Ile Lys Thr Gln Phe Lys Ser Gln Glu
                85                  90                  95

Ile Pro Ala Pro Gln Gly Leu Glu Thr Leu Arg Lys Thr Ser Lys Gly
            100                 105                 110

Thr Cys Lys Asp Ile Tyr Leu Met Thr Val Asp Leu Val Lys Lys Asn
        115                 120                 125

Lys Leu Gln Phe Ala Lys Ala Phe His Gly Ile Ser Ala Glu Ala Ala
    130                 135                 140

Lys Trp Tyr Thr Gln His Lys Gly Asn Val Lys Gly Lys Tyr Gln Lys
145                 150                 155                 160

Ala Ser Glu Phe Cys Lys Ser Lys Asp Asp Glu Cys Arg Leu His Cys
                165                 170                 175

Arg Phe Tyr Tyr Tyr Arg Leu Val Asp Glu Asp Tyr Gln Ile Phe Asn
            180                 185                 190

Arg Asn Leu Lys Ile Asn Gly Ile Ser Asn Ala Gln Leu Gln Gln Cys
        195                 200                 205

Arg Asn Lys Ala Ser Gln Ala Lys Gly Cys Gln Val Ala Lys Val Leu
    210                 215                 220

Arg Gln Cys Leu Lys Asp Ile Asn Pro Glu Asn Val Lys Ala Thr Leu
```

```
                    225                 230                 235                 240

Lys Glu Leu Asp Glu Ile Ser Ala Lys
                245

<210> SEQ ID NO 64
<211> LENGTH: 952
<212> TYPE: DNA
<213> ORGANISM: Phlebotomus perniciosus

<400> SEQUENCE: 64
ccattacggc cgaggagtct ctttcaacgc ttaatatcag caatgaataa cttgttaaca      60
ttctttggag tactttgctt cttgggcttt gctaactctc tgcgattccc tcgtgaccca     120
gaccaaacca gatgggcgga aaagacttgt ctgagagaat ttctcgtgc tccacctagt     180 cttttaaaga aatggcaaca actggacttt cccaatacca atctcaccca ctgcttcatc     240
aagtgcttca cttcgtatct tggagtctac aacgacacga ctaagaaatt taacgtggac     300
ggaattaaaa cccaatttaa aagtcaggaa attcctgcac ctcaaggtct tgagacactt     360
cgtaaaacat ctaaaggaac ctgcaaggat atttatctaa tgactgtgga ccttgtcaag     420
aaaaacaagc tacaattcgc aaaagctttc catggaattt ctgcagaagc tgcaaaatgg     480 tatcccaac ataaaggaaa tgttaaggga agtaccaga aagcatcgga attctgcaaa      540
tctaaagatg atgagtgtag ctccattgc cgattctact actaccgctt agttgacgag     600
gactaccaga tattcaacag aaatttaaaa atcaacggta tttccaacgc tcaacttcag     660
caatgcagga acaaagccag tcaagctaag ggttgccagg tggcaaaggt cctaaggcaa     720
tgtctcaaag acattaatcc tgaaaatgta aaagcgactt tgaaggagtt ggatgagata     780
tcggcgaaat aatatactta aattaacccc atcagcccaa tttagcgtaa tttctcgacc     840
gtagaaaaag gtgtttaact tacgggtgat tgagtgtaag taatttagcg gctgtgggag     900
atgaaatgac tattaaaagg tttatatccc caaaaaaaaa aaaaaaaaaa aa              952

<210> SEQ ID NO 65
<211> LENGTH: 236
<212> TYPE: PRT
<213> ORGANISM: Phlebotomus perniciosus

<400> SEQUENCE: 65

Met Leu Gln Ile Lys His Phe Leu Phe Phe Val Val Leu Leu Val Ile
 1               5                  10                  15

Val His Ala Asn Asp Tyr Cys Gln Pro Lys Leu Cys Thr Asn Gly Lys
                20                  25                  30

Thr Val Lys Pro His Ile Gly Cys Arg Asn Asn Gly Asp Phe Asp Arg
            35                  40                  45

Ser Ala Cys Pro Asn Asp Ala Gln Met Val Glu Met Thr Gln Gln Arg
        50                  55                  60

Lys Glu Leu Phe Leu Lys Ile His Asn Arg Leu Arg Asp Arg Phe Ala
65                  70                  75                  80

Arg Gly Ser Val Pro Asn Phe Lys Ser Ala Ala Lys Met Pro Met Leu
                85                  90                  95

Lys Trp Asp Asn Glu Leu Ala Lys Leu Ala Glu Tyr Asn Val Arg Thr
            100                 105                 110

Cys Lys Phe Ala His Asp Gln Cys Arg Ala Thr Thr Ala Cys Pro Tyr
        115                 120                 125

Ala Gly Gln Asn Leu Gly Gln Met Leu Ser Ser Pro Asp Tyr Leu Asp
    130                 135                 140
```

```
Pro Gly Tyr Ala Ile Lys Asn Ile Thr Arg Glu Trp Phe Leu Glu Tyr
145                 150                 155                 160

Lys Trp Ala Asp Gln Gln Arg Thr Asn Thr Phe Thr Gly Gly Pro Gly
                165                 170                 175

Lys Asp Gly Lys Gln Ile Gly His Phe Thr Ala Phe Val His Glu Lys
            180                 185                 190

Ser Asp Lys Val Gly Cys Ala Val Ala Lys Leu Thr Asn Arg Gln Phe
        195                 200                 205

Asn Met Lys Gln Tyr Leu Ile Ala Cys Asn Tyr Cys Tyr Thr Asn Met
    210                 215                 220

Met Asn Glu Lys Ile Thr Ala Gln Val Pro Pro Phe
225                 230                 235
```

<210> SEQ ID NO 66
<211> LENGTH: 1033
<212> TYPE: DNA
<213> ORGANISM: Phlebotomus perniciosus

<400> SEQUENCE: 66

```
agtaagttta tctgcgcgag cggaaatggg tgccatttag gccggagtcc agttaatatt      60
ccgacatgtt gcaaattaaa catttcttgt tctttgtggt gttactcgtg atcgttcacg     120
ctaacgacta ttgccagccg aaattgtgca caaatggcaa acagtgaag cctcacattg      180
gatgcaggaa taatggagat ttcgatagaa gtgcctgtcc aaatgatgct cagatggttg     240
aaatgactca acagaggaag gagctctttc ttaagattca caatcgcctt cgcgataggt     300
tcgctcgtgg ctcagtgccc aatttcaagt cagccgccaa gatgccaatg ctgaaatggg     360
acaatgaatt ggccaagttg gcagaataca atgtgagaac gtgcaaattt gctcacgatc     420
agtgtcgcgc aaccacagct tgtccttatg ctggtcagaa cttggggcaa atgttgtcat     480
ctccagatta tttggacccc ggctatgcca tcaagaatat caccagggag tggttcttgg     540
agtataagtg ggcagatcaa caacgtacca acacctttac gggaggacct ggtaaagatg     600
gcaaacaaat tggtcacttt actgccttcg tccatgagaa gagcgacaag gttggatgtg     660
ctgttgctaa attaacgaac cgacaattca acatgaagca gtacctcatc gcttgcaact     720
actgctacac gaatatgatg aacgagaaga tcacagcaca ggtgccccog ttctaagtgc     780
cagagtaaaa aatgcgattc caaatacaag aatttgtgcg atgccagtga aaagtcgaa     840
gccatcccag acatcttcct caagaagcgc aggacataat tctctgcttt cccatttgaa     900
aattgtaaaa taatatattgt tttcccttct atcaggtgaa ttggtgaaga tgagaagaaa     960
gaatgtataa gaaataaga aataaacaga aactgagata tcgtaaaaaa aaaaaaaaa    1020
aaaaaaaaaa aaa                                                     1033
```

<210> SEQ ID NO 67
<211> LENGTH: 257
<212> TYPE: PRT
<213> ORGANISM: Phlebotomus perniciosus

<400> SEQUENCE: 67

```
Met Ile Val Lys Gly Leu Leu Gly Val Phe Leu Val Ile Leu Leu Val
1               5                   10                  15

Cys Val Thr Glu Gln Gly Val Asp Gly Tyr His Arg Ala Asn Gly Asp
            20                  25                  30

Tyr Gly Tyr Ser Tyr Glu Asn Arg His His Val Val Asn Gly Asp Glu
        35                  40                  45
```

-continued

```
Glu Glu His Glu Ile Lys His Thr Asn Ser Arg Lys Phe Asp Asp Asp
     50                  55                  60

Asp Tyr Leu Phe Ser His Gly Tyr Ala Ala Tyr Asp Asp Glu Asp Asp
 65                  70                  75                  80

Glu Asp Glu Arg Gln Gly Tyr Ser Arg Gly Gly Gly Ala Gly Asp
                 85                  90                  95

Ser Ser Arg Asp Pro Gly Phe Tyr Arg Arg Gly Ser Gln Glu Gln Ser
                100                 105                 110

Tyr Asp Pro His Ser Gly Gln Thr Ala Pro Gly Tyr Ser Glu Ser Ser
            115                 120                 125

Glu Tyr Glu His Ser Gly Asp Tyr Asp Asn Ser Gln Asn Gln Gln Tyr
        130                 135                 140

Ser Ser Thr Pro Ser Asn Ala Asn Val Asn Leu Ile Asp Gln Tyr Leu
145                 150                 155                 160

His Leu Ile Gln Leu His Ser Ile Pro Ser Asp Leu Val Gln Tyr Ala
                165                 170                 175

Glu Ser Tyr Leu Thr His Ala Lys Asn Ser Ile Arg Tyr Tyr Ala Val
            180                 185                 190

His Ala Lys Asp Phe Glu Arg Ile Arg Pro Cys Leu Glu Ser Val Thr
        195                 200                 205

Lys Tyr Phe Asn Met Leu Asn Asp Asp Leu Ala Arg Glu Tyr Val Arg
210                 215                 220

Cys Gln Arg Gln Cys Tyr Leu Asp Arg Leu Asn Ser Tyr Thr Thr Ala
225                 230                 235                 240

Ile Ser Gln Tyr Thr Val Thr Thr Asn Ala Cys Ile Asn Asn Arg Leu
                245                 250                 255

Asn
```

<210> SEQ ID NO 68
<211> LENGTH: 934
<212> TYPE: DNA
<213> ORGANISM: Phlebotomus perniciosus

<400> SEQUENCE: 68

```
atcagtttca ctttgaccat cgatggtgaa atacttcaat tcattttacg aaatcactct    60
gattgagaaa cgatgatcgt gaagggtctc cttggggtgt ttcttgtgat cttgctcgtg   120
tgcgtgacag aacagggagt ggacggatac cacagggcta atggggacta tggttacagc   180
tacgaaaacc ggcatcacgt agtcaacgga gatgaggagg aacatgaaat aaaacatact   240
aactctcgta aatttgatga tgacgactat ctctttagtc acggctacgc cgcctacgac   300
gacgaagacg atgaagatga acgacagggc tattcaaggg gcggtggggg agccggagac   360
agtagcagag atcccggatt ttatcgtcgt ggaagtcagg aacaatctta cgatccccac   420
agcggtcaga cagctcctgg ctactcagaa tccagtgaat acgaacatag cggagactac   480
gataactccc agaaccagca atattcctca actccctcta acgctaacgt taacctaatc   540
gaccagtatc tccatctaat ccaattacat agcatcccat ccgatttagt ccaatacgcc   600
gaatcctact aacacacgc caagaactcc atccgatact acgccgtgca cgccaaggac   660
tttgagagga ttcgaccctg ccttgaatcc gtcacgaagt acttcaatat gctcaatgac   720
gatctcgcca gggagtacgt cagatgtcaa cgacaatgtt accttgatcg tctcaatagc   780
tacacaacgg ctatctctca gtatactgtc accacaaatg cctgcataaa caaccgtttg   840
aactgaagat gaggcttttt ttgtgaaata tttatttggg tcagtgaaaa taaattttca   900
```
tcaacaaaaa aaaaaaaaaa aaaaaaaaaa aaaa 934

<210> SEQ ID NO 69
<211> LENGTH: 331
<212> TYPE: PRT
<213> ORGANISM: Phlebotomus perniciosus

<400> SEQUENCE: 69

Met Ile Leu Lys Leu Cys Ala Ile Ala Val Leu Phe Phe Leu Ile Gly
1               5                   10                  15

Asp Gly Glu Ala Ala Pro Arg Pro Thr Arg Phe Ile Pro Phe Ala Ile
            20                  25                  30

Ile Ser Asp Leu His Arg Lys Ala Met His Asp Glu Lys Asn Arg Phe
        35                  40                  45

Thr Ser Ile Val Lys Tyr Gly Gln Leu Lys Tyr Asn Gly Glu Lys Tyr
    50                  55                  60

Thr Leu Ser Ile Arg Ser Glu Asn Leu His Tyr Phe Thr Lys Asp Thr
65                  70                  75                  80

Tyr Lys Gly Thr Gly Ala Asp Met Ser Glu Leu Ile Tyr Phe Asn Asp
                85                  90                  95

Lys Leu Tyr Thr Leu Asn Asp Glu Thr Gly Thr Ile Tyr Glu Val Lys
            100                 105                 110

His Gly Gly Glu Leu Ile Pro Trp Ile Thr Leu Lys Asn Asp Asp Gly
        115                 120                 125

Asn Gln Lys Asp Gly Phe Lys Ala Lys Trp Ala Thr Val Lys Gly Asn
    130                 135                 140

Lys Leu Ile Val Gly Ser Ala Gly Met Ala Phe Leu Asp Ala Lys Thr
145                 150                 155                 160

Met Asn Ile Asp Arg Asp Ala Leu Trp Val Lys Glu Ile Ser Glu Ser
                165                 170                 175

Gly His Val Thr Asn Lys Tyr Trp Asp Ser Gln Tyr Lys Lys Val Arg
            180                 185                 190

Asp Ala Met Gly Leu Val Ser Gly Phe Val Trp His Glu Ala Val Asn
        195                 200                 205

Trp Ser Pro Arg Lys Asn Leu Trp Val Phe Met Pro Arg Lys Cys Thr
    210                 215                 220

Asn Glu Pro Tyr Thr Val Arg Leu Asp Lys Lys Thr Gly Cys Asn Gln
225                 230                 235                 240

Ile Ile Thr Ala Asn Glu Asn Phe Asn Asp Val Arg Ala Ile His Ile
                245                 250                 255

Asn Arg Ala Ala Ala Asp Pro Ala Ser Gly Phe Ser Ser Phe Lys Phe
            260                 265                 270

Ile Pro Asn Thr Arg Asn Asn Asp Ile Phe Ala Ile Lys Thr Ile Glu
        275                 280                 285

Arg Asn Gly Gln Thr Ala Thr Tyr Gly Thr Val Ile Asp Ile Asn Gly
    290                 295                 300

Lys Thr Leu Leu Pro Asp Gln Arg Ile Leu Asp Asp Lys Tyr Glu Gly
305                 310                 315                 320

Ile Ala Phe Phe Lys Asp Pro Lys Gly Ile Lys
                325                 330

<210> SEQ ID NO 70
<211> LENGTH: 1102
<212> TYPE: DNA
<213> ORGANISM: Phlebotomus perniciosus

<400> SEQUENCE: 70

```
agtattcagt tgttagagat ctttccaaca tgatattgaa attgtgcgcc attgcggttt    60
tatttttcct tattggagac ggagaagcag ctcctagacc aacaagattc atcccttcg   120
ctatcatctc agatctgcac aggaaggcca tgcacgacga aaagaacaga tttactagta   180
tagtgaaata tggtcaattg aagtacaatg gagagaaata tactctgtcc atcagaagtg   240
agaatctcca ttatttcaca aaggacacct acaaaggaac cggagccgat atgtccgagt   300
tgatctactt caatgacaag ctctacactc ttaacgacga acaggaact atctatgagg    360
tgaaacacgg cggagagctc attccatgga taactctcaa gaatgacgat ggaaatcaaa   420
aggacggctt caaagctaaa tgggcaacag ttaagggtaa caagttgatt gtcggatcag   480
caggaatggc ctttctggac gcgaaaacca tgaatattga cagagacgcc ctctgggtga   540
aggaaatcag cgaatctggc cacgtcacta ataaatattg ggatagtcaa tacaagaaag   600
tgagggacgc catgggactc gtctccggat ttgtctggca tgaggccgta aattggtcac   660
caaggaagaa tctttgggtc ttcatgccca ggaaatgcac aaatgaacca tataccgttc   720
gcttagacaa gaaaaccgga tgcaatcaga ttatcacggc aatgaaaac ttcaatgatg    780
ttagagcaat tcatatcaat cgagccgctg cagatccagc ttctggattc tcctcttca    840
agttcatccc aaacaccaga aacaatgata tcttcgcaat caagacaatc gagaggaacg   900
gccaaacagc cacttatggc acagtgattg acatcaatgg gaagactttg ttgcccgatc   960
agcgaattct cgatgataaa tatgaaggaa ttgcattttt caaggatccc aaaggaatta  1020
agtaaagatg gattataaaa tgttgaaata aaatgtcatg aagcttataa aatgaaaaaa  1080
aaaaaaaaaa aaaaaaaaaa aa                                           1102
```

<210> SEQ ID NO 71
<211> LENGTH: 230
<212> TYPE: PRT
<213> ORGANISM: Phlebotomus perniciosus

<400> SEQUENCE: 71

```
Met Asn Thr Leu Leu Lys Val Ala Val Leu Leu Ser Leu Gly Gly Thr
1               5                   10                  15
Gly Tyr Ser Trp Gln Tyr Pro Arg Asn Ala Asp Gln Thr Leu Trp Ala
            20                  25                  30
Trp Arg Ser Cys Gln Lys Glu His Ile Gly Asp Asp Gln Ala Leu Leu
        35                  40                  45
Lys Lys Trp Leu Lys Phe Glu Ile Pro Asp Asp Lys Val Thr His Cys
    50                  55                  60
Phe Ile Lys Cys Thr Trp Ile His Leu Gly Met Tyr Asp Glu Lys Thr
65                  70                  75                  80
Lys Thr Ile Arg Val Asp Lys Val Lys Gln Gln Phe Glu Gly Arg Lys
                85                  90                  95
Leu Pro Val Pro Ala Glu Ile Ser Lys Leu Glu Gly Pro Thr Asp Gly
            100                 105                 110
Asp Cys Glu Lys Ile Tyr Arg Lys Thr Lys Ala Phe Leu Asp Ala Gln
        115                 120                 125
Met Lys Asn Tyr Arg Ile Ala Phe Tyr Gly Ile Tyr Asp Gly Ser Asp
    130                 135                 140
Ala Trp Phe Ala Glu His Pro Glu Thr Lys Pro Lys Lys Thr Lys Ile
145                 150                 155                 160
```

Ser Glu Phe Cys Lys Gly Arg Glu Gly Lys Glu Gly Thr Cys Lys
            165                 170                 175

His Ala Cys Ser Met Tyr Tyr Tyr Arg Leu Val Asp Glu Asp Asn Leu
            180                 185                 190

Val Ile Pro Phe Arg Lys Leu Pro Gly Ile Ser Glu Ser Asp Leu Lys
        195                 200                 205

Gln Cys Arg Asp Ala Ala Ser Lys Lys Ser Gly Cys Gln Val Ala Asp
    210                 215                 220

Asp Asn Leu Arg Leu Ser
225             230

<210> SEQ ID NO 72
<211> LENGTH: 845
<212> TYPE: DNA
<213> ORGANISM: Phlebotomus perniciosus

<400> SEQUENCE: 72
agttcagttt tctgtggaaa atgaatacct tattgaaagt cgcggttttg ctaagcttgg     60
gaggaactgg gtactcttgg caatatccca ggaatgccga tcaaactctc tgggcttgga    120
gatcgtgtca aaggagcac atcggcgacg accaagcatt attgaagaaa tggttgaaat    180
ttgaaattcc agatgataaa gtaacgcatt gttttattaa atgtacttgg atccatttag    240
gaatgtacga tgaaaaaact aaaaccatta gggttgataa ggtcaagcaa caattcgagg    300
gacgcaaatt accagttcct gctgaaatca gcaaattaga gggtcctaca gatggcgatt    360
gtgaaaaaat ttacagaaaa actaaggctt ttcttgacgc tcaaatgaag aattatcgca    420
ttgcattcta tggcatttat gatggatccg atgcatggtt tgcagaacat cccgaaacta    480
agcccaagaa aacgaagatt tctgaattct gcaaggtcg tgaaggtgga aggaaggaa     540 cttgcaagca tgcttgcagc atgtactact accgcttagt cgatgaggat aatcttgtga    600
ttcccttcag gaagttgcca ggcatctcag agtctgatct taaacaatgc agagatgccg    660
ctagcaagaa agtggatgc caagttgctg atgacaatct acgattgtct aacaagatc      720 aacccgacag gtcttaaaac tgctttaaat acgctcgatg agcaatcatt aacaaattat    780
tagaaaagaa ataaaaattg atttcgagca atcgtaaaaa aaaaaaaaaa aaaaaaaaaa    840
aaaaa                                                                 845

<210> SEQ ID NO 73
<211> LENGTH: 49
<212> TYPE: PRT
<213> ORGANISM: Phlebotomus perniciosus

<400> SEQUENCE: 73

Met Lys Tyr Phe Ser Leu Asn Phe Leu Leu Ile Val Ile Leu Leu Ile
1               5                   10                  15

Val Ala Cys Ser Pro Gln Leu Pro Cys Leu Pro Gln Asp Ser Lys Lys
            20                  25                  30

Lys Pro Ser Asn Pro Arg Pro Lys Leu Ser Ala Arg Ser Gly Leu Ser
        35                  40                  45

Tyr

<210> SEQ ID NO 74
<211> LENGTH: 521
<212> TYPE: DNA
<213> ORGANISM: Phlebotomus perniciosus

<400> SEQUENCE: 74

-continued

```
atcattagtg aagttgttaa caactaagca tgaagtactt ttctctcaat tttcttctaa      60
ttgtgattct attgattgtg gcttgttcac ctcaattacc atgtttaccc caggattcca     120
agaaaaagcc gtccaatcct cgtcctaaat tatcggccag aagtggtttg tcttattgag     180
ttatcacact aggaattcga tgcagtaatt tattacgtgg gcattgtggc ttcatagctg     240
gggccgtaaa aattaaaaga caaaaagaaa ttattacatg acggccgcca taagtcgacg     300
aaaatggaca taacatcctt gactacctat cgtaatgtga atttgaaaaa ttatacaaaa     360
aaataattat gaattagcaa aaataaaaat tatcagagga gcagatctgc tgttatgatt     420 tcttttatg tctcttttat gtaagcaatc actattcttg tacgaatata aaataaaag      480 ttccaactgt gtcaaaaaaa aaaaaaaaaa aaaaaaaaa a                         521
```

<210> SEQ ID NO 75
<211> LENGTH: 82
<212> TYPE: PRT
<213> ORGANISM: Phlebotomus perniciosus

<400> SEQUENCE: 75

```
Met Lys Lys Ile Val Leu Phe Ser Phe Ile Phe Val Ala Leu Val Ile
 1               5                  10                  15

Ser Ala Lys Ala Ile Glu Thr Glu Leu Asp Asp Pro Asp Asp Ala Thr
             20                  25                  30

Lys Gly Arg Asp Val Ala Lys Ala Glu Pro Gly Gln Leu Gly Gln Val
         35                  40                  45

Pro Val Val Pro Asp Leu Asn Pro Ser Asn Thr Arg Lys Arg Arg Asn
     50                  55                  60

Arg Ser Arg Lys Arg Arg Asn Leu Gly Lys Arg Leu Lys Lys Val
 65                  70                  75                  80

Phe Ala
```

<210> SEQ ID NO 76
<211> LENGTH: 379
<212> TYPE: DNA
<213> ORGANISM: Phlebotomus perniciosus

<400> SEQUENCE: 76

```
agtcagttat tgttcgaaaa atgaagaaaa ttgtgctatt cagttttata ttcgttgctt      60
tggtgatcag tgctaaagcc attgagacgg aattggatga tcccgatgat gccactaaag    120
gtcgggatgt tgcgaaggca gaacctggac aactgggaca agttccagtt gtacctgatt    180
taaatccttc gaacacgagg aaacggagga atagatccag aaaaaggcga cgaaatctag    240
gaaagagact caaaaaagtt tttgcataga aattaatact aaaaagatta aaactatgtc    300
aatttgatgc cttttgagca ttcaattaaa aagtatgaca aattattaag aaaaaaaaaa    360
aaaaaaaaaa aaaaaaaa                                                   379
```

<210> SEQ ID NO 77
<211> LENGTH: 293
<212> TYPE: PRT
<213> ORGANISM: Phlebotomus perniciosus

<400> SEQUENCE: 77

```
Met Met Ser Arg Trp Ser Lys Ser Val Lys Phe Val Cys Leu Leu Leu
 1               5                  10                  15

Cys Gly Gly Phe Thr Phe Leu Thr Thr Ser Ala Arg Ala Lys Pro Thr
             20                  25                  30
```

```
Leu Thr Phe Gln Leu Pro Pro Ala Leu Thr Asn Leu Pro Pro Phe Ile
            35                  40                  45

Gly Ile Ser Arg Phe Val Glu Arg Lys Met Gln Asn Asp Gln Met Lys
 50                  55                  60

Thr Tyr Thr Gly Val Arg Gln Thr Asn Asp Ser Leu Val Met Ile Tyr
 65                  70                  75                  80

His His Asp Leu Thr Ile Ala Ile Val Glu Leu Gly Pro Glu Lys Thr
                85                  90                  95

Leu Leu Gly Cys Glu Leu Ile Glu Ile Asn Asn Asp Asp Glu Gly Ala
            100                 105                 110

Lys Val Leu Thr Glu Leu Ala Thr Val Asn Ile Pro Leu Gln Ile Asp
            115                 120                 125

Phe Arg Glu Met Val Lys Leu Met Lys Gln Cys Glu Lys Ile Asp Tyr
            130                 135                 140

Met Arg Lys Val Lys Arg Gln Gly Ala Ser Glu Ser Asp Gln Thr Thr
145                 150                 155                 160

Asn Arg Gln His Gln Thr Gly Tyr Phe Gly Leu Gly Gly Ala Thr Ala
                165                 170                 175

Gly Leu Ser Ile Leu Ser Gly Ile Leu Pro Gly Thr Lys Trp Cys Gly
            180                 185                 190

Thr Gly Asp Ile Ala Lys Thr Tyr His Asp Leu Gly Thr Glu Ala Thr
            195                 200                 205

Met Asp Met Cys Cys Arg Thr His Asp Leu Cys Pro Val Lys Val Arg
            210                 215                 220

Ser Tyr Gln Gln Arg Tyr Asn Leu Ser Asn Asn Ser Ile Tyr Thr Lys
225                 230                 235                 240

Ser Pro Cys Lys Cys Asp Asp Met Leu Phe Asn Cys Leu Lys Arg Thr
                245                 250                 255

Asn Thr Ser Ala Ser Gln Phe Met Gly Thr Ile Tyr Phe Asn Val Val
            260                 265                 270

Gln Val Pro Cys Val Leu Asp Thr Glu Arg Gly Tyr Arg Phe Arg Lys
            275                 280                 285

Ala Arg Thr Phe Ser
290

<210> SEQ ID NO 78
<211> LENGTH: 1613
<212> TYPE: DNA
<213> ORGANISM: Phlebotomus perniciosus

<400> SEQUENCE: 78
acttaatatt ggactgtatt ttgagataga caccccagag tacgatggtg caatgtgaat    60
tcggtggaac accttgtacg actttgaata tttcatatcc aacgatcaag ccactggtga   120
atgcctgagt gttgtgttga gctcagtcgc ggtggagcga cgagccgaga agaatggca   180 aaggtgcaat agagatacta aactagagga aagacttgaa cggtgacaga ggaataggag   240
caagaaagaa gtgttgagaa tttgcgggaa tttctatggc caatattaag tgttgattca   300
aagagttttc tacacagaga aattgcgagg tcacttattg gaaatcaatg agaaagtttt   360
taatgttttt cgtgaaagga gtgaataaaa attgagtgct ttatacatgt gagactcccc   420 ctttctgtg gagagacgat aaaaggaaat tcgatatta tgggaaaagt gatgaattag   480
tgatactggt ggctctcgaa acacaagtca cgaattagaa aacgtccaaa gagtgatttt   540
tgtgctctcc ggtggctgat ataagagaat gtgaagagtg aggatgatgt ctcgctggag   600
```

-continued

```
caaaagtgtg aaatttgtgt gcctcctcct gtgtggcggg ttcacgtttc tcacaacatc    660
agcacgtgcc aaacccacgc tgacctttca gcttccgccc gccctcacga acctaccccc    720
cttcataggc atctcgcgat ttgtcgaacg caaaatgcag aatgaccaga tgaagaccta    780
cactggcgtt cggcagacga acgactctct cgtgatgatc taccaccatg atctgacgat    840
cgccatcgtg gaattgggac cagagaagac tctcttgggt tgtgaattga tagaaattaa    900
caacgatgat gaaggcgcca aagtgctcac agaactggcc accgtgaata taccactgca    960
gatcgacttc cgggagatgg tgaagctcat gaagcagtgc gagaagatcg attacatgcg   1020
gaaagtgaaa cgccagggag catcagagag tgaccagaca acaaatcgtc aacatcagac   1080
gggctacttt ggactcggag cgccaccgc cggtctaagc atcctcagtg catccttcc    1140 cggcaccaag tggtgtggca caggagacat cgccaaaaca taccacgatc tcggcaccga   1200
ggccactatg gacatgtgct gtcgcactca tgatctctgt ccagtgaaag tgcgctcata   1260
tcagcagcgc tacaatctca gcaataactc tatctacaca aaatctccct gcaaatgtga   1320
tgacatgctg ttcaattgcc tcaagaggac caacacgtca gcctcgcaat tcatggggac   1380
catctacttc aacgtggtcc aagtgccatg tgttctggac acagagagag ctacagatt    1440 cagaaaagcg agaaccttct cctgagtatt gcaaaacaac gaaatctgcg gatttttttt   1500
tatttttggg acttttcgtg tgtaaagacc atttcttgtg attttcagct gcggtgctct   1560
ttcaaatgaa ttatttatgt tgctaaaaaa aaaaaaaaa aaaaaaaaaa aaa           1613
```

```
<210> SEQ ID NO 79
<211> LENGTH: 137
<212> TYPE: PRT
<213> ORGANISM: Phlebotomus perniciosus

<400> SEQUENCE: 79

Met Lys Gln Leu Val Val Phe Leu Ala Leu Ile Val Leu Ile Val Ile
1               5                   10                  15

Cys His Ala Lys Arg Pro Ser Arg Lys Cys Arg Ser Gly Met Val Lys
            20                  25                  30

Glu Glu Glu Cys Ile Leu His Cys Glu Tyr Lys Tyr Tyr Gly Phe Thr
        35                  40                  45

Asp Asp Lys Phe Gln Leu Asp Ala Asp Gln Arg Gly Asn Phe Arg Phe
    50                  55                  60

Ala Met Met Asp Tyr Gly Ala Ile Arg Met Asp Gln Glu Gly Gln Met
65                  70                  75                  80

Asp Glu His Leu Lys Lys Cys Ala Asn Glu Ala Glu Lys Ala Pro Val
                85                  90                  95

Cys Ser Lys Val Asp Lys Cys Arg Lys Ile Ile Gln Tyr Tyr Arg Cys
            100                 105                 110

Ala Val Asn Asn Lys Leu Phe Gln Tyr Asn Ala Tyr Ala Lys Ala Ile
        115                 120                 125

Ile Ala Leu Asp Lys Thr Ile Asn Val
    130                 135

<210> SEQ ID NO 80
<211> LENGTH: 518
<212> TYPE: DNA
<213> ORGANISM: Phlebotomus perniciosus

<400> SEQUENCE: 80
gtattagaaa accaatcatg aagcagcttg ttgtattttt ggcgttgata gttctaatag    60
```

```
tgatttgtca cgcaaaacga ccttcgagga agtgtaggag tggaatggtg aaagaggaag    120
agtgtatact ccattgtgag tacaaatatt atggctttac cgatgataag ttccaacttg    180
atgcagatca gagaggaaac tttagatttg ccatgatgga ctatggagca attaggatgg    240
atcaggaggg tcaaatggat gagcatttga aaaaatgtgc caatgaagct gaaaaggctc    300
cagtgtgctc caaggtggat aagtgtagga aaatcattca gtactatcgc tgtgcagtga    360
ataataaact tttccaatat aatgcttatg ccaaagcaat tattgcgctt gataagacaa    420
ttaatgttta aaaagtggaa tgaatcccta aataaagaa ggaaagataa gaactttcaa     480
gaaaacttga aaaaaaaaa aaaaaaaaa aaaaaaa                               518

<210> SEQ ID NO 81
<211> LENGTH: 141
<212> TYPE: PRT
<213> ORGANISM: Phlebotomus perniciosus

<400> SEQUENCE: 81

Met Lys Gln Leu Pro Val Ile Leu Leu Ala Leu Val Phe Leu Ile Ala
1               5                   10                  15

Lys Cys Arg Ser Glu Lys Pro Glu Tyr Lys Cys Arg Arg Asp Phe Lys
            20                  25                  30

Thr Glu Asp Lys Asn Cys Phe Leu Ser Cys Thr Phe Lys Asn Tyr His
        35                  40                  45

Phe Ile Asp Asn Lys Phe Arg Ile Glu Arg Lys Asn Ile Glu Asn Tyr
    50                  55                  60

Lys Lys Phe Ile Thr Asp Tyr Lys Ala Leu Lys Pro Asn Val Ser Asp
65                  70                  75                  80

Asn Asp Leu Glu Lys His Leu Leu Asp Cys Trp Asp Lys Phe Gln Lys
                85                  90                  95

Ser Pro Glu Ala Ser Thr Arg Pro Glu Lys Cys Glu Lys Val Asn Asn
            100                 105                 110

Phe Glu Arg Cys Val Ile Asp Lys Asn Ile Phe Asp Tyr Pro Ile Tyr
        115                 120                 125

Phe Asn Ala Leu Lys Lys Ile Asn Tyr Ile Thr Lys Val
    130                 135                 140

<210> SEQ ID NO 82
<211> LENGTH: 526
<212> TYPE: DNA
<213> ORGANISM: Phlebotomus perniciosus

<400> SEQUENCE: 82
acacacatac gattcattac cagaaatgaa gcagttacca gtgatccttc tggccttagt    60
ctttctgatc gcaaaatgtc gatcagaaaa accggaatat aagtgccgca gagacttcaa   120
gaccgaggat aaaaattgct tcctttcttg tacatttaaa aattaccact tcattgataa   180
caagttcagg attgaaagga agaatattga aaactacaag aagttcataa ctgactataa   240
ggccctgaaa cccaatgtta gcgataatga tttggaaaaa cacctgttgg attgttggga   300
taaattccaa aaatcaccctg aagcatcaac aaggcccgaa aatgtgaaa agtcaacaa    360 ctttgaaaga tgtgttattg acaagaatat ctttgattat cctatttact tcaatgcttt   420
gaagaaaata aattacatta caaaggttta atgaaaaatt gatgaaataa acataatgaa   480
ttattgcatt gaataacaaa aaaaaaaaaa aaaaaaaaa aaaaaa                   526
```

<210> SEQ ID NO 83
<211> LENGTH: 97
<212> TYPE: PRT
<213> ORGANISM: Phlebotomus perniciosus

<400> SEQUENCE: 83

Met Lys Lys Ile Val Leu Phe Ser Val Ile Phe Ile Ala Leu Val Ile
1               5                   10                  15
Ser Ala Lys Ala Ile Glu Asp Glu Asp Asp Asp Asp Asp Asp Asp Glu
            20                  25                  30
Ser Glu Asp Arg Asp Val Ala Arg Ala Glu Arg Glu Gln Gln Glu Glu
        35                  40                  45
Glu Pro Asp Glu Pro Glu Tyr Ile Pro Ser Arg Pro Arg Asn Arg Ser
    50                  55                  60
Lys Met Arg Lys Trp Arg Asn Arg Asn Tyr Arg Lys Tyr Arg Asp Glu
65                  70                  75                  80
Ser Arg Lys Arg Lys Arg Asp Met Val Leu Asp Val Ile Arg Arg Phe
                85                  90                  95
Leu

<210> SEQ ID NO 84
<211> LENGTH: 425
<212> TYPE: DNA
<213> ORGANISM: Phlebotomus perniciosus

<400> SEQUENCE: 84
agttattgtt gggaaaatga agaaaattgt gctgttcagt gttatattca ttgctttggt      60
gatcagtgct aaagccattg aggatgagga tgatgatgat gacgatgatg aatctgaaga     120
tcgggatgtt gcgagggcag aacgtgaaca acaggaagaa gaaccagacg aacctgaata     180
tattccttct agaccgagga tcggtcgaa aatgagaaaa tggaggaata gaaactatag      240
aaaatataga gacgaaagta ggaaaagaaa gcgagatatg gttttggatg ttatcagaag     300 attttttatag aaattaatac taaaagtatt aagtggatca atttgatgcc ttttgagtga    360
ttcattttga actttgaaaa ataaaacaaa gaatgtaaaa aaaaaaaaa aaaaaaaaa       420 aaaaa                                                                 425

<210> SEQ ID NO 85
<211> LENGTH: 22
<212> TYPE: DNA
<213> ORGANISM: Artificial Sequence
<220> FEATURE:
<223> OTHER INFORMATION: Oligonucleotide primer.

<400> SEQUENCE: 85
aagtactcta gcaattgtga gc                                               22

<210> SEQ ID NO 86
<211> LENGTH: 22
<212> TYPE: DNA
<213> ORGANISM: Artificial Sequence
<220> FEATURE:
<223> OTHER INFORMATION: Oligonucleotide primer.

<400> SEQUENCE: 86
ctcttcgcta ttacgccagc tg                                               22

-continued

```
<210> SEQ ID NO 87
<211> LENGTH: 24
<212> TYPE: DNA
<213> ORGANISM: Artificial Sequence
<220> FEATURE:
<223> OTHER INFORMATION: Oligonucleotide primer.

<400> SEQUENCE: 87
tctcgggaag cgcgccattg tgtt                                          24
```

P. ARIASI POLYPEPTIDES, P. PERNICIOSUS POLYPEPTIDES AND METHODS OF USE

PRIORITY CLAIM

This application is the §371 U.S. National Stage of International Application No. PCT/US2003/029833, filed Sep. 18, 2003, which was published in English under PCT Article 21(2), which in turn claims the benefit of U.S. Provisional Application No. 60/412,327, filed Sep. 19, 2002, and U.S. Provisional Application No. 60/425,852, filed Nov. 12, 2002, which are incorporated herein by reference.

FIELD

The disclosure relates to proteins substantially purified from Phlebotomine sand fly salivary glands, or recombinant vectors expressing these proteins, and to an immune response produced to these proteins. This disclosure also relates to the production of an immune response that affects survival of Leishmania.

BACKGROUND

Leishmaniasis is a group of diseases caused by protozoa of the genus Leishmania that affects many millions of people worldwide. In humans, infection with the parasite manifests either as a cutaneous disease caused mainly by L. major, L. tropica, and L. mexicana; as a mucocutaneous disease caused mainly by L. brasiliensis; or as a visceral disease caused mainly by L. donovani and L. chagasi. In canids, Leishmania infections manifest as a visceral disease that can result in high death rates.

All leishmanial diseases are transmitted to their vertebrate hosts by phlebotomine sand flies, which acquire the pathogen by feeding on infected hosts and transmit them by regurgitating the parasite at the site of a subsequent blood meal (Killick-Kendrick, Biology of Leishmania in phlebotomine sand flies. In Biology of the kinetoplastida. W. Lumsden and D. Evans, editors. Academic Press, New York. 395, 1979).

While obtaining a blood meal, sand flies salivate into the host's skin. This saliva contains anticlotting, antiplatelet, and vasodilatory compounds that increase the hemorrhagic pool where sand flies feed (Ribeiro et al., Comp. Biochem. Physiol. 4:683, 1986; Charlab et al., Proc. Natl. Acad. Sci. USA. 26:15155, 1999). Some of these components are additionally immunomodulatory. For example, the New World sand fly Lutzomyia longipalpis contains the 6.5 kDa peptide, maxadilan, which is the most potent vasodilator known (Lerner et al., J. Biol. Chem. 17:11234, 1991). Maxadilan additionally has immunosuppressive activities of its own (Qureshi et al., Am. J. Trop. Med. Hyg. 6:665, 1996), as do many persistent vasodilators such as prostaglandin $E_2$ (Makoul et al., J. Immunol. 134:2645, 1985; Santoli and Zurier, J. Immunol. 143: 1303, 1989; Stockman and Mumford, Exp. Hematol. 2:65, 1974) and calcitonin gene-related peptide (Nong et al., J. Immunol. 1:45, 1989). Old World sand flies do not have maxadilan but instead use adenosine monophosphate and adenosine as vasodilators (Ribeiro et al., J. Exp. Biol. 11:1551, 1999). Adenosine is also an immunomodulatory component, promoting the production of interleukin-10 and suppressing tumor necrosis factor-α and interleukin-12 in mice (Hasko et al., J. Immunol. 10:4634, 1996; Webster, Asian Pac. J. Allergy Immunol. 2:311, 1984; Hasko et al., FASEB J. 14:2065, 2000). Despite what is known about the role of sandfly saliva and disease transmission, much remains unknown, and an effective vaccine does not exist. Thus, there is a need for agents that can be used to induce an immune response to the organisms that cause leishmaniasis.

SUMMARY

The present disclosure relates to salivary proteins from sand fly vectors of Leishmania that are members of the subgenus of Phlebotomus Larroussius, in particular two species, namely Phlebotomus ariasi and Phlebotomus perniciosus, and the nucleic acids that encode these proteins. Methods of producing an immune response in a subject are also disclosed.

Substantially purified salivary P. ariasi polypeptides are disclosed herein. Also disclosed are polynucleotides encoding the P. ariasi polypeptides disclosed herein.

Disclosed herein are substantially purified salivary P. perniciosus polypeptides. Also disclosed are polynucleotides encoding the P. perniciosus polypeptides disclosed herein.

Methods are disclosed for inducing an immune response to a P. ariasi polypeptide using a therapeutically effective amount of the substantially purified salivary P. ariasi polypeptides disclosed herein, or the polynucleotides encoding the P. ariasi polypeptides disclosed herein.

Methods are also disclosed for inducing an immune response to a P. perniciosus polypeptide using a therapeutically effective amount of the P. perniciosus polypeptides disclosed herein, or the polynucleotides encoding the P. perniciosus polypeptides disclosed herein.

In another embodiment, methods are disclosed herein for inhibiting the symptoms of a Leishmania infection or for preventing a Leishmania infection in a subject. The methods include administering to the subject a therapeutically effective amount of a P. ariasi polypeptide, or a polynucleotide encoding a P. ariasi polypeptide.

In yet another embodiment, methods are disclosed herein for inhibiting the symptoms of a Leishmania infection or for preventing a Leishmania infection in a subject. The methods include administering to the subject a therapeutically effective amount of a P. perniciosus polypeptide, or a polynucleotide encoding a P. perniciosus polypeptide.

Pharmaceutical compositions are disclosed including a pharmaceutically acceptable carrier and a P. ariasi polypeptide and/or a P. perniciosus polypeptide.

The foregoing and other features and advantages will become more apparent from the following detailed description of several embodiments, which proceeds with reference to the accompanying figures.

Sequence Listing

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO:1 is the amino acid sequence of a PRL-P4-A10 polypeptide.

SEQ ID NO:2 is the nucleic acid sequence of a polynucleotide encoding a PRL-P4-A10 polypeptide.

SEQ ID NO:3 is the amino acid sequence of PRL-P4-A9 polypeptide.

SEQ ID NO:4 is the nucleic acid sequence of a polynucleotide encoding a PRL-P4-A9 polypeptide.

SEQ ID NO:5 is the amino acid sequence of PRL-P4-C10 polypeptide.

SEQ ID NO:6 is the nucleic acid sequence of a polynucleotide encoding a PRL-P4-C10 polypeptide.

SEQ ID NO:7 is the amino acid sequence of PRL-P4-D6 polypeptide.

SEQ ID NO:8 is the nucleic acid sequence of a polynucleotide encoding a PRL-P4-D6 polypeptide.

SEQ ID NO:9 is the amino acid sequence of PRL-P4-D7 polypeptide.

SEQ ID NO:10 is the nucleic acid sequence of a polynucleotide encoding a PRL-P4-D7 polypeptide.

SEQ ID NO:11 is the amino acid sequence of PRL-P4-E5 polypeptide.

SEQ ID NO:12 is the nucleic acid sequence of a polynucleotide encoding a PRL-P4-E5 polypeptide.

SEQ ID NO:13 is the amino acid sequence of PRL-P4-F3 polypeptide.

SEQ ID NO:14 is the nucleic acid sequence of a polynucleotide encoding a PRL-P4-F3 polypeptide.

SEQ ID NO:15 is the amino acid sequence of PRL-P4-G12 polypeptide.

SEQ ID NO:16 is the nucleic acid sequence of a polynucleotide encoding a PRL-P4-G12 polypeptide.

SEQ ID NO:17 is the amino acid sequence of PRL-P4-G7 polypeptide.

SEQ ID NO:18 is the nucleic acid sequence of a polynucleotide encoding a PRL-P4-G7 polypeptide.

SEQ ID NO:19 is the amino acid sequence of PRL-P6-E11 polypeptide.

SEQ ID NO:20 is the nucleic acid sequence of a polynucleotide encoding a PRL-P6-E11 polypeptide.

SEQ ID NO:21 is the amino acid sequence of PRM-P3-A6 polypeptide.

SEQ ID NO:22 is the nucleic acid sequence of a polynucleotide encoding a PRM-P3-A6 polypeptide.

SEQ ID NO:23 is the amino acid sequence of PRM-P3-F11 polypeptide.

SEQ ID NO:24 is the nucleic acid sequence of a polynucleotide encoding a PRM-P3-F11 polypeptide.

SEQ ID NO:25 is the amino acid sequence of PRM-P5-D6 polypeptide.

SEQ ID NO:26 is the nucleic acid sequence of a polynucleotide encoding a PRM-P5-D6 polypeptide.

SEQ ID NO:27 is the amino acid sequence of PRM-P5-E9 polypeptide.

SEQ ID NO:28 is the nucleic acid sequence of a polynucleotide encoding a PRM-P5-E9 polypeptide.

SEQ ID NO:29 is the amino acid sequence of PRM-P5-F12 polypeptide.

SEQ ID NO:30 is the nucleic acid sequence of a polynucleotide encoding a PRM-P5-F12 polypeptide.

SEQ ID NO:31 is the amino acid sequence of PRM-P5-F2 polypeptide.

SEQ ID NO:32 is the nucleic acid sequence of a polynucleotide encoding a PRM-P5-F2 polypeptide.

SEQ ID NO:33 is the amino acid sequence of PRM-P5-G11 polypeptide.

SEQ ID NO:34 is the nucleic acid sequence of a polynucleotide encoding a PRM-P5-G11 polypeptide.

SEQ ID NO:35 is the amino acid sequence of PRM-P5-H4 polypeptide.

SEQ ID NO:36 is the nucleic acid sequence of a polynucleotide encoding a PRM-P5-H4 polypeptide.

SEQ ID NO:37 is the amino acid sequence of PRS-P1-B11 polypeptide.

SEQ ID NO:38 is the nucleic acid sequence of a polynucleotide encoding a PRS-P1-B11 polypeptide.

SEQ ID NO:39 is the amino acid sequence of PRS-P1-B4 polypeptide.

SEQ ID NO:40 is the nucleic acid sequence of a polynucleotide encoding a PRS-P1-B4 polypeptide.

SEQ ID NO:41 is the amino acid sequence of PRS-P1-E7 polypeptide.

SEQ ID NO:42 is the nucleic acid sequence of a polynucleotide encoding a PRS-P1-E7 polypeptide.

SEQ ID NO:43 is the amino acid sequence of PRS-P1-G9 polypeptide.

SEQ ID NO:44 is the nucleic acid sequence of a polynucleotide encoding a PRS-P1-G9 polypeptide.

SEQ ID NO:45 is the amino acid sequence of PRS-P2-C8 polypeptide.

SEQ ID NO:46 is the nucleic acid sequence of a polynucleotide encoding a PRS-P2-C8 polypeptide.

SEQ ID NO:47 is the amino acid sequence of PRS-P2-G8 polypeptide.

SEQ ID NO:48 is the nucleic acid sequence of a polynucleotide encoding a PRS-P2-G8 polypeptide.

SEQ ID NO:49 is the amino acid sequence of PERL-P7-G8 polypeptide.

SEQ ID NO:50 is the nucleic acid sequence of a polynucleotide encoding a PERL-P7-G8 polypeptide.

SEQ ID NO:51 is the amino acid sequence of PERL-P6-H9 polypeptide.

SEQ ID NO:52 is the nucleic acid sequence of a polynucleotide encoding a PERL-P6-H9 polypeptide.

SEQ ID NO:53 is the amino acid sequence of PERL-P7-C2 polypeptide.

SEQ ID NO:54 is the nucleic acid sequence of a polynucleotide encoding a PERL-P7-C2 polypeptide.

SEQ ID NO:55 is the amino acid sequence of PERL-P6-H1 polypeptide.

SEQ ID NO:56 is the nucleic acid sequence of a polynucleotide encoding a PERL-P6-H1 polypeptide.

SEQ ID NO:57 is the amino acid sequence of PERL-P3-E11 polypeptide.

SEQ ID NO:58 is the nucleic acid sequence of a polynucleotide encoding a PERL-P3-E11 polypeptide.

SEQ ID NO:59 is the amino acid sequence of PERL-P7-G12 polypeptide.

SEQ ID NO:60 is the nucleic acid sequence of a polynucleotide encoding a PERL-P7-G12 polypeptide.

SEQ ID.NO:61 is the amino acid sequence of PERL-P3-C9 polypeptide.

SEQ ID NO:62 is the nucleic acid sequence of a polynucleotide encoding a PERL-P3-C9 polypeptide.

SEQ ID NO:63 is the amino acid sequence of PERM-P2-A10 polypeptide.

SEQ ID NO:64 is the nucleic acid sequence of a polynucleotide encoding a PERM-P2-A10 polypeptide.

SEQ ID NO:65 is the amino acid sequence of PERL-P6-H11 polypeptide.

SEQ ID NO:66 is the nucleic acid sequence of a polynucleotide encoding a PERL-P6-H11 polypeptide.

SEQ ID NO:67 is the amino acid sequence of PERS-P1-H11 polypeptide.

SEQ ID NO:68 is the nucleic acid sequence of a polynucleotide encoding a PERS-P1-H11 polypeptide.

SEQ ID NO:69 is the amino acid sequence of PERM-P2-G11 polypeptide.

SEQ ID NO:70 is the nucleic acid sequence of a polynucleotide encoding a PERM-P2-G11 polypeptide.

SEQ ID NO:71 is the amino acid sequence of PERM-P5-E2 polypeptide.

SEQ ID NO:72 is the nucleic acid sequence of a polynucleotide encoding a PERM-P5-E2 polypeptide.

SEQ ID NO:73 is the amino acid sequence of PERM-P5-C11 polypeptide.

SEQ ID NO:74 is the nucleic acid sequence of a polynucleotide encoding a PERM-P5-C 11 polypeptide.

SEQ ID NO:75 is the amino acid sequence of PERM-P5-H8 (also referred to as P2-G9) polypeptide.

SEQ ID NO:76 is the nucleic acid sequence of a polynucleotide encoding a PERM-P5-H8 (also referred to as P2-G9) polypeptide.

SEQ ID NO:77 is the amino acid sequence of PERL-P3-B3 polypeptide.

SEQ ID NO:78 is the nucleic acid sequence of a polynucleotide encoding a PERL-P3-B3 polypeptide.

SEQ ID NO:79 is the amino acid sequence of PERM-P2-D11 polypeptide.

SEQ ID NO:80 is the nucleic acid sequence of a polynucleotide encoding a PERM-P2-D11 polypeptide.

SEQ ID NO:81 is the amino acid sequence of PERM-P5-E3 polypeptide.

SEQ ID NO:82 is the nucleic acid sequence of a polynucleotide encoding a PERM-P5-E3 polypeptide.

SEQ ID NO:83 is the amino acid sequence of PERM-P2-F11 polypeptide.

SEQ ID NO:84 is the nucleic acid sequence of a polynucleotide encoding a PERM-P2-F11 polypeptide.

SEQ ID NO:85 is the nucleic acid sequence of the PT2F1 primer.

SEQ ID NO:86 is the nucleic acid sequence of the PT2R1 primer.

SEQ ID NO:87 is the nucleic acid sequence of the PT2F3 primer.

DETAILED DESCRIPTION

I. Abbreviations

| | |
|---|---|
| AAV | adeno-associated virus |
| AcNPV | Autographa California Nuclear Polyhedrosis Virus |
| alum | aluminum phosphate or aluminum hydroxide |
| BCG | Bacillus Calmette Guerin |
| BLAST | Basic Local Alignment Search Tool |
| BSA | bovine serum albumin |
| CAV | canine adenovirus |
| CDR | complementarity determining region |
| CHV | canine herpes virus |
| CMV | cytomegalovirus |
| CTL | cytotoxic T lymphocyte |
| DMRIE | N-(2-hydroxyethyl)-N,N-diméthyl-2,3-bis (tetradecyloxy)-1-propanammonium |
| DOPE | dioleoyl-phosphatidyl-ethanolamine |
| DTH | delayed type hypersensitivity |
| fMLP | N-formyl-methionyl-leucyl-phenylalanine |
| GM-CSF | granulocyte-macrophage colony stimulating factor |
| H | heavy chains |
| HLB | hydrophile-lipophile balance |
| ID | intradermal |
| IM | intramuscular |
| ISS | immunostimulating sequence |
| KLH | keyhole limpet hemocyanin |
| L | light chains |
| LB | Luria broth |
| MVA | Modified Vaccinia virus Ankara |
| ORF | open reading frame |
| PCR | polymerase chain reaction |
| polyA | polyadenylation signal |
| PVDF | polyvinylidene difluoride |
| SC | subcutaneous |
| SCA | Single chain antibody |

-continued

| | |
|---|---|
| SDS-PAGE | sodium dodecyl sulfate-polyacrylamide gel electrophoresis |
| sFv | single-chain antigen binding proteins |
| SGH | salivary gland homogenate |
| SPGA | sucrose phosphate glutamate albumin |
| tPA | tissue plasminogen activator |
| $V_H$ | variable region of the heavy chain |
| $V_L$ | variable region of the light chain |
| W/V | weight/volume |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Amplification (of a nucleic acid molecule): A technique that increases the number of copies of a nucleic acid molecule (e.g., a DNA or an RNA) in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP 0320308; gap filling ligase chain reaction amplification, as disclosed in U.S. Pat. No. 5,427,930; and NASBA™ RNA transcription-free amplification, as disclosed in U.S. Pat. No. 6,025,134.

Antibody: immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains inter-connected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the VL, VH, CL, and CH1 domains; (ii) an Fd fragment consisting of the VH and CH1 domains; (iii) an Fv fragment consisting of the VL and VH domains of a single arm of an antibody, (iv) a dAb fragment (Ward et al., *Nature* 341:544-546, 1989) which consists of a VH domain; (v) an isolated complimentarily determining region (CDR); and (vi) a $F(ab')_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055; 4,444,487; WO 88/03565; EP 0256654; EP 0120694; EP 0125023; Faoulkner et al., *Nature* 298:286, 1982; Morrison, *J. Immunol.* 123:793, 1979; Morrison et al., *Ann Rev. Immunol* 2:239, 1984).

Animal: Living multi-cellular vertebrate organisms, a category that includes, for example, mammals and birds. The term mammal includes both human and non-human mammals. Similarly, the term "subject" includes both human and veterinary subjects, such as dogs.

Conservative variants: "Conservative" amino acid substitutions are those substitutions that do not substantially affect or decrease an activity or antigenicity of the *P. ariasi* or *P. perniciosus* polypeptide. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the unsubstituted polypeptide also essentially immunoreact with the substituted polypeptide, or that an immune response can be generated against the substituted polypeptide that is similar to the immune response against the unsubstituted polypeptide. Thus, in one embodiment, non-conservative substitutions are those that reduce an activity or antigenicity.

cDNA (complementary DNA): A piece of DNA lacking internal, non-coding segments (introns) and expression control sequences. cDNA is synthesized in the laboratory by reverse transcription from messenger RNA extracted from cells.

Degenerate variant: A polynucleotide encoding a *P. ariasi* polypeptide or a *P. perniciosus* polypeptide that includes a sequence that is degenerate as a result of the genetic code. There are 20 natural amino acids, most of which are specified by more than one codon. Therefore, all degenerate nucleotide sequences are included in the disclosure as long as the amino acid sequence of the *P. ariasi* polypeptide or *P. perniciosus* polypeptide encoded by the nucleotide sequence is unchanged.

Epitope: An antigenic determinant. These are particular chemical groups or peptide sequences on a molecule that are antigenic, i.e., that elicit a specific immune response. An antibody specifically binds a particular antigenic epitope on a polypeptide. Specific, non-limiting examples of an epitope include a tetra- to penta-peptide sequence in a polypeptide, a tri- to penta-glycoside sequence in a polysaccharide. In the animal most antigens will present several or even many antigenic determinants simultaneously. Such a polypeptide may also be qualified as an immunogenic polypeptide and the epitope may be identified as described further.

Expression Control Sequences: Nucleic acid sequences that control and regulate the expression of a nucleic acid sequence, such as a heterologous nucleic acid sequence, to which it is operably linked. Expression control sequences are operably linked to a nucleic acid sequence when the expression control sequences control and regulate the transcription and, as appropriate, translation of the nucleic acid sequence. Thus expression control sequences can include appropriate promoters, enhancers, transcription terminators, polyA signals, a start codon (i.e., ATG) in front of a protein-encoding polynucleotide sequence, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac-hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. In one embodiment, the promoter is a cytomegalovirus promoter.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Also includes the cells of the subject.

Immune response: A response of a cell of the immune system, such as a B cell, T cell, or monocyte, to a stimulus. In one embodiment, the response is specific for a particular antigen (an "antigen-specific response"). The response can also be a non-specific response (not targeted specifically to salivary polypeptides) such as production of lymphokines. In one embodiment, an immune response is a T cell response, such as a CD4+ response or a CD8+ response. In another embodiment, the response is a B cell response, and results in the production of specific antibodies.

Immunogenic polypeptide: A polypeptide which comprises an allele-specific motif, an epitope or other sequence such that the polypeptide will induce an imunune response. A specific, non-limiting example of an immune response includes binding an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived.

In one embodiment, immunogenic polypeptides are identified using sequence motifs or other methods known in the art. Typically, algorithms are used to determine the "binding threshold" of polypeptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing polypeptide. Within the context of an immunogenic polypeptide, a "conserved residue" is one which appears in a significantly higher frequency than would be expected by random distribution at a particular position in a polypeptide. In one embodiment, a conserved residue is one where the MHC structure may provide a contact point with the immunogenic polypeptide.

Immunogenic composition: A composition that, when administered to a subject, induces an immune response to a Phlebotomus salivary polypeptide. In one embodiment, the immune response is a positive DTH response.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

Label: A detectable compound or composition that is conjugated directly or indirectly to another molecule to facilitate detection of that molecule. Specific, non-limiting examples of labels include fluorescent tags, enzymatic linkages, and radioactive isotopes.

Leishmaniasis: A parasitic disease spread by the bite of infected sand flies. The trypanosomatid parasite of the genus *Leishmania* is the etiological agent of a variety of disease manifestations, which are collectively known as leishmaniasis. Leishmaniasis is prevalent through out the tropical and sub-tropical regions of Africa, Asia, the Mediterranean, Southern Europe (old world), and South and Central America (new world). The old world species are transmitted by the sand fly vector *Phlebotomus* sp. Humans, wild animals and domestic animals (such as dogs) are known to be targets of these sandflies and to act as reservoir hosts or to develop leishmaniasis.

Cutaneous leishmaniasis starts as single or multiple nodules that develop into ulcers in the skin at the site of the bite. The chiclero ulcer typically appears as a notch-like loss of tissue on the ear lobe. The incubation period ranges from days to months, even a year in some cases. The sores usually last months to a few years, with most cases healing on their own. The mucocutaneous type can develop into erosive lesions in the nose, mouth, or throat and can lead to severe disfigurement. Visceral leishmaniasis often has fever occurring in a typical daily pattern, abdominal enlargement with pain, weakness, widespread swelling of lymph nodes, and weight loss, as well as superimposed infections because of a weakened immune system. Visceral leishmaniasis can result in high death rates. The onset of symptoms can be sudden, but more often tends to be insidious.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Oligonucleotide: A linear polynucleotide sequence of up to about 100 nucleotide bases in length.

Open reading frame (ORF): A nucleic acid sequence having a series of nucleotide triplets (codons), starting with a start codon and ending with a stop codon, coding for amino acids without any internal termination codons. These sequences are usually translatable into a polypeptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles or excipients: The pharmaceutically acceptable vehicles or excipients of use are conventional. *Remington's Pharmaceutical Sciences*, by E. W. Martin, Mack Publishing Co., Easton, Pa., 15th Edition (1975), describes compositions and formulations suitable for pharmaceutical delivery of the polypeptides, plasmids, viral vectors herein disclosed.

In general, the nature of the vehicle or excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., freeze-dried pastille, powder, pill, tablet, or capsule forms), conventional non-toxic solid vehicles or excipients can include, for example, pharmaceutical grades of mannitol, lactose, starch, or magnesium stearate. In addition to biologically neutral vehicles or excipients, immunogenic compositions to be administered can contain minor amounts of non-toxic auxiliary substances, such as wetting or emulsifying agents, preservatives, and pH buffering agents and the like, for example sodium acetate or sorbitan monolaurate.

*Phlebotomus ariasi* (*P. ariasi*): A species of *Phlebotomus* (sand flies) genus endogenous to the Old World, in particular to southern Europe and Mediterranean countries, more particularly to Spain and France. This sand fly is a proven vector of visceral leishmaniasis. *P. ariasi* is a member of the subgenera of *Phlebotomus Larroussius*.

*Phlebotomus perniciosus* (*P. perniciosus*): A species of *Phlebotomus* (sand flies) genus endogenous to the Old World, in particular to southern Europe, and Mediterranean countries, more particularly to France, Italy, Greece, Morocco, and Spain. This sand fly is a proven vector of the visceral leishmaniasis. *P. perniciosus* is a member of the subgenera of *Phlebotomus Larroussius*.

Polynucleotide: The term polynucleotide or nucleic acid sequence refers to a polymeric form of nucleotide at least 10 bases in length, thus including oligonucleotides and genes. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The polynucleotides can be ribonucleotides (e.g. RNA), deoxyribonucleotides (e.g. DNA, cDNA), or modified forms of either nucleotide. The term includes single- and double-stranded forms of DNA.

Polypeptide: Any chain of amino acids, regardless of length (thus encompassing oligopeptides, peptides, and proteins) or post-translational modification (e.g., glycosylation, phosphorylation, or acylation). A polypeptide encompasses also the precursor, as well as the mature polypeptide. In one embodiment, the polypeptide is a polypeptide isolated from *P. ariasi*, or encoded by a nucleic acid isolated from *P. ariasi*, such as the *P. ariasi* polypeptides disclosed herein. In another embodiment, the polypeptide is a polypeptide isolated from *P. perniciosus*, or encoded by a nucleic acid isolated from *P. perniciosus*, such as the *P. perniciosus* polypeptides disclosed herein.

Fusion proteins are encompassed by the term polypeptide. Fusion proteins have at least two domains of two different polypeptides fused together. In one embodiment, one domain is a detectable label. The two domains of a fusion protein can be genetically fused together, for instance directly or through the use of a linker oligonucleotide, thereby producing a single fusion-encoding nucleic acid molecule. The translated product of such a fusion-encoding nucleic acid molecule is a fusion protein. In one embodiment, one domain of the fusion protein is a *P. ariasi* or a *P. perniciosus* polypeptide and another domain of the fusion protein is a detectable label. The detectable label can be green fluorescent protein, a myc tag or a histidine tag, or the like.

Polypeptide Modifications: *P. ariasi* polypeptides or *P. perniciosus* polypeptides include synthetic embodiments of polypeptides described herein. In addition, analogues (non-peptide organic molecules), derivatives (chemically functionalized peptide molecules obtained starting with the disclosed polypeptide sequences) and variants (homologs) of these proteins can be utilized in the methods described herein. Each polypeptide of the disclosure is comprised of a sequence of amino acids, which may be either L- and/or D-amino acids, naturally occurring and otherwise.

Polypeptides may be modified by a variety of chemical techniques to produce derivatives having essentially the same activity as the unmodified polypeptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric, and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine, or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a *P. ariasi* polypeptide or a *P. perniciosus* polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," Klegerman & Groves (eds.), 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included are mimetics prepared using such techniques.

Probes and primers: A probe comprises an isolated polynucleotide attached to a detectable label or reporter molecule. Primers are short polynucleotides. In one embodiment, polynucleotides are 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g. by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise at least 15, 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987). Promoters may be cell-type specific or tissue specific.

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Protein Purification: The *P. ariasi* polypeptides and *P. perniciosus* polypeptides disclosed herein can be purified by any of the means known in the art. See, e.g., Guide to Protein Purification, Deutscher (ed.), *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95%, or 98% pure. Thus, in one specific, non-limiting example, a substantially purified protein is 90% free of other proteins or cellular components.

Purified: The term purified does not require absolute purity; rather, it is intended as a relative term. Thus, for example, a purified polypeptide preparation is one in which the polypeptide is more enriched than the polypeptide is in its natural environment. A polypeptide preparation is substantially purified such that the polypeptide represents, in several embodiments, at least 60%, at least 70%, at least 80%, at least 90%, at least 95%, or at least 99%, of the total polypeptide content of the preparation. The same applies for polynucleotides. The polypeptides disclosed herein can be purified by any of the means known in the art (see, e.g., *Guide to Protein Purification*, Deutscher (ed.), *Meth. Enzymol.* 185, Academic Press, San Diego, 1990; and Scopes, *Protein Purification: Principles and Practice*, Springer Verlag, New York, 1982).

Recombinant: A recombinant polynucleotide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the percentage identity between the sequences. The higher the percentage, the more similar the two sequences are. Homologs or variants of a *P. ariasi* polypeptide or a *P. perniciosus* polypeptide will possess a significant degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.*, 6:119, 1994 presents a detailed consideration of sequence alignment methods and identity calculations.

The NCBI Basic Local Aligmnent Search Tool (BLAST) (Altschul et al., *J. Mol. Biol.* 215:403, 1990) is available from several sources, including the National Center for Biotechnology Information (NCBI, Bethesda, Md.) and on the Internet, for use in connection with the sequence analysis programs blastp, blastn, blastx, tblastn, and tblastx. A description of how to determine sequence identity using this program is available on the NCBI website on the internet.

Homologs and variants of a *P. ariasi* polypeptide or a *P. perniciosus* polypeptide are typically characterized by possession of at least 75%, for example at least 80%, sequence identity counted over the full length alignment with the amino acid sequence of the *P. ariasi* polypeptide or the *P. perniciosus* polypeptide using the NCBI Blast 2.0, gapped blastp set to default parameters. The comparison between the sequences is made over the full length alignment with the amino acid sequence given in this present disclosure, employing the Blast 2 sequences function using the default BLOSUM62 matrix set to default parameters, (gap existence cost of 11, and a per residue gap cost of 1).

When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologues and, variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologues could be obtained that fall outside of the ranges provided.

Specific binding agent: An agent that binds substantially only to a defined target. Thus a *P. ariasi* specific binding agent is an agent that binds substantially to a *P. ariasi* polypeptide. Similarly, a *P. perniciosus* specific binding agent is an agent that binds substantially to a *P. perniciosus* polypeptide.

In one embodiment, the specific binding agent is a monoclonal or polyclonal antibody that specifically binds the *P. ariasi* polypeptide. In another embodiment, the specific binding agent is a monoclonal or polyclonal antibody that specifically binds the *P. perniciosus* polypeptide.

Subject: Living multi-cellular vertebrate organisms, a category that includes both human veterinary subjects, including human and non-human mammals. In one embodiment, the subject is a member of the canine family, such as a dog. In another embodiment, the subject is -continued ALLRLYNEVKLSDDVGIACLPSYSQASPGRSEVCKVLGWGQGTRRTKLQ
EADMHIQPANSCKRHYYGTGQLVTRHMLCASSRNYVSDTCGGDSGGPLL
CRDTKSPARPWTLFGITSFGDDCTVSESPGVYARVASFRKWIDSVIECD
GSCDN PRL-P4-A9 (SEQ ID NO: 3)
MNILLKVAILVSLCEIGYSWKYPRNADQTLWAWRSCQKGNYDPELVKKWM
AFEIPDDEVTHCYIKCVWTHLGMYDETSQTIRADRVKQQFKARGLSVPAE
ISHLEGSTGGSCVTIYKKTRAFLETQMPNYRIAFYGTVEESDKWFANNPE
TKPKRIKISDFCKGREAGTEGTCKHACSMYYYRLVDEDNLVIPFRKLPGI
LDSQLEQCRDQASSETGCKVGDTIYNCLNRINPEGLKKALNTLDEQSLTL
Y PRL-P4-C10 (SEQ ID NO: 5)
MKIFLCLFAAVSIQGALASQIEREYAWKNIIYEGIDQGSYNIENSIPTAF
AHDAASKKIFITIPRINQVPITLTEFDSIKYPGGSPPLSKFPGSDNIISV
YQPVIDECRRLWIVDAGQVEYKGDEQKYPKKNPAIIAYDLTKDNYPEIDR
YEIPINIAGNPLGFGGFTVDVTNPKEGCGKTFIYITNFEDNTLIVYDQEK
KDSWKISHGSFKPEHESILIHNGVDHILKLGIFGITLGDRDSEGNRPAYY
LGGSSTKLFEVNTKALKKKEGEIEPITLGDRGPHSEAIALAYDPKTKVIF
FTEYNSKKISCWNIKKPLIHDNMDKIYASPEFIFGTDISVDSESKLWFFS
NGHPPIENLQLSSDKPHIHLISVDTEKAIRGTKCEVKA PRL-P4-D6 (SEQ ID NO: 7)
MKIFMGLIAVVSLQGALAYHVEREYAWKNITFEGIDQASYNIENSIPTAF
VHDALSKKIIIAIPRLYPQVPITLTQLDTTKHPERSPPLEKPGSDKLTS
VYQPMLDECRRLWIVDVGQVEYKGDEQKYPKKNPAIIAYDLTKDNYPEID
RYEIPINIAGNQIGFGGFTVDVTNDKEGCGKTFIYITNFEDNTLIVYDQE
KKDSWKISHGSFKPEHESNFSHNGAQYKYKAGIFGITLGDRDPEGNRPAY
YLGGSSTKLFEVSTEALKKKGAKFDPVRLGDRGRHTEAIALVYDPKTKVI
FFAESDSRQISCWNTQKPLNHKNTDVIYASSKFIFGTDIQIDSDSQLWFL
SNGQPPIDNLKLTFDKPHIRLMRVDTKNSIRRTRCEVKPIKKP PRL-P4-D7 (SEQ ID NO: 9)
MFKEIIVVALAVIVAQCAPPAIPIAKQGNDFPVPIVDEKETDDFFDDRFY
PDIDDERVGARAPVGGKQTSNRGTSSQSDKVPRPQGSNRGPSSQTTDKVP
RPQWPSRGTNSQNDKVPRPQGSSGQTPPRTPGKVEQSGRTNTKDQIPRPL
TNRNPTKNPTEQARRPGNRELLIRDKTPGSQGGKQGTGNRQKLSSYKDAQ
PKLIFKSSQFNTDGQNPYLTRLFKTKKVEEVIAKGSPTDEYVLELLDGKP
DNLSLVIRTNGKTSQAVLRNPTRNRIVGRIKSYNPGPRRMSY PRL-P4-E5 (SEQ ID NO: 11)
MASIKLSTCSFVLLNLILPTISMKVISFDDRDEYLLGKPANSDDELLYST
FDFQRDPCSKSYVKCTNNNTHFILDFVDPKKRCISSIHVFSYPDRPPSFE
EKRIPSKSAIYCQKGGIGKSHCLLVFRKKEPREDALVDIRGIPADQTCSL
KERYTSGDPKKTDAYGMAYQFDRKDDWHIQRTGIKTWKRSGNEIFYRKNG
LMNHQIRYLSKFDKYTVTRELVVKNNAKKFTLEFSNFRQYRISFLDIYWF
QESQRNKPRLPYIYYNGHCLPSNKTCQLVFDTDEPITYAFVKVFSNPDHN
EPRLRHEDLGRG PRL-P4-F3 (SEQ ID NO: 13)
MVIYLTQNISRALLTLLPNPEDVRSAADVLESFTDDLKSFYPPPDDVNEE
VSETESRTKRSLIEQLKESQPLKQIRETVAETTKYLKGFLKTKPSGNQTE
SSNSTSTKTQSRKRRGLTDFIPVNSLKDAISQATSGAMKAFKPSSENKTS
SNPLDFLASLSDISRDLVQNSIKEVSGNLVSSVALIVNSKLDAIKQSIG
IINQEIDRTKKVQQYVMNALQQASNITNSIGEQLKSNNCFAQFINPKLF
EEVITCVKNKIENGLKIAEETFKNLNQALSVPSDIVSEVSKCSQNQNLNP
LTKLLCYLRVPLQLDEEKLLLPIEFARRIREITNYFATMRMDLIQCGIAT
IQSIGDKVENCAIEAILAVKDTLKG PRL-P4-G12 (SEQ ID NO: 15)
MKQFPVILLTLGLLVVKCRSERPEWKCERDFKKIDQNCFRPCTFAIYHFV
DNKFRIARKNIENYKKFLIDYNTVKPEVNDLEKHLLDCWNTIKSIEASSR
TEKCEQVNNFERCVIDKNILNYPVYFNALKKINKNTNV PRL-P4-G7 (SEQ ID NO: 17)
MINPIVLRFTFLLVILLPGKCKSAPKSCTINLPTSIPKKGEPIYLNSNGS
VFRPIGGLTQLNIGDSLSIYCPPLKKLKSVPCSRKFSLESYSCNNSSGSE
LVQTEEEECGQEGKWYNIGFPLPTNAFHTIYRTCFNKQKLTPLYSYHVING
KAVGYHVKQPRGNFRPGKGVYRKININELYKTHISRFKKVFGDKQTFFRK
PLHYLARGHLSPEVDFVFGTEQHATEFYINTAPQYQSINQGNWLRVEKHV
RGLAKALQDNLLVVTGILDILKFSNKRADTEIYLGDGIIPVPQIFWKAIF
HLRTSSAIVFVTSNNPHETTFNNICKDACEMAGFGDKQHGNQNFSNYSLG
FTICCELQDFIGNSKVVLPKDIQVKNHRKLLQLPKPKQ PRL-P6-E11 (SEQ ID NO: 19)
MNALLLCVLLSLSGIGYSWKYPRNADQTLWAYRTCQREGKDPALVSKWMN
WVLPDDPETHCYVKCVWTNLGSYDDNTGSIMINTVATQFITRGMKVPAEV
NNLSGSTSGSCSDIYKKTIGFFKSQKANIQKAYYGTKEESDNWYSKHPNV -continued KPKGTKISDFCKGREGGTEGTYKHACSMYYYRLVDEDNLVIPFRKLKIPG
IPGPKIDECRRKASSKTGCKVADALYKCLKAINGKSFENALKKLDEESSR
TY PRM-P3-A6 (SEQ ID NO: 21)
MIRILFPLFILSLGIYQVTCLMCHSCTLDGELESCEDSINETYVVKIEEK
ECKPAQSCGKVSFTANGTVRIGRGCIRSSSSWKIDCRILAKEVRDEGIAV
THCSLCDTDLCNE PRM-P3-F11 (SEQ ID NO: 23)
MLQIKHFLPFVVLFVVAHSNDYCEPKLCKFNNQVKTHIGCKNDGKFVEST
CPKPNDAQMIDMTEQRKNLFLKIHNRLRDRLARGSVSNFKSAAKMPMLKW
DNELARLAEYNVRTCKFAHDQCRSTKACPYAGQNLGQMLSSPDFLDPNYV
IKNITREWFLEYKWANQGHTDKYMTGSGKNGKAIGHFTAFLHEKSDKVGC
AVAKLTNQQYNMKQYLVACNYCYTNMLKEGIYTTGKPCSQCQGKKCDSVY
KNLCDASEKVDPIPDIFKQSRQQRSRK PRM-P5-D6 (SEQ ID NO: 25)
MIVKSFLGVFLVILLVSVTEQDRGVDGHRRTQDDHDYSELAEYDDEDPHQ
EVIDGDEEEHELSGGRRLSHEDEDDDDRHYGHRGEDRENSRGRNGGSRNR
GSEEQSYDPYSHERAPTYSESSEYDHSGDYDNSNYQQHSSTPSSYSNIDH
YIHLIQLHSVPSDLAQYADSYLQHSKNSIRYYASHAKDFEKIRPCLESVV
KYSNLLNDDLAKEYIRCQRKCYLERLNSYTSAISQYTVTTNACINNRLH PRM-P5-E9 (SEQ ID NO: 27)
MIIKLCAIAVACLLTGDGEAAPRATRFIPPAVISDLDKKSIKSDQKFSTS
IVRYGELKDNGERYTLSIKSENLHYFTRYAYNGRGAELSELLYFNNKLYT
IDDKTGIIFEVKHGGDLIPWVILSNGDGNQKNGFKAEWATVKGDKLIVGS
TGIPWFEEKTQSLNTYSLWVKEISKEGEVTNINWKSQYSKVKNAMGIPSS
VGFVWHEAVNWSPRKNLWVFMPRKCTTEYFTSQVEEKTGCNQIITANEDF
TQVKAIRIDGPVQDQAAGFSSFKFIPGTQNNDIFALKTIERNGQTATYGT
VINIEGKTLLNEKRILDDKYEGVAFFKNPEGII PRM-P5-F12 (SEQ ID NO: 29)
MHFKIIFCSLFIVLLGHMAFAESSESSSSESSSSETSEESSEEVVPSPSP
SPKHRPHFGPHHPHGGRPKPPHPPPPKPEPEPDNGSDGONQDNSNGQDNS
NGNSQNDEQDNSQSGSAKRFRQPAVNIVNLVIPFSTI PRM-P5-F2 (SEQ ID NO: 31)
MFSKIFSLAILALALSTVSSETCSNPQVKGASSYTTTDATIVSQIAFITE
FSLECSNPGAEKVSLFAEVDGRITPVAVIGDTKYQVSWNEEVKKARSGDY
NVRLYDEEGYGAVRKAQRSGEENNAKPLATVVVRHSGSYTGPWFNSEILA
SGLIAVVAYFAFATRSKILS PRM-P5-G11 (SEQ ID NO: 33)
MSNLLTIFGAICFLGVANSLQFPRNPDQTRWAEKTCLKESWAPPNLINKW
KQLEFPSTNLTYCYVKCFVMYLGVYNETTKKFNVDGIRSQFTSQGLRPPN
GLESLQKTSKGTCKDVFRMSAGLIKKYKLEFVKAFHGDSAEAAKWYIEHK
GNVKAKYQKASEFCKTQKDECRLHCRFYYYRLVDEDFQIFNRKFKIYGIS
DSQLRQCRSKASQAKGCKVAKVLKNCLDKIDSEKVKTALKTLDEISANYV

PRM-P5-H4 (SEQ ID NO: 35)
MYFTHTLNFLLLVILLIMAGFSQANPEKRPCTNCERPKLSAKTPL

PRS-P1-B11 (SEQ ID NO: 37)
MTWVILCVALLVASVVAEGGIDAEGNRTKIEKITAGAGSDGKVVYTEGGS
FPEKLEKEQKSVKKELGELPKPTNATFSPPVKVENKTEEVRNATLPVNAT
TEAPKVVNTTASTTTVKLTSTSTTTTTPKPKKPSLTISVEDDPSLLEVPV
KVQHPQTGGRLDVEEPVAQLSHENILEMPVNHRDYIVPIVVLIFAIPMIL
GLATVVIRRFRDYRLTRHYRRMDYLVDGMYNE

PRS-P1-B4 (SEQ ID NO: 39)
MKKILLFSVIFVALLITAEAIPGKRARPKAPAVTKGRDVPKPRPGQGGQV
PVEPDFPMENLRSRI

PRS-P1-E7 (SEQ ID NO: 41)
MAVKNLHKFLLVVGFVSLIHAAYSAAQHRTYLRITEQEFNSLPFDIVLQA
VVSLIILVYSILQVVGEFREIRAAVDLQAKSWETLGNIPSFYMFNHRGKS
LSGQYEDNIDTSAD

PRS-P1-G9 (SEQ ID NO: 43)
MMSRWSKSVKFVCLLLCGGFTFLTTSARAKPTLTFQLPPALTNLPPFVGI
SRFVERKMQNEQMKTYTGVRQTNESLVMIYHHDLTIAIVELGPEKSLLGC
ELIEINNDDEGAKVLKELATVNIPLEIDFREMVKLMKQCEKIDYIRKVKR
QGAPESDQTTNRQHQTGYFTGATAGLSILSGILPGTKWCGTGDIARTYHD
LGTEATMDMCCRTHDLCPVKVRSYQQRYNLTNKSIYTKSHCKCDDMLFNC
LKRTNTSASQFMGTIYFNVVQPCVLDTDRGYRFRKARTFS

-continued

```
PRS-P2-C8                              (SEQ ID NO: 45)
MKLLPIILLALTVLIVTCQAEHPGTKCRREFAIEEECINHCEYKHFGFTD
DQFRIKKHHRENFKNAMSHYGAIRKDQEGELDKLLNRCAKKAKESPATSK
RDKCYRIINYYRCVVVDNNLINYSVYVKAVTKINDSINV

PRS-P2-G8                              (SEQ ID NO: 47)
MKELVVFLTLIVLVVICHAERPSQKCRRELKTEEECILHCEYKHYRFTDD
QFRLNADQRGDFRNLMRRYGALRVDQESQLDKHLKKCANKVAKTPATSRK
DKCRKISRYYHCAVDNKLFKYNDYANAIIKYDKTINV
```

*P. perniciosus* polypeptides include polypeptides having a sequence as set forth as SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, and conservative variants thereof.

Specific, non-limiting examples of an amino acid sequence of a *P. perniciosus* polypeptide are set forth below:

```
PERL-P7-G8                             (SEQ ID NO: 49)
MKIFLCLIAVVFLQGVVGFHVEREYAWKNISYEGVDPALFNIDNIIPTGF
VHDAINKKIFIAVPRRSPQLPFTLTELDTTKHPERSPPLSKFPGSDKLIN
VYQPVIDECRRLWIADVGRVDYKGDEQKYPNQNAVLIAYDLTKENYPEIH
RYEIPSKIAGSNTIPFGGFAVDVTNPKEGCGKTFVYITNFEDNTLIVYDQ
EKKDSWKISHGSFKPEHDSTLSHDGKQYKYRVGLFGITLGDRDPEGNRPA
YYIAGSSTKLFEISTKILKEKGAKFDPVNLGNRGPHTEAVALVYDPKTKV
IFFAESDSRQVSCWNTQKPLNHKNTDVIFASAKFIYGSDISVDSESQLWF
LSTGHPPIPNLKLTFDKIPHIRLMRVDTAKAIRRTRCEVKPRKP

PERL-P6-H9                             (SEQ ID NO: 51)
MKIFLCLIAVVSLQGVLAYDIEREYAWKNISFEGIDPASYSVKNSIVTGF
AHDADSKKIFITIPRLNPVPITLTELDTTKHPEGSPPLSKFPGSDKLISV
YQPVIDECRRLWIVDAGQVEYKGDEQKIPKKNAAIIAYDLTKDNYPEIDR
YEIPNNVAGNPLGFGGFAVDVTNPKEGCGKTFVYITNFEDNTLIVYDQEK
KDSWKISHDSFKPEHESILTHNGAQHILKLGIFGITLGDLDEEGNRQAYY
LGGSSTKLFRVNTKDLKKKAGQIEFTPLGDRGSHSEALALAYDPKTKVIF
FIEYNSKRISCWNTQKSLNPDNIDVIYHSPDFIFGTDISMDSESKLWFFS
NGHPPIENVQLTFDKPHFRLISMDTKKSIHGTKCEVKP

PERL-P7-C2                             (SEQ ID NO: 53)
MFKKFILVALVVVVAQCALPAIPIARQGKDFPVPFVSEDNNPDDYFDDQY
YPDINDAGVGSKAPQGSRKPPNRGTLPPPRGDQVSSGGRTPPGRVGQGTS
PTKDKRARPQINRNPTGTVGQGGSPGTKDKRARPQINRNPTGSGTKPRDR
ELVIRDKPPSGSQGGKPGRQVRGPKEDLSRYQNAPAKLIFKSSNINTAGK
TPKRCEVV

PERL-P6-H1                             (SEQ ID NO: 55)
MTYFKISTCCLVLISLILPIICIKVIRFDDRDEYLLGKPDNTDEELLYST
FDFIKNTCANPKMKCTNNATHFVLDFSDPKKRCISSIHVFSTPDGPVNLE
EENKPRSKSSIYCQVGGIGQSYCLLVFKKKERREDALVDIRGLKTCSLKE
RYTSGDPKKTDAYGMAYKFDKNDNWSIKREGVKQWKRSGNEIFYRKNGLM
NHQIRYLSKFDKYTVTREMVVKHRAKKFTMDFSNYGQYRISFLDVYWFQE
SVKHKPKLPYIYYNGECLPSNKTCQLKTFDADEPITYAFVKVFSNPDHNE
PRLRHADLGRG

PERL-P3-E11                            (SEQ ID NO: 57)
MKLLITIGAVCVLQVVTVSSIFFPIPINIQTGTTSSSSGQPGQQVTTSIS
FSNVSNITDMVIYLTQNISRALLTRVPNPDDIKSAADILESFTGSLKYFQ
TPPDDVDQEESETKSRSKRSFTDIFKQSSPLKEIGERIEEIKKKLKGMLK
PKPQTPSGNQTDSSNTTSETQSRKKRALTDFIPMDSLKDAISKTGEVLIP
SSASANSSPLDFMSKLSDIANDLIQNSMKEISENLASSVAMYQVNSQLDA
IKQSMDIIKQEIDKTQKIQKYVKEALNQAKNATKSLGEKLKSSNCFAQFI
NPFKLFEKGITCVKNKIDNGLKIAKDTFKNLQQAMSVPSDIQSEVSKCSQ
NQQLNPIAKLLCYLRTPLQLDDEKLLLPFEFTRRIREITNYFATMRMDLI
RCGIETIQSIGDKVEDCAREAILAVKDTLKG

PERL-P7-G12                            (SEQ ID NO: 59)
MKQLVVFLALIVLIVICHAEPPSKKCRSGLVKDEECILHCEYKYYGFTDD
NFELDSDLRGHFRTAMRKHGAIRIDQERQLDKIHLKKCAQEAKKSEKCRK
IIQYYRCAVNNKLFQYNAYAKAIIALDKTINV

PERL-P3-C9                             (SEQ ID NO: 61)
MINSTVIQFIFLFVIFLPGKSKSAPKTCEINLPTSIPTKGESIYLLNGNG
SVFRPDGKLTQLNIGDSLSIYCPGQKELKRVPCSPKFSLENITCNSNVHS
ELVDTEEKCGKDGKCYNISFPLPTNTFHTIYRTCFNKQKLTPIYSYHVIN
```

-continued

```
GKAVGYHVKQPRGNFRIPGKGVYRKININELYKTHISRFKRIIGSTQTFF
RKPLHYLARGHLSPEVDFVFGNEQHATEFYINTAPQYQSINQGNWLRVEK
HVRKLAKALQDDLHVVTGIIGILKFSNKRAEREIYLGEGVIPVPQIFWKA
VFHPKTSSAIVFVSSNNPHEKTFNPMCKDVCETARFGGKQHENQNFSNHT
VGFTICCELPDFLGNSKVILPKEFQGKNYRKLLKMPGKP

PERM-P2-A10                            (SEQ ID NO: 63)
MNNLLTFFGVLCFLGFANSLRFPRDPDQTRWAEKTCLREFSRAPPSLLKK
WQQLDFPNTNLTHCFIKCFTSYLGVYNDTTKKFNVDGIKTQFKSQEIPAP
QGLETLRKTSKGTCKDIYLMTVDLVKKNKLQFAKAFHGISAEAAKWYTQH
KGNVKGKYQKASEFCKSKDDECRLHCRFYYYRLVDEDYQIFNRNLKINGI
SNAQLQQCRNKASQAKGCQVAKVLRQCLKDINPENVKATLKELDEISAK

PERL-P6-H11                            (SEQ ID NO: 65)
MLQIKHFLFFVVLLVIVHANDYCQPKLCTNGKTVKPHIGCRNNGDFDRSA
CPNDAQMVEMTQQRKELFLKIHNRLRDRFARGSVPNFKSAAKMPMLKWDN
ELAKLAEYNVRTCKFAHDQCRATTACPYAGQNLGQMLSSPDYLDPGYAIK
NITREWFLEYKWADQQRTNTFTGGPGKDGKQIGHFTAFVHEKSDKVGCAV
AKLTNRQFNMKQYLIACNYCYTNMMNEKITAQVPPF

PERS-P1-H11                            (SEQ ID NO: 67)
MIVKGLLGVFLVILLVCVTEQGVDGYHRANGDYGYSYENRHHVVNGDEEE
HEIKHTNSRKFDDDDYLFSHGYAAYDDEDDEDERQGYSRGGGGAGDSSRD
PGFYRRGSQEQSYDPHSGQTAPGYSESSEYEHSGDYDNSQNQQYSSTPSN
ANVNLIDQYLHLIQLHSIPSDLVQYAESYLTHAKNSIRYYAVHAKDFERI
RPCLESVTKYFNMLNDDLAREYVRCQRQCYLDRLNSYTTAISQYTVTTNA
CINNRLN

PERM-P2-G11                            (SEQ ID NO: 69)
MILKLCAIAVLFFLIGDGEAAIPRPTRFIPFAIISDLHRKAMHDEKNRFT
SIVKYGQLKYNGEKYTLSIRSENLHYFTKDTYKGTGADMSELIYFNDKLY
TLNDETGTIYEVKHGGELIPWITLKNDDGNQKDGFKAKWATVKGNKLWGS
AGMAFLDAKTMNIDRDALWVKEISESGHVTNKYWDSQYKKVRDAMGLVSG
FVWHEAVNWSPRKNLWVFMPRKCTNEPYTVRLDKKTGCNQIITANENFND
VRAIHINRAAADPASGFSSFKFIPNTRNNDLFAIKTIERNGQTATYGTVI
DINGKTLLPDQRILDDKYEGIAFFKDPKGIK

PERM-P5-E2                             (SEQ ID NO: 71)
MNTLLKVAVLLSLGGTGYSWQYPRNADQTLWAWRSCQKEHIGDDQALLKK
WLKFEIPDDKVTHCFIKCTWIHLGMYDEKTKTIRVDKVKQQFEGRKLPVP
AEISKLEGPTDGDCEKIYRKTKAFLDAQMKNYRIAFYGIYDGSDAWFAEH
PETKPKKTKISEFCKGREGGKEGTCKHACSMYYYRLVDEDNLVIPFRKLP
GISESDLKQCRDAASKKSGCQVADDNLRLS

PERM-P5-C11                            (SEQ ID NO: 73)
MKYFSLNFLLIVILLIVACSPQLPCLPQDSKKKPSNPRPKLSARSGLSY

PERM-P5-H8 (also referred to as        (SEQ ID NO: 75)
P2-G9)
MKKIVLFSFIFVALVISAKAIETELDDPDDATKGRDVAKAEPGQLGQVPV
VPDLNPSNTRKRRNRSRKRRRNLGKRLKKVFA PERL-P3-B3                             (SEQ ID NO: 77)
MMSRWSKSVKFVCLLLCGGFTFLTTSARAKPTLTFQLPPALTNLPPFIGI
SRFVERKMQNDQMKTYTGVRQTNDSLVMIYHHDLTIAIVELGPEKTLLGC
ELIEINNDDEGAKVLTELATVNIPLQIDFREMVKLMKQCEKIDYMRKVKR
QGASESDQTTNRQHQTGYFGLGGATAGLSILSGILPGTKWCGTGDIAKTY
HDLGTEATMDMCCRTHDLCPVKVRSYQQRYNLSNNSIYTKSPCKCDDMLF
NCLKRTNTSASQFMGTIYFNVVQVPCVLDTERGYRFRKARTFS PERM-P2-D11                            (SEQ ID NO: 79)
MKQLVVFLALIVLIVICHAKRPSRKCRSGMVKEEECILHCEYKYYGFTDD
KFQLDADQRGNFRFAMMDYGAIRMDQEGQMDEHLKKCANEAEKAPVCSKV
DKCRKIIQYYRCAVNNKLFQYNAYAKAIIALDKTINV PERM-P5-E3                             (SEQ ID NO: 81)
MKQLPVILLALVFLIAKCRSEKPEYKCRRDFKTEDKNCFLSCTFKNYHFI
DNKFRIERKNIENYKKFITDYKALKPNVSDNDLEKHLLDCWDKFQKSPEA
STRPEKCEKVNNFERCVIDKNIFDYPIYFNALKKINYITKV PERM-P2-F11                            (SEQ ID NO: 83)
MKKIVLFSVIFIALVISAKAIEDEDDDDDDDESEDRDVARAEREQQEEEP
DEPEYIPSRPRNRSKMRKWRNRNYRKYRDESRKRKRDMVLDVIRRFL
```

Homologous polypeptides having an amino acid sequence at least 75%, 80%, 85%, 90%, 95%, 98%, or 99% identical to the amino acid sequence as set forth as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, or SEQ ID NO:83 are disclosed herein.

Fragments, variants, and fusions of the *Phlebotomus* polypeptides identified above are disclosed herein and can readily be prepared by one of skill in the art using molecular techniques. In one embodiment, a fragment of a *P. ariasi* polypeptide or a *P. perniciosus* polypeptide includes at least 8, 10, 15, or 20 consecutive amino acids of a *P. ariasi* polypeptide or a *P. perniciosus* polypeptide. In another embodiment, a fragment of a *P. ariasi* polypeptide or a *P. perniciosus* polypeptide includes a specific antigenic epitope found on a full-length *P. ariasi* polypeptide or on a full-length *P. perniciosus* polypeptide.

In one embodiment, a fragment is at least 17 amino acids, at least 23 amino acids, at least 25 amino acids, or at least 30 amino acids in length from any polypeptide (including polypeptides as given in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, or SEQ ID NO:83, conservative variants thereof, and homologues thereof), or any fragment that retains at least an epitope.

One skilled in the art, given the disclosure herein, can purify a *P. ariasi* polypeptide or a *P. perniciosus* polypeptide using standard techniques for protein purification. The substantially pure polypeptide will yield a single major band on a non-reducing polyAcrylamide gel. The purity of the *P. ariasi* polypeptide or the *P. perniciosus* polypeptide can also be determined by amino-terminal amino acid sequence analysis.

Minor modifications of the *P. ariasi* polypeptide or the *P. perniciosus* polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein.

Polynucleotides encoding salivary polypeptides from sand fly species of the subgenera of *Phlebotomus Larroussius*, in particular *P. ariasi* and *P. perniciosus*, are disclosed herein. Also provided are nucleic acid sequences encoding a *P. ariasi* or a *P. perniciosus* polypeptide. Specific, non-limiting examples of *P. ariasi* nucleic acid sequences include SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, or SEQ ID NO:48, and degenerate variants thereof. Specific, non-limiting examples of *P. perniciosus* nucleic acid sequences include SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, or SEQ ID NO:84, and degenerate variants thereof. These polynucleotides include DNA, cDNA, and RNA sequences that encode a *P. ariasi* polypeptide or a *P. perniciosus* polypeptide. It is understood that all polynucleotides encoding a *P. ariasi* polypeptide or a *P. perniciosus* polypeptide are also included herein, as long as they encode a polypeptide with the recognized activity, such as the binding to an antibody that recognizes the polypeptide, the induction of an immune response to the polypeptide, an effect on survival of *Leishmania* when administered to a subject having leishmaniasis, or who undergoes a decrease in a sign or a symptom of *Leishmania* infection.

The polynucleotides of the disclosure include sequences that are degenerate as a result of the genetic code. There are 20 natural amino acids, most of which are specified by more than one codon. Therefore, all degenerate nucleotide sequences are included in the disclosure as long as the amino acid sequence of the *P. ariasi* polypeptide or the *P. perniciosus* polypeptide encoded by the nucleotide sequence is functionally unchanged.

Specific, non-limiting examples of a polynucleotide encoding a *P. ariasi* polypeptide are set forth below:

```
PRL-P4-A10                                    (SEQ ID NO: 2)
    ACTTGTCGATCACTTTTCACTCGCTCCAGACGCATTTTTGCGCTCT
TCAGCCGTGATTAGCACAAAGTGTTTTAGAATTTGGTGAAAAAATAGCA
AGATAAGGATGAAATTAGTGCCATTGTGTATTTTAGTGTGTTTTCTAATC
ATCGCGCAGCAGGTGGCTCAGAATGAAGCATCTCCCGCCAAAAGCCAAG
ACGCCATGTACGGTGATTGGAGTCGTTGGAGCTCCTGTGACGAGACTTG
CGATCAGACGAAGGTGAGATCGTGCCTAGGGGCTGTCTGTGAGCGGAAT
CGACTGATGAAGGAGCGAAAATGTCCAGGATGTGGTACAAAAGTGCGA
ATTGTACAGAAACTTCTTCAGCTCTTCGGCATGGGAGACTCCATAGAGAC
TGACTATGAAGATGACTATGGAGAGCACTGGCTAACTGATGACAGAGTC
ATTAGTTCTAGGAATGATCCTGAAAGTGCAGAAAGTGATGAATTGGGAT
CATTCTTCAGGGATTTCTTCCATTCATTCGATTTTGAGTGGAAAAATCCA
TTTAGCAATCCCCATGAGAACAATGATGTGGACTTGGAGGTGGAGGAAG
ATGAGGAAGTTGAAGAACTTCCCGAAATTAGGACTTCTAATGAGGAGGA
TTCTGTCTCTGGGGCGGATCACGTGTGTGGAGTGACCAAGAATGAGAGA
TCTTCAGGGATGATGGCAAAAACTATCGGCGGGAGGAACTCGAAGAAG
GGTCGATGGCCCTGGCAAGTGGCTCTTTATAACCAGGAATATGAGAATT
TCTTCTGCGGCGGGACTCTTATCTCAAAATACTGGGTCATAACGGCCGCT
CACTGTCTGATATCTGACTTCGGCAGTGACATCACGATCTTCTCCGGCCT
GTACGACACCGGAGATCTCGTGGAGTCGCCCTACAGCATCCACCTGGTG
CGGGATCGAGTGATTCATCCGCGCTACGACGCCGAAACCAATGACAATG
ATATCGCCCTGCTGAGGCTCTACAACGAAGTGAAATTGAGCGATGATGT
GGGTATCGCTTGTCTGCCCAGCTACTCGCAAGCCTCCCCGGGACGCAGTG
AGGTGTGCAAGGTGCTGGGCTGGGGCCAAGGGACACGTCGAACCAAACT
CCAGGAGGCCGACATGCACATCCAACCCGCCAACTCCTGCAAGCGCCAC
TACTACGGCACCGGACAACTCGTCACGCGTCACATGCTGTGCGCCTCCTC
CCGGAACTACGTCAGCGACACGTGTGGCGGTGATTCCGGTGGACCACTG
CTGTGTCGCGACACCAAATCCCCCGCCCGACCCTGGACGCTGTTCGGCAT
CACGAGCTTCGGTGACGATTGCACGGTGAGCGAGAGTCCGGGTGTTTAT
GCGCGCGTCGCCTCCTTCCGGAAGTGGATTGACTCCGTCATCGAGTGCGA
CGGCTCTTGTGACAATTAATAAACTCACAATATTATCAGTGAAAAAATA
AATTAGCAAATTTAATGCAAAAAAAAAAAAAAAAAAAAAAAAAAAAAA

PRL-P4-A9                                     (SEQ ID NO: 4)
    AAAATGAATATCTTATTGAAAGTTGCGATTTTGGTGAGCTTGTGC
GAAATTGGGTACTCTTGGAAATATCCCAGGAATGCCGATCAAACTCTCT
GGGCTTGGAGATCATGCCAAAAGGGAAACTATGACCCAGAATTAGTGAA
GAAATGGATGGCTTTTGAAATCCCAGACGACGAAGTAACTCATTGTTAC
ATTAAGTGTGTTTGGACTCATTTGGGAATGTACGATGAAACTAGCCAAA
CTATTAGAGCTGATAGAGTCAAGCAACAATTCAAGGCTCGTGGACTATC
AGTTCCTGCTGAAATAAGCCATTTAGAGGGATCTACAGGAGGATCCTGT
GTAACGATTTTACAAAAAAACTAGGGCTTTCCTTGAAACTCAAATGCCGA
ATTATCGCATTGCATTCTATGGCACTGTGGAAGAATCAGATAAGTGGTTC
GCGAATAATCCCGAAACTAAACCCAAGAGAATTAAGATTTCTGACTTCT
GCAAAGGTCGCGAAGCTGGAACGGAAGGAACTTGCAAGCATGCTTGCA
GCATGTACTACTACCGCTTAGTCGATGAGGATAATCTTGTGATTCCCTTC
```

AGGAAGTTGCCAGGAATCTTAGATTCCCAACYEGAACAATGCAGGGATC
AAGCTAGTTCGGAAACTGGATGCAAAGTTGGTGATACAATCTACAATTG
TCTTAACAGAATTAATCCGGAAGGTCTTAAAAAAGCATTGAATACACTC
GATGAACAATCATTGACGTTGTATTAGAAAGCAATAAACTTGATTAAGA
AAAACAAAAAAAAAAAAAAAAAAAAAAAAAAAAA

PRL-P4-C10 (SEQ ID NO: 6)
GTCAGTCTTTTGGAAACAAAACATGAAGATCTETCTGTGCCTTTTT
GCTGCAGTTTCCATTCAGGGAGGTTTAGCTTCTCAAATTGAAAGGGAATA
CGCGTGGAAAAACATTATTTATGAAGGGATAGATCAAGGATCCTACAAC
ATTGAAAACAGCATCCCAACTGCTTTCGCTCACGATGCAGCTAGTAAGA
AGATTTTCATCACTATTCCAAGAATAAACCAAGTACCAATAACCCTAACT
GAATTTGATAGCATCAAGTATCCGGGAGGTTCTCCTCCTCTTAGCAAATT
CCCTGGAAGCGATAACATAATTTCCGTTTATCAACCGGTCATTGACGAAT
GTCGTAGACTTTGGATTGTGGACGCTGCACAGGTGAGTACAAGGGAGA
TGAGCAGAAGTATCCCAAGAAAAATCCTGCTATCATAGCTTATGACCTG
ACTAAGGACAATTATCCTGAGATTGATCGATACGAAGATACCGATTAATA
TTGCTGGTAATCCATTAGGATTTGGAGGATTACCGTTGATGTTACCAAT
CCGAAGGAGQGATGTGGTAAAACTTTTATCTACATCACAAACTTCGAAG
ACAACACTCTGATTGTGTACGATCAGGAGAAGAAAGATTCTTGGAAGAT
CAGTCATGGTTCATTTAAACCCGAACATGAGTCGATTCTAATCCATAACG
GGGTTGATCATATTTTAAAACTGGGTATTTTCGGAATCACCCTTGGAGAT
CGGGATTCGGAGGGAAACCGTCCGGCTTACTACTTAGGAGGAAGCAGTA
CGAAGCTCTTTGAAGTCAACACAAAGGTTCTTAAGAAGAAGGAGGGTGA
AATCGAACCAATCACTCTGGGAGATCGTGGACCTCATTCCGAAGCCATT
GCTTTGGCATACGATCCCAAGACCAAAGTGATTTTCTTCACTGAATATAA
CTCTAAGAAGATCTCATGCTGGAACATCAAGAAACCCCTTATTCATGAC
AACATGGATAAGATTTATGCTAGTCCTGAATTTATTTCGGCACTGATAT
TTCGGTTGATAGTGAATCCAAATTGTGGTTCTTCTCCAACGGACATCCAC
CCATTGAGAATCTGCAGTTGAGCTCTGATAAGCCTCATATTCATCTTATA
AGCGTGGATACGGAAAAGGCAATTCGTGGCACTAAATGTGAAGTGAAG
GCCTAAGTCAAAAATATAACAATTTTACAACAAATTGTAAATTTAACGA
TGATAATAAAAAAAAAAAAAAAAAAAAAAAAAAAAA

PRL-P4-D6 (SEQ ID NO: 8)
GTCTTTTTGGAAACAAAGATGAAGATCTTTATGGGCCTAATTGCT
GTGGTTCCCTTCAGGGAGCTTTAGCTTATCACGTTGAAAGGGAGTACGC
GTGGAAGAACATTACTTTTGAAGGGATAGATCAAGCATCCTACAACATT
GAAAACAGCATCCCAACTGCATTCGTTCACGATGCACTTAGTAAGAAGAT
TATCATCGCTATTCCTAGGCTATATCCTCAGGTGCCAATTACTTTAACTC
AACTTGATACCACCAAGCATCCGGAACGTTCTCCTCCTCTCGAAAAATTC
CCTGGAAGCGATAAATTAACCTCTGTTTATCAACCGATGCTTGACGAATG
TCGTAGACTTTGGATTGTTGACGTTGGACAGGTCGAGTACAAGGGAGAT
GAGCAGAAGTACCCAAGAAAAATCCTGCTATCATAGCCTATGACCTGA
CTAAGGACAATTATCCAGAGATTGATCGATATGAGATACCGATTAATAT
TGCTGGTAATCAAATAGGATTTGGAGGATTTACCGTTGATGTTACGAATC
CGAAGGAGGGATGTGGTAAAACCTTTATCTACATCACGAACTTCGAAGA
CAACACTCTGATTGTGTACGATCAGGAGAAGAAAGATTCTTGGAAGATC
AGTCATGGTTCATTTAAACCCGAACATGAGTCTAATTTCTCCCACAACGG
TGCTCAGTACAAGTACAAAGCGGGTATTTTCGGAATCACCCTTGGAGAT
CGGGATCCGGAGGGAAATCGTCCGGCTTACTACTTAGGAGGAAGCAGTA
CGAAGCTCTTTGAAGTGAGCACTGAGGCTCTCAAGAAGAAGGGTGCAAA
GTTCGATCCTGTTCGTCTGGGTGATCGTGGGCGTCACACTGAAGCCATTG
CTCTGGTATATGATCCCAAGACTAAAGTTATTTTCTTTGCTGAATCTGAC
TCGAGACAAATCTCATGCTGGAACACCCAGAAGCCACTAAATCATAAGA
ATACTGATGTAATTTATGCGAGTTCCAAATTTATTTTCGGCACCGACATT
CAAATTGACAGTGACTCCCAATTGTGGTTCTTATCCAACGGACAACCCCC
CATTGATAATCTCAAATTGACTTTTGATAAGCCCCATATTCGTCTTATGA
GGGTAGATACGAAAAATTCAATTCGTAGGACTAGATGTGAAGTGAAGCC
CATCAAGAAGCCATAAGACACTCTATTAAAAGATGTAACAATTTCCCCAA
AAAAAGAAATTGTAAATTTACGATGATAATAAAAAAATTTTATGCTTGT
GAAAAAAAAAAAAAAAAAAAAA

PRL-P4-D7 (SEQ ID NO: 10)
ATTCAGTCATAAACCTGGGGTAATGTTTAAGGAAATTATCGTAGT
GGCTCTAGCCGTGATCGTGGCACAATGTGCTCCTCCTGCAATTCCAATTG
CAAAACAGGGAAACGATTTCCCTGTCCCAATTGTTGATGAAAAGAAC
GGATGATTTCTTTGACGATCGATTCTATCCGGACATGATGATGAGCGTG
TAGGTGCTAGGGCTCCGGTGGGTGGCAAACAGACATCTAATAGAGGAAC
CAGTTCTCCAGAGTGATAAGGTTCCTCGTCCTCAAGGGTCAATAGAGGG
CCTAGCTCTCAGACTACTGACAAGGTTCCCCGTCCTCAATGGCCCATAG
AGGAACCAATTCTCAGAATGACAAGGTTCCTCGTCCTCAAGGGTCTAGT
GGACAAACTCCACCTAGAACGCCTGGAAAGGTTGAACAAAGTGGAAGG
ACCAACACAAAGGACCAAATACCTCGTCCACTGACTAACAGAAACCCAA
TCATTAGGGATAAAACCCCAGGGAGTCAAGGTGGAAAACAGGGAACAG
GCAATAGGCAGAAACTGTCGAGTTATAAAGACGCTCAGCCGAAGTTGAT
TTTCAAATCGAGTCAATTCAATACTGATGGCCAAAATCCATATTTAACGA
GGTTGTTCAAGACGAAGAAAGTCGAAGAAGTTATAGCTAAAGGAAGTCC
CACTGATGAATATGTCCTGGAGCTTTTGGATGGAAAGCCAGATAATCTG

PRL-P4-E5 (SEQ ID NO: 12)
TAACGCTCAAGCTTTTGTCTTCAATATGGCTTCCATCAAGCTCAGT
ACTTGCTCTTTCGTTTTGCTAAACCTCATTCTACCAACAATCTCTATGAA
AGTTATCAGTTTCGACGATAGAGATGAGTATCTACTTGGTAAACCTGCAA
ATTCTGACGATGAACTTCTCTATfCAACCTTTTGACTTCCAGAGAGATCC
CTGTTCTAAGTCTTACGTGAAGTGCACCAACAACAACACCCACTTTATTC
TGGATTTCGTTGATCCGAAGAAGAGATGCATCTCTTCAATTCACGTTTTC
TCCTACCCCGATAGACTCCCAGCTTTGAGGAGAAGAGGATTCCCTCGAA
GAGTGCAATTTACTGCCAAAAGGGGGCATTGGGAAGAGTCACTGTTTGC
TGGTGTTCAGGAAGAAGGAACCTCGAGAGGACGCACTGGTTGATATCCGG
GGAATCCCCGCTGATCAAACATGCTCTCCCTCAAGGAGCGCTACACATCGG
GAGATCTAAGACAAACCGATGCTTACGGAATGGCCTATCAGTTTGATAG
AAAAGATGATTGGCACATTCAAAGAACAGGTATCAAGACATGGAAAAG
ATCAGGAAACGAGATCTTCTACCGTAAGAATGGTTTAATGAACCATCAA
ATAAGGTACTTGACCAAGTTCGACAAATACACGGTTACCAGAGAATTGG
TGGTGAAGAACAACGCTAAGAAATTCACCTTGGAATTTTCAAACTTCCGT
CAATACCGAATCAGTTTCTTGGACATCTACTGGTTCCAGGAGTCTCAGAG
GAATAAACCCAGATTACCTTATATTTACTACAACGGTCATTGCTTGCCTA
GCAACAAGACATGCCAGTTGGTCTTCGACACTGATGAGCCTATTACTTAT
GCTTTTGTGAAAGTGTTTAGTAATCCGGATCACAATGAACCACGACTAA
GACATGAAGATCTAGGACGAGGGTAAGAATGGACTAGTCCGGGGTTGA
AAAATCGCCTAAAATATGGGGAATCTATTATTGAAAAAAAAAAAAAAAA
AAAAAAAAAAAAAA

PRL-P4-F3 (SEQ ID NO: 14)
ATGTATCAAACATCACGGATATGGTGATTTATCTCACGCAGAATA
TCAGTAGAGCTCTTCTCACGCTTCTACCAAATCCTGAAGATGTCCGATCA
GCAGCGGATTCTCTAGAAAGTTTTACAGACGACCTCAAGTCTTTCTACCC
ACCTCCTGATGATGTGAATGAAGAGGTATCAGAGACAGAGTCAAGAACT
AAGAGGATCATTGATTGAGCAACTCAAAGAGTCGCAACCTCTAAAACAAA
TCAGAGAAACAGTTGCTGAGACAACCAAGTACCTAAGGGATTCTTAAA
AACGAAACCTTCTGGAAATCAACCGGAGAGTTCTAACTCAACAAGTACG
AAGACTCAGTCAAGAAAGAGACGTGGATTAACTGATTTTATACCAGTGA
ATTCTCTAAAGGATGCAATTTCACAAGCAACTTCAGGTGCCATGAAAGC
GTTCAAACCTTCAAGTGAAAATAAAACAAGGTTCAAATCCTGTAGATTTCC
TCGCAAGCCTCTCAGATATTCCAGAGATCTTGTACAAAAATTCAATTAAG
GAAGTCTCTGGCAATTTAGTTTCAAGCGTTGCTTTATACCAAGTCAACTC
AAAGTTAGATGCCATTAAACAATCCATTGGTATCATAAATCAAGAAATT
GATAGGACCAAAAAAGTTCAGCAATACGTCATGAATGCTCTTCAACAAG
CCAGCAATATTACTAACTCGGAGACAACTCAAGTCCAACAACTG
TTTCGCACAATTTATAAACCCATTCAAACTTTTCGAAGAAGTAATAACTT
GTGTGAAAAATAAAATCGAAAATGGATTGAAAATTGCGGAAGAGACATT
TAAAAATTTAAATCAGGCTTTAAGTGTGCCCTCAGATATTGTAAGTGAAG
TGTCCAAATGTTCCCAAAACCAGAACTTGAATCCCTTGACGAAACTTCTG
TGCTACTTGAGGGTACCCCTGCAATTGGATGAGGAGAAACTGCTGCTTCC
TATTGAATTTGCGAGGCGAATTAGAGAAATAACCAACTATTTTGCCACC
ATGAGAATGGACCTCATTCAATGTGGCATAGCTATTCAATCAATCG
GAGACAAGGTTGAGAATTGTGCAATAGAAGCAATATTGGCTGTAAAGGA
CACTTTGAAGGGATAAAGTCCGTATTTTATGCTGTCCAATTGGGCTAACC
CAATCATTGATATACCGAATTGTGTATGTATATTGAGAAAATGAATAAAT
GCTTCAAATGAAAAAAAAAAAAAAAAAAA

PRL-P4-G12 (SEQ ID NO: 16)
ACATACGATTCCTAACCAACCATGAAGCAGTTCCCAGTGATCCTT
TTGACCTTAGGCCTTTTGGTCGTGAAATGCCGATCAGAACGGCCGGAAT
GGAAATGTGAAAGAGACTTCAAGAAAATCGACCAAAATTGCTTTCGTCC
TTGTACATTTGCAATTTACCACTTTGTTGATAACAAGTTCAGGATTGCCA
GGAAGAATATTGAAAACTACAAGAAGTTCTTAATTGACTATAACACCGT
GAAGCCCGAAGTTAATGATTTGGAAAAACACCTGTTAGATTGTTGGAAT
ACAATCAAATCCATTGAAGCATCATCCAGGACGGAAAAATGTGAACAAG
TTAACAACTTTGAACGATGTGTTATTGACAAGAACATTCTTAATTATCCT
GTTTACTTCAATGCTTTGAAGAAATAAATAAGAATACAAATGTTTAATT
AAATAAGATGTGAAATATTGCAGTGCACAAATATAAAAAAAAAAAAA
AAAAAAAAAAAAAAAAAAAAAAAAAAAAAAAAAA

PRL-P4-G7 (SEQ ID NO: 18)
AGAAGTTATTTACACCTGTGCAATGATAAACCCAATAGTGCTGAG
ATTTACTTTTCTCTTGGTGATTTTGTTGCCTGGCAAATGTAAAAGTGCCC
CAAAGTCTTGCACCATTAATCTTCCCACCAGCATTCCCAAGAAAGGTGA
ACCGATTTACCTCAACAGTAATGGATCAG3TTTCCGACCTATTGGAGGTT
TAACTCAACTCAACATTGGGGACTCCCTCTCCATCTACTGTCCACCACTG
AAGAAGCTCAAGAGTGTTCCTTGCAGTCGAAAATTCTCCCTTGAGAGCT
ACTCTTGCAACAACAGCTCTCAGAGTGAACTCGTGCAGACGGAGGAGGA
GTGCGGACAAGAGGGGAAATGGTACAACATTGGCTTTCCATTGCCCACA

-continued

AATGCCTTCCACACAATCTACAGAACTTGCTTCAATAAGCAGAAACTAA
CACCAATTTACTCTTATCACGTCATCAATGGAAAGGCCGTTGGATATCAC
GTGAAGCAGCCGCGAGGAAACTTCCGACCAGGAAAAGGTGTCTACAGG
AAAATCAACATCAATGAGCTGTACAAGACGCACATTTCGCGCTTCAAGA
AAGTCTTCGGTGACAAACAGACATTCTTCCGGAAGCCACTGCACTACCT
GGCTCGCGGACATCTCTCCCCTGAAGTGGACTTTGTCTCGGCACCGAAC
AACACGCCACTGAGTTCTACATCAACACCGCCCCCCAGTATCAGTCCATC
AACCAGGGAAATTGGCTGCGAGTTGAAAAACACGTGCGCGGTCTGGCCA
AGGCGCTCCAGGACAATCTCCTCGTCGTCACTGGCATTTTGGACATCCTA
AAGTTCTCAAACAAACGAGCCGACACAGAAATCTACTTGGGCGACGGAA
TAATTCCTGTTCCGCAAATATTCTGGAAGGCAATCTTCCACCTCAGAACA
TCTTCCGCCATTGTCTTTGTCACCTCCAACAACCCTCACGAGACGACCTT
CAACAATATCTGCAAGGACGCGTGTGAAATGGCAGGATTCGGAGACAA
CAACATGGAAATCAAAATTTTTCCAACTACTCCTTGGGATTCACCATCTG
TTGCGAACTACAGGACTTCATTGGGAACTCGAAAGTTGTTCTTCCAAAGG
ATATTCAAGTCAAAAACCACCGCAAACTTCTTCAGTTGCCAAAACCGAA
GCAATAAACTTTAATTTTGGTCTTGCAAAGTGTGAGTATATTTTAAATAA
ACAGCAAATCAAAAAAAAAAAAAAAAAAAAAAAAA

PRL-P6-E11    (SEQ ID NO: 20)
AGTCTCTCCCAGGGTTTTATTGTGGAAAATGAACGCTTTATTGCTT
TGTGTTTTGTTGAGTTTAAGTGGAATAGGGTACTCTTGGAAATACCCTAG
GAATGCCGATCAAACTCTCTGGGCTTACAGAACGTGCCAAAGAGAAGGG
AAAGATCCGGCATTAGTATCCAAGTGGATGAATTGGGTGTTACCAGATG
ATCCGGAAACTCACTGCTACGTTAAGTGCGTTTGGACCAATTTAGGATCC
TACGATGATAACACCGGTTCCATTATGATTAACACAGTGGCTACACAATT
TATAACACGCGGCATGAAAGTCCCAGCCGAAGTAAATAATTTAAGTGGG
TCGACAAGTGGATCTTGTTCAGATATTTACAAGAAAACCATTGGGTTCTT
CAAAAGTCAAAGGCGAACATACAGAAAGCGTATTACGGAACTAAGGA
AGAGTCAGATAACTGGTATTCGAAACATCCAAATGTAAACTCCGAAAGGA
ACGAAGATTTCTGACTTCTGCAAAGGTCGCGAAGGTGGAACGGAAGGAA
CTTACAAGCATGCTTGCAGCATGTACTACTACCGCTTAGTCGATGAGGAT
AATCTTGTGATTCCGTTCAGGAAGTTGAAAATTCCGGGAATTCCAGGACC
CAAAATAGATGAGTGTAGGAGGAGGCTAGCTCGAAAACTGGATGCAA
AGTTGCCGATGCACTATACAAATGTCTTAAGGCTATAAACGGTAAAGT
TTTGAAAATGCTTTAAAGAAGTTGGACGAAGAATCATCCAGAACTTATT
AAAATAAAAGAAACTTGAGTTGCTAAAAAAAAAAAAAAAAAAAAAA
AAAAA

PRM-P3-A6    (SEQ ID NO: 22)
ATATCTAGAGGAAAATATTAAGTGAAAAGTGAAATGATTAGGATTC
TGTTTCCTCTCTTTATTCTTAGTCTTGGAATTTATCAAGTAACTTGCTT
ATGTGCCACTCATGTACTCTTGATGGGGAGCTTGAGTCATGTGAAGATTC
TATCAATGAGACTTATGTAGTTAAGATTGAGGAAAAGGAGTGCAAACCT
GCGCAATCTTGCGGAAAAGTCTCATTTACTGCAATGGAACAGTTCGAA
TCGGAAGAGGATGTATTCGCTCAAGCAGTAGTTGGAAATCGATTGCAG
AATACTTGCAAAGGAAGTTAGAGATGAAGGCATTGCGGTAACACACTGT
TCCTTATGCGACACGGACTTGTGCAATGAATAAATAAAATTGTGAAGAA
AAAAGTATTGTAACTGTTACTGGAAAAACAATTTCAGAAATATCCACAA
TAAAAAGAGAGCATTTCGCTGTAAAAAAAAAAAAAAAAAAAAAAAAAA
AAAA

PRM-P3-F11    (SEQ ID NO: 24)
TCCAGTTAATATTCCGACATGTTGCAAATTAAACACTTCTTGTTCT
TTGTGGTGTTGTTCGTTGTCGCTCACTCCAATGATTATTGTGAGCCGAAA
TTGTGCAAATTTAACAACCAAGTGAAGACTCACATTGGATGCAAGAATG
ATGGAAAGTTCGTGGAAAGCACTTGCCCAAAACCAAATGATGCTCAAAT
GATTGATATGACTGAACAGAGGAAGAATCTCTTTCTCAAGATTCACAAT
CGCCTTCGCGATAGGCTCGCTCGTGGTTCTGTGTCTTATTGCAGTCAGC
CGCCAAGATGCCAATGCTGAAATGGGACAATGAATTGGCCAGGTTGGCA
GAATACAATGTGAGAACGTGCAAATTTGCTCACGATCAGTGTCGCTCAA
CCAAGGCTTGTCCTTATGCTGGCCAGAACTTGGGCCAAATGTTGTCTTCT
CCAGATTTCTTGGACCCCAACTATGTCATCAAGAATATCACTAGGGAGTG
GTTCTTGGAGTATAAGTGGCAAATCAAGGACATACTGATAAATATATG
ACAGGATCTGGTAAGAATGGCAAAGCAATTGGTCACTTTACTGCCTTCAT
CCATGAGAAAGCGACAAGGTTGGATGCGCTGTTGCTAAATTAACCAAC
CAGCAGTACAACATGAACAGTACCTCGTGGCCTGCACTACTGCTACA
CGAATATGCTAAAGGAAGGGATCTACACGACAGGAAAGCCTTGTTCTCA
GTGCCAGGGAAAGAAGTGTGATTCCGTCTACAAGAACTTATGCGATCG
AGTGAGAAAGTCGATCCCATCCCAGACATCTTTAAGCAATCGAGACAAC
AGAGGAGCAGGAAATAATTCTCTGCTTTCCCATTTGGTATAAAATGTTAA
ATTTATTGTTTTCCCATCTATTGGGTGAATTGGCGAAAAAGGTGAAGATG
AAAAAAGGTATAAATAAGAGATAAACAGAAACTGAGATATCTGA
AAAAAAAAAAAAAAAAAAAAAAAAAAAAAAAAAAAAAAAAAAAA
AAAACCCAAAAAAAAAAAAAAAAAAAAAAAAAAA

PRM-P5-D6    (SEQ ID NO: 26)
TCAGTTTCACTTTGACCATCGATGGTGCAATTACTTCAATTCAATT
TACGAAATCACTTTGATTGAGAAACGATGATCGTGAAGAGTTTCCTTGG
GGTGTTTCTTGTGATCTTGCTCGTGTCCGTGACAGAACAGGATCGTGGAG

-continued

TAGACGGACACAGGAGGACTCAAGATGACCATGATTACAGCGAATTGGC
GGAATATGACGACGAAGATCCTCATCAAGAGGTAATTGACGGTGATGAG
GAGGAACATGAGTTGTCCGGAGGACGTCGACTATCCCACGAAGACGAAG
ACGACGACGACAGACACTATGGCCATCGTGGAGAGGATCGAGAGAATTC
TCGAGGACAGAAATGGTGGATCTCGTAATCGTGGTAGTGAGGAACAATCA
TACGATCCCTACAGCCACGAGAGAGCTCCTACCTACTCAGAATCCAGTG
AATACGACCACAGCGGTGACTACGACAATTCCAACTACCAGCAACATTC
CTCCACTCCCTCCTCCTACAGCAACATCGATCACTATCTCCATCTCATCC
AATTGCACAGCGTCCCCAGTGATTTAGCCCAGTACGCCGATTCCTACCTT
CAACACTCCAAGAACTCCATCAGATACTACGCTTCGCATGCCAAAGACT
TTGAGAAGATTCGACCCTGTCTGGAGAGCGTCGTGAAGTACTCCAATCTC
CTCAATGACGATCTTGCCAAGGAGTACATCAGATGCCAACGAAAGTGTT
ACCTTGAACGTCTCAATAGCTACACATCGGCTATCTCTCAGTACACAGTC
ACCACAAATGCCTGCATAAACAACCGATTGCATTAAAGCTGAGGATTAT
CTTGTGAAATATTTATTTGAATCGATCAGTGAAAATAAATTTCCAATAGC
AAAAAAAAAAAAACAAAAAAAAAAAAAAAA

PRM-P5-E9    (SEQ ID NO: 28)
AAAGTATTCAGTTGTGAGAAATCTTTCCAAATACACATCATGATT
ATCAAATTGTGCGCTATTGCTGTTGCTTGTCTCCTCACTGGAGATGGAGA
AGCAGCTCCCAGAGCAACAAGATTCATCCCTTTCGCTGTTATCTCCGACT
TGGACAAGAAGTTCCATTAAATCCGATCAGAAGAGTTTCACCAGCATCGT
GAGATATGGCGAATTGAAGGACAATGGAGAGAGATATACGT1ATCCATC
AAGAGTGAAAATCTTCACTACTTCACGCGATACGCTTACAATGGACGCG
GAGCCGAATTATCTGAATTGTTGTACTTCAACAACAAACTCTACACCATT
GATGACAAAACAGGAATTATCTTTGAGGTGAAACATGGTGGGCTATCTCA
TTCCATGGGTGATCCTGTCGAATGGCGATGGAAATCAAAAGAATGGCTT
TAAAGCCGAATGGGCGACAGTTAAGGGTGACAAGTTGATTGTCGGATCA
ACAGGAATCCCCTGGTTTGAGGAGAAAACCCAGTCTCTTAACACCTACA
GCCTTTGGTGAAAGAGATCAGCAAGGAAGGCGAAGTCACCAACATCA
ATTGGAAGAGTCAATACAGCAAAGTGAAGAATGCAATGGGAATTCCTTC
CTCTGTGGGATTCGTCTGGCATGAGGCTGTAAATTGGTCACCGAGGAAG
AATCTATGGGTCTTCATGCCCAGAAAATGTACAACTGAATATTTCACCAG
TCAAGTGGAAGAGAAAACTGGATGCAATCAGATTATCACGGCTAATGAA
GATTTCACTCAAGTGAAAGCAATTAGGATGCTGATGGACCTGTTCAGGATC
AAGCTGCTGGATTCTCCTCCTTTAAGTTCATCCCAGGCACTCAAACAAT
GATATCTTCGCACTGAAGACTATCGAGAGGAACGGCCAAACAGCCACTT
ACGGGACAGTAATTAACATCGAAGGGAGACTATGTTGAACGAAAAACG
AATTCTCGATGATAAATACGAAGGAGTTGCATTTTTCAAGAATCCCGAA
GGCATTATATAAAATAATAATGATGGAGTGAAAAACAAATTGAAATAAA
ATGCTAAAGCTCATAAAATTAAAAAAAAAAAAAAAAAAAAAAAAAAA
AAAAAAAAAAAAAAAAAAAAAAAAAAAAAAAAA

PRM-P5-F12    (SEQ ID NO: 30)
ATCAATTGTTATTGAAATAATCTTCAAGATGCATTTCAAGATTATC
TTCTTCTCCCTCTTCATTGTCCTGCTGGGACATATGCGGTTTGCTGAATC
TTCTGAGTCATCATCTTCAGATCGTCGTCTTCAGAAACATCTGAAGAGT
CATCTGAAGAAGTTGTTCCATCCCCTTCTCCCTCACCTAAGCATCGGCCG
CATTTTGGTCCCCATCACCCACATGGAGGCCGACCTAAGCCTCCCCATCC
GCCGCCACCGAAACCTGAGCCGGAGCCAGATAATGGCTCAGATGGTGCA
ATCAGGATAATTCAAATGGTCAGGATAACTCTAATGGAAACTCTCAGAA
TGATGAACAGGATAACTCTCAATCGGGATCCGCTAAGCGATTCAGACAAC
CTGCAGTGAATATTGTTAATCTTGTGATTCCTTTTTCTACGATTTAACTT
TCCTTTTGTGTACTTTAATCACTTTAATGCACGTAATAATAAAAAATACT
TTCAGCAAAAAAAAAAAAAAAAAAAAAAAAAAAAA

PRM-P5-F2    (SEQ ID NO: 32)
TTTCTCAATTTGTGTGTGATTGCTCTAGACGTGGCCGGTGAATTTTC
CCAAAATGTTTTCCAAAATCTTCTTTGGCTATCCTCGCTCTCGCCTTG
TCCACTGTGTCCAGTGAGACTTGCAGTAATCCTCAAGTGAAGGCGCTTC
CTCCTACACAACCACGGATCAACGATAGTCAGCCAAATTGCCTTCATC
ACTGAATTCTCACTGGAGTGCTCGAATCCCGGAGCTGAGAAGGTCTCCCT
GTTCGCCGAAGTTGACGGACGGATCACTCCAGTTGCGGTAATTGGAGAT
ACTAAATATCAGGTGAGCTGGAATGAGGAGGTCAAGAAGGCTCGCAGTG
GAGATTACAATGTAAGACTGTACGACGAGGAGCGATACGGAGCTGTGCG
CAAAGCCCAGAGATCAGGAGAGGAGAACAATGCGAAGCCACTGGCTAC
AGTTGTTGTTCGCCATTCCGGATCCTACTACTGGCCCTTGGTTCAATTCTG
AAATCTTAGCCTCCGGTCTCATCGCCGTCGTAGCATATTTTGCTTTCGCC
ACCAAGACAAATTCCTGTCGTAGAGACGCATCAATAATTTCACAAAAA
TGTAGCCAGAAGGCTGTTCTTGGCACTCAGACTGTTTCTGTGAAATAGAA
CAACATATCAAAAAAAAAAAAAAAAAAAAAAAA

PRM-P5-G11    (SEQ ID NO: 34)
GTTTCTTATACATCACTTTGAAGCAGCAATGAGTAACTTGCTAACT
ATCTTTGGGCAATTTGTTTCTTGGGCGTTGCCAACTCTCTGCAATTCCC
TCGGAACCCACAACCAAACCAGATGGGCAGAAAAGACATGTTTAAAAGAA
TCTTGGGCACCACCTAATCTGATAACAAGTGGAAGCAATTGGAATTTC
CCAGTACCAATCTCACCTACTGCTACGTGAAGTGCTTTGTTATGTATTTA
GGAGTCTACAACGAGACGACCAAGAAATTCAACGTAGACGGTATCAGAT
CCCAATTTACAAGTCAAGGACTTCGTCCACCTAACGGTCTAGAGAGCCT

-continued

ACAAAAGACATCTAAAGGAACCTGCAAGGATGTCTTCCGAATGTCCGCT
G6CCTAATCAAGAAGTACAAATTGGAATTCGTAAAAGCTTTCCATGGAG
ATTCTGCCGAAGCTGCGAAGTGGTACATCGAACATAAAGGAAATGTTAA
GGCAAAGTATCAGAAAGCTTCGGAATTCTGCAAAACTCAGAAGGATGAG
TGTAGGCTGCATTGTCGTTTCTACTACTACCGCTTAGTTGACGAAGACTT
CCAAATATTCAATAGAAAATTCAAGATCTACGGCATTTCGGACTCACAG
CTACGGCAGTGTAGGAGTAAAGCCAGTCAAGCTAAGGGTTGCAAGGTTG
CCAAAGTCCTTAAAAATTGCCTCGACAAGATTGATTCTGAGAAAGTGAA
AACCGCTCTTAAGACTTTGGATGAGATATCAGCAAATTACGTTTAACAGT
AATCTCCAAGTTAGCCCCATCAGCCTAATTTAGCGCCACCTTTAAATCAA
CCCCCAGCTAATTTCTCGAACGTTAGAAAAAGGTGTTTAACTTACGGGTG
ATTGAGTGTAAGTAATTTAGCGGCTGTGGAGATGAAATGACTATTAAAT
CGTGCACAATGGGGCAAAAAAAAAAAAAAAAAAAAAAAAAAA

PRM-P5-H4 (SEQ ID NO: 36)

ACAATTCATATTTCCTTTAGTGAAGTTGTTGAAAATCAAGCAAGAT
GTACTTTACCCATACCCTCAATTTTCTTCTTCTTGTAATTCTATTAATAA
TGGCTGGTTTTEICCCAGGCAAATCCCGAGAAAAGGCCCTGCACAAACTG
TGAGCGTCCCAAGTTATCGGCTAAAACTCCTTTGTAACCCTTTTAAATCA
TATAATCGGTGATTAAAGATTTACCAGCAGAGCTACCGCAATGTGAAAT
CGAAAAATTATACCTACCTACAGAAAAACTAAAATGTAATAAGAATTAG
AAAAAATAAAAATGATCCAAGAACAAAAAAAAAAAAAAAAAAAAAA
AAAAAA

PRS-P1-B11 (SEQ ID NO: 38)

ATCGCGATTCTGTTGCAACGTCACAGAGTACTTCCTTCTTTTCCTT
TCGGTTTCCTATCATTTCATTTGTTATCTCGCACCCAAATGACGTGGGTG
ATTCTTTGTGTCGCCCTCCTGGTTGCTTCCGTTGTCGCGGAGGGCGGAAT
CGATGCGGAGGGGAATCGCACGAAAATCGAGAAGATAACCGCGGGTGC
AGGAAGTGATGGCAAGGTGGTCTACACAGAGGGTGGAAGCTTCCCGGA
GAAGCTAGAGAAGGAGCAGAAGAGCGTGAAGAAGGAGCTTGGAGAATT
GCCAAAGCCCACAAATGCCACATTTCACCTCCCGTGAAGGTGGAGAAT
AAGACGGAGGAGGTGAGGAATGCTACACTGCCGGTGAATGCCACAACT
GAGGCCCCTAAGGTGGTCAATACGACAGCCAGCACCACCACGGTGAAGC
TAACATCCACCAGCACCACAACAACTACTCCCAAGCCCAAGAAGCCCAG
CCTCACGATTAGCGTGGAGGACGATCCGAGCCTCCTGGAGGTGCCAGTC
AAGGTGCAGCATCCACAGACCGGAGGACGACTGGATGTGGAGGAGCCT
GTGGCTCAGCTGTCGCATGAGAACATCCTGGAGATGCCCGTGAATCACCG
GGACTACATTGTTCCCATTGTGGTGCTTATCTTTGCCATTCCCATGATCC
TGGGACTCGCCACTGTTGTCATCCGACGTTTCAGGGACTACCGGCTCACT
CGCCACTACCGCCGGATGGACTACCTCGTGGATGGAATGTATAATGAGT
AGTTTCCGGCTCGCACTAACCGCCCAAGCAATAATCTAATTAATGCTTAA
TCGTTTTATACTATGTAAATAAATGTACATTTTAATAATAAAAAAAAAAA
AAAAAAAAAAAAAAAAA

PRS-P1-B4 (SEQ ID NO: 40)

GTCAGTTTGTTGAAAGTTGGGAAAATGAAGAAAATTCTGCTATT
CAGTGTTATATTCGTGCTTTGTTGATCACTGCCGAAGCCATTCCGGGAA
AACGGGCAAGACCGAAAGCTCCCGCGGTCACTAAAGGTCGGGATGTTCC
AAAACCAAGACCTGGTCAAGGAGGACAAGTGCCAGTTGAACCAGATTTT
CCTATGGAAAACTTAAGAAGTAGAATTTAGTAGATCTTCAGCTTTCTCGG
CCCCTTTAATAAAATTCGTCTACTGATAAAAAAAAAAAAAAAAAAAAAA
AAAAAAAAAA

PRS-P1-E7 (SEQ ID NO: 42)

ATATATCTATCGATTTCTCGTGTTTTGATTTGCTTAGGTGGCCCCA
TTTTTCCAAGAAAATTCCTGAAATGGCAGTTAAAAATCTTCACAAATTCC
TCCTGGTCGTGGGATTCGTGTCCCTGATCCATGCGGCTTATTCGGCAGCA
CAGCACAGAACGTACCTGAGAATCACGGAGCAGGAGTTTAATTCTCTCC
CATTTGACATTGTGCTCCAAGCTGTGGTGAGTCTGATCATTCTGGTGTAC

-continued

AGCATTCTGCAGGTTGTTGGGGAGTTCCGGGAGATTCGAGCAGCTGTGG
ACTTGCAAGCGAAATCATGGGAGACTTTGGGTAACATCCCCTCCTTCTAC
ATGTTCAATCACCGTGGGAAGAGCCTATCCGGCCAGTATGAGGATAACA
TTGACACGAGTGCCGATTGAATGCCCGGAAGAAGCCTTCCCGTAAATCT
ATTTGAATGTAAGGAATCCGATTAATTGAATTAACACCAAAGGAGAGCT
GAGGGAAAAAAAAAAAAAAAAAAAAAAAAAAAAAAAAAAAAAAAA

PRS-P1-G9 (SEQ ID NO: 44)

CACGAATTAGAAAACGGTCCCAGTGATTCTCTCGGTGGCTGATTT
ATAAGAGAATGTGAAGAGTTGAGGATGATGTCTCGCTGGAGCAAAAGTG
TGAAATTTGTGTGCCTCCTCCTGTGTGGCGGATTCACGTTTCTCACAACA
TCAGCACGTGCCAAACCCACACTGACCTTTCAGCTACCGCCCGCACTCAC
GAACCTACCCCCCTTCGTGGGCATCTCACGATTCGTCGAACGCAAAATGC
AGAATGAGCAGATGAAGACCTACACTGGCGTTCGGCAGACGAATGAGTC
TCTCGTGATGATCTACCACCATGATCTGACGATCGCCATCGTGGAATTGG
GACCAGAGAAGAGTCTCTTGGGTTGTGAATTGATAGAAATTAACAACGA
TGACGAAGGCGCCAAAGTGCTGAAAGAACTGGCCACGGTGAATATACCA
CTGGAGATCGACTTCCGGGAGATGGTGAAGCTCATGAAGCAGTGCGAGA
AGATCGATTACATACGGAAAGTGAAACGCCAAGGAGCACCAGAGAGTG
ACCAGACGACAAATCGTCAACACCAGACGGGCTACTTCACGGGCGCCAC
TGCCGGCCTGAGTATCCTCAGTGGCATCCTTCCCGGCACCAAGTGGTGTG
GCACAGGAGACATCGCCAGGACATATCACGATCTCGGCACAGAGGCTAC
CATGGACATGTGCTGTCGCACTCACGATCTCTGTCCAGTGAAAGTGCGCT
CATATCAGCAACGCTACAATCTCACCAATAAGTCAATCTACACAAAATC
TCACTGTAAATGTGATGACATGCTGTTCAATTGCCTCAAGAGGACCAAC
ACGTCAGCCTCGCAATTCATGGGGACCATCTACTTCAACGTGGTCCAAGT
GCCATGTGTTCTGGACACAGACAGAGGCTACAGATTCAGAAAAGCGAGA
ACCTTCTCCTGATCATCGCAATGCAACGAAATCTGAGGATATTTTATTTT
TGGGGACTTTTTTTTGCGTGTAAAGACCATTTCTGTGATTTTCAGCTGAG
GTGCTCTTTCAAATGAATTATTTATATGTTACAAAAAAAAAAAAAAAA
AAAAA

PRS-P2-C8 (SEQ ID NO: 46)

AACATATCTGAACCAGCCATGAAGTTGTTACCTATAATTCTGTTG
GCGTTGACAGTCTTGATCGTGACTTGTCAAGCTGAACATCCCGGTACTAA
GTGTAGAAGAGAATTCGCAATAGAAGAAGAATGTATCAATCATTGTGAA
TACAAACACTTTGGCTTCACAGATGACCAATTCCGGATTAAAAAGCATC
ATAGAGAAAATTTCAAAAACGCTATGAGTCATTACGGTGCAATCAGAAA
GGATCAAGAAGGTGAACTGGATAAGCTTTTGAATAGATGTGCCAAGAAA
GCCAAAGAGTCTCCTGCTACATCGAAAAGAGACAAATGTTACAGAATTAT
TAACTACTACCGTTGTGTTGTTGTAGATAATAATCTGATCAATTATTCTG
TTTACGTCAAAGCTGTTACCAAGATTAATGATTCAATCAATGTATAAAAA
TCAAATATTACTTTGAAATAAAAGAAGAAACAATGTTGTATGCAAGGCC
AAAAAAAAAAAAAAAAAAAAAAAAAAA

PRS-P2-G8 (SEQ ID NO: 48)

ATAGAAATCGAATCATGAAGGAGCTTGTTGTATTTTTGACACTGA
TAGTTTTGGTCGTGATTTGTCACGCAGAACGACCTTCACAAAAGTGTAGG
AGGGAACTGAAGACAGAGGAAGAGTGTATACTGCATTGTGAGTACAAA
CATTATCGCTTTACTGATGACCAGTTTCGACTTAACGCAGATCAAAGAGG
AGACTTTAGGAATATCATGAGGAGGTACGGCGCAATTAGGGTGGATCAG
GAAAGTCAATTGGATAAGCATTTGAAAAAATGTGCCAACAAAGTTGCTA
AGACTCCGCCAACATCGAGGAAGGATAAGTGTAGGAAAATTTCTCGGTA
CTATCACTGTGCTGTGCATAATAAACTTTTCAAATATAATGATTATGCCA
ATGCCATAATTAAATATGATAAGACAATAAATGTTTAAAGATGAATGTA
TCGCTCAAATAAAGAAGCAAAGCTAACCATATTCAAATCAAAAAAAAAA
AAAAAAAAAAAAAAAAAA

Specific, non-limiting examples of a polynucleotide encoding a *P. perniciosus* polypeptide are set forth below:

PERL-P7-G8 (SEQ ID NO:50)

TATATATAACTTTTGAAATGTTCAGTCAGTCTTTTGGAAGCAAAGATGAA
GATCTTTCTGTGCCTAATTGCTGTGGTTTTCCTTCAGGGAGTTGTAGGCTT
TCACGTTGAACGAGAATATGCGTGGAAAAACATTAGTTACGAAGGAGTA
GATCCAGCATTATTCAATATTGATAATATCATTCCGACTGGTTTCGTTCA
CGATGCAATTAATAAGAAGATTTTCATTGCTGTTCCAAGGAGATCTCCTC
AAATACCATTTACCCTAACTGAACTTGATACCACCAAGCATCCGGAACG
TTCTCCTCCTCTAAGCAAATTTCCTGGTAGCGATAAATTAATCAACGTTT
ATCAACCGGTCATTGACGAATGTCGCCGACTTTGGATTGCGGACGTCGG
ACGGGTTGACTACAAGGGCGATGAGCAGAAGTATCCAAACCAAAATGCT
GTTCTCATAGCTTATGACCTGACGAAGGAAAATTACCCAGAGATTCATC
GATACGAGATACCAAGTAAAATTGCTGGTTCAAATACAATTCCATTTGG
AGGATTTGCCGTTGATGTTACGAATCCGAAGGAGGGATGCGGCAAAACC
TTTGTCTACATCACGAACTTCGAAGACAACACTCTGATTGTGTACGATCA
GGAGAAGAAAGATTCTTGGAAGATCAGTCATGGGTCATTCAAACCAGAG

-continued

```
CATGACTCGACTCTCTCCCATGACGGTAAACAGTACAAGTATAGAGTGG
GTTTATTCGGAATTACTCTTGGAGATCGGGATCCGGAAGGAAATCGTCC
GGCTTTACTACATAGCCGGAAGCAGTACGAAGCTCTTTGAGATCAGCACT
AAGATTTTGAAGGAGAAGCGTGCCAAATTTGATCCTGTTAATTTGGGAA
ATCGTGGTCCCCACACTGAAGCTGTTGCCCTGGTATATGATCCCAAGACA
AAAGTTATCTTCTTTGCTGAATCTGACTCCAGGCAGGTCTCTTGCTGGAA
TACCCAGAAGCCACTGAATCATAAGAACACTGATGTGATTTTTGCCAGT
GCCAAATTTATTTACGGCTCCGATATTTCAGTTGATAGTGAATCTCAATT
GTGGTTCTTATCCACGGACATCCACCCATTCCTAATCTCAAGTTGACCT
TTGATAAACCCCATATTCGTCTTATGAGGGTGGATACGGCTAAAGCAATT
CGTAGAACTAGATGCGAAGTGAAGCCCCGCAAGCCATAAGACGAATATC
TAATATCAAAAATGTTACAATTCTGCTAAAATGTCTAAAAATAAAGATA
ATAATAAATAAATAAAAATATTGTGCAACACACAGAAACAAACCAAAA
AAAAAA

PERL-P6-H9                              (SEQ ID NO:52)
CAAGATGAAAATCTTTCTGTGCCTAATTGCTGTGGTTTCCCTTCAGGGAG
TTTTAGCTTATGATATTGAGAGGGAATACGCGTGGAAAAACATCAGTTTT
GAAGGAATAGACCCAGCATCCTACAGCGTTAAAAATAGTATCGTAACTG
GTTTCGCTCACGATGCAGATAGTAAGAAGATTTTCATTACTATTCCAAGG
CTAAACCCAGTTCCGATTACTCTAACTGAACTGGATACCACTAAGCATCC
GGAAGGATCTCCTCCACTAAGCAAATTTCCTGGTAGTGATAAATTAATCT
CTGTTTATCAACCGGTCATTGACGAATGTCGCCGACTTTGGATTGTGGAC
GCTGGACAGGTTGAGTACAAAGGAGATGAGCAGAAGATTCCCAAGAAA
AATGCTGCTATTATAGCTTATGATCTGACGAAGGACAATTATCCAGAAAT
TGATCGATACGAGATACCGAATAATGTTGCTGGTAATCCACTTGGATTTG
GAGGATTTGCCGTTGATGTTACAAATCCGAAAGAGGGATGTGGTAAAAC
CTTTGTCTACATCACGAACTTCGAAGACAACACTCTAATAGTGTATGATC
AGGAGAAGAAAGATTCCTGGAAGATCAGTCATGATTCATTCAAACCTGA
GCATGAATCGATCCTGACCCACAACGGTGCTCAACACATTTTAAAGTTG
GGTATATTCGGAATCACCTTTAGGAGATCTGGATGAGGAGGGAAATCGTC
AGGCTTACTACTTGGGAGGTAGTAGTACGAAGCTCTTTAGAGTGAACAC
CAAGGATCTCAAGAAGAAAGCCGGTCAAATTGAATTCACTCCTCTGGGA
GATCGTGGATCTCACTCTGAAGCCCTTGCTCTGGCTTATGATCCCAAGAC
TAAAGTTATCTTTTTCATTGAATATAATTCTAAGCGAATCTCCTGCTGGA
ACACTCAGAAATCACTAAATCCTGACAACATTGATGTGATTTATCACAGT
CCTGATTTTATCTTCGGCACTGATATTTCAATGGATAGTGAATCCAAAT
TGTGGTTCTTTTCCAACGGTCATCCACCAATTGAGAATGTTCAACTAACT
TTTGATAAGCCACATTTTCGTCTTATAAGCATGGATACGAAAAAATCAAT
TCATGGTACTAAATGCGAAGTAAAACCTTAAGTCAAACTTGGAAAATAA
AACACTTCTTAAAGAAATTGTAATTTTTATGATGGTAATAAATTTTTGTG
TGCCGAAAAAAAAAAAAAAAAAAAAAAAAAAAA

PERL-P7-C2                              (SEQ ID NO:54)
CACTTTAGTCTCAAATCTTGGATCATGTTTAAGAAATTTATCTTGGTGGC
CCTTGTCGTTGTCGTGGCACAATGTGCTCTTCCCGCAATCCCAATTGCAA
GACAGGGAAAAGATTTCCCCGTCCCGTTTGTAAGTGAAGATAATAATCC
GGATGATTATTTTGACGATCAGTACTATCCGGACATAAACGATGCGGGT
GTAGGTTCAAAGGCTCCGCAGGGAAGCAGAAAGCCACCCAATAGAGGC
ACCATCCCTCCTCCTCGTGGTGACCAAGTGTCATCTGGTGGACGAACTCC
ACCCGGAAGGGTTGGACAGGGTACAAGCCCTACAAAGGATAAAAGAGC
TCGTCCTCAGATTAACAGAAACCCAACCGGAACGGTTGGACAGGGTGGA
AGCCCTGGTACAAAGGATAAAAGAGCTCGTCCTCAGATTAACAGAAACC
CAACCGGAAGTGGTACAAAACCCAGAGATAGGGAGCTTGTGATTAGGG
ATAAGCCCCCATCCGGAAGTCAAGGTGGTAAACCTGGAAGACAGGTCAG
AGGCCCAAAGGAAGATTTGTCGCGTTATCAAAACGCTCCGGCAAAGTTG
ATTTTCAAATCGAGTAATATCAATACTGCTGGTAAAACCCCGAAGCGCT
GTGAAGTTGTTTAAGACGAAGAAGGACAAAACAGTTGTTGCTAAGGGAG
GTCCCAACGATGTTTATGAGGTGGAGCTTCTCGATGGAAATTTCAATAAT
ATGAGCTTGAGGATCCAGATAATGGACAGGAAGAGCAGCACAGCGATC
CTCAGCAATCCAGATCGCAACTTAATTGTTGGCCGTGTCAAGACGTACCG
CGGATTAAGATGAGGTGCTGAATTTTTAAATTTTATTTTATTTTTTGCTC
CTAAATCCAAAATCCCCCCAAATAAATCAGTTTGAACGCAAAAAAAAAA
AAAAAAAAAAAAAAAAAAA

PERL-P6-H1                              (SEQ ID NO:56)
GGCCATTACGGCCAGGGGGAATAAGTTAGTGTCTTCACGTTTATTGAAG
CTTTCACTTCAATATGACTTACTTCAAGATCAGTACTTGTTGTTTAGTTTT
AATAAGCCTCATTCTACCTATAATTTGTATTAAAGTTATTCGTTTTGATGA
TAGAGATGAATATCTTCTTGGTAAACCTGATAATACTGATGAAGAACTCC
TCTATTCAACCTTTGACTTCATTAAGAATACCTGCGCTAATCCTAAAATG
AAATGCACCAATAACGCCACTCATTTCGTTCTGGATTTCTCTGATCCGAA
GAAGAGATGTATCCTCCATCCATGTATTTTCCACTCCCGATGGACCTG
TTAATCTTGAGGAGGAGAATAAGCCTCGATCAAAGAGTTCAATTTACTG
CCAAGTGGGCGGCATTGGACAGAGTTACTGTTTGCTGGTGTTTAAAAAG
AAGGAACGTCGTGAGGATGCTCTGGTTGATATCCGGGGACTCAAAACAT
GCTCCCTCAAGGAGCGCTACACATCTGGAGATCCCAAGAAAACCGATGC
TTACGGAATGCCATACAAATTCGACAAGAATGATAATTGGAGCATCAAG
AGAGAAGGTGTTAAGCAATGGAAAAGATCAGGAAATGAGATCTTCTACC
GCAAGAATGGTTTGATGAACCATCAAATAAGATACTTGAGCAAGTTTGA
```

-continued
```
TAAGTACACGGTTACCAGAGAAATGGTCGTGAAGCACCGCGCTAAGAAA
TTCACCATGGACTTCTCCAACTATGGCCAGTACAGAATCAGTTTCTTGGA
CGTCTACTGGTTCCAGGAGTCCGTGAAGCACAAGCCGAAGTTACCCTAC
ATCTACTACAATGGCGAATGCTTGCCTAGCAATAAGACGTGTCAGTTGGT
TTTCGACGCTGATGAGCCTATTACTTATGCTTTTGTGAAAGTGTTCAGTA
ATCCGGACCACAACGAACCACGATTGAGGCATGCAGATCTGGGACGAGG
ATAGGAGTGGATTAGTCCGTTGTTGAAATTTGAATAAAATGCTATGAAG
ATGTTAAATTTGCCTCAAAAAAAAAAAAAAAAAAAAAAAAAA PERL-P3-E11                                 (SEQ ID NO:58)
AAAACATCTTCGCGTTTTCGTGCTATTTGAAACGGAGAACATCGAGTAA
AGAATATGAAGTTACTAATTACTATCGGTGCGGTTTGTGTGTTACAAGTC
GTTACAGTATCATCCATCTTCTTTCCCATTCCAATCAACATCCAAACAGG
GACGACATCATCATCATCAGGACAACCAGGACAGCAAGTTACAACGAGT
ATAAGTTTCAGTAATGTATCAAACATCACGGATATGGTGATTTATCTCAC
GCAGAATATCAGTAGAGCTCTCCTTACGCGTGTACCAAACCCTGATGAT
ATCAAATCAGCAGCGGATATCTTGGAAAGTTTTACAGGAAGCCTCAAGT
ATTTCCAAACACCTCCGGATGATGTGGATCAAGAGGAATCAGAGACAAA
GTCACGATCTAAGAGATCATTTACTGATATATTCAAACAATCTTCGCCTT
TAAAAGAAATCGGAGAAAGGATCGAAGAAATAAAAAAGAAACTAAAAG
GAATGCTCAAACCAAAACCGCAAACACCTTCTGGAAATCAAACTGATAG
CTCGAACACAACTTCGGAGACTCAATCGAGAAAGAAACGGGCTTTAACT
GACTTTATACCAATGGATTCTCTGAAAGATGCGATTTCAAAAACAGGGG
AAGTGTTGATACCTTCAAGTGCAAGTGCAAACTCTAGTCCTCTAGATTTT
ATGTCAAAACTATCCGATATCGCAAATGATCTTATTCAAAACTCAATGAA
GGAAATCTCCGAAAATTTAGCCTCAAGCGTTGCTATGTACCAAGTCAACT
CACAGTTAGATGCCATTAAACAATCCATGGATATTATAAAACAAGAAT
TGATAAGACCCAAAAGATCCAGAAATACGTAAAGGAAGCTCTTAATCAA
GCCAAAAATGCTACTAAATCTTTAGGAGAAAAGCTTAAGTCCAGTAACT
GTTTCGCTCAATTTATAAATCCCTTTAAACTTTTTGAAAAAGGAATTACT
TGTGTGAAAAATAAAATCGATAATGGATTAAAAATCGCAAAAGACACCT
TTAAGAATTTACAACAGGCAATGAGTGTGCCCTCAGATATTCAAAGTGA
AGTGTCCAAATGCTCCCAAAATCAGCAATTGAATCCCATTGCCAAACTCC
TGTGCTACTTGAGGACACCACTGCAATTGGACGACGAGAAGTTGCTGCT
TCCCTTTGAATTTACGAGGAGAATTAGAGAAATAACTAACTATTTTGCCA
CCATGAGAATGGACCTCATTCGTTGTGGCATAGAAACTATTCAGTCGATC
GGAGACAAGGTTGAGGATTGTGCAAGAGAAGCAATATTGGCTGTAAAG
GACACTCTGAAGGGATAAAGTCCGCATTTTCTGGCTGTCCAATTGGGACT
AACCCAATCATTGATGATGCCGAGCTATTGTATGTTGGAGAAAATGAAT
AAAAGGCTTCGCAAAAAAAAAAAAAAAAAAAAAAAAAAA PERL-P7-G12                                 (SEQ ID NO:60)
ATTAGAAAACCAATCATGAAGCAGCTTGTTGTATTTTTGGCGTTGATAGT
TCTGATAGTGATTTGTCACGCAGAACCACCTTCGAAGAAGTGTAGGAGT
GGACTGCTGAAAGATGAGGAGTGTATACTCCATTGTGAATACAAATACT
ATGGCTTTACTGATGATAATTTCGAACTTGATTCAGATCTAAGAGGACAC
TTTAGAACTGCTATGAGGAAGCACGGCGCAATTAGGATCGATCAGGAAA
GACAACTTGATAAGCATTTGAAAAAATGTGCTCAGGAAGCTAAAAAGTC
GGAAAAGTGTAGGAAAATCATTCAGTACTATCGCTGTGCTGTGAATAAT
AAACTTTTCCAATATAATGCTTATGCTAAAGCAATTATTGCGCTTGATAA
GACAATAAATGTTTAAAAAAGAAAGTGAAATGTATCTATCGCTCAAATA
AAGAAGGAAGCTAAGATCGTTGAAAGAAAAAAAAAAAAAAAAAAAA
AAAAAAAA PERL-P3-C9                                  (SEQ ID NO:62)
GCTTTAGAAGTTATTTTACATCTGTGCAATGATTAACTCAACAGTGATTC
AATTTATTTTTCTTTTTGTGATTTTTCTTCCTGGAAAATCTAAAAGTGCCC
CAAAGACTTGCGAAATTAATCTTCCCACCAGTATTCCGACAAAAGGTGA
ATCAATTTATCTTTCTCAATGGAAATGGATCGGTCTTCCGACCGGATGGAA
AATTGACTCAACTCAATATTGGGGATTCCCTGTCCATCTACTGTCCTGGA
CAGAAGGAGCTCAAGAGAGTCCCTTGCAGTCCCAAATTTTCCCTTGAGA
ACATCACTTGCAACAGCAATGTTCACAGTGAATTGGTTGACACGGAGGA
AAAGTGCGGAAAAGATGGAAAATGTTACAATATTAGCTTTCCATTGCCA
ACAAATACCTTCCATACAATCTACAGAACTTGCTTCAACAAGCAGAAAC
TAACACCAATCTATTCTTATCACGTCATCAATGGAAAGGCAGTTGGATAT
CATGTGAAACAGCCACGAGGAAACTTTCGACCGGGAAAAGGTGTCTACA
GGAAGATCAACATCAATGAGCTCTACAAGACCCACATTTCGCGCTTCAA
GAGAATCATCGGATCCACCCAGACATTCTTCCGGAAGCCCCTGCACTATC
TGGCTCGTGGACATCTCTCACCTGAAGTGGACTTTGTCTTTGGCAACGAA
CAACACGCCACTGAGTTCTACATCAACACCGCCCCCCAATATCAATCCAT
CAACCAGGGAAATTGGCTTCGAGTGGAGAAACACGTGCGCAAACTGGCC
AAGGCCCTCCAGGATGATCTCCACGTTGTCACTGGAATTTTGGGCATCCT
CAAGTTCTCAAACAAACGAGCCGAAAGAGAAATCTATCTGGGCGAAGG
AGTTATTCCTGTACCGCAAATATTTTGGAAGGCTGTCTTCCACCCTAAAA
CCTCTTCCGCCATTGTCTTCGTGTCCTCTAACAACCCTCATGAGAGGACC
TTCAATCCAATGTGCAAGGATGTTTTGTGAAACAGCAAGATTCGGAGGCA
AACAACATGAAAATCAAAATTTTTCCAATCACACAGTGGGATTCACCAT
CTGTTGTGAATTACCAGACTTTCTTGGAAACTCAAAAGTTATTCTTCCTA
AGGAGTTTCAAGGCAAAAACTACCGCAAGTTGCTTAAAATGCCAGGAAA
GCCATAAAAAACTTTCATCTTATGGTGTTGTCACACGGCAATAGTTTTGAC
```

-continued
AACAGATCCTAGCTCAAACGGAATTCAATAGCATTTTCCTTTAGAAAACT
ATCATATTTTCATCGAAAAACAGTCTCTTACAATTCTGAGGATTTTTAAA
AAAGAATTTCAATTGAATCAGAATCTCTTTTAAGCACTGAAGAGAATCTC
CTGTCATTTTCTGATCTTCTATGGGTCTTTTCCAGAAAATTCTTGATTATT
CCTAAGAAGAAATTGATMTTAGTGAAGACTGTAATTGTTTAGCATTCAA
CAGTAAAAATTTGTTGACAGAGCTATAATTCCGTGTGACAACACCATTA
GTGGAAGACTCAACAAATCGATAAAAAAAATGATTTCAAAATGGTATAA
TAGTAAAAATAAAAACCTTTCCGCCAATAAATTATTCCTTTGAGGATCAC
AATGTCCTGAATATTCACACAGTGACTGAGTTTTAAGATTATTTTACTCT
CAAATCGTATAATAAAGGACAAAAACATGCGTAAATAAAGAAATTTGC
AGTACGTAAAAAAAAAAAAAAAAAAAAAAAAAAAA PERM-P2-A10                                (SEQ ID NO:64)
CCATTACGGCCGAGGAGTCTCTTTCAACGCTTAATATCAGCAATGAATAA
CTTGTTAACATTCTTTGGAGTACTTTGCTTCTTGGGCTTTGCTAACTCTCT
GCGATTCCCTCGTGACCCAGACCAAACCAGATGGGCGGAAAAGACTTGT
CTGAGAGAATTTTCTCGTGCTCCACCTAGTCTTTTAAAGAAATGGCAACA
ACTGGACTTTCCCAATACCAATCTCACCCACTGCTTCATCAAGTGCTTCA
CTTCGTATCTTGGAGTCTACAACGACACGACTAAGAAATTTAACGTGGA
CGGAATTAAAACCCAATTTAAAAGTCAGGAAATTCCTGCACCTCAAGGT
CTTGAGACACTTCGTAAAACATCTAAAGGAACCTGCAAGGATATTTATCT
AATGACTGTGGACCTTGTCAAGAAAAACAAGCTACAATTCGCAAAAGCT
TTCCATGGAATTTCTGCAGAAGCTGCAAAATGGTATACCCAACATAAAG
GAAATGTTAAGGGAAAGTACCAGAAAGCATCGGAATTCTGCAAATCTAA
AGATGATGAGTGTAGGCTCCATTGCCGATTCTACTACTACCGCTTAGTTG
ACGAGGACTACCAGATATTCAACAGAAATTTAAAAATCAACGGTATTTC
CAACGCTCAACTTCAGCAATGCAGGAACAAAGCCAGTCAAGCTAAGGGT
TGCCAGGTGGCAAAGGTCCTAAGGCAATGTCTCAAAGACATTAATCCTG
AAAATGTAAAAGCGACTTTGAAGGAGTTGGATGAGATATCGGCGAAATA
ATATACTTAAATTAACCCCATCAGCCCAATTTAGCGTAATTTCTCGACCG
TAGAAAAAGGTGTTTAACTTACGGGTGATTGAGTGTAAGTAATTTAGCG
GCTGTGGGAGATGAAATGACTATTAAAAGGTTTATATCCCCAAAAAAAA
AAAAAAAAAAAA PERL-P6-H11                                (SEQ ID NO:66)
AGTAAGTTTATCTGCGCGAGCGGAAATGGGTGCCATTTAGGCCGGAGTC
CAGTTAATATTCCGACATGTTGCAAATTAAACATTTCTTGTTCTTTGTGGT
GTTACTCGTGATCGTTCACGCTAACGACTATTGCCAGCCGAAATTGTGCA
CAAATGGCAAAACAGTGAAGCCTCACATTGGATGCAGGAATAATGGAG
ATTTCGATAGAAGTGCCTGTCCAAATGATGCTCAGATGGTTGAAATGACT
CAACAGAGGAAGGAGCTCTTCCTTAAGATTCACAATCGCCTTCGCGATA
GGTTCGCTCGTGGCTCAGTGCCCAATTTCAAGTCAGCCGCCAAGATGCCA
ATGCTGAAATGGGACAATGAATTGGCCAAGTTGGCAGAATACAATGTGA
GAACGTGCAAATTTGCTCACGATCAGTGTCGCGCAACCACAGCTTGTCCT
TATGCTGGTCAGAACTTGGGGCAAATGTCGTCATCTCCAGATTATTTGGA
CCCCGGCTATGCCATCAAGAATATCACCAGGGAGTGGTTCTTGGAGTAT
AAGTGGGCAGATCAACAACGTACCAACACCTTTACGGGAGGACCTGGTA
AAGATGGCAAACAAATTGGTCACTTTACTGCCTTCGTCCATGAGAAGAG
CGACAAGGTTGGATGTGCTGTTGCTAAATTAACGAACCGACAATTCAAC
ATGAAGCAGTACCTCATCGCTTGCAACTACTGCTACACGAATATGATGA
ACGAGAAGATCACAGCACAGGTGCCCCCGTTCTAAGTGCCAGAGTAAAA
AATGCGATTCCAAATACAAGAATTTGTGCGATGCCAGTGAGAAAGTCGA
AGCCATCCCAGACATCTTCCTCAAGAAGCGCAGGACATAATTCTCTGCTT
TCCCATTTGAAAATTGTAAAATAAATATTGTTTTCCCTTCTATCAGGTGA
ATTGGTGAAGATGAGAAGAAAGAATGTATAAGAAAATAAGAAATAAAC
AGAAACTGAGATATCGTAAAAAAAAAAAAAAAAAAAAAAAAAA PERS-P1-H11                                (SEQ ID NO:68)
ATCAGTTTTCACTTTGACCATCGATGGTGAAATACTTCAATTCATTTTACG
AAATCACTCTGATTGAGAAACGATGATCGTGAAGGGTCTCCTTGGGGTG
TTTCTTGTGATCTTGCTCGTGTGCGTGACAGAACAGGGAGTGGACGGATA
CCACAGGGCTAATGGGGACTATGGTTACAGCTAGGAAAACCGGCATCAC
GTAGTCAACGGAGATGAGGAGGAACATGAAATAAAACATACTAACTCTC
GTAAATTTGATGATGACGACTATCTCTTTAGTCACGGCTACGCCGCCTAC
GACGACGAAGACGATGAAGATGAACGACAGGGCTATTCAAGGGGCGGT
GGGGGAGCCGGAGACAGTAGCAGAGATCCCGGATTTTATCGTCGTGGAA
GTCAGGAACAATCTTACGATCCCCACAGCGTCAGACAGCTCCTGGCTA
CTCAGAATCCAGTGAATACGAACATAGCGGAGACTACGATAACTCCCAG
AACCAGCAATATTCCTCAACTCCCTCTAACGCTAACGTTAACCTAATCGA
CCAGTATCTCCATCTAATCCAATTACATAGCATCCCATCCGATTTAGTCC
AATACGCCGAATCCTACTTAACACACGCCAAGAACTCCATCCGATACTA
CGCCGTGCACGCCAAGGACTTTGAGAGGATTCGACCCTGCCTTGAATCC
GTCACGAAGTACTTCAATATGCTCAATGACGATCTCGCCAGGGAGTACG
TCAGATGTCAACGACAATGTTACCTTGATCGTCTCAATAGCTACACAACG
GCTATCTCTCAGTATACTGTCACCACAAATGCCTGCATAAACAACCGTTT
GAACTGAAGATGAGGCTTTTTTTTGTGAAATATTTATTTGGGTCAGTGAAA
ATAAATTTTCATCAACAAAAAAAAAAAAAAAAAAAAAAAAAAA

```
PERM-P2-G11                              (SEQ ID NO:70)
AGTATTCAGTTGTTAGAGATCTTTCCAACATGATATTGAAATTGTGCGCC
ATTGCGGTTTTATTTTTCCTTATTGGAGACGGAGAAGCAGCTCCTAGACC
AACAAGATTCATCCCTTTCGCTATCATCTCAGATCTGCACAGGAAGGCCA
TGCACGACGAAAAGAACAGATTTACTAGTATAGTGAAATATGGTCAATT
GAAGTACAATGGAGAGAAATATACTCTGTCCATCAGAAGTGAGAATCTC
CATTTATTTCACAAAGGACACCTACAAAGGAACCGGAGCCGATATGTCCG
AGTTGATCTACTTCAATGACAAGCTCTACACTCTTAACGACGAAACAGG
AACTATCTATGAGGTGAAACACGGCGGAGAGCTCATTCCATGGATAACT
CTCAAGAATGACGATGGAAATCAAAAGGACGGCTTCAAAGCTAAATGG
GCAACAGTTAAGGGTAACAAGTTGATTGTCGGATCAGCAGGAATGGCCT
TTCTGGAGGCGAAAACCATGAATATTGACAGAGACGCGCTCTGGGTGAA
GGAAATCAGCGAATCTGGCCACGTCACTAATAAATATTGGGATAGTCAA
TACAAGAAAGTGAGGGACGCCATGGGACTCGTCTCCGGATTTGTCTGGC
ATGAGGCCGTAAATTGGTCACCAAGGAAGAATCTTTGGGTCTTCATGCC
CAGGAAATGCACAAATGAACCATATACCGTTCGCTTAGACAAGAAAACC
GGATGCAATCAGATTATCACGGCCAATGAAAACTTCAATGATGTTAGAG
CAATTCATATCAATCGAGCCGCTGCAGATCCAGCTTCTGGATTCTCCTCT
TTCAAGTTCATCCCAAACACCAGAAACAATGATATCTTCGCAATCAAGA
CAATCGAGAGGAACGGCCAAACAGCCACTTATGGCACAGTGATTGACAT
CAATGGGAAGACTTTGTTGCCCGATCAGCGAATTCTCGATGATAAATAT
GAAGGAATTGCATTTTTCAAGGATCCCAAAGGAATTAAGTAAAGATGGA
TTATAAAATGTTGAAATAAAATGTCATGAAGCTTATAAAATGAAAAAAA
AAAAAAAAAAAAAAAAAAAAAA

PERM-P5-E2                               (SEQ ID NO:72)
AGTTCAGTTTTCTGTGCAAAATGAATACCTTATTGAAAGTCGCGGTTTTG
CTAAGCTTGGGAGGAACTGGGTACTCTTGGCAATATCCCAGGAATGCCG
ATCAAACTCTCTGGGCTTGGAGATCGTGTCAAAAGGAGCACATCGGCGA
CGACCAAGCATTATTGAAGAAATGGTTGAAATTTGAAATTCCAGATGAT
AAAGTAACGCATTGTTTTATTAAATGTACTTGGATCCATTTAGGAATGTA
CGATGAAAAACTAAAACCATTAGGGTTGATAAGGTCAAGCAACAATTC
GAGGGACGCAAATTACCAGTTCCTGCTGAAATCAGCAAATTAGAGGGTC
CTACAGATGGCGATTGTGAAAAAATTTACAGAAAAACTAAGGCTTTTCT
TGACGCTCAAATGAAGAATTATCGCATTGCATTCTATGGCATTTATGATG
GATCCGATGCATGGTTTGCAGAACATCCCGAAACTAAGCCCAAGAAAAC
GAAGATTTCTGAATTCTGCAAAGGTCGTGAAGGTGGAAAGGAAGGAACT
TGCAAGCATGCTTGCAGCATGTACTACTACCGCTTAGTCGATGAGGATA
ATCTTGTGATTCCCTTCAGGAAGTTGCCAGGCATCTCAGAGTCTGATCT
TAAACAATGCAGAGATGCCGCTAGCAAGAAAGTGGATGCCAAGTTGCT
GATGACAATCTACGATTGTCTTAACAAGATCAACCCGACAGGTCTTAAA
ACTGCTTTAAATACGCTCGATGAGCAATCATTAACAAATTATTAGAAAA
GAAATAAAAATTGATTTCGAGCAATCGTAAAAAAAAAAAAAAAAAAAA
AAAAAAAAA

PERM-P5-C11                              (SEQ ID NO:74)
ATCATTAGTGAAGTTGTTAACAACTAAGCATGAAGTACTTTTCTCTCAAT
TTTCTTCTAATTGTGATTCTATTGATTGTGGCTTGTTCACCTCAATTACCA
TGTTTACCCCAGGATTCCAAGAAAAAGCCGTCCAATCCTCGTCCTAAATT
ATCGGCCAGAAGTGGTTTGTCTTATTGAGTTATCACACTAGGAATTCGAT
GCAGTAATTTATTACGTGGGCATTGTGGCTTCATAGCTGGGGCCGTAAA
ATTAAAAGACAAAAGAAATTATTACATGACGGCCGCCATAAGTCGACG
AAAATGGACATAACATCCTTGACTACCTATCGTAATGTGAATTTGAAAA
ATTATACAAAAAAATAATTATGAATTAGCAAAAATAAAAATTATCAGAG
GAGCAGATCTGCTGTTATGATTTCTTTTTATGTCTCTTTTATGTAAGCAAT
CACTATTCTTGTACGAATATATAAATAAAAGTTCCAACTGTGTCAAAAAA
AAAAAAAAAAAAAAAAAAAAAA

PERM-P5-H8 (also referred to as P2-G9)   (SEQ ID NO:76)
AGTCAGTTATTGTTCGAAAAATGAAGAAAATTGTGCTATTCAGTTTTATA
TTCGTTGCTTTGGTGATCAGTGCTAAAGCCATTGAGACGGAATTGGATGA
TCCCGATGATGCCACTAAAGGTCGGGATGTTGCGAAGGCAGAACCTGGA
CAACTGGGACAAGTTCCAGTTGTACCTGATTTAAATCCTTCGAACACGAG
GAAACGGAGGAATAGATCCAGAAAAAGGCGACGAAATCTAGGAAAGAG
ACTCAAAAAAGTTTTTGCATAGAAATTAATACTAAAAAGATTAAAACTA
TGTCAATTTGATGCCTTTTGAGCATTCAATTAAAAAGTATGACAAATTAT
TAAGAAAAAAAAAAAAAAAAAAAAAAAAAAAAA PERT-P3-B3                               (SEQ ID NO:78)
ACTTAATATTGGACTGTATTTTGAGATAGACACCCCAGAGTACGATGGTG
CAATGTGAATTCGGTGGAACACCTTGTACGACTTTGAATATTTCATATCC
AACGATCAAGCCACTGGTGAATGCCTGAGTGTTGTGTTGAGCTCAGTCG
CGGTGGAGCAGCGAGCCGAGAAAGAATGGCAAAGGTGCAATAGAGATA
CTAAACTAGAGGAAAGACTTGAACGGTGACAGAGGAATAGGAGCAAGA
AAGAAGTGTTGAGAATTTTGCGGGAATTTCTATGGCCAATATTAAGTGTTG
ATTCAAAGAGTTTTCTACACAGAGAAATTGCGAGGTCACTTATTGGAAA
TCAATGAGAAAGTTTTTAATGTTTTTCGTGAAAGGAGTGAATAAAAATTG
AGTGCTTTATACATGTGAGACTCCCCCTTTTCTGTGGAGAGACGATAAAA
GGAAATTCGATATTTATGGGAAAAGTGATGAATTAGTGATACTGGTGGC
TCTCGAAACACAAGTCACGAATTAGAAAACGTCCAAAGAGTGATTTTTG
```

```
                            -continued
TGCTCTCCGGTGGCTGATATAAGAGAATGTGAAGAGTGAGGATGATGTC
TCGCTGGAGCAAAAGTGTGAAATTTGTGTGCCTCCTCCTGTGTGGCGGG
TTCACGTTTCTCACAACATCAGCACGTGCCAAACCCACGCTGACCTTTCA
GCTTCCGCCCGCCCTCACGAACCTACCCCCCTTCATAGGCATCTCGCGAT
TTGTCGAACGCAAAATGCAGAATGACCAGATGAAGACCTACACTGGCGT
TCGGCAGACGAACGACTCTCTCGTGATGATCTACCACCATGATCTGACG
ATCGCCATCGTGGAATTGGGACCAGAGAAGACTCTCTTGGGTTGTGAAT
TGATAGAAATTAACAACGATGATGAAGGCGCCAAAGTGCTCACAGAACT
GGCCACCGTGAATATACCACTGCAGATCGACTTCCGGGAGATGGTGAAG
CTCATGAAGCAGTGCGAGAAGATCGATTACATGCGGAAAGTGAAACGCC
AGGGAGCATCAGAGAGTGACCAGACAACAAATCGTCAACATCAGACGG
GCTACTTTGGACTCGGAGGCGCCACCGCCGGTCTAAGCATCCTCAGTGG
CATCCTTCCCGGCACCAAGTGGTGTGGCACAGGAGACATCGCCAAAACA
TACCACGATCTCGGCACCGAGGCCACTATGGACATGTGCTGTCGCACTC
ATGATCTCTGTCCAGTGAAAGTGCGCTCATATCAGCAGCGCTACAATCTC
AGCAATAACTCTATCTACACAAAATCTCCCTGCAAATGTGATGACATGCT
GTTCAATTGGCTCAAGAGGACCAACACGTCAGCCTCGCAATTCATGGGG
ACCATCTACTTCAACGTGGTCCAAGTGCCATGTGTTCTGGACACAGAGA
GAGGCTACAGATTCAGAAAAGCGAGAACCTTCTCCTGAGTATTGCAAAA
CAACGAAATCTGCGGATTTTTTTTATTTTTGGGACTTTTCGTGTGTAAAG
ACCATTTCTTGTGATTTTCAGCTGCGGTGCTCTTTCAAATGAATTATTTAT
GTTGCTAAAAAAAAAAAAAAAAAAAAAAAAAAAAAA PERM-P2-D11                                      (SEQ ID NO:80)
GTATTAGAAAACCAATCATGAAGCAGCTTGTTGTATTTTTGCCGTTGATA
GTTCTAATAGTGATTTGTCACGCAAAACGACCTTCGAGGAAGTGTAGGA
GTGGAATGGTGAAAGAGGAAGAGTGTATACTCCATTGTGAGTACAAATA
TTATGGCTTTACCGATGATAAGTTCCAACTTGATGCAGATCAGAGAGGA
AACTTTAGATTTGCCATGATGGACTATGGAGCAATTAGGATGGATCAGG
AGGGTCAAATGGATGAGCATTTGAAAAAATGTGCCAATGAAGCTGAAAA
GGCTCCAGTGTGCTCCAAGGTGGATAAGTGTAGGAAAATCATTCAGTAC
TATCGCTGTGCAGTGAATAATAAACTTTTCCAATATAATGCTTATGCCAA
AGCAATTATTGCGCTTGATAAGACAATTAATGTTTAAAAAGTGGAATGA
ATCCCTAAAATAAAGAAGGAAAGATAAGAACTTTCAAGAAAAGTTGAA
AAAAAAAAAAAAAAAAAAAAAAAAAAA PERM-P5-E3                                       (SEQ ID NO:82)
ACACACATACGATTCATTACCAGAAATGAAGCAGTTACCAGTGATCCTT
CTGGCCTTTAGTCTTTCTGATCGCAAAATGTCGATCAGAAAAACCGGAAT
ATAAGTGCCGCAGAGACTTCAAGACCGAGGATAAAAATTGCTTCCTTTC
TTGTACATTTAAAAATTACCACTTCATTGATAACAAGTTCAGGATTGAAA
GGAAGAATATTGAAAACTACAAGAAGTTCATAACTGACTATAAGGCCCT
GAAACCCAATGTTAGCGATAATGATTTGGAAAAACACCTGTTGGATTGT
TGGGATAAATTCCAAAATCACCTGAAGCATCAAGAAGGCCCGAAAAAT
GTGAAAAAGTCAACAACTTTGAAAGATGTGTTATTGACAAGAATATCTT
TGATTATCCTATTTACTTCAATGCTTTGAAGAAAATAAATTACATTACAA
AGGTTTAATGAAAAATTGATGAAATAAACATAATGAATTATTGCATTGA
ATAACAAAAAAAAAAAAAAAAAAAAAAAAAAAA PERM-P2-F11                                      (SEQ ID NO:84)
AGTTATTGTTGGGAAAATGAAGAAAATTGTGCTGTTCAGTGTTATATTCA
TTGCTTTGGTGATCAGTGCTAAAGCCATTG
       AGGATGAGGATGATGATGATGACGATGATGAATCTGAAGATCGG
GATGTTGCGAGGGCAGAACGTGAACAACAGGAAGAAGAACCAGACGAA
CCTGAATATATTCCTTCTAGACCGAGGAATCGGTCGAAAATGAGAAAAT
GGAGGAATAGAAACTATAGAAAATATAGAGACGAAAGTAGGAAAAGAA
AGCGAGATATGGTTTTGGATGTTATCAGAAGATTTTTATAGAAATTAATA
CTAAAAGTATTAAGTGGATCAATTTGATGCCTTTTGAGTGATTCATTTTG
AACTTTGAAAAATAAAACAAAGAATGTAAAAAAAAAAAAAAAAAAAA
AAAAAAAA
```

Also included are fragments of the above-described nucleic acid sequences that are at least 33 bases, at least 36 bases, at least 42 bases or at least 48 bases in length, which is sufficient to permit the fragment to selectively hybridize to a polynucleotide that encodes a disclosed *P. ariasi* polypeptide or that encodes a disclosed *P. perniciosus* polypeptide under physiological conditions. The term "selectively hybridize" refers to hybridization under moderately or highly stringent conditions, which excludes non-related nucleotide sequences.

Also disclosed herein are open reading frames (ORFs) encoding a *P. ariasi* or a *P. perniciosus* polypeptide. These ORFs are delimited by a start codon and by a stop codon. This also includes the degenerate variants and nucleotide sequences encoding conservative variants and homologs. Specific, non-limiting examples of ORFs encoding a *P. ariasi* or a *P. perniciosus* polypeptide include a nucleic acid sequence from position 104 to position 1444 (104-1444) of SEQ ID NO:2, 4-759 of SEQ ID NO:4, 23-1189 of SEQ ID NO:6, 19-1200 of SEQ ID NO:8, 23-901 of SEQ ID NO:10, 25-963 of SEQ ID NO:12, 21-1148 of SEQ ID NO:14, 22438 of SEQ ID NO:16, 24-1190 of SEQ ID NO:18, 29-787 of SEQ ID NO:20, 34-375 of SEQ ID NO:22, 19-852 of SEQ ID NO:24, 73-822 of SEQ ID NO:26, 40-1041 of SEQ ID NO:28, 29-442 of SEQ ID NO:30, 53-565 of SEQ ID NO:32, 29-781 of SEQ ID NO:34, 45-182 of SEQ ID NO:36, 85-783 of SEQ ID NO:38, 26-223 of SEQ ID NO:40, 69-413 of SEQ ID NO:42, 70-945 of SEQ ID NO:44, 19438 of SEQ ID NO:46, 15428 of SEQ ID NO:48, 46-1227 of SEQ ID NO:49, 5-1171 of SEQ ID NO:51, 25-651 of SEQ ID NO:53, 63-995 of SEQ ID NO:55, 55-1350 of SEQ ID NO:57, 16411 of SEQ ID NO:59, 29-1195 of SEQ ID NO:61, 43-792 of SEQ ID NO:63, 66-776 of SEQ ID NO:65, 73-846 of SEQ ID NO:67, 30-1025 of SEQ ID NO:69, 21-713 of SEQ ID NO:71, 30-179 of SEQ ID NO:73, 21-269 of SEQ ID NO:75, 584-1465 of SEQ ID NO:77, 18-431 of SEQ ID NO:79, 26451 of SEQ ID NO:81, 17-310 of SEQ ID NO:83.

In several embodiments:

The PRL-P4-A10 mature protein is 426 amino acids long (21446 of SEQ ID NO:1) and is encoded by the nucleic acid sequence 164-1441 of SEQ ID NO:2.

The PRL-P4-A9 mature protein is 232 amino acids long (20-251 of SEQ ID NO:3) and is encoded by the nucleic acid sequence 61-756 of SEQ ID NO:4.

The PRL-P4-C10 mature protein is 370 amino acids long (19-388 of SEQ ID NO:5) and is encoded by the nucleic acid sequence 77-1186 of SEQ ID NO:6.

The PRL-P4-D6 mature protein is 375 amino acids long (19-393 of SEQ ID NO:7) and is encoded by the nucleic acid sequence 73-1197 of SEQ ID NO:8.

The PRL-P4-D7 mature protein is 275 amino acids long (18-292 of SEQ ID NO:9) and is encoded by the nucleic acid sequence 74-898 of SEQ ID NO:10.

The PRL-P4-E5 mature protein is 290 amino acids long (23-312 of SEQ ID NO:11) and is encoded by the nucleic acid sequence 91-960 of SEQ ID NO:12.

The PRL-P4-F3 mature protein is 350 amino acids long (26-375 of SEQ ID NO:13) and is encoded by the nucleic acid sequence 96-1145 of SEQ ID NO:14.

The PRL-P4-G12 mature protein is 118 amino acids long (21-138 of SEQ ID NO:15) and is encoded by the nucleic acid sequence 82435 of SEQ ID NO:16.

The PRL-P4-G7 mature protein is 365 amino acids long (24-388 of SEQ ID NO:17) and is encoded by the nucleic acid sequence 93-1187 of SEQ ID NO:18.

The PRL-P6-E11 mature protein is 234 amino acids long (19-252 of SEQ ID NO:19) and is encoded by the nucleic acid sequence 83-784 of SEQ ID NO:20.

The PRM-P3-A6 mature protein is 93 amino acids long (21-113 of SEQ ID NO:21) and is encoded by the nucleic acid sequence 94-372 of SEQ ID NO:22.

The PRM-P3-F11 mature protein is 258 amino acids long (20-277 of SEQ ID NO:23) and is encoded by the nucleic acid sequence 76-849 of SEQ ID NO:24.

The PRM-P5-D6 mature protein is 228 amino acids long (22-249 of SEQ ID NO:25) and is encoded by the nucleic acid sequence 136-819 of SEQ ID NO:26.

The PRM-P5-E9 mature protein is 313 amino acids long (21-333 of SEQ ID NO:27) and is encoded by the nucleic acid sequence 100-1038 of SEQ ID NO:28.

The PRM-P5-F12 mature protein is 116 amino acids long (22-137 of SEQ ID NO:29) and is encoded by the nucleic acid sequence 92439 of SEQ ID NO:30.

The PRM-P5-F2 mature protein is 150 amino acids long (21-170 of SEQ ID NO:31) and is encoded by the nucleic acid sequence 113-562 of SEQ ID NO:32.

The PRM-P5-G11 mature protein is 231 amino acids long (20-250 of SEQ ID NO:33) and is encoded by the nucleic acid sequence 86-778 of SEQ ID NO:34.

The PRM-P5-H4 mature protein is 21 amino acids long (2545 of SEQ ID NO:35) and is encoded by the nucleic acid sequence 117-179 of SEQ ID NO:36.

The PRS-P1-B11 mature protein is 215 amino acids long (18-232 of SEQ ID NO:37) and is encoded by the nucleic acid sequence 136-780 of SEQ ID NO:38.

The PRS-P1-B4 mature protein is 45 amino acids long (21-65 of SEQ ID NO:39) and is encoded by the nucleic acid sequence 86-220 of SEQ ID NO:40.

The PRS-P1-E7 mature protein is 93 amino acids long (22-114 of SEQ ID NO:41) and is encoded by the nucleic acid sequence 132410 of SEQ ID NO:42.

The PRS-P1-G9 mature protein is 262 amino acids long (30-291 of SEQ ID NO:43) and is encoded by the nucleic acid sequence 157-942 of SEQ ID NO:44.

The PRS-P2-C8 mature protein is 119 amino acids long (21-139 of SEQ ID NO:45) and is encoded by the nucleic acid sequence 79435 of SEQ ID NO:46.

The PRS-P2-G8 mature protein is 118 amino acids long (20-137 of SEQ ID NO:47) and is encoded by the nucleic acid sequence 72425 of SEQ ID NO:48.

The PERL-P7-G8 mature protein is 375 amino acids long (19-393 of SEQ ID NO:49) and is encoded by the nucleic acid sequence 100-1224 of SEQ ID NO:50.

The PERL-P6-H9 mature protein is 370 amino acids long (19-388 of SEQ ID NO:51) and is encoded by the nucleic acid sequence 59-1168 of SEQ ID NO:52.

The PERL-P7-C2 mature protein is 191 amino acids long (18-208 of SEQ ID NO:53) and is encoded by the nucleic acid sequence 76-648 of SEQ ID NO:54.

The PERL-P6-H1 mature protein is 282 amino acids long (29-310 of SEQ ID NO:55) and is encoded by the nucleic acid sequence 147-992 of SEQ ID NO:56.

The PERL-P3-E11 mature protein is 411 amino acids long (21-431 of SEQ ID NO:57) and is encoded by the nucleic acid sequence 115-1347 of SEQ ID NO:58.

The PERL-P7-G12 mature protein is 112 amino acids long (20-131 of SEQ ID NO:59) and is encoded by the nucleic acid sequence 73-408 of SEQ ID NO:60.

The PERL-P3-C9 mature protein is 365 amino acids long (24-388 of SEQ ID NO:61) and is encoded by the nucleic acid sequence 98-1192 of SEQ ID NO:62.

The PERM-P2-A10 mature protein is 230 amino acids long (20-249 of SEQ ID NO:63) and is encoded by the nucleic acid sequence 100-789 of SEQ ID NO:64.

The PERL-P6-H11 mature protein is 217 amino acids long (20-236 of SEQ ID NO:65) and is encoded by the nucleic acid sequence 123-773 of SEQ ID NO:66.

The PERS-P1-H11 mature protein is 232 amino acids long (26-257 of SEQ ID NO:67) and is encoded by the nucleic acid sequence 148-843 of SEQ ID NO:68.

The PERM-P2-G11 mature protein is 311 amino acids long (21-331 of SEQ ID NO:69) and is encoded by the nucleic acid sequence 90-1022 of SEQ ID NO:70.

The PERM-P5-E2 mature protein is 211 amino acids long (20-230 of SEQ ID NO:71) and is encoded by the nucleic acid sequence 78-710 of SEQ ID NO:72.

The PERM-P5-C11 mature protein is 24 amino acids long (26-49 of SEQ ID NO:73) and is encoded by the nucleic acid sequence 105-176 of SEQ ID NO:74.

The PERM-P5-H8 (also referred to P2-G9) mature protein is 62 amino acids long (21-82 of SEQ ID NO:75) and is encoded by the nucleic acid sequence 81-266 of SEQ ID NO:76.

The PERL-P3-B3 mature protein is 264 amino acids long (30-293 of SEQ ID NO:77) and is encoded by the nucleic acid sequence 671-1462 of SEQ ID NO:78.

The PERM-P2-D11 mature protein is 118 amino acids long (20-137 of SEQ ID NO:79) and is encoded by the nucleic acid sequence 75428 of SEQ ID NO:80.

The PERM-P5-E3 mature protein is 121 amino acids long (21-141 of SEQ ID NO:81) and is encoded by the nucleic acid sequence 86-448 of SEQ ID NO:82.

The PERM-P2-F11 mature protein is 77 amino acids long (21-97 of SEQ ID NO:83) and is encoded by the nucleic acid sequence 77-307 of SEQ ID NO:84.

Another specific, non-limiting example of a polynucleotide encoding a *P. ariasi* polypeptide is a polynucleotide having at least 75%, 85%, 90%, 95%, or 99% homologous to one of the sequences set forth above that encodes a polypeptide having an antigenic epitope or function of a *P. ariasi* polypeptide or a *P. perniciosus* polypeptide. Yet another specific, non-limiting example of a polynucleotide encoding a *P. ariasi* polypeptide or a *P. perniciosus* polypeptide is a polynucleotide that encodes a polypeptide that is specifically bound by an antibody that specifically binds the *P. ariasi* polypeptide or the *P. perniciosus* polypeptide.

The *P. ariasi* polynucleotides and *P. perniciosus* polynucleotides include a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single and double forms of DNA.

Recombinant vectors are also disclosed herein that include a polynucleotide encoding a polypeptide or a fragment thereof according to the disclosure. Recombinant vectors include plasmids, viral vectors, and bacterial vectors and may be used for in vitro or in vivo expression.

A plasmid may include a DNA transcription unit, a nucleic acid sequence that permit it to replicate in a host cell, such as an origin of replication (prokaryotic or eukaryotic). A plasmid may also include one or more selectable marker genes and other genetic elements known in the art. Circular and linear forms of plasmids are encompassed in the present disclosure.

For in vivo expression, the promoter is generally of viral or cellular origin. In one embodiment, the cytomegalovirus (CMV) early promoter (CMV-IE promoter), including the promoter and enhancer, is of use. The CMV-IE promoter can be of human or murine origin, or of other origin such as rat or guinea pig (see EP 0260148; EP 0323597; WO 89/01036; Pasleau et al., *Gene* 38:227-232, 1985; Boshart M. et al., *Cell* 41:521-530, 1985). Functional fragments of the CMV-E promoter may also be used (WO 98/00166). The SV40 virus early or late promoter and the Rous Sarcoma virus LTR promoter are also of use. Other promoters include but are not limited to, a promoter of the cytoskeleton gene, such as (but not limited to) the desmin promoter (Kwissa M. et al., *Vaccine* 18 (22):2337-2344, 2000), or the actin promoter (Miyazaki J. et al., *Gene* 79 (2):269-277, 1989). When several genes are present in the same plasmid, they may be provided in the same transcription unit or in different units.

The plasmids may also comprise other transcription regulating elements such as, for example, stabilizing sequences of the intron type. In several embodiments the plasmids include the first intron of CMV-IE (WO 89/01036), the intron II of the rabbit β-globin gene (van Ooyen et al., *Science* 206: 337-344, 1979), the signal sequence of the protein encoded by the tissue plasminogen activator (tPA; Montgomery et al., *Cell. Mol. Biol.* 43:285-292, 1997), and/or a polyAdenylation signal (polyA), in particular the polyA of the bovine growth hormone (bGH) gene (U.S. Pat. No. 5,122,458) or the polyA of the rabbit β-globin gene or of SV40 virus.

In a specific, non-limiting example, the pVR1020 plasmid (VICAL Inc.; Luke C. et al., *Journal of Infectious Diseases* 175:91-97, 1997; Hartikka J. et al., *Human Gene Therapy* 7:1205-1217, 1996)) can be utilized as a vector for the insertion of such a polynucleotide sequence, generating recombinant plasmids such as, but not limited to, PJV001, PJV002, PJV003, PJV004, PJV005, PJV006, PJV007, PJV008, PJV009, PJV010, PJV011, PJV012, PJV013, PJV014, PJV015, PJV016, PJV017, PJV018, PJV019, PJV020, PJV021, PJV022, PJV023, PJV024, PJV025, PJV026, PJV027, PJV028, PJV029, PJV030, PJV031, PJV032, PJV033, PJV034, PJV035, PJV036, PJV037, PJV038, PJV039, PJV040, PJV041, or PJV042. The plasmids are evaluated in dogs in order to determine their efficacy against a *Leishmania* infection (Vidor E. et al., *P*3.14, XXIV World Veterinary Congress, R10 de Janeiro, Brazil, 18-23 August 1991).

Various viral vectors are also of use with a polynucleotide encoding a *P. ariasi* or a *P. perniciosus* polypeptide. A specific, non-limiting example includes recombinant poxvirus, including avipox viruses, such as the canarypox virus. Another specific, non-limiting example includes vaccinia viruses (U.S. Pat. No. 4,603,112), such as attenuated vaccinia virus such as NYVAC (see U.S. Pat. No. 5,494,807) or Modified Vaccinia virus Ankara (MVA, Stickl H. and Hochstein-Mintzel V., *Munch. Med. Wschr.* 113:1149-1153, 1971; Sutter G. et al., *Proc. Natl. Acad. Sci. U.S.A.* 89:10847-10851, 1992; Carroll M. W. et al., *Vaccine* 15 (4):387-394, 1997; Stittelaar K. J. et al., *J. Virol.* 74 (9):4236-4243, 2000; Sutter G. et al., *Vaccine* 12 (11):1032-1040, 1994). When avipox viruses are used, canarypox viruses (U.S. Pat. No. 5,756,103) and fowlpox viruses (U.S. Pat. No. 5,766,599) are of use, such as attenuated viruses. For recombinant canarypox virus vectors, the insertion sites may be in particular in the ORFs C3, C5 or C6. When the expression vector is a poxvirus, the heterologous polynucleotide can be inserted under the control of a poxvirus specific promoter, such as the vaccinia virus 7.5 kDa promoter (Cochran et al., *J. Virology* 54:30-35, 1985), the vaccinia virus I3L promoter (Riviere et al., *J. Virology* 66:3424-3434, 1992), the vaccinia virus HA promoter (Shida, *Virology* 150:451-457, 1986), the cowpox virus ATI promoter (Funahashi et al., *J. Gen. Virol.* 69:35-47, 1988), other vaccinia virus H6 promoter (Taylor et al., *Vaccine* 6:504-508, 1988; Guo et al., *J. Virol.* 63:4189-4198, 1989; Perkus et al., *J. Virol.* 63:3829-3836, 1989).

Other viral vectors of use are herpes virus or adenovirus vectors. Specific, non-limiting examples include a canine herpes virus (CHV) or canine adenovirus (CAV) vector (for example, see U.S. Pat. No. 5,529,780; U.S. Pat. No. 5,688,920; Published PCT Application No. WO 95/14102). For CHV, the insertion sites may be in particular in the thymidine kinase gene, in the ORF3, or in the UL43 ORF (see U.S. Pat. No. 6,159,477). For CAV, the insertion sites may be in particular in the E3 region or in the region located between the E4 region and the right ITR region (see U.S. Pat. No. 6,090,393; U.S. Pat. No. 6,156,567). In one embodiment in CHV or CAV vectors the insert is in general under the control of a promoter (as described above for the plasmids), such as CMV-IE promoter.

Multiple insertions can be done in the same vector using different insertion sites or using the same insertion site. When the same insertion site is used, each polynucleotide insert is inserted under the control of different promoters. The insertion can be done tail-to-tail, head-to-head, tail-to-head, or head-to-tail. IRES elements (Internal Ribosome Entry Site, see European Patent EP 0803573) can also be used to separate and to express multiple inserts operably linked to the same promoter. Bacterial vectors may also be used for in vivo expression.

Any polynucleotide according to the disclosure can be expressed in vitro by DNA transfer or expression vectors into a suitable host cell. The host cell may be prokaryotic or eukaryotic. The term "host cell" also includes any progeny of the subject host cell. Methods of stable transfer, meaning that the foreign polynucleotide is continuously maintained in the host cell, are known in the art. Host cells can include bacteria (e.g. *Escherichia coli*), yeast, insect cells, and vertebrate cells. Methods of expressing DNA sequences in eukaryotic cells are well known in the art.

As a method for in vitro expression, recombinant Baculovirus vectors (e.g., *Autographa California* Nuclear Polyhedrosis Virus (AcNPV)) can be used with the nucleic acids disclosed herein. For example, polyhedrin promoters can be utilized with insect cells (for example *Spodoptera frugiperda* cells, like Sf9 available at the ATCC under the accession number CRL 1711, Sf21) (see for example, Smith et al., *Mol. Cell Biol.* 3:2156-2165, 1983; Pennock et al., *Mol. Cell Biol.* 4: 399-406, 1994; Vialard et al., *J. Virol.* 64:37-50, 1990; Verne A., *Virology* 167:56-71, 1988; O'Reilly et al., "Baculovirus expression vectors, A laboratory manual," New York Oxfore, Oxfore University Press, 1994; Kidd 1. M. & Emery V. C., "The use of baculoviruses as expression vectors," *Applied Biochemistry and Biotechnology* 42:37-159, 1993; European Patent No. EP 0370573; European Patent No. EP 0265785; U.S. Pat. No. 4,745,051). For expression the BaculoGold™ Starter Package (Cat # 21001K) from Pharmingen (Becton Dickinson) can be used.

As a method for in vitro expression, recombinant *E. coli* can be used with a vector. For example, when cloning in bacterial systems, inducible promoters such as arabinose promoter, pL of bacteriophage lambda, plac, ptrp, ptac (ptrp-lac hybrid promoter), and the like may be used.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, methods of transduction of DNA such as calcium phosphate coprecipitates, conventional mechanical procedures such as microinjection, electroporation, insertion of a plasmid encased in liposomes, or virus vectors may be used. Eukaryotic cells can also be cotransformed with *P. ariasi* polynucleotide sequences or *P. perniciosus* polynucleotide sequences, and a second foreign DNA molecule encoding a selectable phenotype, such as the herpes simplex thymidine kinase gene. Another method is to use a eukaryotic viral vector (see above), such as a herpes virus or adenovirus (for example, canine adenovirus 2), to transiently transduce eukaryotic cells and express the protein (see for example, Eukaryotic Viral Vectors, Cold Spring Harbor Laboratory, Gluzman ed., 1982).

Isolation and purification of recombinantly expressed polypeptides may be carried out by conventional means including preparative chromatography (e.g., size exclusion, ion exchange, affinity), selective precipitation and ultra-filtration. Such a recombinantly expressed polypeptide is part of the present disclosure. The methods for production of such a polypeptide are also encompassed, in particular the use of a host cell and a recombinant expression vector comprising a polynucleotide according to the disclosure.

Antibodies

A polypeptide of the disclosure or a fragment thereof according to the disclosure can be used to produce antibodies. Polyclonal antibodies, antibodies which consist essentially of pooled monoclonal antibodies with different epitopic specificities, as well as distinct monoclonal antibodies are included. Without being bound by theory, antibodies are of use as markers for exposure, and as immunodiagnostic tools to follow the development of the immune response to Phlebotomus salivary proteins.

The preparation of polyclonal antibodies is well-known to those skilled in the art. See, for example, Green et al., "Production of Polyclonal Antisera," *Immunochemical Protocols*, pp. 1-5, Manson, ed., *Humana Press,* 1992; Coligan et al., "Production of Polyclonal Antisera in Rabbits, Rats, Mice and Hamsters," *Current Protocols in Immunology*, section 2.4.1, 1992.

The preparation of monoclonal antibodies likewise is conventional. See, for example, Kohler & Milstein, *Nature* 256: 495, 1975; Coligan et al., sections 2.5.1-2.6.7; and Harlow et al., *Antibodies: A Laboratory Manual*, p. 726, Cold Spring Harbor Pub., 1988. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., "Purification of Immunoglobulin G (IgG)," *Methods in Molecular Biology*, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes, or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. In one embodiment, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from subhuman primates. General techniques for raising therapeutically useful antibodies in baboons can be found, for example, in WO 91/11465, 1991, and Losman et al., *Int J. Cancer* 46:310, 1990.

Alternatively, an antibody that specifically binds a polypeptide can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989. Techniques for producing humanized monoclonal antibodies are described, for example, by Jones et al, *Nature* 321:522, 1986; Riechmann et al., *Nature* 332:323, 1988; Verhoeyen et al, *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993.

Antibodies can be derived from human antibody fragments isolated from a combinatorial immunoglobulin library. See, for example, Barbas et al., *Methods: a Companion to Methods in Enzymology*, Vol. 2, p. 119, 1991; Winter et al., *Ann. Rev. Immunol.* 12:433, 1994. Cloning and expression vectors that are useful for producing a human immunoglobulin phage library can be obtained, for example, from STRATAGENE Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int Immunol.* 6:579, 1994.

Antibodies include intact molecules as well as fragments thereof, such as Fab, F(ab')$_2$, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain (L) and a portion of one heavy chain (H);

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain ($V_L$) and the variable region of the heavy chain ($V_H$) expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York, 1988).

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and in one embodiment, a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Nat'l Acad. Sci. USA* 69:2659, 1972). Alternatively, the variable chains can be linked by an intermolecular disulfide bond or cross-linked by chemicals such as glutaraldehyde. See, e.g., Sandhu, supra. In one embodiment, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larick et al., *Methods: a Companion to Methods in Enzymology*, Vol. 2, page 106, 1991).

Antibodies can be prepared using an intact polypeptide or fragments containing small peptides of interest as the immunizing antigen: The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize an animal (e.g., a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991).

It is also possible to use the anti-idiotype technology to produce monoclonal antibodies which mimic an epitope. For example, an anti-idiotypic monoclonal antibody made to a first monoclonal antibody will have a binding domain in the hypervariable region that is the "image" of the epitope bound by the first mono-clonal antibody.

In view of the large number of methods that have been reported for attaching a variety of radiodiagnostic compounds, radiotherapeutic compounds, label (e.g., enzymes or fluorescent molecules) drugs, toxins, and other agents to antibodies one skilled in the art will be able to determine a suitable method for attaching a given agent to an antibody or other polypeptide.

In one embodiment, an antibody that binds a *P. ariasi* polypeptide or a *P. perniciosus* polypeptide can be used to assess whether a subject has been bitten by a sand fly. In one specific, non-limiting example, a sample is obtained from a subject of interest, such as a human or a dog. The sample can be a body fluid (e.g., blood, serum, urine, saliva, etc.) or a tissue biopsy. The sample or a fraction thereof is contacted with the antibody, and the ability of the antibody to form an antigen-antibody complex is assessed. One of skill in the art can readily detect the formation of an antigen-antibody complex. For example, ELISA or radio-immune assays can be utilized.

Immunogenic Compositions, Vaccines and Methods of Use

Immunogenic compositions and vaccines are disclosed herein. In one embodiment the immunogenic compositions and vaccines include a polypeptide. In another embodiment, the immunogenic compositions and vaccines include a recombinant vector, such as a viral vector or a plasmid. When administered to a subject such an immunogenic composition or vaccine generates an immune response to the sand fly's salivary protein(s), and surprisingly a reduction of the leishmaniasis symptoms and a decrease of the *leishmania* parasite load. Thus, without being bound by theory, a cellular response, such as a Th1 response, produced to the salivary protein can indirectly kill a *Leishmania* parasite. For example, a Th1 type response can allow macrophages to take up *Leishmania* antigens and present them to T cells in a Th1 context. The induction of the Th1 response can produce an anti-*Leishmania* immune response, or can prime the immune system of the mammalian host for anti-*Leishmania* immunity in response to a later infection.

In one embodiment, the immunogenic composition or the vaccine includes an effective amount of at least one *P. ariasi* polypeptide disclosed herein. The immunogenic composition and the vaccine can include a pharmaceutically acceptable excipient and/or an adjuvant. In one embodiment, the immunogenic composition or vaccine includes a polypeptide having an amino acid sequence as set forth as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or SEQ ID NO:47, a conservative variant, a fusion protein, a homolog, or an immunogenic fragment thereof, or any combination thereof. In another embodiment, the composition includes a polypeptide having a sequence as set forth as SEQ ID NO:1, SEQ ID NO:3, SEQ ID NO:7, SEQ ID NO:9, SEQ ID NO:11, SEQ ID NO:15, SEQ ID NO:17, SEQ ID NO:19, SEQ ID NO:29, SEQ ID NO:33, SEQ ID NO:35, SEQ ID NO:39, or SEQ ID NO:43, a conservative variant, a fusion protein, a homolog, or an immunogenic fragment thereof, or any combination thereof. In another embodiment, the immunogenic composition or vaccine includes a polypeptide having an amino acid sequence as set forth as SEQ ID NO:1, SEQ ID NO:11, SEQ ID NO:19, SEQ ID NO:35, or SEQ ID NO:39, a conservative variant, a fusion protein, a homolog, or an immunogenic fragment thereof, or any combination thereof. In yet another embodiment, the immunogenic composition or vaccine includes a polypeptide having an amino acid sequence as set forth as SEQ ID NO:11, SEQ ID NO:19, SEQ ID NO:35, or SEQ ID NO:39, a conservative variant, a fusion protein, a homolog, or an immunogenic fragment thereof, or any combination thereof. In a particular embodiment the immunogenic composition or vaccine comprises the five polypeptides as set forth as SEQ ID NO:1, SEQ ID NO:11, SEQ ID NO:19, SEQ ID NO:35, and SEQ ID NO:39. In a particular embodiment the immunogenic composition or vaccine comprises the four polypeptides as set forth as SEQ ID NO:11, SEQ ID NO:19, SEQ ID NO:35, and SEQ ID NO:39.

In another embodiment, the immunogenic composition or the vaccine includes an effective amount of at least one *P. perniciosus* polypeptide disclosed herein. The immunogenic composition or the vaccine can include a pharmaceutically acceptable excipient and/or an adjuvant. In one embodiment, the immunogenic composition or vaccine includes a polypeptide having an amino acid sequence as set forth as SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, or SEQ ID NO:83, a conservative variant, a fusion protein, a homolog, or an immunogenic fragment thereof, or any combination thereof. In another embodiment, the immunogenic composition or vaccine includes a polypeptide having a sequence as set forth as SEQ ID NO:55, SEQ ID NO:63, SEQ ID NO:73, or SEQ ID NO:75, a conservative variant, a fusion protein, a homolog, or an immunogenic fragment thereof, or any combination thereof. In yet another embodiment, the immunogenic composition or vaccine includes a polypeptide having an amino acid sequence as set forth as SEQ ID NO:73, or SEQ ID NO:75, a conservative variant, a fusion protein, a homolog, or an immunogenic fragment thereof, or any combination thereof. In a particular embodiment the immunogenic composition or vaccine comprises the four polypeptides as set forth as SEQ ID NO:55, SEQ ID NO:63, SEQ ID NO:73, and SEQ ID NO:75. In another particular embodiment the immunogenic composition or vaccine comprises the two polypeptides as set forth as SEQ ID NO:73 and SEQ ID NO:75. In another particular embodiment the immunogenic composition or vaccine comprises the polypeptide as set forth as SEQ ID NO:75.

In a further embodiment, the immunogenic compositions and the vaccines may comprise a combination including at least one *P. ariasi* polypeptide disclosed herein and at least one *P. perniciosus* polypeptide disclosed herein. In one embodiment, the immunogenic composition or vaccine includes a combination of polypeptides including a *P. ariasi* polypeptide having an amino acid sequence as set forth as SEQ ID NO:1, SEQ ID NO:11, SEQ ID NO:19, SEQ ID NO:35, SEQ ID NO:39, a conservative variant, a fusion protein, a homolog, or an immunogenic fragment thereof, or any combination thereof, and a *P. perniciosus* polypeptide having an amino acid sequence as set forth as SEQ ID NO:55, SEQ ID NO:63, SEQ ID NO:73, SEQ ID NO:75, a conservative variant, a fusion protein, a homolog, or an immunogenic fragment thereof, or any combination thereof. In another embodiment, the immunogenic composition or vaccine includes a combination of polypeptides including a *P. ariasi* polypeptide having an amino acid sequence as set forth as SEQ ID NO:1, SEQ ID NO:19, SEQ ID NO:35, SEQ ID NO:39, a conservative variant, a fusion protein, a homolog, or an immunogenic fragment thereof, or any combination thereof, and a *P. perniciosus* polypeptide having an amino acid sequence as set forth as SEQ ID NO:55, SEQ ID NO:63, SEQ ID NO:73, SEQ ID NO:75, a conservative variant, a fusion protein, a homolog, or an immunogenic fragment thereof, or any combination thereof. In yet another embodiment, the immunogenic composition or vaccine includes a combination of polypeptides including a *P. ariasi* polypeptide having an amino acid sequence as set forth as SEQ ID NO:11, SEQ ID NO:19, SEQ ID NO:35, SEQ ID NO:39, a conservative variant, a fusion protein, a homolog, or an immunogenic fragment thereof, or any combination thereof, and a *P. perniciosus* polypeptide having an amino acid sequence as set forth as SEQ ID NO:73, SEQ ID NO:75, a conservative variant, a fusion protein, a homolog, or an immunogenic fragment thereof, or any combination thereof. In yet another embodiment, the immunogenic composition or vaccine includes a combination of polypeptides including a *P. ariasi* polypeptide having an amino acid sequence as set forth as SEQ ID NO:11, SEQ ID NO:19, SEQ ID NO:35, SEQ ID NO:39, a conservative variant, a fusion protein, a homolog, or an immunogenic fragment thereof, or any combination thereof, and a *P. perniciosus* polypeptide having an amino acid sequence as set forth as SEQ ID NO:75 a conservative variant, a fusion protein, a homolog, or an immunogenic fragment thereof, or any combination thereof. In a further embodiment, the immunogenic composition or vaccine includes a combination of four *P. ariasi* polypeptides as set forth as SEQ ID NO:11, SEQ ID NO:19, SEQ ID NO:35, SEQ ID NO:39, a conservative variant, a fusion protein, a homolog, or an immunogenic fragment thereof, or any combination thereof, and two *P. perniciosus* polypeptides as set forth as SEQ ID NO:73, SEQ ID NO:75, a conservative variant, a fusion protein, a homolog, or an immunogenic fragment thereof, or any combination thereof. In another embodiment, the immunogenic composition or vaccine includes a combination of four *P. ariasi* polypeptides as set forth as SEQ ID NO:11, SEQ ID NO:19, SEQ ID NO:35, SEQ ID NO:39, a conservative variant, a fusion protein, a homolog, or an immunogenic fragment thereof, or any combination thereof, and one *P. perniciosus* polypeptide as set forth as SEQ ID NO:75, a conservative variant, a fusion protein, a homolog, or an immunogenic fragment thereof, or any combination thereof.

In one embodiment, the immunogenic composition or the vaccine comprises an effective amount of a recombinant vector expressing at least one *P. ariasi* polypeptide disclosed herein and a pharmaceutically acceptable vehicle or excipient. In one specific, non-limiting example the recombinant vector encodes at least a polypeptide having a sequence as set forth as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or SEQ ID NO:47, a conservative variant, a fusion protein, a homolog, or an immunogenic fragment thereof, or any combination thereof. In another specific, non-limiting example the recombinant vector encodes a polypeptide having a sequence as set forth as SEQ ID NO:1, SEQ ID NO:3, SEQ ID NO:7, SEQ ID NO:9, SEQ ID NO:11, SEQ ID NO:15, SEQ ID NO:17, SEQ ID NO:19, SEQ ID NO:29, SEQ ID NO:33, SEQ ID NO:35, SEQ ID NO:39, or SEQ ID NO:43, a conservative variant, a fusion protein, a homolog, or an immunogenic fragment thereof, or any combination thereof. In yet another specific, non-limiting example the recombinant vector encodes at least a polypeptide having a sequence as set forth as SEQ ID NO:1, SEQ ID NO:11, SEQ ID NO:19, SEQ ID NO:35, or SEQ ID NO:39, a conservative variant, a fusion protein, a homolog, or an immunogenic fragment thereof, or any combination thereof. In yet another specific, non-limiting example the recombinant vector encodes at least a polypeptide having a sequence as set forth as SEQ ID NO:11, SEQ ID NO:19, SEQ ID NO:35, or SEQ ID NO:39, a conservative variant, a fusion protein, a homolog, or an immunogenic fragment thereof, or any combination thereof. In a particular embodiment the immunogenic composition or vaccine comprises recombinant vector(s) expressing at least the five polypeptides as set forth as SEQ ID NO:1, SEQ ID NO:11, SEQ ID NO:19, SEQ ID NO:35, and SEQ ID NO:39. In a particular embodiment the immunogenic composition or vaccine comprises recombinant vector(s) expressing at least the four polypeptides as set forth as SEQ ID NO:11, SEQ ID NO:19, SEQ ID NO:35, and SEQ ID NO:39.

In another embodiment, the immunogenic composition or the vaccine comprises an effective amount of a recombinant vector expressing at least one *P. perniciosus* polypeptide disclosed herein and a pharmaceutically acceptable vehicle or excipient. In one specific, non-limiting example the recombinant vector encodes at least a polypeptide having a sequence as set forth as SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, or SEQ ID NO:83, a conservative variant, a fusion protein, a homolog, or an immunogenic fragment thereof, or any combination thereof. In another specific, non-limiting example the recombinant vector encodes at least a polypeptide having a sequence as set forth SEQ ID NO:55, SEQ ID NO:63, SEQ ID NO:73, or SEQ ID NO:75, a conservative variant, a fusion protein, a homolog, or an immunogenic fragment thereof, or any combination thereof. In yet another specific, non-limiting example the recombinant vector encodes at least a polypeptide having a sequence as set forth as SEQ ID NO:73, or SEQ ID NO:75, a conservative variant, a fusion protein, a homolog, or an immunogenic fragment thereof, or any combination thereof. In a particular embodiment the immunogenic composition or vaccine comprises recombinant vector(s) expressing at least the four polypeptides as set forth as SEQ ID NO:55, SEQ ID NO:63, SEQ ID NO:73, and SEQ ID NO:75. In a particular embodiment the immunogenic composition or vaccine comprises recombinant vector(s) expressing at least the two polypeptides as set forth as SEQ ID NO:73, and SEQ ID NO:75. In a particular embodiment the immunogenic composition or vaccine comprises a recombinant vector expressing at least the polypeptide as set forth as SEQ ID NO:75.

In a further embodiment, the immunogenic composition or the vaccine comprises a combination including a recombinant vector encoding at least one *P. ariasi* polypeptide disclosed herein and encoding at least one *P. perniciosus* polypeptide disclosed herein. In one embodiment, the combination includes a recombinant vector encoding at least a *P. ariasi* polypeptide having an amino acid sequence as set forth as SEQ ID NO:1, SEQ ID NO:11, SEQ ID NO:19, SEQ ID NO:35, SEQ ID NO:39, a conservative variant, a fusion protein, a homolog, or an immunogenic fragment thereof, or any combination thereof, and at least a *P. perniciosus* polypeptide having an amino acid sequence as set forth as SEQ ID NO:55, SEQ ID NO:63, SEQ ID NO:73, SEQ ID NO:75 a conservative variant, a fusion protein, a homolog, or an immunogenic fragment thereof, or any combination thereof. In another embodiment, the combination includes a recombinant vector encoding at least a *P. ariasi* polypeptide having an amino acid sequence as set forth as SEQ ID NO:11, SEQ ID NO:19, SEQ ID NO:35, SEQ ID NO:39, a conservative variant, a fusion protein, a homolog, or an immunogenic fragment thereof, or any combination thereof, and at least a *P. perniciosus* polypeptide having an amino acid sequence as set forth as SEQ ID NO:55, SEQ ID NO:63, SEQ ID NO:73, SEQ ID NO:75, a conservative variant, a fusion protein, a homolog, or an immunogenic fragment thereof, or any combination thereof. In another embodiment, the combination includes a recombinant vector encoding at least a *P. ariasi* polypeptide having an amino acid sequence as set forth as SEQ ID NO:11, SEQ ID NO:19, SEQ ID NO:35, SEQ ID NO:39, a conservative variant, a fusion protein, a homolog, or an immunogenic fragment thereof, or any combination thereof, and at least a *P. perniciosus* polypeptide having an amino acid sequence as set forth as SEQ ID NO:73, SEQ ID NO:75, a conservative variant, a fusion protein, a homolog, or an immunogenic fragment thereof, or any combination thereof. In yet another embodiment, the combination includes a recombinant vector encoding at least a *P. ariasi* polypeptide having an amino acid sequence as set forth as SEQ ID NO:11, SEQ ID NO:19, SEQ ID NO:35, SEQ ID NO:39, a conservative variant, a fusion protein, a homolog, or an immunogenic fragment thereof, or any combination thereof, and at least a *P. perniciosus* polypeptide having an amino acid sequence as set forth as SEQ ID NO:75, a conservative variant, a fusion protein, a homolog, or an immunogenic fragment thereof, or any combination thereof. In a further embodiment, the combination includes recombinant vector(s) encoding at least four *P. ariasi* polypeptides as set forth as SEQ ID NO:11, SEQ ID NO:19, SEQ ID NO:35, SEQ ID NO:39, a conservative variant, a fusion protein, a homolog, or an immunogenic fragment thereof, or any combination thereof, and at least two *P. perniciosus* polypeptides as set forth as SEQ ID NO:73, SEQ ID NO:75, a conservative variant, a fusion protein, a homolog, or an immunogenic fragment thereof, or any combination thereof. In another embodiment, the combination includes recombinant vector(s) encoding at least four *P. ariasi* polypeptides as set forth as SEQ ID NO:11, SEQ ID NO:19, SEQ ID NO:35, SEQ ID NO:39, a conservative variant, a fusion protein, a homolog, or an immunogenic fragment thereof, or any combination thereof, and at least the *P. perniciosus* polypeptide as set forth as SEQ ID NO:75, a conservative variant, a fusion protein, a homolog, or an immunogenic fragment thereof, or any combination thereof.

In one embodiment, the *P. ariasi* polypeptide(s) having an amino acid sequence as set forth as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or SEQ ID NO:47, a conservative variant, a fusion protein, a homolog, or an immunogenic fragment thereof, or any combination thereof, and the *P. perniciosus* polypeptide(s) having an amino acid sequence as set forth as SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, or SEQ ID NO:83, a conservative variant, a fusion protein, a homolog, or an immunogenic fragment thereof, or any combination thereof, are encoded by the same recombinant vector. In another embodiment, the *P. ariasi* polypeptide(s) having an amino acid sequence as set forth as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or SEQ ID NO:47, a conservative variant, a fusion protein, a homolog, or an immunogenic fragment thereof, or any combination thereof, and the *P. perniciosus* polypeptide(s) having an amino acid sequence as set forth as SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, or SEQ ID NO:83, a conservative variant, a fusion protein, a homolog, or an immunogenic fragment thereof, or any combination thereof, are encoded by different recombinant vectors.

The *P. ariasi* polypeptide or a *P. perniciosus* polypeptide can be administered by any means known to one of skill in the art (See Banga, A., "Parenteral Controlled Delivery of Therapeutic Peptides and Proteins," *Therapeutic Peptides and Proteins*, Technomic Publishing Co., Inc., Lancaster, Pa., 1995) such as by intramuscular, intradermal, subcutaneous, or intravenous injection, but even oral, nasal, or, anal administration is contemplated. In one embodiment, administration is by subcutaneous, intradermal, or intramuscular injection using a needleless injector (Biojector, Bioject, Oregon, USA).

To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banja, supra). A particulate carrier based on a synthetic polymer has been shown to act as an adjuvant to enhance the immune response, in addition to providing a controlled release. Aluminum salts may also be used as adjuvants to produce a humoral immune response. Thus, in one embodiment, a *P. ariasi* polypeptide or a *P. perniciosus* polypeptide is administered in a manner to induce a humoral response.

In another embodiment, a *P. ariasi* polypeptide or a *P. perniciosus* polypeptide is administered in a manner to direct the immune response to a cellular response (that is, a CTL response), rather than a humoral (antibody) response. A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinylseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, the two compositions can be combined to elicit both humoral and cell-mediated responses where that is deemed desirable.

In yet another embodiment, an MHC class II-restricted T-helper epitope is added to the polypeptide of the disclosure to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," Powell, et al., (eds.), *Vaccine Design, the Subunit and Adjuvant Approach*, Plenum Press, New York, 1995).

An immunogenic composition or a vaccine according to the disclosure can be prepared in accordance with standard techniques well known to those skilled in the pharmaceutical or veterinary art. Such compositions can be administered in dosages and by techniques well known to those skilled in the medical or veterinary arts, taking into consideration such factors as the age, sex, weight, species, and condition of the particular subject, and the route of administration. The immunogenic composition or the vaccine can be administered alone, or in combination with adjuvant(s) and/or with other antigen(s). The other antigen(s) can be a *Leishmania* antigen. In one embodiment, the Leishmania antigen is the A2 antigen, such as the A2 antigen from *L. infantum* (see PCT Patent Application WO 95/06729 and in particular the sequence given in SEQ ID NO:2). The other antigen(s) can be present in the composition as a protein, or as an immunological fragment thereof (e.g., an epitope), or as an insert in an expression vector (e.g., recombinant viral vector, recombinant plasmid, in particular the pVR1012 (Vical Inc.; Hartikka J. et al., *Human Gene Therapy* 7:1205-1217, 1996)).

Any immunogenic composition, vaccine, or therapeutic composition according to the disclosure can be mixed with an adjuvant.

Polypeptide-Based Compositions:

In several embodiments, the polypeptide-based immunogenic compositions and vaccines according to the disclosure are formulated with (1) vitamin E, saponin (e.g., Quil A™, QS21™), aluminum hydroxide, aluminum phosphate, aluminum oxide ("Vaccine Design, The subunit and adjuvant approach," *Pharmaceutical Biotechnology*, vol. 6, Edited by Micheal F. Powell and Mark J. Newman, 1995, Plenum Press New York), (2) an acrylic acid or methacrylic acid polymer, a polymer of maleic anhydride and of alkenyl derivative, (3) an immunostimulating sequence (ISS), in particular an oligodeoxyribonucleotidic sequence bearing one or more non-methylated CpG groups (Klinman D. M. et al., *Proc. Natl. Acad. Sci. USA* 93:2879-2883, 1996; WO 98/16247), (4) to formulate the immunogenic or vaccine preparation in the form of an oil-in-water emulsion, in particular the SPT emulsion described on page 147 of "Vaccine Design, The Subunit and Adjuvant Approach" edited by M. Powell and M. Newman, Plenum Press, 1995, and the emulsion MF59 described on page 183 of this same book, (5) cytokines, or (6) combinations or mixtures thereof.

The cytokine (5) could be added to the composition, such as, but not limited to, GM-CSF or cytokines inducing Th1 (e.g., IL12). All these cytokines can be added to the composition as a protein or as a vector encoding this cytokine protein. In one embodiment, the cytokines are from canine origin, e.g., canine GM-CSF, for which a gene sequence has been deposited at the GenBank database (accession number S49738). This sequence can be used to create the vector in a manner similar to what was made in the PCT Patent Application WO 00/77210.

In one specific, non-limiting example the adjuvant contains two or more of an emulsifier, a micelle-forming agent, or an oil. Suitable emulsifiers, micelle-forming agents, and oils are detailed in U.S. Pat. Nos. 5,585,103; 5,709,860; 5,270,202; and 5,695,770. An emulsifier is any molecule that allows the components of the emulsion to remain as a stable emulsion. Such emulsifiers include polysorbate 80 (Sorbitan-mono-9-octadecenoate-poly(oxy-1,2-ethanediyl); manufactured by ICI Americas, Wilmington, Del.), polysorbate 20, polysorbate 21, polysorbate 40, polysorbate 60, polysorbate 61, polysorbate 85, dodecyl-N,N-dimethyl-3-ammonio-1-propanesulfonate, TEEPOL HB7™, and SPAN 80™ SPAN85™, ethoxylated fatty alcohols, ethoxylated fatty acids, ethoxylated castor oil (hydrogenated or not). In one embodiment, these emulsifiers are provided in an amount of approximately 0.05 to approximately 0.5%. In another embodiment, these emulsifiers are provided in an amount of approximately 0.2%. A micelle forming agent is an agent which is able to stabilize the emulsion formed with the other components such that a micelle-like structure is formed.

Examples of such agents include polymer surfactants described by BASF Wyandotte publications, e.g., Schmolka, *J. Am. Oil. Chem. Soc.* 54:110, 1977, and Hunter et al., *J. Immunol.* 129:1244, 1981, PLURONIC™ L62LF, L101, L121, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between about 0 and about 2, as defined by Hunter and Bennett, *J. Immun.* 133:3167, 1984. In one embodiment, the agent can be provided in an effective amount, for example between about 0.5 and about 10%. In another embodiment, the agent can be provided in an effective amount, for example between about 1.25 and about 5%.

In one embodiment, the oil included in the composition is chosen to promote the retention of the antigen in an oil-in-water emulsion, i.e., to provide a vehicle for the desired antigen. In another embodiment, the oil has a melting temperature of less than about 65° C. such that emulsion is formed either at room temperature (about 20° C. to about 25° C.), or once the temperature of the emulsion is brought down to room temperature.

The oil-in-water emulsion (4) can be based in particular on light liquid paraffin oil (European Pharmacopea type); isoprenoid oil such as squalane, squalene, EICOSANE™ or tetratetracontane; oil resulting from the oligomerization of alkenes, in particular of isobutene or decene; esters of acids or of alcohols containing a linear alkyl group, more particularly plant oils, ethyl oleate, propylene glycol di(caprylate/caprate), glyceryl tri(caprylate/caprate) or propylene glycol dioleate; esters of branched fatty acids or alcohols, in particular isostearic acid esters. The oil is used in combination with emulsifiers to form the emulsion. In several embodiments, the emulsifiers are nonionic surfactants, in particular esters of sorbitan, mannide (e.g., anhydromannitol oleate), glycerol, polyglycerol, propylene glycol, and oleic, isostearic, ricinoleic, or hydroxystearic acid, which are for example, ethoxylated, and polyoxypropylene-polyoxyethylene copolymer blocks, in particular the Pluronic® products, especially L121. In one specific, non-limiting example, the oil is provided in an amount between about 1 and about 60%. In another specific, non-limiting example, the oil is provided in an amount between about 5 and about 30%. In one embodiment, the adjuvant is a mixture of emulsifiers, micelle-forming agent, and oil available under the name Provax® (IDEC Pharmaceuticals, San Diego, Calif.).

The acrylic acid or methacrylic acid polymers (2) can be cross-linked in particular with polyAlkenyl ethers of sugars or of polyAlcohols. These compounds are known under the term "carbomer" (*Pharmeuropa*, Vol. 8, No. 2, June 1996). A person skilled in the art may also refer to U.S. Pat. No. 2,909,462 describing such acrylic polymers cross-linked with a polyhydroxylated compound containing at least 3 hydroxyl groups. In one embodiment, a polyhydroxylated compound contains not more than 8 hydroxyl groups. In another embodiment, the hydrogen atoms of at least 3 hydroxyls are replaced with unsaturated aliphatic radicals containing at least 2 carbon atoms. In other embodiments, radicals contain from about 2 to about 4 carbon atoms, e.g., vinyls, allyls, and other ethylenically unsaturated groups. The unsaturated radicals can themselves contain other substituents, such as methyl. The products sold under the name Carbopol® (Noveon Inc., Ohio, USA) are particularly suitable. They are cross-linked with an allyl sucrose or with allylpentaerythritol. Among these, mention may be made of the products Carbopol® 974P, 934P, and 971P.

Among the copolymers of maleic anhydride and of an alkenyl derivative, such as the EMA® products (Monsanto) which are copolymers of maleic anhydride and of ethylene, which may be linear or cross-linked, for example cross-linked with divinyl ether. Reference may be made to J. Fields et al., *Nature* 186:778-780, 1960. In one embodiment, the acrylic acid or methacrylic acid polymers and the EMA® products are formed from units based on the following formula:

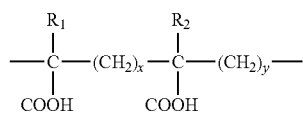

in which:
R$_1$ and R$_2$, which may be identical or different, represent H or CH$_3$
x=0 or 1, in one embodiment, x=1
y=1 or 2, with x+y=2.
For the EMA® products, x=0 and y=2. For the carbomers, x=y=1.

In one embodiment, the dissolution of these polymers in water leads to an acid solution, which is neutralized to physiological pH, in order to give the adjuvant solution into which the immunogenic composition or the vaccine itself is incorporated. The carboxyl groups of the polymer are then partly in COO$^-$ form.

In one embodiment, a solution of adjuvant, especially of carbomer, is prepared in distilled water. In another embodiment, a solution of adjuvant, especially of carbomer, is prepared in the presence of sodium chloride, the solution obtained being at acidic pH. In another embodiment, this stock solution is diluted by adding it or a substantial part thereof, to the desired quantity (for obtaining the desired final concentration) of water charged with NaCl. In yet another embodiment, stock solution is diluted by adding it to the desired quantity of physiological saline (NaCl 9 g/l) with concomitant or subsequent neutralization (pH 7.3 to 7.4). In one embodiment, the stock solution is neutralized with NaOH. This solution, at physiological pH, is used as is for mixing with the immunogenic composition or with the vaccine, which may be stored in freeze-dried, liquid or frozen form.

In one embodiment, the polymer concentration in the final vaccine composition is from about 0.01% to about 1.5% weight/volume (W/V). In another embodiment, the final vaccine composition is from about 0.05 to about 1% W/V. In yet another embodiment, the final vaccine composition is from about 0.1 to about 0.4% W/V.

Lipids have been identified as agents capable of stimulating the immune response for various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinylseryl-serine, can be used.

To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banja, supra). A particulate excipient based on a synthetic polymer has been shown to act as an adjuvant to enhance the immune response, in addition to providing a controlled release.

Plasmid-Based Compositions:

In one embodiment, the plasmid-based compositions is formulated with cationic lipids, in particular with cationic lipids containing a quaternary ammonium salt having the following formula:

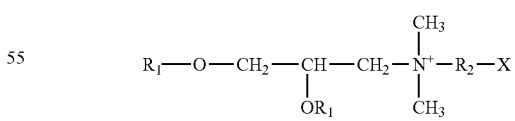

in which R1 is a saturated or unsaturated linear aliphatic radical from 12 to 18 carbon atoms, R2 is another aliphatic radical comprising from 2 to 3 carbon atoms, and X is an hydroxyl or amine group.

In one embodiment, DMRIE (N-(2-hydroxyethyl)-N,N-dimethyl-2,3-bis(tetradecyloxy)-1-propanammonium; WO 96/34109) is the cationic lipid. In another embodiment, the cationic lipid is in association with a neutral lipid, for example DOPE (dioleoyl-phosphatidyl-ethanolamine; Behr J. P., *Bioconjugate Chemistry* 5:382-389, 1994), in order to form the DMRIE-DOPE. In yet another embodiment, the mixture is made extemporaneously about 10 minutes to about 60 minutes before administration. In another embodiment, the mixture is made extemporaneously about 30 minutes before administration. In one embodiment, the molar ratio of DMRIE/DOPE is from about 95/5 to about 5/95. In another embodiment, the molar ratio of DMRIE/DOPE is about 1/1. In one embodiment, the weight ratio of plasmid/DMRIE or of DMRIE-DOPE adjuvant is from about 50/1 to about 1/10. In another embodiment, the weight ratio of plasmid/DMRIE or of DMRIE-DOPE adjuvant is from about 10/1 to about 1/5. In yet another embodiment, the weight ratio of plasmid/DMRIE or of DMRIE-DOPE adjuvant is from about 1/1 to about 1/2.

In one embodiment, a cytokine or non-methylated CpG groups is added to the composition, as described above for polypeptide-based compositions. The addition can be done advantageously by a plasmid encoding the cytokine.

Viral Vector-Based Composition:

The recombinant viral vector-based composition can be supplemented with fMLP (N-formyl-methionyl-leucyl-phenylalanine; U.S. Pat. No. 6,017,537) and/or acrylic acid or methacrylic acid polymer adjuvant as described above for polypeptide-based compositions. They can also be formaluted with emulsions as described above.

In one embodiment, cytokines, non-methylated CpG groups, or emulsions are added to the composition as described above for polypeptide-based compositions. The addition can be done advantageously by a viral vector encoding said cytokine.

The immunogenic compositions and vaccines according to the disclosure are conserved and stored either in formulated form at 5° C., or in lyophilized form. In one embodiment, the immunogenic compositions and vaccines according to the disclosure are conserved and stored either in formulated form at 5° C., or in lyophilized form with a stabilizer. Freeze-drying can be done according to well-known standard freeze-drying procedures. The pharmaceutically acceptable stabilizers may be SPGA (sucrose phosphate glutamate albumin) (Bovarnik et al., *J. Bacteriology* 59:509, 1950), carbohydrates (e.g., sorbitol, mannitol, lactose, sucrose, glucose, dextran, trehalose), sodium glutamate (Tsvetkov T et al., *Cryobiology* 20 (3):318-23, 1983; Israeli E et al., *Cryobiology* 30 (5):519-23, 1993), proteins such as peptone, albumin, or casein, protein containing agents such as skimmed milk (Mills C K et al., *Cryobiology* 25 (2):148-52, 1988; Wolff E et al., *Cryobiology* 27 (5):569-75, 1990), and buffers (e.g., phosphate buffer, alkaline metal phosphate buffer). An adjuvant may be used to make soluble the freeze-dried preparations.

Methods of Immunization

The present disclosure provides methods for inducing an immune response to a Phlebotomus polypeptide in a subject. The present disclosure provides further methods for inhibiting or preventing leishmaniasis in a subject.

These methods include the administration of at least one immunogenic composition or vaccine according to the disclosure.

An immunogenic composition or a vaccine according to the disclosure can be prepared in accordance with standard techniques well known to those skilled in the pharmaceutical or veterinary art. Such compositions can be administered in dosages and by techniques well known to those skilled in the medical or veterinary arts, taking into consideration such factors as the age, sex, weight, species, and condition of the particular subject, and the route of administration.

If more than one administration is required, they can be administered concurrently (e.g., different compositions given during the same period of time via the same or different routes, or a same composition given in the same period of time via different routes), or sequentially (e.g., the same or different compositions given at least two times via the same or different routes). In one embodiment, the delay between two sequential administrations is from about 1 week to about 6 months. In another embodiment, the delay is from about 3 weeks to about 6 weeks. In yet another embodiment, the delay is from about 4 weeks. Following vaccination, annual boost administrations may be done. In a prime-boost vaccination schedule advantageously, at least one primo-administration can be done with a composition containing a plasmid according to the disclosure, following by at least one booster administration done with a composition containing a recombinant viral vector according to the disclosure, on the condition that a same Phlebotomus salivary polypeptide is present twice, coded by the plasmid and by the viral vector. Alternatively, the booster administration can be done with a composition containing a polypeptide according to the disclosure, on the condition that a same Phlebotomus salivary polypeptide is present twice, coded by the primo-administration plasmid and in the booster polypeptide-based composition.

In such compositions the antigen(s) may be in admixture with a suitable vehicle or excipient such as sterile water, physiological saline, glucose, or the like. The compositions can contain auxiliary substances such as wetting or emulsifying agents, pH buffering agents, adjuvants, gelling, or viscosity enhancing additives, preservatives, flavoring agents, colors, and the like, depending upon the route of administration and the preparation desired. Standard texts, such as Remington's Pharmaceutical Science, 17th edition, 1985, may be consulted to prepare suitable preparations, without undue experimentation. The compositions can also be lyophilized.

Suitable dosages can also be based upon the examples below. For polypeptide-based compositions, the route of administration can be intradermal (ID), intramuscular (IM), or subcutaneous (SC), intravenous, oral, nasal, or anal. This administration can be made with a syringe and a needle or with a needle-less apparatus like, for example, Biojector (Bioject, Oregon, USA). In several embodiments, polypeptide dosages can be from about 1 to 250 µg/ml, from about 15 to about 150 µg/dose, or from about 20 to about 100 µg/dose. In another embodiment, using a needle-less apparatus, the volume of a dose can be between about 0.1 ml and about 0.5 ml. In yet another embodiment, using a needle-less apparatus, the volume of a dose can be about 0.25 ml. Administration with multiple points of injection is preferred. In one embodiment, for conventional injection with a syringe and a needle, the volumes are from about 0.1 to about 2 ml. In another embodiment, for conventional injection with a syringe and a needle, the volumes are from about 0.5 to about 1 ml.

For plasmid-based compositions, the route of administration can be ID, IM, SC, intravenous, oral, nasal, or anal. This administration can be made with a syringe and a needle or with a needle-less apparatus like, for example, Biojector. The dosage is from about 50 µg to about 500 µg per plasmid. When DMRIE-DOPE is added, about 100 µg per plasmid is preferred. In one embodiment, when canine GM-CSF or other cytokine is used, the plasmid encoding this protein is present at a dosage from about 200 µg to about 500 µg. In another embodiment, the plasmid encoding this protein is present at a dosage of about 200 µg. In one embodiment, using a needleless apparatus, the volume of a dose can be between about 0.1 ml and about 0.5 ml. In another embodiment, the volume of a dose can be about 0.25 ml. In yet another embodiment, administration is performed using multiple points of injection. In one embodiment, for conventional injection with a syringe and a needle, the volumes are from about 0.1 to about 2. In another embodiment, the volumes are from about 0.5 to about 1 ml. The dosages are the same as mentioned above.

For recombinant viral vector-based compositions, the route of administration can be ID, IM, SC, intravenous, oral, nasal, or anal. This administration can be made with a syringe and a needle or with a needle-less apparatus like, for example, Biojector. The dosage is from about $10^3$ pfu to about $10^9$ pfu per recombinant poxvirus vector. In one embodiment, when the vector is a canarypox virus, the dosage is from about $10^5$ pfu to about $10^9$ pfu. In another embodiment, when the vector is a canarypox virus, the dosage is from about $10^6$ pfu to about $10^8$ pfu. In one embodiment, the volume of needle-less apparatus doses is between about 0.1 ml and about 0.5 ml. In another embodiment, the volume of needle-less apparatus dose is 0.25 ml. In yet another embodiment, administration is performed using multiple points of injection. In one embodiment, for conventional injection with a syringe and a needle, the volumes are from about 0.1 to about 2. In another embodiment, the volumes are from about 0.5 to about 1 ml. The dosages are the same as mentioned above. In one embodiment, when a syringe with a needle is used, the injection is IM.

In one embodiment, for the prime-boost administration regimen, the prime-administration is made with a plasmid-based composition and the boost administration is made with a recombinant viral vector-based composition. In one embodiment, the boost administration is made with a canarypox vector. Both priming and boosting administrations include vectors encoding at least one identical Phlebotomus salivary antigen, and in one specific, non-limiting example, a Leishmania A2 antigen. The dosage of plasmids and recombinant viral vectors are the same as described above. In one embodiment, the boost administration is done with a polypeptide-based composition. In specific, non-limiting examples, the dosage of polypeptide is from about 1 to about 250 µg/ml, from about 15 to about 150 µg/dose, or from about 20 to about 100 µg/dose.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response) and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, Immunol. Today 12:383, 1991). Doses of antigen as low as 1 µg encapsulated in ISCOMS™ have been found to produce class I mediated CTL responses (Takahashi et al., Nature 344:873, 1990).

In another approach to using nucleic acids for immunization, a P. ariasi or a P. perniciosus polypeptide, or an immunogenic peptide thereof, can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, Nature 351:456-460, 1991).

In one embodiment, a nucleic acid encoding a P. ariasi or a P. perniciosus polypeptide, or an immunogenic fragment thereof, is introduced directly into cells. For example, the nucleic acid may be loaded onto gold microspheres by standard methods and introduced into the skin by a device such as Bio-Rad's Helios™ Gene Gun. A needless injector can also be utilized, such as a Bioinjector2000™. The nucleic acids can be "naked," consisting of plasmids under control of a strong promoter. Typically, the DNA is injected into muscle, although it can also be injected directly into other sites. Exemplary dosages for injection are around 0.5 μg/kg to about 50 mg/kg, and typically are about 0.005 mg/kg to about 5 mg/kg (see, e.g., U.S. Pat. No. 5,589,466). In one embodiment, a prime-boost strategy for immunization is utilized. Thus, in one embodiment, a nucleic acid encoding a *P. ariasi* or a *P. perniciosus* polypeptide is administered to the subject, followed by immunization with an attenuated or inactivated form of *Leishmania*.

The immunogenic compositions and the vaccines disclosed herein can be administered for preventative and therapeutic treatments. In therapeutic applications, compositions are administered to a subject suffering from a disease, such as Leishmaniasis, in a therapeutically effective amount, which is an amount sufficient to cure or at least partially arrest the disease or a sign or symptom of the disease. Amounts effective for this use will depend upon the severity of the disease and the general state of the subject's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity in the subject.

As noted above, the dosage of the composition varies depending on the weight, age, sex, and method of administration. The dosage can also be adjusted by the individual physician as called for based on the particular circumstances. The compositions can be administered conventionally as vaccines containing the active composition as a predetermined quantity of active material calculated to produce the desired therapeutic or immunologic effect in association with the required pharmaceutically acceptable carrier or diluent (i.e., carrier or vehicle). For example, about 50 μg of a DNA construct vaccine of the present disclosure can be injected intradermally three times at two week intervals to produce the desired therapeutic or immunologic effect. In another embodiment, about 1 mg/Kg dosage of a protein vaccine of the present disclosure can be injected intradermally three times at two week intervals to produce the desired therapeutic or immunologic effect.

A vaccine is provided herein that includes a *P. ariasi* or *P. perniciosus* polypeptide or polynucleotide. Administration of the vaccine to a subject, such as a human or veterinary subject, results in resistance to infection with *Leishamania*. In one embodiment, the subject is a human subject. In another embodiment, the subject is a canine subject, such as a dog.

The disclosure is illustrated by the following non-limiting Examples.

EXAMPLES

Example 1

Library Construction

Sand Flies and Preparation of salivary gland homogenate (SGH). Salivary extracts are prepared directly from sand flies captured in the wild in the Cevennes in Southern France (close to Vallerauge (Gard)) which is known to be a valid biotope for the *P. ariasi* sand fly species. Unfed females are captured by aspiration immediately after they land on the outside walls of a tent in which a dog has been placed. Captures are done at the end of July, shortly after dusk on dry days and in the absence of wind. Outside temperatures should be between 20 and 25° C. Alternatively, salivary extracts of *P. perniciosus* are prepared directly from sand flies captured in the wild in Southern France (near the city of Marseille) which is known to be a valid biotope for the *P. perniciosus* sand fly species. The identification of the sand fly specimen is performed by the visual observation (20× microscope) of the morphology of the spermatheca after dissection, as described in Leger et al. *Ann. Parasitol. Hum. Comp. t*58 (6):611-623, 1983).

Salivary glands dissected under a dissection microscope and collected in microfuge tubes in sterile phosphate saline buffer, pH 7.0, are stored in dry ice and transferred to −70° C. until use.

The salivary gland of *P. ariasi* is a sac-like structure consisting of a unicellular epithelium layer surrounding a large lumen (Adler and Theodor, *Ann. Trop. Med. Parasitol.* 20:109, 1926). After a blood meal, the gland total protein content decreases to half or less from its ~1 µg value (Ribeiro et al., *Insect Biochem.* 19:409-412, 1989). Thus, most of the protein from the fly SGH must be destined for secretion. Sodium dodecylsulfate-polyAcrylamide gel electrophoresis (SDS-PAGE) of SGH reveals a low complexity composition consisting of ~12 major bands varying from 10-100 kDa (Valenzuela et al., *J. Exp. Med.* 194:331-42, 2001). For SDS-PAGE, Tris-glycine gels (16%), 1 mm thick, or NUPAGE 12% BIS-tris gels were used (Invitrogen). Gels were run with either Tris-glycine or MOPS Nupage running buffer according to the manufacturer's instructions. To estimate the molecular weight of the samples, See BlueJ markers from Invitrogen (myosin, BSA, glutamic dehydrogenase, alcohol dehydrogenase, carbonic anhydrase, myoglobin, lysozyme, aprotinin, and insulin, chain B) were used. SGH were treated with equal parts of 2×SDS sample buffer (8% SDS in Tris-HCl buffer, 0.5M, pH 6.8, 10% glycerol and 1% bromophenol blue dye). Thirty pairs of homogenized salivary glands per lane (approximately 30 µg protein) were applied when visualization of the protein bands by Coomassie blue staining was desired. For amino terminal sequencing of the salivary proteins, 40 homogenized pairs of glands were electrophoresed and transferred to polyvinylidene difluoride (PVDF) membrane using 10 mM CAPS, pH 11, 10% methanol as the transfer buffer on a Blot-Module for the XCell II Mini-Cell (Invitrogen). The membrane was stained with Coomassie blue in the absence of acetic acid. Stained bands were cut from the PVDF membrane and subjected to Edman degradation using a Procise sequencer (Perkin-Elmer Corp.).

Salivary Gland cDNA Library Construction. *P. ariasi* salivary gland mRNA was isolated from 100 salivary gland pairs from adult females. The Micro-FastTrack mRNA isolation kit (Invitrogen, San Diego, Calif.) was used, yielding approximately 100 ng poly (A)+mRNA. The PCR-based cDNA library was made following the instructions for the SMART cDNA library construction kit (Clontech, Palo Alto, Calif.). One hundred nanograms of *P. ariasi* salivary gland mRNA was reverse transcribed to cDNA using Superscript II RNase H— reverse transcriptase (Gibco-BRL, Gaithersburg, Md.) and the CDS/3' primer (Clontech, Palo Alto, Calif.) for 1 hour at 42° C. Second strand synthesis was performed using a PCR-based protocol by using the SMART III primer (Clontech, Palo Alto, Calif.) as the sense primer, and the CDS/3' primer as anti-sense primer. These two primers, additionally, create at the ends of the nascent cDNA, SfiI A and B sites respectively. Double strand cDNA synthesis was done on a Perkin Elmer 9700 Thermal cycler (Perkin Elmer Corp., Foster City, Calif.) using the Advantage Klen-Taq DNA polymerase (Clontech, Palo Alto, Calif.). PCR conditions were the following: 940° C. for 2 minutes; 19 cycles of 94° C. for 10 seconds and 68° C. for 6 minutes. Double stranded cDNA was immediately treated with proteinase K (0.8 µg/µl) for 20 minutes at 45° C. and washed three times with water using Amicon filters with a 100 kD cut off (Millipore Corp., Bedford Mass.). The double stranded cDNA was then digested with Sfi I for 2 hours at 50° C. (The Sfi I sites were inserted to the cDNA during the second strand synthesis using the SMART III and the CDS/3' primer). The cDNA was then fractionated using columns provided by the manufacturer (Clontech, Palo Alto, Calif.). Fractions containing cDNA of more than 400 bp were pooled, concentrated, and washed three times with water using an Amicon filter with a 100 kDa cut-off. The cDNA was concentrated to a volume of 7 µl. The concentrated cDNA was then ligated into a lambda triplex2 vector (Clontech, Palo Alto, Calif.), and the resulting ligation reaction was packed using the Gigapack gold III from Stratagene/Biocrest (Cedar Creek, TE) following manufacturer's specifications. The obtained library was plated by infecting log phase XL1-blue cells (Clontech, Palo Alto, Calif.) and the amount of recombinants was determined by PCR using vector primers flanking the inserted cDNA and visualized on a 1.1% agarose gel with ethidium bromide (1.5 µg/ml)

Massive Sequencing of *P. ariasi* Salivary Gland cDNA Library. *P. ariasi* salivary gland cDNA library was plated to approximately 200 plaques per plate (150 mm Petri dish). The plaques were randomly picked and transferred to a 96 well polypropylene plate containing 100 µl of water per well. The plate was covered and placed on a gyrator shaker for 1 hour at room temperature. Four microliters of a phage sample was used as a template for a PCR reaction to amplify random cDNAs. The primers used for this reaction were sequences from the triplex2 vector, the primers were named PT2F1 (5'-AAGTACTCT AGCAAT TGTGAGC-3') (SEQ ID NO:85) which is positioned upstream of the cDNA of interest (5' end), and PT2R1 (5'-CTCTTCGCTATTACGCCAGCT G-3') (SEQ ID NO:86) which is positioned downstream of the cDNA of interest (3' end). Platinum Taq polymerase (Gibco-BRL, Gaithersburg, Md.) was used for these reactions. Amplification conditions were: 1 hold of 75° C. for 3 minutes, 1 hold of 94° C. for 3 minutes, and 34 cycles of 94° C. for 30 seconds, 49° C. for 30 seconds and 72° C. for 1 minute and 20 seconds. Amplified products were visualized on a 1.1% agarose gel with ethidium bromide. Clean PCR was used as a template for a cycle sequencing reaction using the DTCS labeling kit from Beckman Coulter Inc. (Fullerton, Calif.). The primer used for sequencing (PT2F3) (5'-TCTCGG-GAAGCGCGCCATTGTGTT-3') (SEQ ID NO:87) is upstream of the inserted cDNA and downstream of the primer PT2F1. Sequencing reaction was performed on a Perkin Elmer 9700 thermacycler. Conditions were 75° C. for 2 minutes, 94° C. for 4 minutes, and 30 cycles of 96° C. for 20 seconds, 50° C. for 20 seconds and 60° C. for 4 minutes.

After cycle sequencing the samples, a cleaning step was done using the multi-screen 96 well plate cleaning system from Millipore (Bedford, Mass.). The 96 well multi-screening plate was prepared by adding a fixed amount (according to the manufacturer's specifications) of Sephadex-50 (Amersham Pharmacia Biotech, Piscataway, N.J.) and 300 µl of deionized water. After 1 hour of incubation at room temperature, the water was removed from the multi screen plate by centrifugation at 750 g for 5 minutes. After the Sephadex in the multi-screen plate was partially dried, the whole cycle sequencing reaction was added to the center of each well, centrifuged at 750 g for 5 minutes and the clean sample was collected on a sequencing microtiter plate (Beckman Coulter, Fullerton, Calif.). The plate was then dried on Speed-Vac SC 110 model with a microtiter plate holder (Savant Instruments Inc, Holbrook, NY). The dried samples were immediately resuspended with 25 µl of deionized ultrapure formamide (J. T. Baker, Phillipsburg, N.J.), and one drop of mineral oil was added to the top of each sample. Samples were sequenced immediately on a CEQ 2000 DNA sequencing instrument (Beckman Coulter Inc., Fullerton, Calif.) or stored at −30° C. The entire cDNA of selected genes was fully sequenced using custom primers using a CEQ 2000 DNA sequencing instrument (Beckman Coulter Inc., Fullerton, Calif.), as described above.

Accordingly, a cDNA library was also constructed with *P. perniciosus* salivary glands and sequenced.

DNA Vaccine Construction and Description of the VR1020 Vector. The genes coding for the predicted secreted proteins were amplified from *P. ariasi* specific cDNA and from *P. perniciosus* specific cDNA by PCR using Platinum Taq polymerase (GIBCO BRL) and specific primers carrying the Predicted N-terminus (Forward primer); and the stop codon (Reverse primer) of the selected cDNA.

The PCR product was immediately cloned into the custom made VR-2001-TOPO (derived from VR1020 vector) cloning vector following the manufacturer's specifications (Invitrogen). The ligation mixture was used to transform TOP10 cells (Invitrogen) and the cells were incubated overnight at 370° C. Eight colonies were picked and mixed with 10 µl of sterile water. Five µl of each sample were transferred to Luria broth (LB) with ampicillin (100 µg/ml) and grown at 37° C. The other 5 µl were used as a template for a PCR reaction using two vector-specific primers from the PCRII vector to confirm the presence of the insert and for sequencing analysis. After visualization of the PCR product on a 1.1% agarose gel, the eight PCR products were completely sequenced as described above using a CEQ2000 DNA sequencing instrument (Beckman Coulter). Cells containing the plasmid carrying the selected *P. ariasi* gene were grown overnight at 37° C. on Luria broth with ampicillin (100 µg/ml), and plasmid isolation was performed using the Wizard Miniprep kit (Promega). The VR-2001-TOPO (a variant of the VR1020 plasmid from Vical) plasmid contains a kanamycin resistance gene, the human cytomegalovirus promoter, and the tissue plasminogen activator signal peptide upstream of the TOPO TA cloning site. The sample that contained the sequence from the start codon to the stop codon in the right orientation and in the correct open-reading-frame following the nucleotide sequence encoding the tissue plasminogen activator signal peptide was chosen.

Plasmids were transformed into the SCS-1 strain of *E. coli* (Stratagene, La Jolla, Calif.) according to the manufacturer's instructions. The transformed bacteria were grown in LB medium and the plasmid was subsequently purified using a commercial plasmid purification kit (Qiagen, Courtaboeuf, France). Individual plasmids were quality controlled for identity based on a restriction profile.

These plasmids were named and encoded the following proteins:

TABLE 1

| Plasmid name | Protein encoded |
| --- | --- |
| PJV001 | PRL-P4-A10 |
| PJV002 | PRL-P4-D6 |
| PJV003 | PRL-P4-E5 |
| PJV004 | PRL-P4-G7 |
| PJV005 | PRM-P5-D6 |
| PJV006 | PRM-P5-E9 |
| PJV007 | PRM-P5-F12 |
| PJV008 | PRM-P5-F2 |
| PJV009 | PRM-P5-G11 |
| PJV010 | PRM-P5-H4 |
| PJV011 | PRS-P1-B11 |
| PJV012 | PRS-P1-B4 |
| PJV013 | PRS-P1-E7 |
| PJV014 | PRS-P1-G9 |
| PJV015 | PRS-P2-C8 |
| PJV016 | PRS-P2-G8 |
| PJV017 | PRL-P4-A9 |
| PJV018 | PRL-P4-C10 |
| PJV019 | PRL-P4-D7 |
| PJV020 | PRL-P4-F3 |
| PJV021 | PRL-P4-G12 |
| PJV022 | PRL-P6-E11 |
| PJV023 | PRM-P3-A6 |
| PJV024 | PRM-P3-F11 |
| PJV031 | PERL-P7-G8 |
| PJV032 | PERL-P6-H9 |
| PJV033 | PERL-P7-C2 |
| PJV034 | PERL-P6-H1 |
| PJV035 | PERL-P3-E11 |
| PJV036 | PERL-P7-G12 |
| PJV037 | PERL-P3-C9 |
| PVJ038 | PERM-P2-A10 |
| PVJ039 | PERL-P6-H11 |
| PJV040 | PERS-P1-H11 |
| PJV041 | PERM-P2-G11 |
| PJV042 | PERM-P5-E2 |
| PJV025 | PERM-P5-C11 |
| PJV026 | PERM-P5-H8 |
| PJV027 | PERL-P3-B3 |
| PJV028 | PERM-P2-D11 |
| PJV029 | PERM-P5-E3 |
| PJV030 | PERM-P2-F11 |

Example 2

DNA and Predicted Protein Sequence Analysis

DNA data derived from the mass sequencing project were analyzed by an in-house program written in VisualBASIC (Microsoft). This program removed vector and primer sequences from the raw sequence. Stripped sequences were compared to the NCBI non-redundant protein database using the program BlastX using the BLOSUM-62 matrix (Altschul et al. *Nucleic Acids Research* 25:3389, 1997). DNA sequences were clustered by blasting the database against itself with a preselected threshold cutoff, usually $1e^{-10}$ (BlastN program) (Altschul et al. *Nucleic Acids Research*

25:3389, 1997). Sequences from the same cluster were aligned using ClustalX (Jeanmougin et al, *Trends Biochem. Sci* 23:403, 1998). To find the cDNA sequences corresponding to the amino acid sequence obtained by Edman degradation of the proteins transferred to PVDF membranes from SDS-PAGE gels, a search program was written that checked these amino acid sequences against the three possible protein translations of each cDNA sequence obtained in the mass sequencing project. This was written using the same approach used in the BLOCKS (Henikoff et al., *Bioinformatics* 15:471, 1999) or Prosite (Bairoch, *Nucleic Acids Res.* 19 (Suppl.): 2241, 1991) programs. Protein translations of the full-length clones were further processed to identify the predicted signal peptides using the Signal P program (Nielsen et al., *Protein Eng.* 10: 1, 1997), available online. Predicted signal peptide cleaved sites were compared to the N-terminus sequence obtained from Edman degradation of *Phlebotomus* salivary proteins. Estimation of isoelectric point and molecular weight of translated protein was performed using the DNA STAR program (DNASTAR). Full-length translated protein sequence information was compared with the non-redundant protein database of NCBI using the BLAST-P program (Altschul et al. *Nucleic Acids Research* 25:3389, 1997) and searched for motifs by submitting each sequence to the electronic database.

To characterize the primary structure of the main proteins of *P. ariasi* and *P. perniciosus* SGH, SDS-PAGE gels were transferred to PVDF membranes, and the amino terminal sequence of each cut band by Edman degradation was estimated.

Example 3

DNA Vaccination in Mice

For genetic immunization, Swiss Webster mice were purchased from Taconic Farms. Mice were maintained in the NIAID Animal Care Facility under pathogen-free conditions. Mice were inoculated in the right ear with 30 μg of the plasmid encoding the selected cDNA from *P. ariasi* suspended in 5 μl of PBS. Each group was boosted 2 wk later using the same regimen. Mice were challenged on the opposite ear with salivary gland homogenate of *P. ariasi* and delayed type hypersensitivity (DTH) response was measured 24 hours after the injection by measuring thickness and redness of ear (++: at least 2 mice with a good DTH response, +++: at least three mice had a good DTH response, Table 2).

TABLE 2

| Plasmid name | DTH response |
|---|---|
| PJV002 | − |
| PJV016 | − |
| PJV008 | − |
| PJV017 | − |
| PJV021 | +++ |
| PJV013 | − |
| PJV024 | +++ |
| PJV022 | +++ |
| PJV007 | − |
| PJV005 | +++ |
| PJV009 | +++ |
| PJV023 | ++ |
| PJV010 | − |
| PJV012 | +++ |
| PJV003 | − |
| PJV014 | − |
| PJV015 | ++ |

TABLE 2-continued

| Plasmid name | DTH response |
|---|---|
| PJV019 | − |
| PJV018 | − |
| PJV011 | − |
| PJV020 | +++ |
| PJV001 | +++ |
| PJV006 | +++ |
| PJV004 | ++ |

Example 4

Production of an Immune Response in Dogs

In a first experiment DTH (delayed type hypersensitivity) reaction was performed in dogs with natural immunity against the leishmaniasis in order to determine which *P. ariasi* salivary proteins are recognized by a protective immune response. Dogs with natural immunity survived without symptoms after two years of exposure in an endemic area. In a second experiment, naïve dogs were immunized with the 24 *P. ariasi* salivary gland proteins expressed by a plasmid in order to evaluate the capability to induce a cellular immune response measured by DTH.

Twelve dogs approximately three years old with natural immunity against Leishmaniasis were injected, via an intradermial route (ID) in the back after shaving, with 100 μg of each individual plasmid suspended in 100 μl of PBS. Each plasmid was injected at a different point. The points were separated by at least 3 cm to avoid interference between DTH responses. The negative control (100 μl of buffer) was also inoculated by ID route.

The DTH response was assessed 72 hours after injection by measuring the larger diameter of the skin tumefaction area (see Table 3). The results are expressed as the mean value of the tumefaction area for all the dogs and as a percentage of dogs having a positive DTH response. A positive DTH is a tumefaction area diameter greater than or equal to 4 mm at 72 hours after injection.

TABLE 3

| Plasmids | Mean diameter of the tumefaction area (mm) | Percentage of dogs with a tumefaction diameter ≧ 4 mm |
|---|---|---|
| PJV018 | 1.1 | 18% |
| PJV016 | 1.4 | 20% |
| PJV005 | 2.0 | 27% |
| PJV006 | 1.4 | 27% |
| PJV008 | 2.0 | 27% |
| PJV011 | 1.6 | 27% |
| PJV013 | 1.7 | 27% |
| PJV020 | 1.4 | 27% |
| PJV023 | 1.5 | 27% |
| PJV015 | 2.4 | 36% |
| PJV024 | 2.1 | 36% |
| PJV004 | 2.3 | 40% |
| PJV009 | 2.9 | 46% |
| PJV014 | 2.7 | 46% |
| PJV019 | 2.9 | 46% |
| PJV002 | 2.8 | 46% |
| PJV021 | 3.3 | 55% |
| PJV007 | 3.3 | 55% |
| PJV017 | 3.9 | 58% |
| PJV001 | 4.4 | 64% |
| PJV022 | 4.1 | 64% |
| PJV003 | 6.0 | 82% |

TABLE 3-continued

| Plasmids | Mean diameter of the tumefaction area (mm) | Percentage of dogs with a tumefaction diameter ≧ 4 mm |
|---|---|---|
| PJV012 | 6.1 | 91% |
| PJV010 | 6.3 | 100% |

The data in Table 3 can be divided into three groups: a first group corresponding to plasmids number PJV001, PJV022, PJV003, PJV012, and PJV010 showing a strong DTH response, a second group corresponding to PJV018, PJV016, PJV005, PJV006, PJV008, PJV011, PJV013, PJV020, PJV023, PJV015, and PJV024 showing a low DTH response, and a last group (with PJV004, PJV009, PJV014, PJV019, PJV002, PJV021, PJV007, and PJV017) showing an intermediate DTH response.

In a second study, 10 naïve dogs 4 to 6 months old were immunized by ID injection in 10 points (100 µl per point) in the right ear with a pool of the 24 plasmids (PJV001 to PJV024), 100 µg for each one suspended in 1000 µl of PBS. On day 21, dogs were injected in 10 points (100 µl per point) in the left ear and in 10 points (100 µl per point) in the belly with a pool of the 24 plasmids, 100 µg for each one suspended in 2000 µl of PBS. All dogs were challenged on day 35 by inoculation by ID route in the back (after shaving), with 100 µg of each individual plasmid suspended in 100 µl of PBS. Each plasmid was injected at a different point. The points were separated by at least 3 cm to avoid interference. As a negative control, 100 µl of buffer was inoculated intradermally. The DTH response was assessed 72 hours after challenge, by measuring the larger diameter of the skin tumefaction area (see Table 4). The results are expressed as the mean value of the tumefaction area for all the dogs and as a percentage of dogs having a positive DTH response. A positive DTH is a tumefaction area diameter higher or equal of 4 mm at 72 hours after injection.

TABLE 4

| Plasmids | Mean diameter of the tumefaction area (mm) | Percentage of dogs with a tumefaction diameter ≧ 4 mm |
|---|---|---|
| PJV018 | 4.2 | 60% |
| PJV016 | 3.2 | 56% |
| PJV005 | 3.9 | 60% |
| PJV006 | 3.3 | 50% |
| PJV008 | 3.9 | 70% |
| PJV011 | 4.9 | 89% |
| PJV013 | 3.2 | 56% |
| PJV020 | 2.5 | 50% |
| PJV023 | 3.9 | 67% |
| PJV015 | 2.7 | 44% |
| PJV024 | 5.3 | 78% |
| PJV004 | 3.8 | 56% |
| PJV009 | 3.7 | 70% |
| PJV014 | 2.9 | 44% |
| PJV019 | 1.8 | 33% |
| PJV002 | 2.7 | 50% |
| PJV021 | 4.2 | 70% |
| PJV007 | 3.5 | 70% |
| PJV017 | 3.1 | 56% |
| PJV001 | 2.1 | 40% |
| PJV022 | 6.4 | 100% |
| PJV003 | 4.3 | 70% |
| PJV012 | 3.2 | 60% |
| PJV010 | 2.4 | 40% |

The results of this table show that all plasmids can induce cellular immunity in dogs after injection, as revealed by a DTH response. The variation of the DTH response level may be due to the variation of the expression of the insert.

It will be apparent that the precise details of the methods described may be varied or modified without departing from the spirit of the described disclosure. We claim all such modifications and variations that fall within the scope and spirit of the claims below.

We claim:

1. A substantially purified salivary *Phlebotomus ariasi* polypeptide, wherein the polypeptide comprises: a) residues 23-312 of the SEQ ID NO: 11; b) an amino acid sequence that is at least 95% identical to residues 23-312 of SEQ ID NO: 11; or c) an immunogenic fragment comprising at least fifteen contiguous amino acids of residues 23-312 of SEQ ID NO: 11.

2. A substantially purified salivary *Phlebotomus ariasi* polypeptide, wherein the polypeptide comprises an amino acid sequence that is at least 95% identical to residues 23-312 of SEQ ID NO: 11.

3. A substantially purified salivary *Phlebotomus ariasi* polypeptide of claim 2, wherein the polypeptide comprises an amino acid sequence at least 99% identical to residues 23-312 of SEQ ID NO: 11.

4. An immunogenic fragment of the polypeptide of claim 3, wherein the immunogenic fragment comprises at least fifteen contiguous amino acids of residues 23-312 of SEQ ID NO: 11.

5. An immunogenic composition comprising an effective amount of the polypeptide of claim 1 and a pharmaceutically acceptable carrier.

6. A substantially purified salivary *Phlebotomus ariasi* polypeptide of claim 3, wherein the polypeptide comprises residues 23-312 of SEQ ID NO: 11.

7. An immunogenic composition comprising an effective amount of the polypeptide of claim 2 and a pharmaceutically acceptable carrier.

8. The substantially purified salivary *P. ariasi* polypeptide of claim 6, wherein the polypeptide comprises SEQ ID NO: 11.

9. The substantially purified salivary *P. ariasi* polypeptide of claim 1, wherein the polypeptide comprises SEQ ID NO: 11.

10. A substantially purified salivary *Phlebotomus ariasi* polypeptide of claim 2, wherein the polypeptide comprises an amino acid sequence at least 98% identical to residues 23-312 of SEQ ID NO: 11.

* * * * *

UNITED STATES PATENT AND TRADEMARK OFFICE
CERTIFICATE OF CORRECTION

| | | |
|---|---|---|
| PATENT NO. | : 7,741,437 B2 | |
| APPLICATION NO. | : 10/527500 | |
| DATED | : June 22, 2010 | |
| INVENTOR(S) | : Valenzuela et al. | |

It is certified that error appears in the above-identified patent and that said Letters Patent is hereby corrected as shown below:

Column 14, line 41, "parameters, (gap" should read --parameters (gap--.

Column 14, line 52, "and, variants" should read --and variants--.

Column 55, line 42, "Among the copolymers of" should read --Copolymers of--.

Column 55, line 45, "which may be linear" should read --may be linear--.

Column 61, line 45, "dodecylsulfate-polyAcrylamide" should read --dodecylsulfate-polyacrylamide--.

Signed and Sealed this
Thirtieth Day of October, 2012

David J. Kappos
*Director of the United States Patent and Trademark Office*